United States Patent [19]
Yamamoto et al.

[11] Patent Number: 4,830,660
[45] Date of Patent: May 16, 1989

[54] IMIDAZOLESULFONAMIDE DERIVATIVES AND HERBICIDES

[75] Inventors: Susumu Yamamoto; Takuya Kakuta; Toshiaki Sato; Katsushi Morimoto; Eiichi Oya, all of Funabashi; Takashi Ikai, Shiraoka; Tsutomu Nawamaki, Shiraoka; Kenji Hattori, Shiraoka, all of Japan

[73] Assignee: Nissan Chemical Industries, Ltd., Tokyo, Japan

[21] Appl. No.: 59,608

[22] Filed: Jun. 8, 1987

[30] Foreign Application Priority Data

Jun. 19, 1986 [JP] Japan ................................ 61-143446
Jul. 28, 1986 [JP] Japan ................................ 61-177327

[51] Int. Cl.$^4$ ................. C07D 401/14; C07D 403/14; A01N 43/54; A01N 43/66
[52] U.S. Cl. ............................................ 71/92; 77/90; 544/212; 544/182; 544/298; 544/296; 544/320; 544/321; 544/324; 544/331; 544/278; 544/316; 544/317; 544/319; 544/327; 544/328
[58] Field of Search .................. 71/92, 90; 544/212, 544/182, 295, 296, 320, 321, 324, 331, 278, 316, 317, 319, 327, 328

[56] References Cited

FOREIGN PATENT DOCUMENTS

| 0095925 | 7/1983 | European Pat. Off. . |
| 0096003 | 7/1983 | Fed. Rep. of Germany . |
| 58-162587 | 9/1983 | Japan . |
| 60-45572 | 3/1985 | Japan . |

Primary Examiner—John M. Ford
Attorney, Agent, or Firm—Frishauf, Holtz, Goodman & Woodward

[57] ABSTRACT

There is disclosed imidazolesulfonamide derivatives represented by the general formula (I):

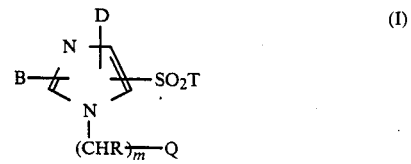

wherein Q, m, R, B, D and T represent a group as specified in the specification and
herbicides containing the same as an active ingredient.

21 Claims, No Drawings

IMIDAZOLESULFONAMIDE DERIVATIVES AND HERBICIDES

BACKGROUND OF THE INVENTION

This invention relates to a novel imidazolesulfonamide derivative, a process for preparing the compound and a herbicide containing the compound as an active ingredient.

In order to protect important crops such as rice plants, wheat, corn, soybean, cotton, beat, etc. from damages by weeds to achieve an increased yield, it is indispensable to use a herbicide. In recent years in particular, a herbicide having selectivity (or discriminativity) is sought after as it can kill only weeds selectively without damages to crops even when a foliage treatment with the herbicide is applied simultaneously on crops and weeds in a cultivated land wherein useful crops and weeds are grown together. Also, from viewpoints of prevention of environmental pollution, the transportation, and the economical cost reduction in application of chemicals, studies and researches have been made over many years on such compounds that may achieve a higher herbicidal activity with use of chemicals in a lower amount. Some of the compounds having such a property are presently used as the herbicide having selectivity. Still, however, there are further demands for new compounds having such a property.

SUMMARY OF THE INVENTION

The present inventors have made researches over many years to develop herbicides having the selectivity on important crops, and have examined herbicidal properties of a number of compounds to create compounds having a higher herbicidal effect and the selectivity. As a result, it was found that an imidazolesulfonamide derivative represented by general Formula (I) (hereinafter referred to as "the compound of this invention"):

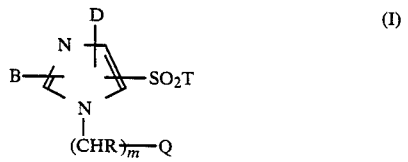    (I)

wherein Q represents a group of;

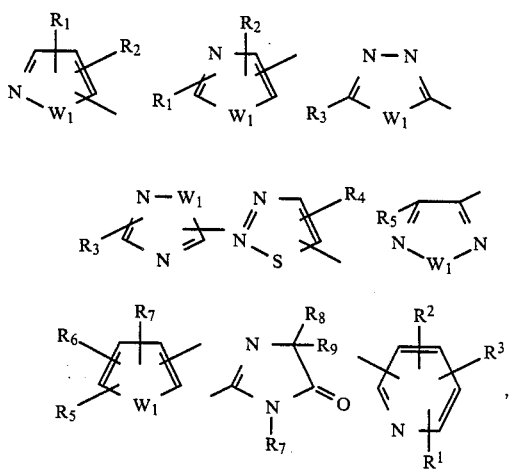

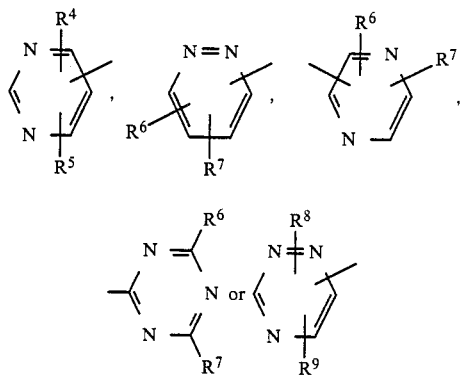

wherein $R^1$, $R^2$ and $R^3$ each independently represent a hydrogen atom, a halogen atom, a nitro group, a lower alkyl group, a halogenated lower alkyl group, a cyano group, a group of $COOR^{10}$, a group of $S(O)_nR^{11}$, a group of $NR^{12}R^{13}$, a lower alkoxy group, a group of $SO_2NR^8R^9$, a group of $SO_2OR^{11}$ or a phenyl group which may be substituted (the substituent is selected from a halogen atom, a nitro group, a group of $COOR^{10}$, a lower alkoxy group and a lower alkyl group);

$R^4$ and $R^5$ each independently represent a hydrogen atom, a halogen atom, a lower alkyl group, a halogenated loweralkyl group, a nitro group, a cyano group, a group of $COOR^{10}$, a group of $S(O)_nR^{11}$, a lower alkoxy group or a phenyl group which may be substituted (the substituent is selected from a halogen atom, a group of $COOR^{10}$, a nitro group, a lower alkoxy group and a lower alkyl group);

$R^6$ and $R^7$ each independently represent a hydrogen atom, a halogen atom, a lower alkyl group, a lower alkoxy group, a nitro group or a group of $COOR^{10}$;

$R^8$ and $R^9$ each independently represent a hydrogen atom, a lower alkyl group or a phenyl group;

$W^1$ represents an oxygen atom, a sulfur atom or a group of $N-R^{10}$;

$R^{10}$ represents a hydrogen atom or a lower alkyl group;

$R^{11}$ represents a lower alkyl group and n represents an integer of 0, 1 or 2; and $R^{12}$ and $R^{13}$ each independently represent a hydrogen atom or a lower alkyl group, m represents an integer of 0, 1 or 2;

R repesents a hydrogen atom or a lower alkyl group;

B and D each independently represent a hydrogen atom, a halogen atom, a nitro group, a lower alkyl group, an aralkyl group, a lower alkoxy group, a halogenated alkyl group, a halogenated alkenyl group, a lower alkoxyalkyl group, an alkylcarbonyl group, a group of $COOR^{14}$, a group of $CONR^{15}R^{16}$, a group of $S(O)_nR^{17}$, a cyano group, a group of $NR^{18}R^{19}$, a group of $SO_2NR^{20}R^{21}$, a hydroxy group, a benzoyl group which may be substituted (the substituent is selected from a halogen atom and a lower alkyl group) or a phenyl group which may substituted (the substituent is selected from a halogen atom, a nitro group, a group of COOR$^{10}$, a lower alkoxy group and a lower alkyl group);

R$^{14}$ represents a hydrogen atom, a lower alkyl group which may be substituted (the substituent is selected from a lower alkoxy group which may be substituted by a group of OR$^{10}$, a halogen atom, a halogenated lower alkoxy group, a cyano group, a phenoxy group, a lower alkoxycarbonyl group, a group of NR$^{10}$R$^{11}$, a lower cycloalkyl group, a lower alkylthio group and a lower alkylcarbonyl group), a lower alkenyl group, a halogenated lower alkenyl group, a lower alkynyl group, a halogenated lower alkynyl group, a halogenated lower cycloalkyl group or a benzyl group;

R$^{15}$ represents a hydrogen atom, a lower alkyl group or a phenyl group; and R$^{16}$ represents a hydrogen atom, a lower alkyl group or a lower alkoxy group;

R$^{17}$ represents a lower alkyl group, a lower alkoxy group, a phenyl group, a halogenated alkyl group, a lower alkenyloxy group or a lower alkynyloxy group; and n represents an integer of 0, 1 or 2;

R$^{18}$ and R$^{19}$ each independently represent a hydrogen atom, a lower alkyl group, a lower alkylcarbonyl group or a lower alkylsulfonyl group;

R$^{20}$ and R$^{21}$ each independently represent a hydrogen atom, a lower alkyl group, a lower alkenyl group or a lower alkynyl group;

T represents a group of

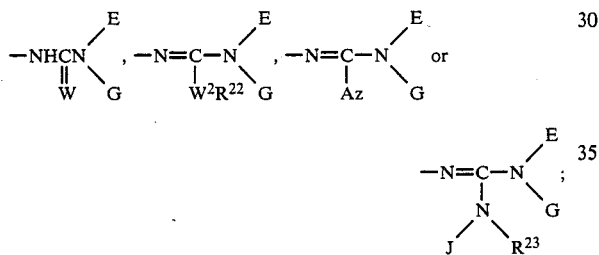

E represents a hydrogen atom, a lower alkyl group, a lower alkenyl group, a lower alkynyl group or a lower alkoxy group;

G represents a group of;

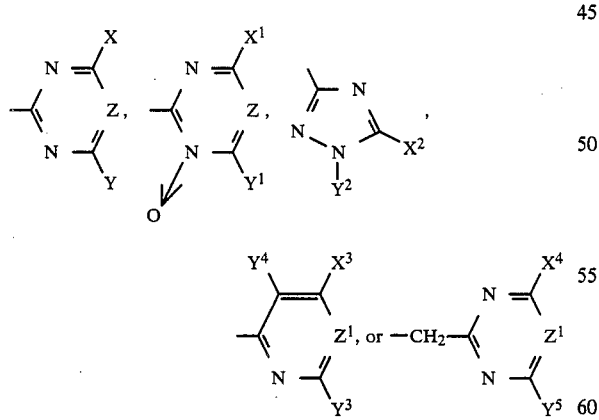

wherein X and Y each independently represent a hydrogen atom, a halogen atom, a lower alkyl group, a lower alkoxy group, a lower alkoxyalkyl group, a halogenated alkyl group, a halogenated lower alkoxy group, a group of NR$^{24}$R$^{25}$, a group of OCH(R$^{10}$)COOR$^{10}$, a group of COOR$^{10}$, a cyclopropyl group, a group of CH(OR$^{26}$)$_2$, a lower alkylthio group or a halogenated lower alkylthio group, R$^{24}$ and R$^{25}$ each independently represents a hydrogen atom, a lower alkyl group or a lower alkoxy group;

R$^{26}$ represents a lower alkyl group;

X$^1$ and Y$^1$ each independently represent a hydrogen atom, a halogen atom, a lower alkyl group, a halogenated alkyl group or a lower alkoxy group;

X$^2$ represents a lower alkyl group, a lower alkylthio group or a lower alkoxy group, and Y$^2$ represents a lower alkyl group;

Z represents a nitrogen atom or a group of C—R$^{27}$,

R$^{27}$ represents a hydrogen atom, a lower alkyl group, a halogenated lower alkyl group, a halogen atom, a lower alkoxy group or a 5-membered ring structure containing an oxygen atom together with Y or Y$^1$;

X$^3$ represents a lower alkyl group, a lower alkoxy group, a lower alkoxyalkyl group or a halogen atom;

Y$^3$ represents a lower alkyl group, a lower alkoxy group, a halogen atom, a monoalkylamino group or a dialkylamino group;

Y$^4$ represents a cyano group, a group of CO$_2$R$^{10}$, a nitro group, a group of S(O)$_n$R$^{11}$, an alkyl group or a halogenated alkyl group;

Z$^1$ represents a nitrogen atom or a group of CH;

X$^4$ and Y$^5$ each independently represent a lower alkyl group or a lower alkoxy group;

W represents an oxygen atom, a sulfur atom or a group of N—R$^{28}$ (wherein R$^{28}$ represents a hydrogen atom or a lower alkoxy group);

W$^2$ represents an oxygen atom or a sulfur atom;

R$^{22}$ represents a lower alkyl group;

Az represents a halogen atom, a nitro group, or an imidazolyl group, an imidazolynyl group, a pyrazolyl group, a triazolyl group or a benzimidazolyl group each of which may be mono-, di- or tri-substituted by a lower alkyl group;

J represents a lower alkyl group or a group of

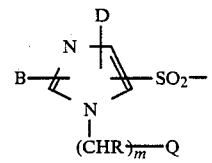

wherein Q, R, m, B and D have the same meanings as defined above;

and R$^{23}$ represents a hydrogen atom, a lower alkyl group or a lower alkoxy group, has a strong herbicidal effect to various weeds while retaining high safety to the important crops in either case of the soil treatment or the foliage treatment, whereby this invention has been accomplished. The compound of this invention shows a high herbicidal activity in an application of a very low amount of the active ingredient as compared with the conventional herbicides, and accordingly it is useful also as a herbicide for orchards and uncultivated lands.

DESCRIPTION OF THE PREFERRED EMBODIMENTS

As a prior technique, for example, Japanese Provisional Patent Publication No. 162587/1983 and No. 1480/1984 disclose imidazolesulfonylurea which has the structure similar to the compound of this invention. However, there has been disclosed no compound wherein a heterocyclic ring is substituted on an imidazole ring as the compound of this invention. Thus, the compound of this invention can be said to be a novel one.

In the present invention, preferred componds represented by the formula (I) are as follows:

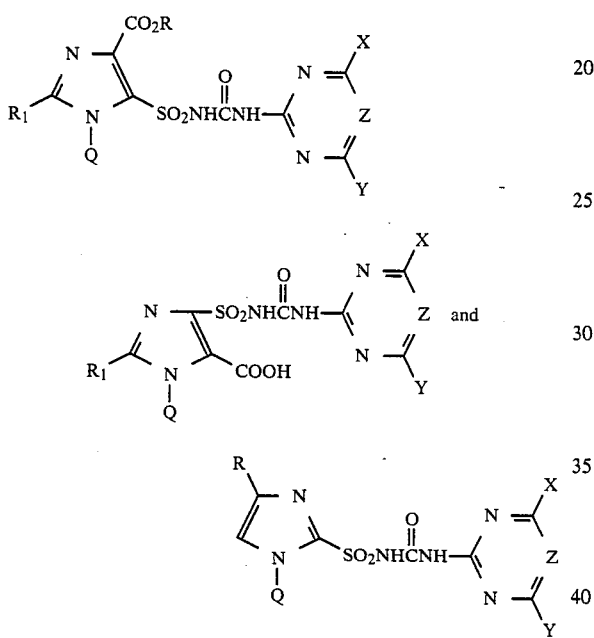

wherein $R_1$ represents a hydrogen atom, a methyl group, a halogen atom or a nitro group; R represents a methyl group or an ethyl group; Q is selected from the group of Q5, Q6, Q7, Q9, Q15, Q21, Q26, Q29, Q32, Q50, Q54, Q61, Q68, Q88, Q127, Q138Q142, Q188, Q189, Q201, Q202, Q204, Q205, Q209, Q222, Q225, Q229, Q230, Q246 and Q250 as mentioned on pages 45 to 57 hereinbelow;

X and Y are each independently a halogen atom, a methyl group, a methoxy group; and Z is —CH= or —N=.

The compound of this invention, represented by general formula (I) can be readily prepared by selecting any of reaction schemes 1 to 7 shown below.

Reaction scheme 1

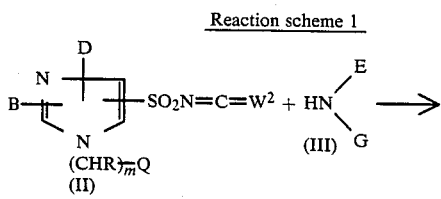

-continued
Reaction scheme 1

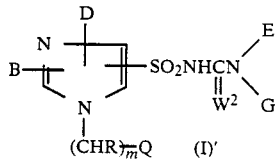

wherein B, D, E, G, Q, R, $W^2$ and m have the same meanings as defined above.

More specifically, the imidazolesulfonyl(thio)isocyanate derivative (II) is dissolved in a sufficiently dried inert solvent such as dioxane and acetonitrile and thereto is added a pyrimidine, triazine or triazole derivative represented by Formula (III), with stirring. Thus, the reactants generally are reacted with each other rapidly to give the compound (I)' which is part of the compound of this invention. In cases where it is difficult for the reaction to proceed, a trace or small amount of suitable base, such as triethylamine, triethylenediamine, pyridine, a sodium alkoxide, sodium hydride and the like, may be added to the reaction system to allow the reaction to proceed readily.

Reaction scheme 2

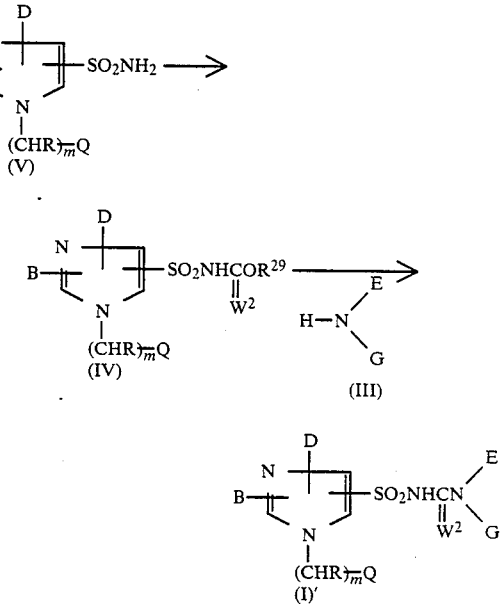

wherein B, D, E, G, Q, R, $W^2$ and m have the same meanings as defined above. $R^{29}$ represents a lower alkyl group or a phenyl group.

More specifically, the imidazolesulfonamide derivative (V) is reacted with a chloroformic acid (thio)ester or a carbonic acid (thio)ester in a solvent such as acetone, methyl ethyl ketone and acetonitrile in the presence of a base such as potassium carbonate to give the compound (IV). Subsequently, the resulting (IV) is heated with the compound (III) in a solvent such as tolune to give the compound (I)' which is a part of the compound of this invention.

Reaction scheme 3

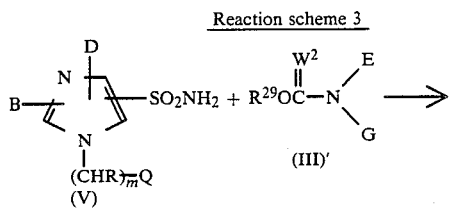
(V)    (III)'

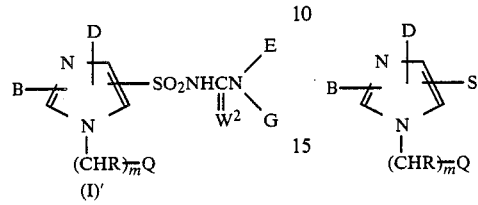
(I)' wherein B, D, E, G, Q, R, W² and m have the same meanings as defined above. R²⁹ represents a lower alkyl group or a phenyl group.

More specifically, by reacting the imidazolesulfonamide derivative (V) with an N-heterocylic carbamate (III)' in the presence of an inorganic salts such as hydroxides, hydrides, etc., or an organic bases such as alkylamine, pyridine, 1,8-diazabicyclo(5.4.0)-7-undecene in an inert solvent such as methylene chloride, tetrahydrofuran, acetonitrile, etc., the compound (I)' which is a part of the compound of this invention can be obtained.

Reaction scheme 4

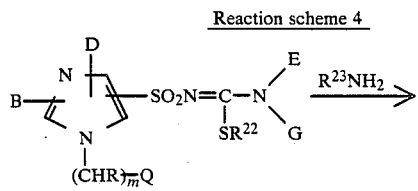

-continued
Reaction scheme 4

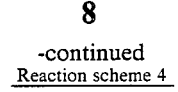

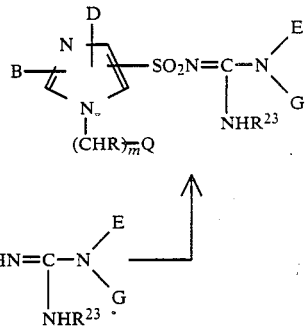

wherein B, D, E, G, Q, R, m, R²² and R²³ have the same meanings as defined above.

Reaction scheme 5

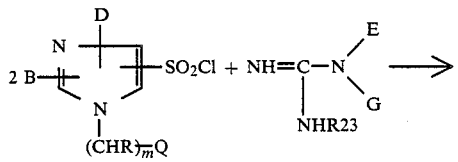

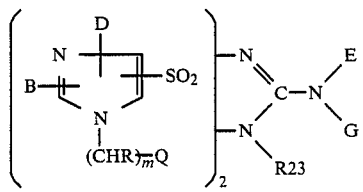

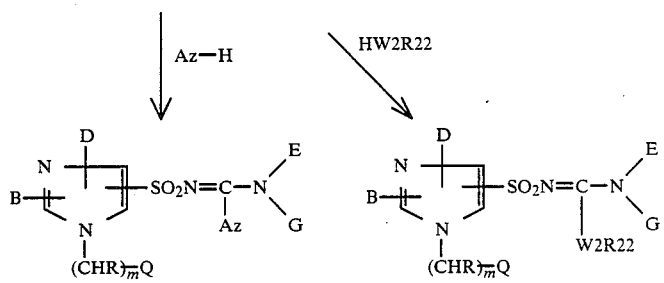

wherein Az, B, D, E, G, Q, R, W², m, R²² and R²³ have the same meanings as defined above.

Reaction scheme 6

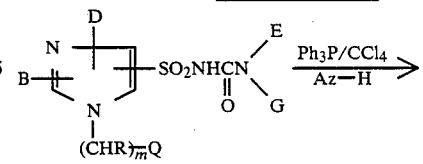

wherein Az, B, D, E, G, Q, R and m have the same meanings as defined above.

More specifically, the above imidazolesulfonamide derivative in any of Reaction schemes 4 to 6, which is a part of the compound of this invention can be synthesized in accordance with the process disclosed in Japanese Provisional Patent Publications No. 167570/1984, No. 6654/1985, No. 36467/1985, No. 60670/1986, No. 60684/1986 and No. 72783/1986.

the resulting product to the desired product with reference to the methods as described in European Patent Publication No. 87,780 (EP-A0 087 780) and Japanese Provisional Patent Publication No. 13266/1980.

The imidazolesulfonamide which is an intermediate to be used in the present invention is also a novel compound, which can be obtained by optionally selecting one of the following Reaction schemes 8 to 12 and the methods described in Japanese Provisional Patent Publications No. 162587/1983, No. 1480/1984, etc.

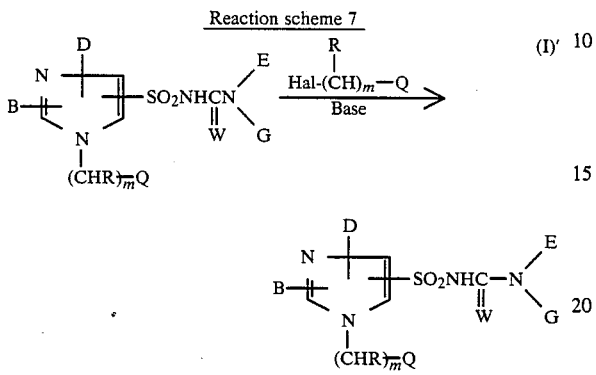

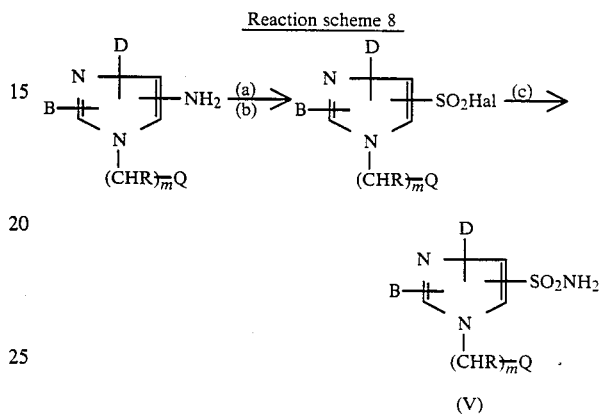

wherein B, D, E, G, Q, R, W and m have the same meanings as defined above; and Hal represents a halogen atom.

More specifically, 1H-imidazolesulfonylurea is reacted with a Hal—(CHR)$_m$—Q in the presence of an appropriate base to give the compound (I)' which is a part of the compound of this invention. Be noted that in case where m is 0, Q desirably has an electron attractive group such as a nitro group, CF$_3$, a halogen atom or the like as a substituent therefor in many occasions and the Hal-group is required to have high reactivity.

The starting material, the imidazolesulfonyl(thio)isocyanate (II) or the imidazolesulfonyl(thio)carbamate derivative (IV) which is used in Reaction schemes 1 and 2 may be synthesized by optionally selecting the methods as will be described hereinafter to synthesize the imidazolesulfonamide (V) and further converting

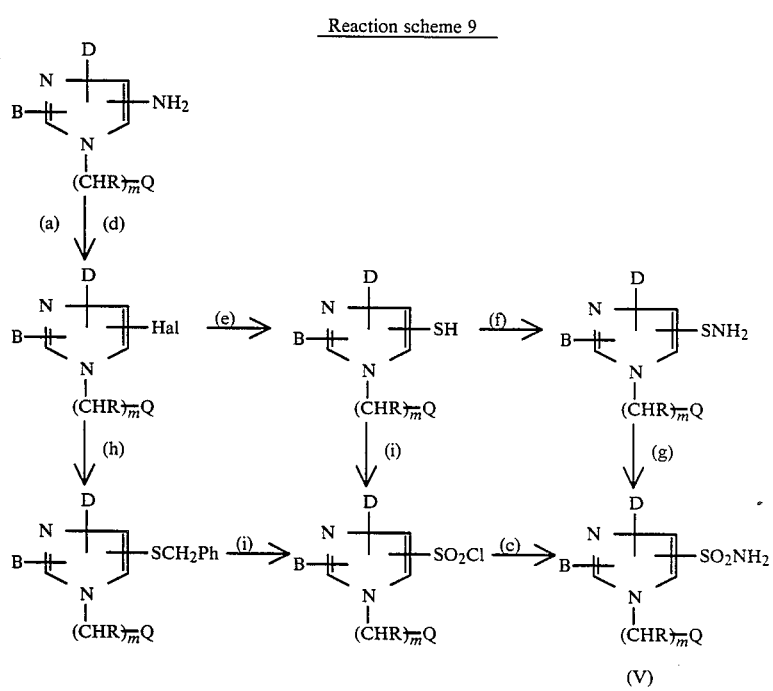

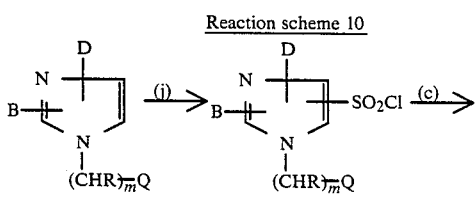

-continued
Reaction scheme 10

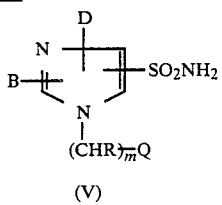

Reaction scheme 11

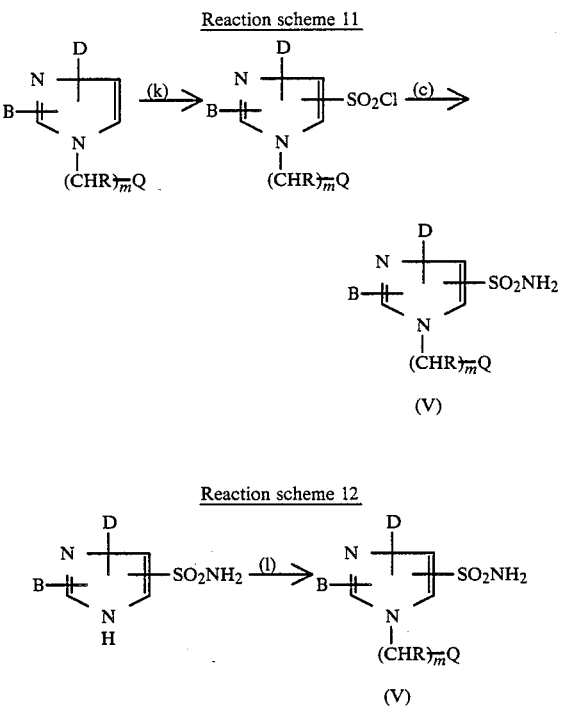

Reaction scheme 12

(a) $NaNO_2 \cdot HCl$ or $NaNO_2 \cdot HBr$
(b) $SO_2 \cdot Cu$ salt
(c) $NH_4OH$ or ammonium carbonate
(d) Cu salt
(e) NaSH
(f) $NaOH \cdot NH_4OH/NaOCl$
(g) Oxidizing agent
(h) $NaSCH_2Ph$
(i) $Cl_2/CH_3CO_2H \cdot H_2O$ or $NaOCl/HCl$
(j)
  (1) $ClSO_3H$
  (2) $SOCl_2$ or $PCl_5$
(k)
  (1) BuLi or $LiN(i-Pr)_2$
  (2) $SO_2$
  (3) N-chlorosuccinimide
(l) Q—$(CHR)_m$—Hal/base In Reaction schemes 8 to 12, B, D, Q, R and m have the same meanings as defined above; and Hal represents a halogen atom.

The imidazolesulfonamide (V) may usually be obtained by reacting a corresponding imidazolesulfonyl chloride with an aqueous ammonia or ammonium carbonate. In order to introduce a sulfonyl group into an imidazole ring, there may be adopted such methods as follows:

(1) The amino group is subjected to diazonium decomposition in the presence of sulfur dioxide to give a imidazolesulfonyl chloride;

(2) A sulfur atom is introduced into the imidazole ring by a nucleophilic substitution reaction with a halogen atom or the like and optionally the resulting compound is further oxidized to given an imidazolesulfonyl chloride;

(3) A carbanion of an imidazole is formed by using a base and sulfur dioxide is reacted therewith followed by halogenation to give an imidazolesulfonyl chloride; and (4) Chlorosulfonic acid or the like is used to directly give an imdazolesulfonyl chloride in an electrophilic substitution reaction.

More specifically, (1) according to Reaction scheme 8, an aminoimidazole is converted into a diazonium salt by using sodium nitrite or the like in hydrochloric acid, hydrobromic acid or the like and then sulfur dioxide is reacted with the resulting diazonium salt in the presence of a catalyst which is usually used for diazonium decomposition such as a copper salt or the like, to afford a corresponding imidazolesulfonyl chloride. With the resulting compound was reacted an aqueous ammonia to give the desired pyrazolesulfonamide (V).

(2) According to Reaction scheme 9, a halogenated imidazole is treated with sodium hydrosulfide, sodium salt of benzylmercaptan or the like to introduce a sulfur atom into the imidazole ring, followed by oxidation with chlorine in a solvent such as acetic acid/water to give an imidazolesulfonyl chloride. As in Reaction scheme 8, a reaction with an aqueous ammonia gives the desired pyrazolesulfonamide (V). The desired imidazolesulfonamide may also be obtained by converting the intermediate of mercaptopyrazole into a sulfenamide which is then oxidized. The starting material, the halogenated imidazole, may be obtained by diazodecomposition of an aminopyrazole; by the reaction of a hydroxyimidazole with phosphorus oxychloride or phosphorus oxybromide; or by formation of an anion by using a strong base such as butyl lithium, lithium diisopropylamide or the like, followed by halogenation.

(3) According to Reaction scheme 11, an anion may be formed by using a strong base such as butyl lithium, lithium diisopropylamide or the like, and the resulting anion may further be treated with sulfur dioxide and subsequently with an N-halogenosuccinimide to form an imidazolesulfonyl chloride which is then treated with an aqueous ammonia to give the desired imidazolesulfonamide (V).

(4) According to Reaction scheme 10, use of chlorosulfonic acid may give directly an imidazolesulfonyl chloride.

In addition to the above schemes, according to Reaction scheme 12, the desired imidazolesufonamide (V) may be obtained by allowing an imidazolesulfonamide having no substituent on the 1-position to react with an appropriate halogen derivative Hal—$(CHR)_m$—Q (wherein Q, R, m and Hal have the same meanings as defined above) in the presence of a suitable base. The reaction may be carried out in accordance with Reaction scheme 7. In reactions in Reaction schemes 10 to 12, isomers may possibly be formed in admixture with the desired compound depending upon occasion. However, such isomers may be separated by recrystallization, column chromatography or the like and used as an intermediate for the compound of this invention. General literatures for the chemistry on the imidazoles used as starting materials in the above-mentioned reactions include the following ones. M. R. Grimmett, Advanced Heterocyclic Chemistry, Vol. 12, p. 104 (1970); R. C. Elderfield, Heterocyclic Compounds, Vol. V, p. 194 (1957), published by John Wiley and Sons, Inc., New York; K. Schofield, M. R. Grimmett and B. R. T. Keene, Heteroaromatic Nitrogen Compounds The Azoles, published by Cambridge University Press, (1976); M. R. Grimmett, Comprehensive Heterocyclic Chemistry, Vol. 5, p. 345 (1984), published by Pergamon Press.

The mercaptoimidazole derivative, for example, may be synthesized, as shown in Reaction scheme 13, according to methods described in R. G. Jones, E. C. Kornfeld, K. C. McLaughlin and R. C. Anderson, J. Am. Chem. Soc., Vol. 71, p. 4000 (1949).

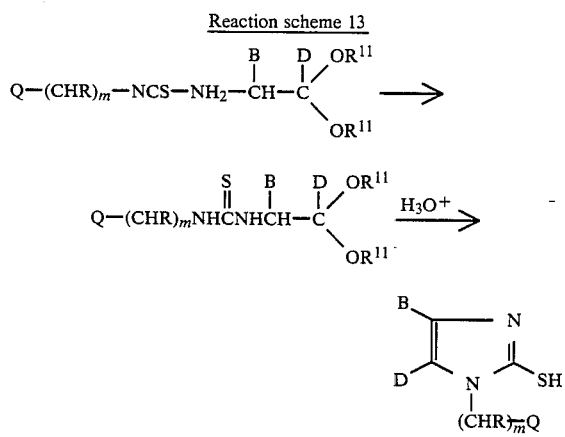

Reaction scheme 13 wherein Q, R, $R^{11}$ and m have the same meanings as defined above; and B and D each independently represent a hydrogen atom or a lower alkyl group.

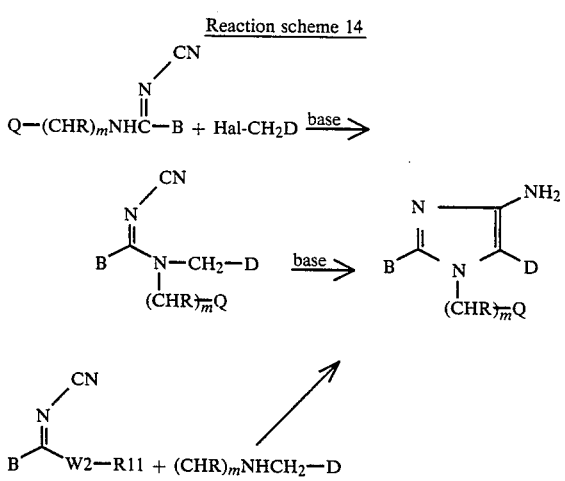

Reaction scheme 14 wherein Q, R, $R^{11}$, $W^2$, m and Hal have the same meanings as defined above; B represents a hydrogen atom, a lower alkyl group or a lower alkylmercapto group; D represents an alkylcarbonyl group, a benzoyl group, a cyano group, an alkylsulfonyl group, a phenylsulfonyl group, a group of $COOR^{14}$ or a group of $CONR^{15}R^{16}$; wherein $R^{14}$, $R^{15}$ and $R^{16}$ have the same meanings as defined above.

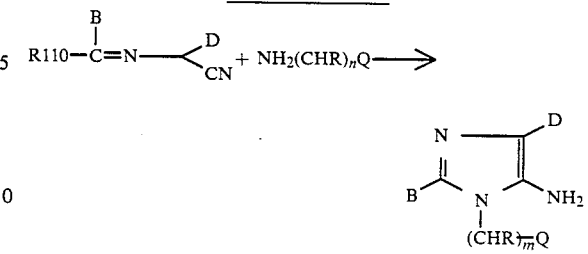

Reaction scheme 15 wherein Q, R, $R^{11}$ and m have the same meanings as defined above; B represents a hydrogen atom or a lower alkyl group; D represents a hydrogen atom, an alkylcarbonyl group, a benzoyl group, a cyano group, an alkylsulfonyl group, a phenylsulfonyl group, a group of $COOR^{14}$ or a group of $CONR^{15}R^{16}$, in which $R^{14}$, $R^{15}$ and $R^{16}$ have the same meanings as defined above.

An aminoimidazole may be synthesized, as shown in Reaction scheme 14, according to methods described in K. Gewald and G. Heinhold, Monatsh. Chem., Vol. 107, p. 1413 (1976), specification of East German Pat. No. 118,640 and A. Edenhofer, Helv. Chim. Acta., Vol. 58, p. 2192 (1975) to give 4-aminoimidazole derivatives having various substituents. Also, 5-aminoimidazole may be synthesized, as shown in Reaction scheme 15, according to methods described in D. H. Robinson and G. Shaw, J. Chem. Soc., Perkin Trans. I, p. 1715 (1972).

Further, a heterocyclic isothiocyanate which is a raw material to be used in a reaction of Reaction scheme 13 may be synthesized, for example as shown in Reaction scheme 16, according to methods desribed in D. J. LeCount, D. J. Dewsbury and W. Grundy, Synthesis, p. 582 (1977).

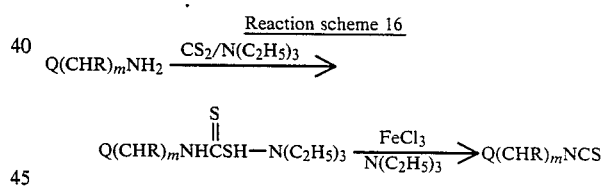

Reaction scheme 16 wherein Q, R and m have the same meanings as defined above.

Generally, a person skilled in the art would be able to obtain an intermediate for the compound of the present invention by investigating experimental conditions and the like taking into consideration the above descriptions and the prior art technologies as mentioned above. Hereinafter, there will be described Synthesis examples of the present compounds and the intermediate imidazolesulfonamide therefor by way of Examples or Reference examples, which, however, should not be construed to limit the present invention.

REFERENCE EXAMPLE 1

Synthesis of 1-methyl-3-pyrazolylisothiocyanate

To a mixture of 29.1 g of 3-amino-1-methylpyrazole and 45 ml of triethylamine was added dropwise 18 ml of carbon disulfide and the resulting mixture was stirred at 40° C. for 30 minutes to precipitate solids. To the reaction mixture was added ether, followed by pulverization of solids. After filtration, the thus pulverized solids were washed with ether to give 67 g of triethylamine salt of 1-methyl-3-pyrazolyldithiocarbamic acid (melting point: 79° to 82° C.) 31.8 g of the thus obtained triethylamine salt of dithiocarbamic acid and 11.7 g of triethylamine were dissolved in 150 ml of methylene chloride. To the resulting solution was added at one time 34.5 g of ferric chloride 6 hydrate dissolved in 100 ml of water, followed by vigorous stirring for 10 minutes. The reaction mixture was filtered to remove insoluble solids. The organic layer was separated and then the aqueous layer was extracted with methylene chloride. After the organic layers were combined, washed with water and dried, the solvent was distilled off under reduced pressure. To the thus obtained residue was added ether to filter the insoluble solids off and the filtrate was concentrated under reduced pressure to give 9.0 g of oil. The thus obtained oil was evaporated under reduced pressure to give 6.5 g of the desired compound. b.p.: 135° to 138° C./23 mmHg.

REFERENCE EXAMPLE 2

Synthesis of 1-(1-methylpyrazol-3-yl)imidazole-2-thiol

To 6.6 g of 2,2-diethoxyethylamine dissolved in 100 ml of ethanol was added 6.3 g of 1-methyl-3-pyrzolylisothiocyanate, followed by stirring at room temperature over night. Crystals precipitated were filtered out and washed with a small amount of ethanol to give 10.3 g of N-2,2-diethoxyethyl-N'-(1-methylpyrazol-3-yl)thiourea (m.p.: 152° to 155° C.). 10.0 g of the crystals thus obtained were suspended in 70 ml of water. To the resulting suspension was added 15 ml of conc. hydrochloric acid, followed by stirring under reflux with heating for 30 minutes. The reaction mixture was cooled and adjusted to pH to 4 to 6 with use of 50% aqueous sodium hydroxide solution to precipitate crystals. The crystals precipitated were filtered out, washed with water and dried to give 6.0 g of the desired compound. m.p.: 126° to 128° C.

REFERENCE EXAMPLE 3

Synthesis of 1-(4-chloro-1-methylpyrazol-3-yl)imidazole-2-sulfonamide

To a mixture of 5.8 g of 1-(1-methylpyrazol-3-yl)imidazole-2-thiol, 30 ml of water, 60 ml of chloroform and 27 g of conc. hydrochloric acid was added dropwise 192 g of aqueous sodium hypochlorite solution (content of 6%) under vigorous stirring at −10° to 0° C. over about 4 hours. After completion of the dropwise addition, the resulting mixture was stirred at the same temperature for 1 hour. Then, the organic layer was separated and the aqueous layer was extracted with chloroform. The organic layers were combined and washed with water. Then, to the organic layer was added dropwise 20 ml of 28% aqueous ammonia under ice-cooling, followed by stirring at room temperature for 1.5 hours. Crystals precipitated by concentrating the resulting mixture under reduced pressure, were filtered out, washed with water and subsequently with ether to give 2.9 g of the desired compound. m.p.: 208° to 210° C.

REFERENCE EXAMPLE 4

Synthesis of 1-methyl-5-pyrazolylisothiocyanate

Using 5-amino-1-methylpyrazole as a starting material, triethylamine salt of 1-methyl-5-pyrazolyldithiocarbamic acid (m.p.: 89° to 94° C.) was synthesized, following the procedures described in Reference Example 1. Ferric chloride was allowed to act upon the resulting product to yield the desired compound. Oily substance.

REFERENCE EXAMPLE 5

Synthesis of 1-(1-methylpyrazol-5-yl)imidazole-2-thiol

Using 1-methyl-5-pyrazolylisothiocyanate as a starting material, the desired compound was obtained via N-2,2-diethoxyethyl-N'-(1-methylpyrazol-5-yl)thiourea (m.p.: 148° to 149° C.) as an intermediate, following the procedures described in Reference Example 2. m.p.: 247° to 251° C.

REFERENCE EXAMPLE 6

Synthesis of 1-(1-methylpyrazol-5-yl)imidazole-2-sulfonamide

To a mixture of 5.0 g of 1-(1-methylpyrazol-5-yl)imidazole-2-thiol, 30 ml of water, 60 ml of chloroform and 23 g of conc. hydrochloric acid, was added dropwise 100 g of aqueous sodium hypochlorite (content of 6%) under vigorous stirring at −10° to 0° C. over 2.5 hours. After completion of the dropwise addition, the resulting mixture was stirred at the same temperature for 0.5 hour. Then the organic layer was separated and the aqueous layer was extracted with chloroform. After the organic layers were combined and washed with water, to the organic layer was added dropwise 20 ml of 28% aqueous ammonia under ice-cooling, followed by stirring at room temperature for 1.5 hours. Crystals precipitated by concentrating the resulting mixture under reduced pressure, were filtered out, washed with water and subsequently with ether to give 3.4 g of the desired compound. m.p.: 230° to 233° C.

REFERENCE EXAMPLE 7

Synthesis of 5-amino-4-ethoxycarbonyl-1-(1-methylpyrazol-3-yl)imidazole

In 200 ml of acetonitrile, 6.7 g of ethyl-aminocyanoacetate, 8.5 g of ethyl orthoformate and 5.6 g of 3-amino-1-methylpyrazole were refluxed under heating for 4.5 hours. After completion of the reaction, the solvent was distilled off under reduced pressure. Crystals precipitated was filtered out, followed by washing with ether to give 7.5 g of the desired compound. m.p.: 168° to 170° C.

REFERENCE EXAMPLE 8

Synthesis of 5-chloro-4-ethoxycarbonyl-1-(1-methylpyrazol-3-yl)imidazole 7.4 g of 5-amino-4-ethoxycarbonyl-1-(1-methylpyrazol-3-yl)imidazole was dissolved in 40 ml of conc. hydrochloric acid and the resulting solution was cooled to −5° C. Subsequently, 2.6 g of sodium nitrite was dissolved in 10 ml of water and the resulting solution was added dropwise to the previously prepared solution while maintaining the temperature at −5° C. or lower. After completion of the dropwise addition, the resulting mixture was stirred at the same temperature for 0.5 hour. The thus obtained solution was added dropwise at around 5° C. to 120 ml of a solution of chloroform containing 0.5 g of cuprous chloride and 17 g of sulfur dioxide. After the resulting mixture was stirred at room temperature for 1 hour, was added thereto 200 ml of water and the organic layer was separated. The aqueous layer was extracted with chloroform and the organic layers were combined, washed with water and dried. The solvent was then removed by distillation to give 8.0 g of 5-chloro-6-ethoxycarbonyl-1-(1-methylpyrazol-3-yl)imidazole as an oil.

REFERENCE EXAMPLE 9

Synthesis of 1-(4-chloro-1-methylpyrazol-3-yl)-4-ethoxycarbonylimidazole-5-sulfonamide 7.5 g of 5-chloro-4-ethoxycarbonyl-1-(1-methylpyrazol-3-yl)imidazole was dissolved in 30 ml of dimethylformamide. To the resulting solution was added 5.9 g of sodium hydrosulfide (content of 70%), followed by stirring of the resulting mixture at 70° to 80° C. for 1.5 hours. After completion of the reaction, 100 ml of ice-cold water was added to the reaction mixture and the resulting mixture was made weakly acidic with use of conc. hydrochloric acid. Subsequently, 100 ml of chloroform was added to the mixture and chlorine was introduced into the resulting mixture little by little at $-10°$ to $0°$ C. over 2 hours. After completion of the reaction, the organic layer was separated and the aqueous layer was extracted with chloroform. After the organic layers were combined and washed with water, 20 ml of 28% aqueous ammonia was added dropwise under ice-cooling, followed by stirring of the resulting mixture at room temperature for 1.5 hours. Crystals precipitated by concentrating the reaction mixture under reduced pressure were filtered out and washed with water and subsequently with ether to give 7.6 g of the desired compound. m.p.: 167° to 168° C.

REFERENCE EXAMPLE 10

Synthesis of 5-amino-4-ethoxycarbonyl-1-(thiazol-2-yl)imidazole

Following the procedure described in Reference Example 7, the desired compound was synthesized using ethyl α-aminocyanoacetate, ethyl orthoformate and 2-aminothiazole as raw materials. m.p.: 120° to 123° C.

REFERENCE EXAMPLE 11

Synthesis of 5-chloro-4-ethoxycarbonyl-1-(thiazol-2-yl)imidazole

Following the procedure described in Reference Example 8, the desired compound was synthesized using 5-amino-4-ethoxycarbonyl-1-(thiazol-2-yl)imidazole as a raw material. m.p.: 128° to 131° C.

REFERENCE EXAMPLE 12

Synthesis of 4-ethoxycarbonyl-1-(thiazol-2-yl)imidazole-5-thiol 8.0 g of 5-chloro-4-ethoxycarbonyl-1-(thiazol-2-yl)imidazole was dissolved in 30 ml of dimethylformamide. To the resulting solution was added 6.2 g of sodium hydrosulfide (content of 70%), followed by stirring of the resulting mixture at 60° C. for 1 hour. After completion of the reaction, the reaction mixture was poured into ice water and the resulting solution was made weakly acidic with conc. hydrochloric acid. Crystals precipitated were filtered out, washed and dried to give 7.5 g of the desired compound. m.p.: 155° to 158° C.

REFERENCE EXAMPLE 13

Synthesis of 4-ethoxycarbonyl-1-(thiazol-2-yl)imidazole-5-sulfonamide

The desired compound was synthesized following the procedures described in Reference Example 6 by using 4-ethoxycarbonyl-1-(thiazol-2-yl)imidazole-5-thiol as a raw material. m.p.: 84° to 85° C.

REFERENCE EXAMPLE 14

Synthesis of 5-amino-4-ethoxycarbonyl-1-(4-methylthiazol-2-yl)imidazole

The desired compound was synthesized following the procedures described in Reference Example 7 by using ethyl α-aminocyanoacetate, ethyl orthoformate and 2-amino-4-methylthiazole as raw materials. m.p.: 152° to 155° C.

REFERENCE EXAMPLE 15

Synthesis of 5-chloro-4-ethoxycarbonyl-1-(4-methylthiazol-2-yl)imidazole

The desired compound was synthesized following the procedures described in Reference Example 8 by using 5-amino-4-ethoxycarbonyl-1-(4-methylthiazol-2-yl)imidazole as a raw material. m.p.: 98° to 101° C.

REFERENCE EXAMPLE 16

Synthesis of 4-ethoxycarbonyl-1-(4-methylthiazol-2-yl)imidazole-5-thiol

The desired compound was synthesized following the procedures described in Reference Example 12 by using 5-chloro-4-ethoxycarbonyl-1-(4-methylthiazol-2-yl)imidazole as a raw material. m.p.: 193° to 195° C.

REFERENCE EXAMPLE 17

Synthesis of 4-ethoxycarbonyl-1-(5-chloro-4-methylthiazol-2-yl)imidazole-5-sulfonamide A mixture consisting of 4.2 g of 4-ethoxycarbonyl-1-(4-methylthiazol-2-yl)imidazole-5-thiol, 3.2 g of anhydrous potassium carbonate, 2.2 g of benzyl chloride, 20 ml of dimethylformamide and 100 ml of acetonitrile was stirred at room temperature for 2 hours. After the reaction, solid materials were separated by filtration, and the filtrate was condensed under reduced pressure to obtain crude 5-benzylthio-4-ethoxycarbonyl-1-(4-methylthiazol-2-yl)imidazole as oily product. The resulting oily product was dissolved in 100 ml of chloroform and after addition of 13 g of conc. hydrochloric acid and 30 ml of water, 28 g of a 10% sodium hypochlorite solution was added dropwise to the mixture at $-10°$ C. to $-5°$ C. over 15 minutes. After the reaction mixture was stirred at 0° C. or lower for 20 minutes, an organic layer was separated and an aqueous layer was extracted with chloroform. After the organic layers were combined and washed with water, 60 ml of tetrahydrofuran was added to the organic layer and then 20 ml of a 28% aqueous ammonia was added dropwise under ice-cooling, and the mixture was stirred at room temperature for 1.5 hours. After the reaction mixture was concentrated under reduced pressure, ethyl acetate and water were added thereto, an organic layer was separated and an aqueous layer was extracted with ethyl acetate. The organic layers were combined and dried, and then concentrated under reduced pressure to obtain oily product. The resulting oily product was identified as 5-benzylsulfinyl-4-ethoxycarbonyl-1-(5-chloro-4-methylthiazol-2-yl)imidazole by NMR and MS analyses.

The resulting oily product was again treated with sodium hypochlorite in accordance with the above-mentioned method, and reacted with an aqueous ammonia to obtain 0.86 g of the title compound. m.p.: 136° to 139° C.

REFERENCE EXAMPLE 18

Synthesis of 5-amino-4-ethoxycarbonyl-1-(1,3,4-thiadiazol-2-yl)imidazole

The desired compound was synthesized following the procedures described in Reference Example 7 by using ethyl α-aminocyanoacetate, ethyl orthoformate and 2-amino-1,3,4-thiadiazole as raw materials. m.p.: 181° to 183° C.

REFERENCE EXAMPLE 19

Synthesis of 5-chloro-4-ethoxycarbonyl-1-(1,3,4-thiadiazol-2-yl)imidazole

The desired compound was synthesized following the procedures described in Reference Example 8 by using 5-amino-4-ethoxycarbonyl-1-(1,3,4-thiadiazol-2-yl)imidazole as a raw material. m.p.: 184° to 185° C.

REFERENCE EXAMPLE 20

Synthesis of 4-ethoxycarbonyl-1-(1,3,4-thiadiazol-2-yl)imidazole-5-thiol

The desired compound was synthesized following the procedures described in Reference Example 12 by using 5-chloro-4-ethoxycarbonyl-1-(1,3,4-thiadiazol-2-yl)imidazole as a raw material. m.p.: 182° to 185° C.

REFERENCE EXAMPLE 21

Synthesis of 4-ethoxycarbonyl-1-(1,3,4-thiadiazol-2-yl)imidazole-5-sulfonamide

The desired compound was synthesized following the precedures described in Reference Example 17 by using 4-ethoxycarbonyl-1-(1,3,4-thiadiazol-2-yl)imidazole-5-thiol as a raw material and via 5-benzylthio-4-ethoxycarbonyl-b 1-(1,3,4-thiadiazol-2-yl)imidazole (m.p.: 113° to 115° C.) as an indermediate. m.p.: 168° to 171° C.

REFERENCE EXAMPLE 22

Synthesis of 1-(thiazol-2-yl)imidazole-2-thiol

To 200 ml of acetonitrile, 14.6 g of N-(thiazol-2-yl)methyldithiocarbamate and 12 g of 2,2-diethoxyethylamine were added and the mixture was refluxed under heating for 12 hours. After removing acetonitrile, diisopropyl ether was added to the residue and precipitated crystals were collected by filtration to obtain 9.5 g of N-2,2-diethoxyethyl-N'-(thiazol-2-yl)thiourea (m.p.: 118° to 119° C.). In 55 ml of water was suspended 8.5 g of the resulting crystals, and 25 ml of conc. hydrochloric acid was added thereto and then the mixture was refluxed under heating for 5 hours. The reaction mixture was cooled and then the precipitated crystals were collected by filtration. The resulting crystals were dissolved in 30 ml of a 20% aqueous sodium hydroxide solution and a pH thereof was adjusted to 7 to 6 to precipitate crystals. The precipitated crystals were collected by filtration, washed with water and then dried to obtain 5.0 g of the title compound. m.p.: 211° to 213° C.

REFERENCE EXAMPLE 23

Synthesis of 1-(thiazol-2-yl)imidazole-2-sulfonamide

The desired compound was synthesized following the procedures described in Reference Example 6 by using 1-(thiazol-2-yl)imidazole-2-thiol as a raw material. m.p.: 157° to 162° C.

REFERENCE EXAMPLE 24

Synthesis of 1-(2-pyridyl)imidazole-2-sulfonamide (1) Synthesis of 1-(2-pyridyl)imidazole-2-thiol To a solution of 11.1 g of 2-pyridylisothiocyanate dissolved in 100 ml of ethanol, was added 10.0 g of aminoacetaldehyde diethylacetal, followed by stirring of the resulting mixture under reflux with heating for 40 minutes. After completion of the reaction, the solvent was distilled off under reduced pressure. Crystals precipitated were collected by filtration to give 13.8 g of N-2,2-diethoxyethyl-N'-(2-pyridyl)thiourea (m.p.: 132° to 133° C.). To the thus obtained crystals was added 120 ml of 10% diluted hydrochloric acid, followed by stirring of the resulting mixture under reflux with heating for 30 minutes. The reaction mixture was cooled and adjusted to pH of 5 to 6 with use of 50% aqueous sodium hydroxide to precipitate crystals. The crystals precipitated were filtered out, washed with water and dried to give 8.3 g of the desired compound. m.p.: 162° to 163° C.

(2) Synthesis of 1-(2-pyridyl)imidazole-2-sulfonamide

A mixture consisting of 5.1 g of 1-(2-pyridyl)imidazole-2-thiol, 5.2 g of anhydrous potassium carbonate, 3.7 g of benzyl chloride and 50 ml of acetonitrile was stirred at room temperature for 4 hours. After completion of the reaction, solids were filtered off and the filtrate was concentrated under reduced pressure. Crystals precipitated were collected by filtration to give 7.1 g of 2-benzylthio-1-(2-pyridyl)imidazole (m.p.: 76° to 77° C.). To a mixture consisting of 7.1 g of the thus obtained crystals, 50 ml of methylene chloride, 50 ml of water and 22 g of conc. hydrochloric acid was added dropwise 80 g of 6% sodium hypochlorite solution under vigorous stirring at −10° to 0° C. over 1 hour. After completion of the dropwise addition, the resulting mixture was stirred at the same temperature for 30 minutes. Then, the organic layer was separated and the aqueous layer was extracted with methylene chloride. After the organic layers were combined and washed with water, to the organic layer was added dropwise 10 ml of a 28% aqueous ammonia under ice-cooling while vigorous stirring. After completion of the dropwise addition, the resulting mixture was stirred at room temperature for 1.5 hours. The reaction mixture was concentrated to dryness and the thus obtained concentrated residue was extracted with ethyl acetate. The organic layer was concentrated under reduced pressure to give 3.0 g of a crude product of the desired compound. Crystals precipitated from the resulting crude product were collected by filtration to give 0.8 g of the desired compound. m.p.: 187° to 188° C.

REFERENCE EXAMPLE 25

Synthesis of 4-ethoxycarbonyl-1-(2-pyridyl)imidazole-5-sulfonamide (1) Synthesis of 5-amino-4-ethoxycarbonyl-1-(2-pyridyl)imidazole In 230 ml of acetonitrile, 8.5 g of ethyl α-aminocyanoacetate, 10.8 g of ethyl orthoformate and 6.2 g of 2-aminopyridine were heated under reflux for 1.5 hours. After completion of the reaction, the solvent was distilled off under reduced pressure and crystals precipitated were filtered off and washed with benzene to give 11.0 g of the desired compound. m.p.: 129° to 131° C.

(2) Synthesis of 4-ethoxycarbonyl-1-(2-pyridyl)imidazole-5-thiol 11.0 g of 5-amino-4-ethoxycarbonyl-1-(2-pyridyl)imidazole was dissolved in 60 ml of conc. hydrochloric acid and the resulting solution was cooled to −5° C. Subsequently, 3.9 g of sodium nitrite was dissolved in 10 ml of water and the resulting solution was added dropwise to the previously prepared solution while maintaining the temperature at −5° C. or lower. After completion of the dropwise addition, the resulting mixture was stirred at the same temperature for 0.5 hour. The thus obtained solution was added dropwise at around 5° C. to 150 ml of a solution of chloroform containing 1.0 g of cuprous chloride and 12 g of sulfur dioxide. After the resulting mixture was stirred at room temperature for 1 hour, was added thereto 300 ml of water and the organic layer was separated. The aqueous layer was extracted with chloroform and the organic layers were combined, washed with water and dried. The solvent was then removed by distillation to give 11.6 g of 5-chloro-4-ethoxycarbonyl-1-(2-pyridyl)imidazole as an oil.

The thus obtained 11.6 g of 5-chloroimidazole derivative was dissolved in 30 ml of dimethylformamide. To the resulting solution was added 9.2 g of sodium hydrosulfide (content of 70%), followed by stirring of the resulting mixture at room temperature for 1 hour. The reaction mixture was poured into ice water and insolubles were filtered out. Then the filtrate was made weakly acidic with use of conc. hydrochloric acid. Crystals precipitated were collected by filtration, washed with water and dried to give 10.6 g of the desired compound. m.p.: 84° to 87° C.

(3) Synthesis of 4-ethoxycarbonyl-1-(2-pyridyl)imidazole-5-sulfonamide

To a mixture consisting of 10.6 g of 4-ethoxycarbonyl-1-(2-pyridyl)imidazole-5-thiol, 50 ml of water, 100 ml of chloroform and 35.5 g of conc. hydrochloric acid, was added dropwise 128 g of sodium hypochlorite solution (content of 6%) under vigorous stirring at −10° to 0° C. over 1 hour. After completion of the dropwise addition, the resulting mixture was stirred at the same temperature for 0.5 hour. Then, the organic layer was separated and the aqueous layer was extracted with chloroform. After the organic layers were combined and washed with water, to the organic layer was added dropwise 10 ml of 28% aqueous ammonia under ice-cooling, followed by stirring of the resulting mixture at room temperature for 1.5 hours. The reaction mixture was concentrated to dryness under reduced pressure and the residue was extracted with ethyl acetate.

After the solvent was distilled off, crystals precipitated were collected by filtration to give 4.1 g of the desired compound. m.p.: 138° to 139° C.

Specific examples of synthesizing the present compounds using the intermediate obtained in the above Reference Examples will be given below.

EXAMPLE 1

Synthesis of N-[(4,6-dimethoxypyrimidin-2-yl)aminocarbonyl]-1-(4-chloro-1-methylpyrazol-3-yl)imidazole-2-sulfonamide In 50 ml of acetonitrile, 2.8 g of 1-(4-chloro-1-methylpyrazol-3-yl)imidazole-2-sulfonamide, 1,4 g of ethyl chloroformate and 2.2 g of anhydrous potassium carbonate were heated under reflux for 2 hours. After completion of the reaction, the solvent was removed by distillation under reduced pressure and ice water was added to the residue and then extracted with chloroform. The aqueous layer was separated and was made acidic with diluted hydrochloric acid. Crystals thus precipitated were filtered, washed with water and dried to give 2.1 g of N-[1-(4-chloro-1-methylpyrazol-3-yl)imidazole-2-sulfonyl]ethyl carbamate. m.p.: 150° to 151° C.

0.7 g of ethyl carbamate thus obtained and 0.32 g of 2-amino-4,6-dimethoxypyrimidine were refluxed under heating in 30 ml of toluene for 2 hours while removing toluene by distillation little by little. After completion of the reaction, the residue was left for cooling and crystals precipitated were filtered out and washed with benzene to give 0.6 g of the desired compound. m.p.: 164° to 165° C.

EXAMPLE 2

Synthesis of N-[(4,6-dimethoxypyrimidin-2-yl)aminocarbonyl]-1-(2-pyridyl)imidazole-2-sulfonamide In 15 ml of acetonitrile, 0.8 g of 1-(2-pyridyl)imidazole-2-sulfonamide, 0.5 g of methyl chloroformate and 0.75 g of anhydrous potassium carbonate were refluxed under heating for 1 hour. After the reaction, the solvent was removed by distillation under reduced pressure and ice water was added to the residue, followed by extraction with methylene chloride. The aqueous layer was made weakly acidic with use of diluted hydrochloric acid and concentrated under reduced pressure to precipitate crystals. Crystals thus precipitated were filtered, washed with water and dried to give 0.46 g of N-[1-(2-pyridyl)imidazole-2-sulfonyl]methyl carbamate. m.p.: 154° to 156° C.

0.46 g of methyl carbamate thus obtained and 0.25 g of 2-amino-4,6-dimethoxypyrimidine were refluxed under heating in 30 ml of toluene for 1.5 hours while removing toluene little by little by distillation. After the reaction, the filtration was carried out during hot. Crystals precipitated from the filtrate were filtered out to give 0.3 g of the desired compound. m.p.: 146° to 149° C.

EXAMPLE 3

Synthesis of N-[(4,6-dimethoxypyrimidin-2-yl)aminocarbonyl]-4-ethoxycarbonyl-1-(1,3,4-thiadiazol-2-yl)imidazole-5-sulfonamide 0.23 g of 1,8-diazobicyclo(5,4,0)-7-undecene was added dropwise to a mixture of 0.45 g of 4-ethoxycarbonyl-1-(1,3,4-thiadiazol-2-yl)imidazole-5-sulfonamide, 0.41 g of N-(4,6-dimethoxypyrimidine-2-yl)phenylcarbamate and 5 ml of acetonitrile. After stirring the reaction mixture at room temperature for 20 minutes, 20 ml of ice water was added thereto and the mixture was filtered. The filtrate was made acidic with use of conc. hydrochloric acid, and resulting precipitated crystals were collected by filtration, washed with water and ethyl ether, and dried to obtain 0.45 g of the title compound. m.p.: 169° to 171° C.

Chemical structures and physical properties of compounds synthesized according to Examples in addition to the compound synthesized in Examples will be given below.

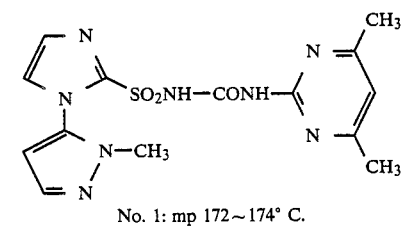

No. 1: mp 172~174° C.

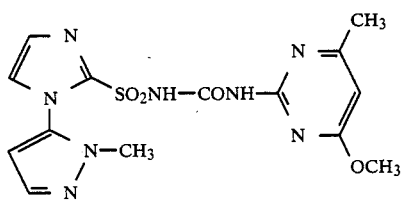

No. 2: mp 169~170° C.

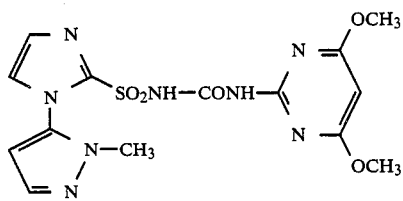

No. 3: mp 167~169° C.

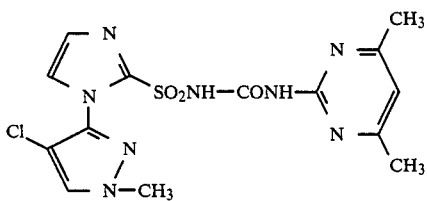

No. 4: mp 207~211° C.

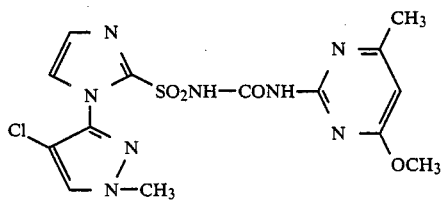

No. 5: mp 116~118° C.

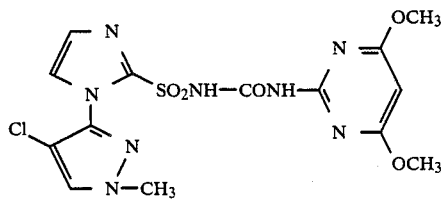

No. 6: mp 164~165° C.

-continued

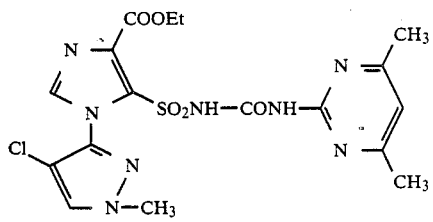

No. 7: mp 156~158° C.

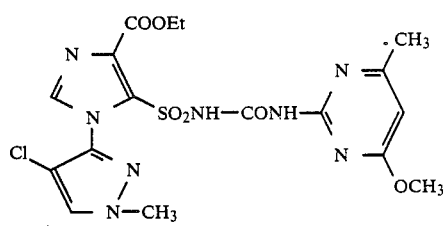

No. 8: mp 126~129° C.

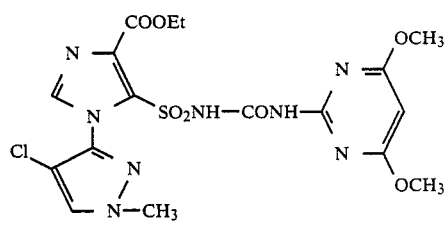

No. 9: mp 113~115° C.

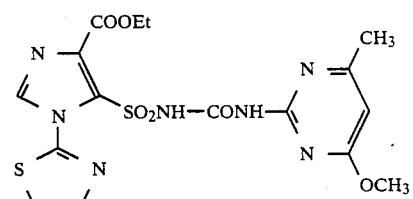

No. 10: mp. 139–141° C.

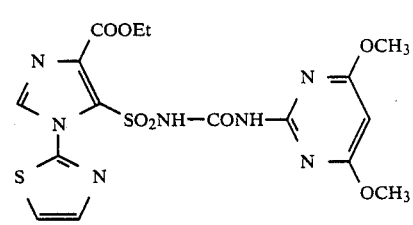

No. 11: mp. 169–171° C.

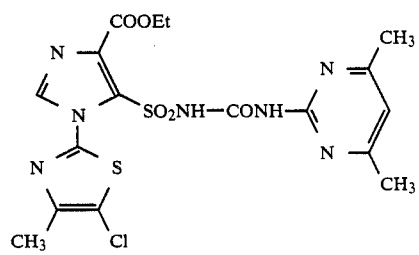

No. 12: mp. 162–165° C.

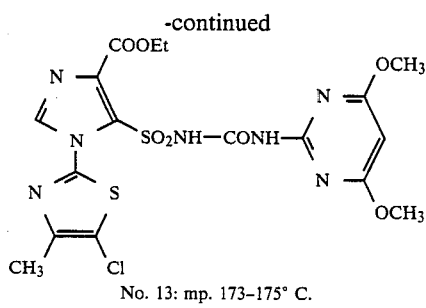

No. 13: mp. 173-175° C.

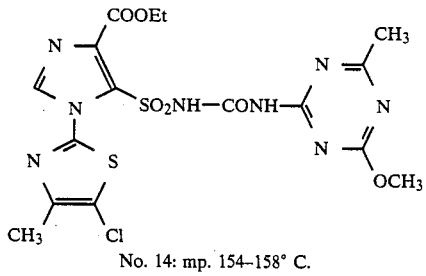

No. 14: mp. 154-158° C.

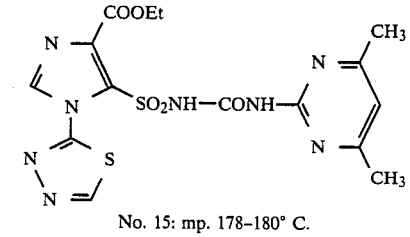

No. 15: mp. 178-180° C.

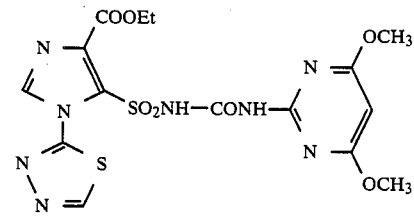

No. 16: mp. 169-171° C.

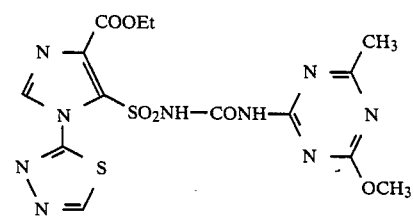

No. 17: mp. 158-160° C.

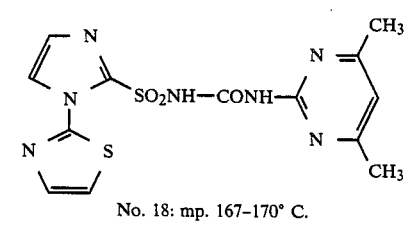

No. 18: mp. 167-170° C.

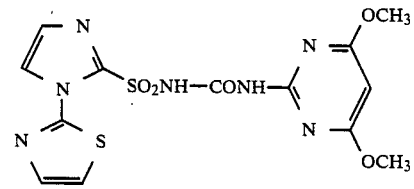

No. 19: mp. 155-157° C.

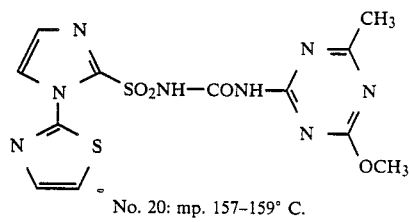

No. 20: mp. 157-159° C.

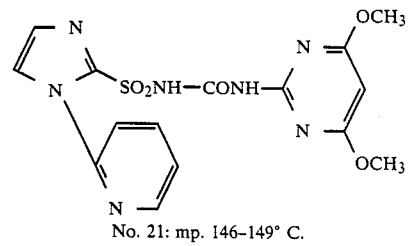

No. 21: mp. 146-149° C.

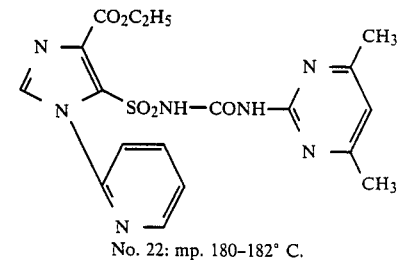

No. 22: mp. 180-182° C.

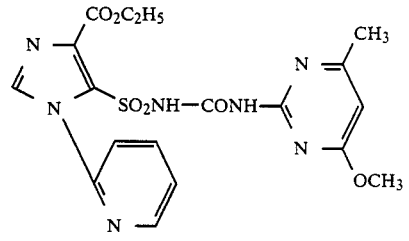

No. 23: mp. 182-183° C.

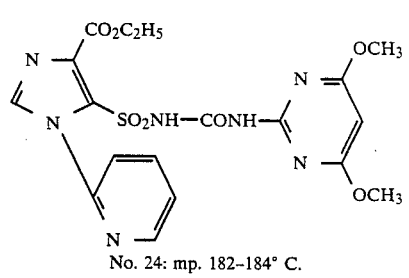

No. 24: mp. 182-184° C.

Examples of compounds to be included in the compound of this invention are shown below in Table 1 to Table 15 in addition to the compounds synthesized in the above Example, which, however, should not be construed to limit this invention.

Be noted that the symbols in Tables have the meanings as shown below.

Me: methyl group, Et: ethyl group, Pr-n: n-propyl group, Pr-i: isopropyl group, Ph: phenyl group Gn represents the following groups.

Ga=G1 to G35, Gb=G1 to G6, Gc=G1 to G3

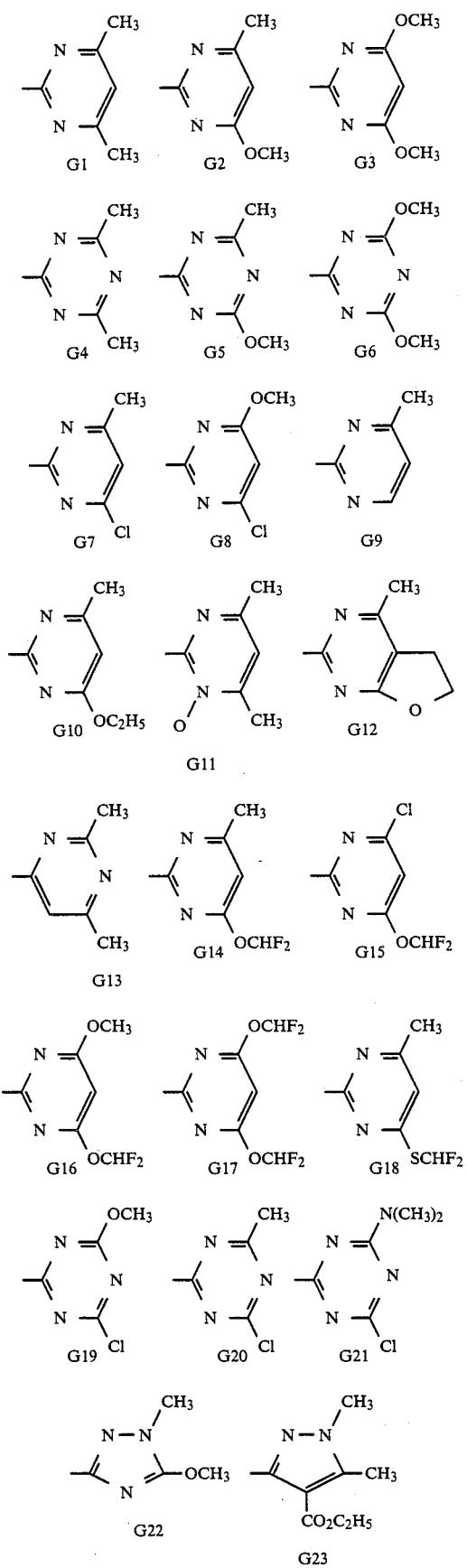
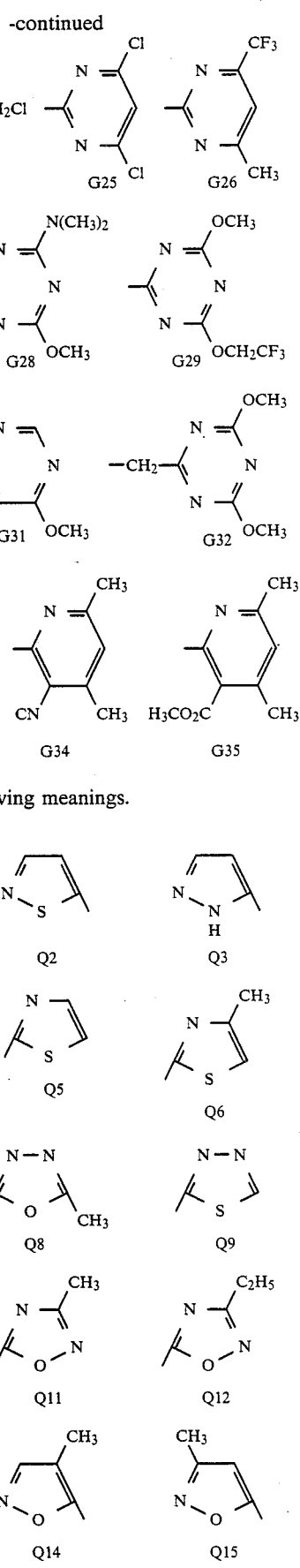
Qn have the following meanings.

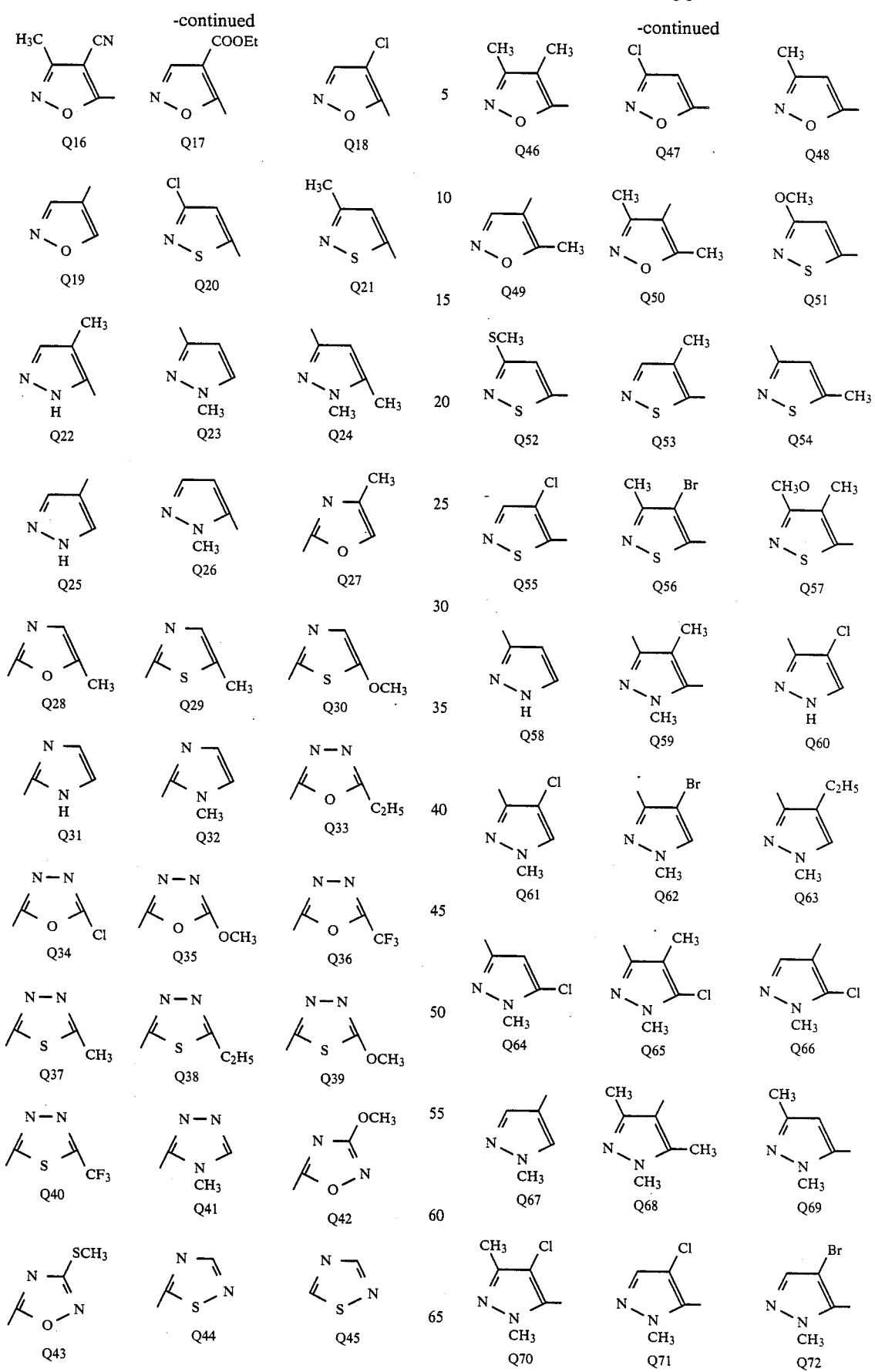

-continued
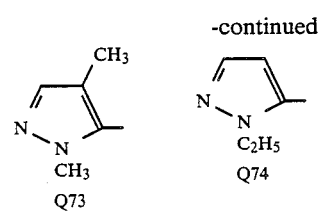
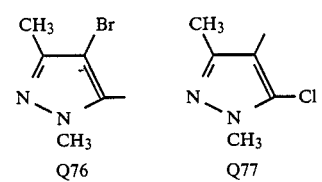
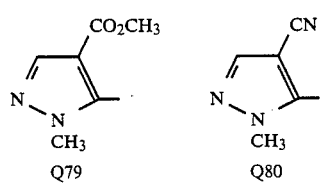
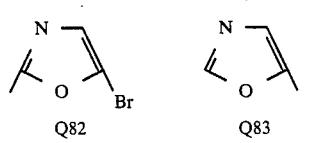
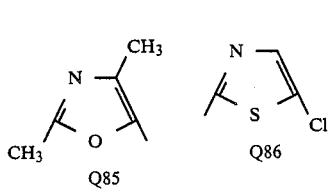
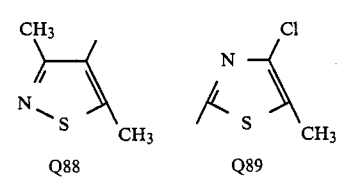
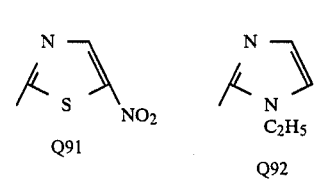
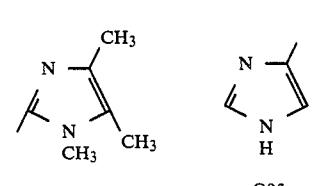
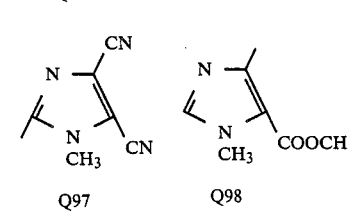
-continued
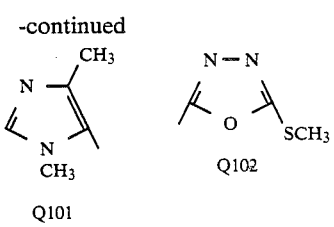
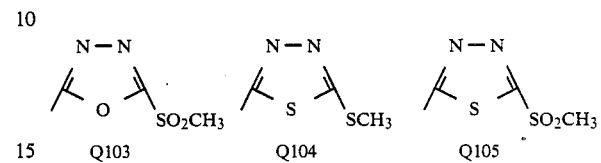
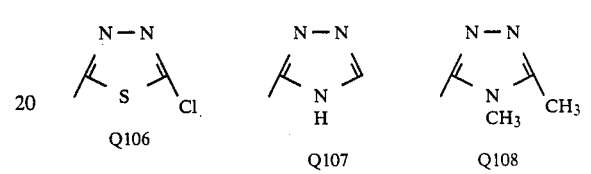
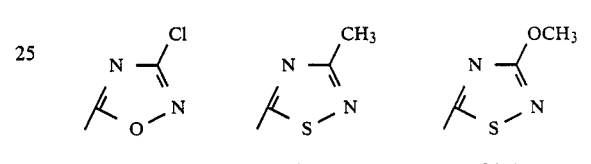
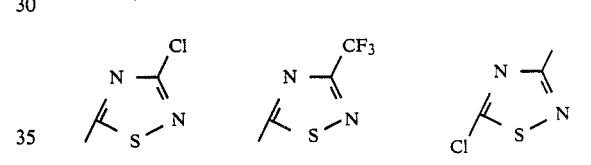
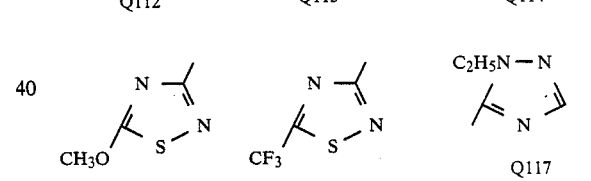
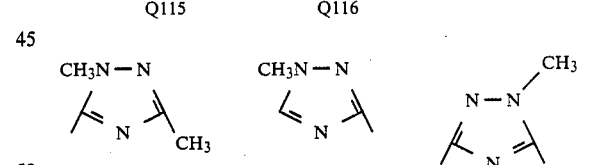
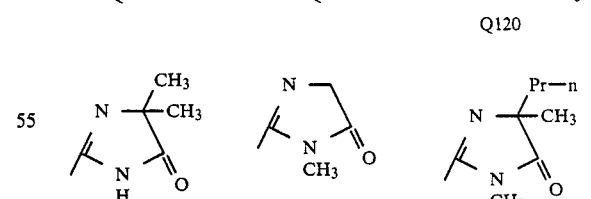
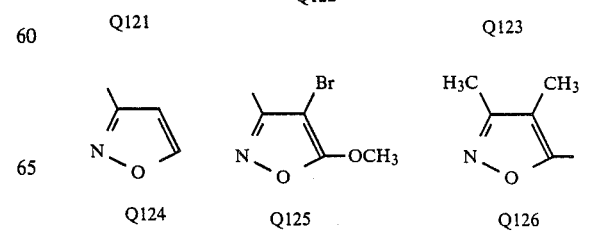

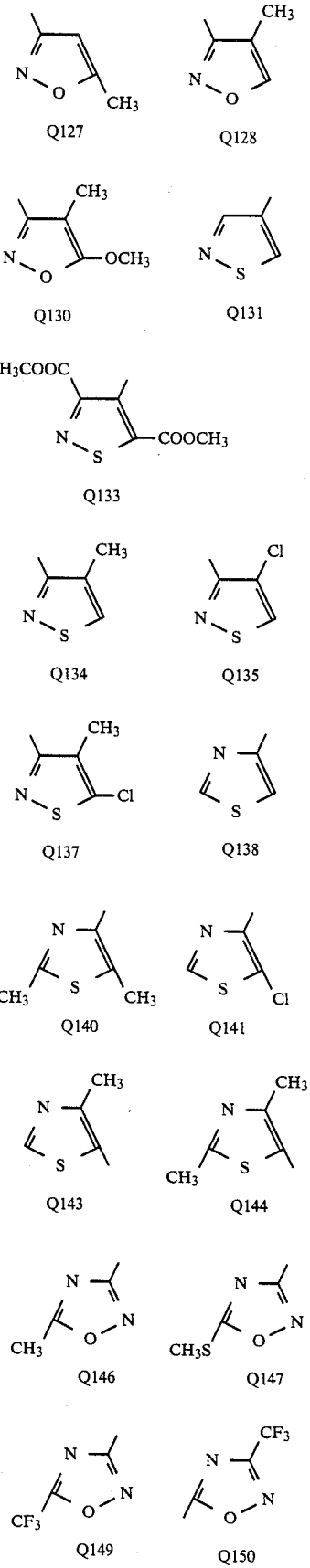
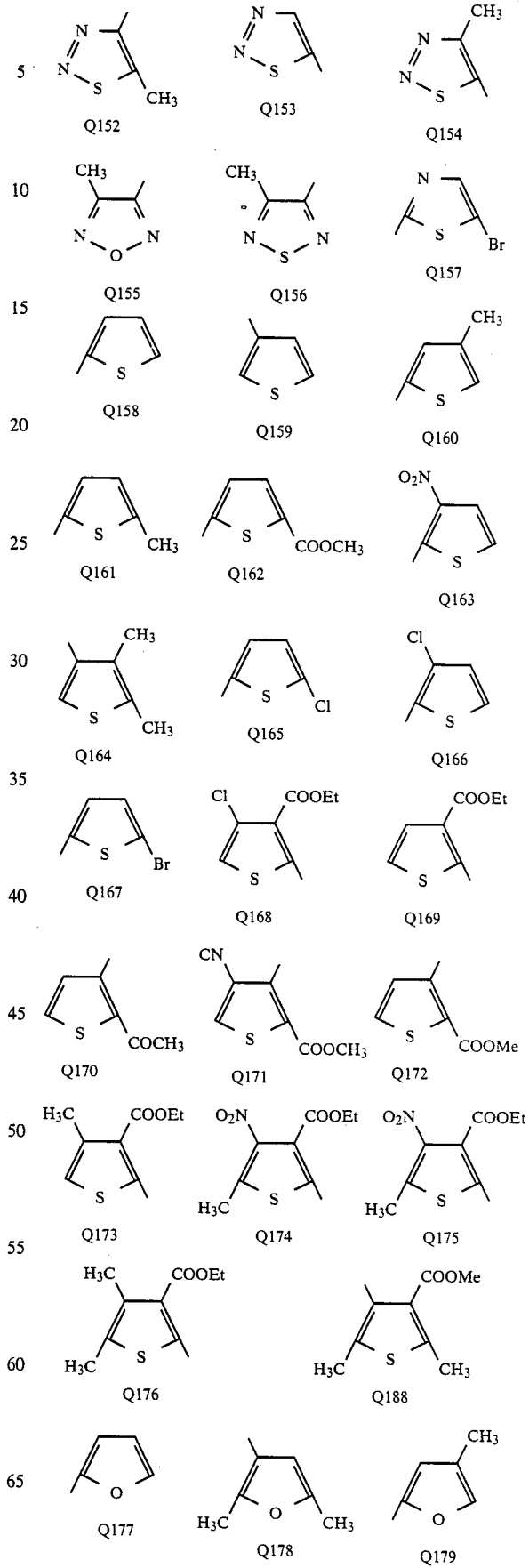

-continued

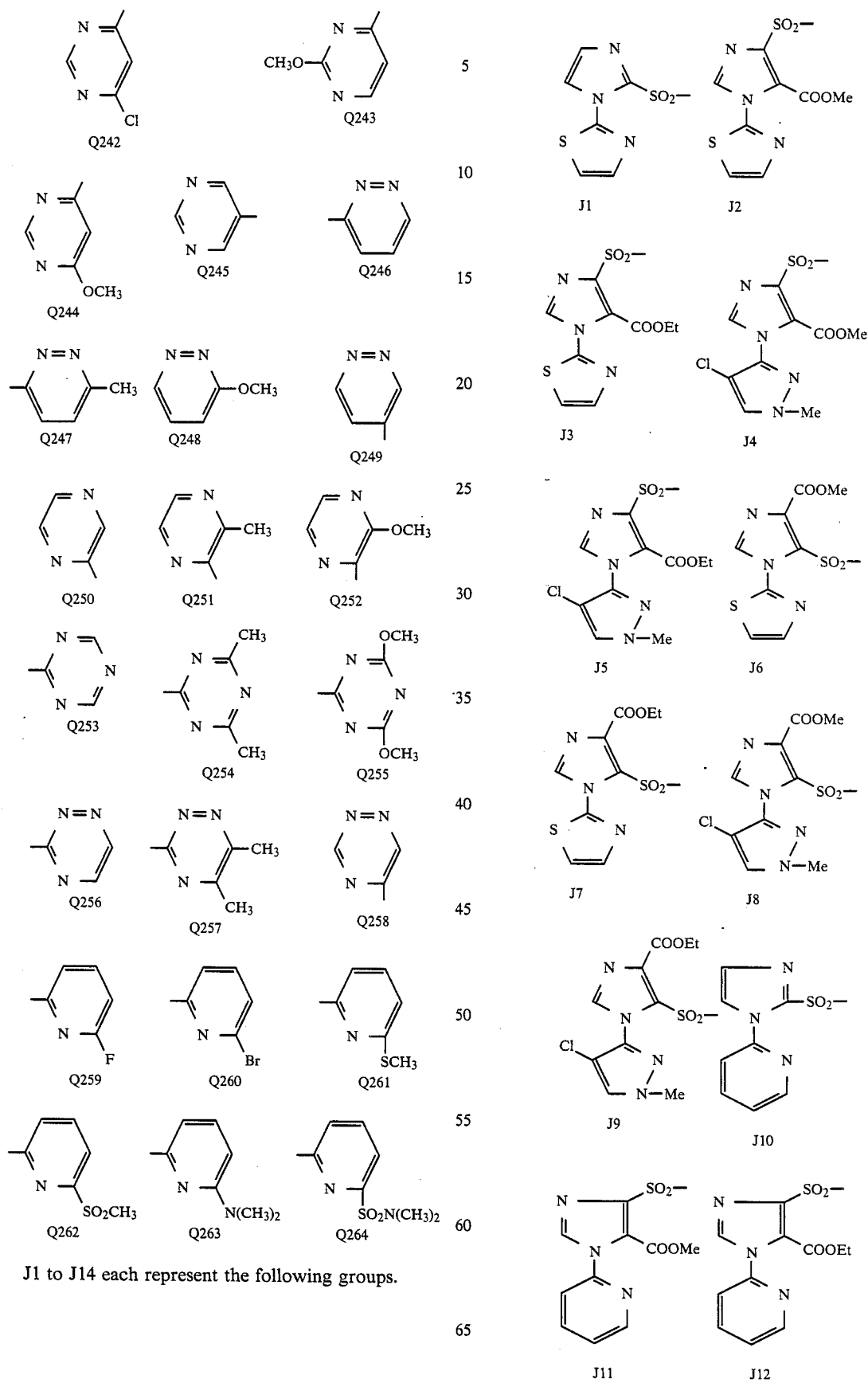
J1 to J14 each represent the following groups.

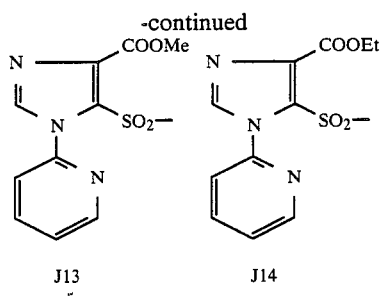

J13  J14

TABLE 1

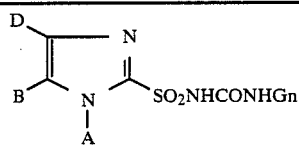

| A | B | D | Gn |
|---|---|---|----|
| Q1 | H | H | Gb |
| CH$_2$- Q1 | H | H | Gc |
| CHMe- Q1 | H | H | G3 |
| Q2 | H | H | Gb |
| Q3 | H | H | Gb |
| Q4 | H | H | Gb |
| Q5 | H | H | Ga |
| CH$_2$ - Q5 | H | H | Gc |
| CHMe - Q5 | H | H | G3 |
| Q6 | H | H | G3 |
| Q7 | H | H | G3 |
| Q8 | H | H | G3 |
| Q9 | H | H | Gc |
| CH$_2$ - Q9 | H | H | Gc |
| Q10 | H | H | Gc |
| Q11 | H | H | G3 |
| Q12 | H | H | G3 |
| Q13 | H | H | G3 |
| Q14 | H | H | G1 |
| Q15 | H | H | G3 |
| Q16 | H | H | Gc |
| Q17 | H | H | Gc |
| Q18 | H | H | G3 |
| Q19 | H | H | Gc |
| Q20 | H | H | Gc |
| Q21 | H | H | Gc |
| Q22 | H | H | G3 |
| Q23 | H | H | Gc |
| CH$_2$ - Q23 | H | H | G3 |
| Q24 | H | H | Gc |
| Q25 | H | H | Gb |
| Q26 | H | H | Gb |
| CH$_2$ - Q26 | H | H | G3 |
| CHMe - Q26 | H | H | G3 |
| Q27 | H | H | G3 |
| Q28 | H | H | G3 |
| Q29 | H | H | Gc |
| CH$_2$ - Q29 | H | H | G3 |
| Q30 | H | H | G3 |
| Q31 | H | H | Gc |
| Q32 | H | H | Gc |
| CH$_2$ - Q32 | H | H | G3 |
| Q33 | H | H | G3 |
| Q34 | H | H | G3 |
| Q35 | H | H | G3 |
| Q36 | H | H | G3 |
| Q37 | H | H | Gc |
| Q38 | H | H | Gc |
| Q39 | H | H | G3 |
| Q40 | H | H | Gc |
| Q41 | H | H | Gc |
| Q42 | H | H | Gc |
| Q43 | H | H | G3 |
| Q44 | H | H | Gc |
| Q45 | H | H | Gc |
| Q46 | H | H | Gc |
| Q47 | H | H | Gc |
| Q48 | H | H | Gc |

TABLE 1-continued

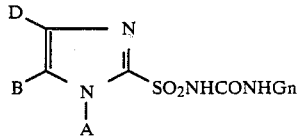

| A | B | D | Gn |
|---|---|---|----|
| Q49 | H | H | G3 |
| Q50 | H | H | Gc |
| CH$_2$ - Q50 | H | H | G3 |
| Q51 | H | H | Gc |
| Q52 | H | H | G3 |
| Q53 | H | H | G3 |
| Q54 | H | H | Gc |
| Q55 | H | H | Gc |
| Q56 | H | H | Gc |
| Q57 | H | H | G3 |
| Q58 | H | H | Gc |
| Q59 | H | H | Gc |
| CH$_2$ - Q59 | H | H | G3 |
| Q60 | H | H | Gc |
| Q61 | H | H | Ga |
| CH$_2$ - Q61 | H | H | Gb |
| CHMe - Q61 | H | H | Gc |
| Q62 | H | H | Gc |
| Q63 | H | H | Gc |
| Q64 | H | H | Gb |
| CH$_2$ - Q64 | H | H | G3 |
| CHMe - Q64 | H | H | G3 |
| Q65 | H | H | G3 |
| Q66 | H | H | G3 |
| Q67 | H | H | G3 |
| Q68 | H | H | G3 |
| Q69 | H | H | Gc |
| Q70 | H | H | Gc |
| Q71 | H | H | Gc |
| Q72 | H | H | Gc |
| CH$_2$ - Q72 | H | H | G3 |
| CHMe - Q72 | H | H | G3 |
| Q73 | H | H | Gc |
| CH$_2$ - Q73 | H | H | G3 |
| Q74 | H | H | Gc |
| Q75 | H | H | G3 |
| Q76 | H | H | G3 |
| Q77 | H | H | Gc |
| CH$_2$ - Q77 | H | H | G3 |
| Q78 | H | H | Gc |
| Q79 | H | H | Gc |
| Q80 | H | H | Gc |
| Q81 | H | H | G3 |
| Q82 | H | H | G3 |
| Q83 | H | H | G1 |
| Q84 | H | H | G2 |
| Q85 | H | H | G3 |
| Q86 | H | H | Gc |
| Q87 | H | H | G2 |
| Q88 | H | H | Gc |
| Q89 | H | H | Gc |
| Q90 | H | H | Gc |
| Q91 | H | H | Gc |
| Q92 | H | H | G3 |
| Q93 | H | H | Gc |
| Q94 | H | H | G3 |
| Q95 | H | H | Gc |
| Q96 | H | H | G3 |
| Q97 | H | H | Gc |
| Q98 | H | H | Gc |
| Q99 | H | H | Gc |
| Q100 | H | H | Gc |
| Q101 | H | H | Gc |
| CH$_2$ - Q101 | H | H | G3 |
| Q102 | H | H | G3 |
| Q103 | H | H | G3 |
| Q104 | H | H | G3 |
| Q105 | H | H | Gc |
| Q106 | H | H | G3 |
| Q107 | H | H | Gc |
| Q108 | H | H | G1 |
| Q109 | H | H | G3 |
| Q110 | H | H | G3 |

TABLE 1-continued

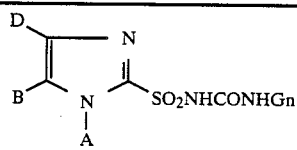

| A | B | D | Gn |
|---|---|---|---|
| Q111 | H | H | G3 |
| Q112 | H | H | Gc |
| Q113 | H | H | Gc |
| Q114 | H | H | G2 |
| Q115 | H | H | Gc |
| Q116 | H | H | Gc |
| Q117 | H | H | Gc |
| Q118 | H | H | G3 |
| Q119 | H | H | Gc |
| Q120 | H | H | Gc |
| Q121 | H | H | G2 |
| Q122 | H | H | Gc |
| Q123 | H | H | Gc |
| Q124 | H | H | Gc |
| Q125 | H | H | Gc |
| Q126 | H | H | Gc |
| Q127 | H | H | Gc |
| Q128 | H | H | Gc |
| Q129 | H | H | Gc |
| Q130 | H | H | G2 |
| Q131 | H | H | Gc |
| Q132 | H | H | Gc |
| Q133 | H | H | G3 |
| Q134 | H | H | G3 |
| Q135 | H | H | Gc |
| Q136 | H | H | G3 |
| Q137 | H | H | G1 |
| Q138 | H | H | Gc |
| CH2 - Q138 | H | H | G3 |
| Q139 | H | H | G3 |
| Q140 | H | H | G1 |
| Q141 | H | H | G3 |
| Q142 | H | H | Gc |
| Q143 | H | H | Gc |
| CH2 - Q143 | H | H | G3 |
| Q144 | H | H | G3 |
| Q145 | H | H | Gc |
| Q146 | H | H | Gc |
| Q147 | H | H | G3 |
| Q148 | H | H | G1 |
| Q149 | H | H | G3 |
| Q150 | H | H | G3 |
| Q151 | H | H | G2 |
| Q152 | H | H | G1 |
| Q153 | H | H | Gc |
| Q154 | H | H | Gc |
| Q155 | H | H | G3 |
| Q156 | H | H | G3 |
| Q157 | H | H | Gc |
| Q158 | H | H | Gc |
| CH2 - Q158 | H | H | G3 |
| CHMe - Q158 | H | H | G3 |
| Q159 | H | H | G3 |
| Q160 | H | H | Gc |
| Q161 | H | H | Gc |
| Q162 | H | H | Gc |
| Q163 | H | H | G3 |
| Q164 | H | H | Gc |
| Q165 | H | H | Gc |
| Q166 | H | H | Gc |
| Q167 | H | H | G3 |
| Q168 | H | H | G3 |
| Q169 | H | H | Gc |
| CH2 - Q169 | H | H | G3 |
| CHMe - Q169 | H | H | G3 |
| Q170 | H | H | Gc |
| Q171 | H | H | Gc |
| Q172 | H | H | Gc |
| Q173 | H | H | Gc |
| Q174 | H | H | Gc |
| Q175 | H | H | Gc |
| Q176 | H | H | Gc |
| Q177 | H | H | Gc |

TABLE 1-continued

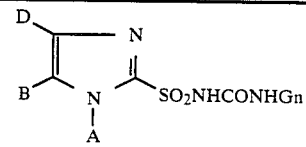

| A | B | D | Gn |
|---|---|---|---|
| CH2 - Q177 | H | H | G3 |
| CHMe - Q177 | H | H | G3 |
| Q178 | H | H | G3 |
| Q179 | H | H | G3 |
| Q180 | H | H | Gc |
| CH2 - Q180 | H | H | G3 |
| Q181 | H | H | G1 |
| Q182 | H | H | G3 |
| Q183 | H | H | G3 |
| Q184 | H | H | Gc |
| CH2 - Q184 | H | H | G3 |
| CHMe - Q184 | H | H | G3 |
| Q185 | H | H | G3 |
| Q186 | H | H | G3 |
| Q187 | H | H | G3 |
| Q188 | H | H | Gb |
| Q189 | H | H | Gb |
| Q1 | H | Me | G3 |
| Q2 | H | Me | G3 |
| Q4 | H | Me | G3 |
| Q5 | H | Me | G3 |
| Q7 | H | Me | G3 |
| Q9 | H | Me | G3 |
| Q10 | H | Me | G3 |
| Q19 | H | Me | G3 |
| Q23 | H | Me | G3 |
| Q26 | H | Me | G3 |
| Q32 | H | Me | G3 |
| Q41 | H | Me | G3 |
| Q45 | H | Me | G3 |
| Q50 | H | Me | G3 |
| Q61 | H | Me | G3 |
| Q69 | H | Me | G3 |
| Q79 | H | Me | G3 |
| Q83 | H | Me | G3 |
| Q96 | H | Me | G3 |
| Q124 | H | Me | G3 |
| Q131 | H | Me | G3 |
| Q132 | H | Me | G3 |
| Q135 | H | Me | G3 |
| Q138 | H | Me | G3 |
| Q142 | H | Me | G3 |
| Q157 | H | Me | G3 |
| Q158 | H | Me | G3 |
| Q159 | H | Me | G3 |
| Q177 | H | Me | G3 |
| Q180 | H | Me | G3 |
| Q184 | H | Me | G3 |
| Q188 | H | Me | Gb |
| Q189 | H | Me | Gb |
| Q1 | Me | H | G3 |
| Q2 | Me | H | G3 |
| Q4 | Me | H | G3 |
| Q5 | Me | H | G3 |
| Q7 | Me | H | G3 |
| Q9 | Me | H | G3 |
| Q10 | Me | H | G3 |
| Q19 | Me | H | G3 |
| Q23 | Me | H | G3 |
| Q26 | Me | H | G3 |
| Q32 | Me | H | G3 |
| Q41 | Me | H | G3 |
| Q45 | Me | H | G3 |
| Q50 | Me | H | G3 |
| Q61 | Me | H | G3 |
| Q69 | Me | H | G3 |
| Q79 | Me | H | G3 |
| Q83 | Me | H | G3 |
| Q96 | Me | H | G3 |
| Q124 | Me | H | G3 |
| Q131 | Me | H | G3 |
| Q132 | Me | H | G3 |
| Q135 | Me | H | G3 |

TABLE 1-continued

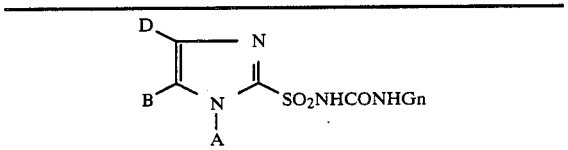

| A | B | D | Gn |
|---|---|---|---|
| Q138 | Me | H | G3 |
| Q142 | Me | H | G3 |
| Q157 | Me | H | G3 |
| Q158 | Me | H | G3 |
| Q159 | Me | H | G3 |
| Q177 | Me | H | G3 |
| Q180 | Me | H | G3 |
| Q184 | Me | H | G3 |
| Q188 | Me | H | Gb |
| Q189 | Me | H | Gb |
| Q4 | Me | Me | G3 |
| Q5 | Me | Me | G3 |
| Q7 | Me | Me | G3 |
| Q9 | Me | Me | G3 |
| Q23 | Me | Me | G3 |
| Q26 | Me | Me | G3 |
| Q32 | Me | Me | G3 |
| Q61 | Me | Me | G3 |
| Q96 | Me | Me | G3 |
| Q142 | Me | Me | G3 |
| Q158 | Me | Me | G3 |
| Q188 | Me | Me | Gb |
| Q189 | Me | Me | Gb |
| Q201 | H | H | Ga |
| CH2 - Q201 | H | H | Ga |
| CHMe - Q201 | H | H | Gc |
| Q202 | H | H | Gb |
| Q203 | H | H | Gb |
| Q204 | H | H | Gb |
| Q205 | H | H | Gb |
| CH2 - Q205 | H | H | Gc |
| Q206 | H | H | G3 |
| Q207 | H | H | Gc |
| Q208 | H | H | G3 |
| Q209 | H | H | Gc |
| CH2 - Q209 | H | H | Gc |
| Q210 | H | H | Gc |
| Q211 | H | H | G3 |
| Q212 | H | H | Gc |
| Q213 | H | H | Gc |
| Q214 | H | H | G1 |
| Q215 | H | H | Gc |
| Q216 | H | H | Gc |
| Q217 | H | H | Gc |
| Q218 | H | H | G3 |
| Q219 | H | H | Gc |
| Q220 | H | H | Gc |
| Q221 | H | H | G2 |
| Q222 | H | H | Gb |
| CH2 - Q222 | H | H | Gc |
| Q223 | H | H | G3 |
| Q224 | H | H | Gc |
| Q225 | H | H | Gb |
| CH2 - Q225 | H | H | Gc |
| Q226 | H | H | G3 |
| Q227 | H | H | Gc |
| Q228 | H | H | Gc |
| Q229 | H | H | Gb |
| CH2 - Q229 | H | H | Gc |
| Q230 | H | H | Gc |
| Q231 | H | H | Gc |
| CH2 - Q231 | H | H | Gc |
| Q232 | H | H | Gc |
| Q233 | H | H | G3 |
| Q234 | H | H | Gc |
| Q235 | H | H | Gc |
| Q236 | H | H | G1 |
| Q237 | H | H | Gc |
| Q238 | H | H | Gc |
| Q239 | H | H | G3 |
| Q240 | H | H | Gc |
| Q241 | H | H | Gc |
| Q242 | H | H | Gc |
| Q243 | H | H | G3 |
| Q244 | H | H | Gc |
| Q245 | H | H | Gc |
| Q246 | H | H | Gb |
| CH2 - Q246 | H | H | Gc |
| Q247 | H | H | Gc |
| Q248 | H | H | G2 |
| Q249 | H | H | Gc |
| Q250 | H | H | Gc |
| CH2 - Q250 | H | H | Gc |
| Q251 | H | H | Gc |
| Q252 | H | H | G3 |
| Q253 | H | H | Gc |
| Q254 | H | H | Gc |
| Q255 | H | H | G2 |
| Q256 | H | H | Gc |
| Q257 | H | H | Gc |
| Q258 | H | H | Gc |
| Q259 | H | H | Gc |
| CH2 - Q259 | H | H | G3 |
| Q260 | H | H | Gc |
| CH2 - Q60 | H | H | Gc |
| Q261 | H | H | G1 |
| Q262 | H | H | Gc |
| Q263 | H | H | Gc |
| Q264 | H | H | G1 |
| Q201 | H | Me | Gc |
| Q202 | H | Me | G3 |
| Q205 | H | Me | Gc |
| Q209 | H | Me | G1 |
| Q222 | H | Me | Gc |
| Q225 | H | Me | G3 |
| Q229 | H | Me | Gc |
| Q231 | H | Me | Gc |
| Q246 | H | Me | G3 |
| Q260 | H | Me | Gc |
| Q201 | Me | H | Gc |
| Q202 | Me | H | G3 |
| Q205 | Me | H | Gc |
| Q209 | Me | H | Gc |
| Q222 | Me | H | Gc |
| Q225 | Me | H | G2 |
| Q229 | Me | H | Gc |
| Q231 | Me | H | Gc |
| Q246 | Me | H | G1 |
| Q260 | Me | H | Gc |
| Q201 | Me | Me | Gc |
| Q202 | Me | Me | G3 |
| Q205 | Me | Me | Gc |
| Q209 | Me | Me | G3 |
| Q222 | Me | Me | Gc |
| Q225 | Me | Me | Gc |
| Q229 | Me | Me | Gc |
| Q231 | Me | Me | G1 |
| Q246 | Me | Me | Gc |
| Q260 | Me | Me | G3 |
| Q201 | Cl | H | Gc |
| Q205 | Cl | H | Gc |
| Q222 | Cl | H | G3 |
| Q229 | Cl | H | Gc |
| Q201 | H | Cl | Gc |
| Q205 | H | Cl | G1 |
| Q201 | Cl | Me | Gc |
| Q205 | Cl | Me | Gc |
| Q201 | Cl | Cl | Gc |
| Q205 | Cl | Cl | Gc |
| Q222 | Cl | Cl | G3 |
| Q229 | Cl | Cl | Gc |
| Q201 | Br | H | Gc |
| Q205 | Br | H | Gc |
| Q222 | Br | H | G2 |
| Q229 | Br | H | Gc |
| Q201 | H | Br | Gc |

TABLE 1-continued

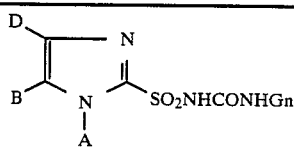

| A | B | D | Gn |
|---|---|---|---|
| Q205 | H | Br | G3 |
| Q201 | Br | Me | Gc |
| Q205 | Br | Me | G3 |
| Q201 | Br | Br | Gc |
| Q205 | Br | Br | G3 |
| Q6 | H | Me | Gb |
| Q15 | H | Me | Gc |
| Q21 | H | Me | G3 |
| Q29 | H | Me | Gb |
| Q54 | H | Me | Gb |
| Q68 | H | Me | Gb |
| Q88 | H | Me | G3 |
| Q127 | H | Me | G3 |
| Q204 | H | Me | G3 |
| Q230 | H | Me | G3 |
| Q250 | H | Me | G3 |
| Q5 | H | Cl | G3 |
| Q6 | H | Cl | G3 |
| Q7 | H | Cl | G3 |
| Q9 | H | Cl | G3 |
| Q15 | H | Cl | G3 |
| Q21 | H | Cl | G3 |
| Q26 | H | Cl | G3 |
| Q29 | H | Cl | G3 |
| Q32 | H | Cl | G3 |
| Q50 | H | Cl | G3 |
| Q54 | H | Cl | G3 |
| Q61 | H | Cl | G3 |
| Q68 | H | Cl | G3 |
| Q88 | H | Cl | G3 |
| Q127 | H | Cl | G3 |
| Q138 | H | Cl | G3 |
| Q142 | H | Cl | G3 |
| Q188 | H | Cl | G3 |
| Q189 | H | Cl | G3 |
| Q202 | H | Cl | G3 |
| Q204 | H | Cl | G3 |
| Q209 | H | Cl | G3 |
| Q222 | H | Cl | G3 |
| Q225 | H | Cl | G3 |
| Q229 | H | Cl | G3 |
| Q230 | H | Cl | G3 |
| Q246 | H | Cl | G3 |
| Q250 | H | Cl | G3 |
| Q5 | H | $NO_2$ | G3 |
| Q6 | H | NHCOMe | G3 |
| Q7 | H | $NO_2$ | G3 |
| Q9 | H | $NO_2$ | G3 |
| Q15 | H | $NMe_2$ | G3 |
| Q21 | H | $NMe_2$ | G3 |
| Q26 | H | NHCOMe | G3 |
| Q29 | H | $NO_2$ | G3 |
| Q32 | H | $NMe_2$ | G3 |
| Q50 | H | $NO_2$ | G3 |
| Q54 | H | $NMe_2$ | G3 |
| Q61 | H | $NO_2$ | G3 |
| Q68 | H | $NO_2$ | G3 |
| Q88 | H | $NO_2$ | G3 |
| Q127 | H | $NMe_2$ | G3 |
| Q138 | H | NHCOMe | G3 |
| Q142 | H | $NO_2$ | G3 |
| Q188 | H | $NO_2$ | G3 |
| Q189 | H | $NO_2$ | G3 |
| Q201 | H | $NMe_2$ | G3 |
| Q202 | H | NHCOMe | G3 |
| Q204 | H | $NO_2$ | G3 |
| Q205 | H | NHCOMe | G3 |
| Q209 | H | $NMe_2$ | G3 |
| Q222 | H | $NO_2$ | G3 |
| Q225 | H | $NMe_2$ | G3 |
| Q229 | H | NHCOMe | G3 |
| Q230 | H | $NO_2$ | G3 |
| Q246 | H | $NMe_2$ | G3 |

TABLE 1-continued

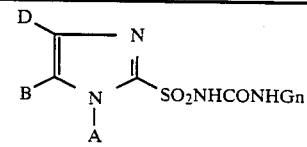

| A | B | D | Gn |
|---|---|---|---|
| Q250 | H | $NO_2$ | G3 |

TABLE 2

| A | B | D | Gn |
|---|---|---|---|
| Q1 | H | COOMe | Gb |
| $CH_2$ - Q1 | H | COOMe | Gc |
| CHMe - Q1 | H | COOMe | G3 |
| Q2 | H | COOMe | Gb |
| Q3 | H | COOMe | Gb |
| Q4 | H | COOMe | Gb |
| Q5 | H | COOMe | Ga |
| $CH_2$ - Q5 | H | COOMe | Gc |
| CHMe - Q5 | H | COOMe | G3 |
| Q6 | H | COOMe | G3 |
| Q7 | H | COOMe | G3 |
| Q8 | H | COOMe | G3 |
| Q9 | H | COOMe | Gc |
| $CH_2$ - Q9 | H | COOMe | Gc |
| Q10 | H | COOMe | Gc |
| Q11 | H | COOMe | G3 |
| Q12 | H | COOMe | G3 |
| Q13 | H | COOMe | G3 |
| Q14 | H | COOMe | G1 |
| Q15 | H | COOMe | G3 |
| Q16 | H | COOMe | Gc |
| Q17 | H | COOMe | Gc |
| Q18 | H | COOMe | G3 |
| Q19 | H | COOMe | Gc |
| Q20 | H | COOMe | Gc |
| Q21 | H | COOMe | Gc |
| Q22 | H | COOMe | G3 |
| Q23 | H | COOMe | Gc |
| $CH_2$ - Q23 | H | COOMe | G3 |
| Q24 | H | COOMe | Gc |
| Q25 | H | COOMe | Gb |
| Q26 | H | COOMe | Ga |
| $CH_2$ - Q26 | H | COOMe | G3 |
| CHMe - Q26 | H | COOMe | G3 |
| Q27 | H | COOMe | G3 |
| Q28 | H | COOMe | G3 |
| Q29 | H | COOMe | Gc |
| $CH_2$ - Q29 | H | COOMe | G3 |
| Q30 | H | COOMe | G3 |
| Q31 | H | COOMe | Gc |
| Q32 | H | COOMe | Gc |
| $CH_2$ - Q32 | H | COOMe | G3 |
| Q33 | H | COOMe | G3 |
| Q34 | H | COOMe | G3 |
| Q35 | H | COOMe | G3 |
| Q36 | H | COOMe | G3 |
| Q37 | H | COOMe | Gc |
| Q38 | H | COOMe | Gc |
| Q39 | H | COOMe | G3 |
| Q40 | H | COOMe | Gc |
| Q41 | H | COOMe | Gc |
| Q42 | H | COOMe | Gc |
| Q43 | H | COOMe | G3 |
| Q44 | H | COOMe | Gc |
| Q45 | H | COOMe | Gc |
| Q46 | H | COOMe | Gc |
| Q47 | H | COOMe | Gc |
| Q48 | H | COOMe | Gc |
| Q49 | H | COOMe | G3 |

TABLE 2-continued structure: imidazole with N-A, C-B, C=C, with SO₂NHCONHGn on one carbon and D on other

| A | B | D | Gn |
|---|---|---|---|
| Q50 | H | COOMe | Gc |
| CH₂ - Q50 | H | COOMe | G3 |
| Q51 | H | COOMe | Gc |
| Q52 | H | COOMe | G3 |
| Q53 | H | COOMe | G3 |
| Q54 | H | COOMe | Gc |
| Q55 | H | COOMe | Gc |
| Q56 | H | COOMe | Gc |
| Q57 | H | COOMe | G3 |
| Q58 | H | COOMe | Gc |
| Q59 | H | COOMe | Gc |
| CH₂ - Q59 | H | COOMe | G3 |
| Q60 | H | COOMe | Gc |
| Q61 | H | COOMe | Ga |
| CH₂ - Q61 | H | COOMe | Gb |
| CHMe - Q61 | H | COOMe | Gc |
| Q62 | H | COOMe | Gc |
| Q63 | H | COOMe | Gc |
| Q64 | H | COOMe | Gb |
| CH₂ - Q64 | H | COOMe | G3 |
| CHMe - Q64 | H | COOMe | G3 |
| Q65 | H | COOMe | G3 |
| Q66 | H | COOMe | G3 |
| Q67 | H | COOMe | G3 |
| Q68 | H | COOMe | G3 |
| Q69 | H | COOMe | Gc |
| Q70 | H | COOMe | Gc |
| Q71 | H | COOMe | Gc |
| Q72 | H | COOMe | Gc |
| CH₂ - Q72 | H | COOMe | G3 |
| CHMe - Q72 | H | COOMe | G3 |
| Q73 | H | COOMe | Gc |
| CH₂ - Q73 | H | COOMe | G3 |
| Q74 | H | COOMe | Gc |
| Q75 | H | COOMe | G3 |
| Q76 | H | COOMe | G3 |
| Q77 | H | COOMe | Gc |
| CH₂ - Q77 | H | COOMe | G3 |
| Q78 | H | COOMe | Gc |
| Q79 | H | COOMe | Gc |
| Q80 | H | COOMe | Gc |
| Q81 | H | COOMe | G3 |
| Q82 | H | COOMe | G3 |
| Q83 | H | COOMe | G1 |
| Q84 | H | COOMe | G2 |
| Q85 | H | COOMe | G3 |
| Q86 | H | COOMe | Gc |
| Q87 | H | COOMe | G2 |
| Q88 | H | COOMe | Gc |
| Q89 | H | COOMe | Gc |
| Q90 | H | COOMe | Gc |
| Q91 | H | COOMe | Gc |
| Q92 | H | COOMe | Gc |
| Q93 | H | COOMe | Gc |
| Q94 | H | COOMe | G3 |
| Q95 | H | COOMe | Gc |
| Q96 | H | COOMe | G3 |
| Q97 | H | COOMe | Gc |
| Q98 | H | COOMe | Gc |
| Q99 | H | COOMe | Gc |
| Q100 | H | COOMe | Gc |
| Q101 | H | COOMe | Gc |
| CH₂ - Q101 | H | COOMe | G3 |
| Q102 | H | COOMe | G3 |
| Q103 | H | COOMe | G3 |
| Q104 | H | COOMe | G3 |
| Q105 | H | COOMe | Gc |
| Q106 | H | COOMe | G3 |
| Q107 | H | COOMe | Gc |
| Q108 | H | COOMe | G1 |
| Q109 | H | COOMe | G3 |
| Q110 | H | COOMe | G3 |
| Q111 | H | COOMe | G3 |
| Q112 | H | COOMe | Gc |
| Q113 | H | COOMe | Gc |
| Q114 | H | COOMe | Gc |
| Q115 | H | COOMe | G2 |
| Q116 | H | COOMe | Gc |
| Q117 | H | COOMe | Gc |
| Q118 | H | COOMe | G3 |
| Q119 | H | COOMe | Gc |
| Q120 | H | COOMe | Gc |
| Q121 | H | COOMe | G2 |
| Q122 | H | COOMe | Gc |
| Q123 | H | COOMe | Gc |
| Q124 | H | COOMe | Gc |
| Q125 | H | COOMe | Gc |
| Q126 | H | COOMe | Gc |
| Q127 | H | COOMe | Gc |
| Q128 | H | COOMe | Gc |
| Q129 | H | COOMe | Gc |
| Q130 | H | COOMe | G2 |
| Q131 | H | COOMe | Gc |
| Q132 | H | COOMe | Gc |
| Q133 | H | COOMe | G3 |
| Q134 | H | COOMe | G3 |
| Q135 | H | COOMe | Gc |
| Q136 | H | COOMe | G3 |
| Q137 | H | COOMe | G1 |
| Q138 | H | COOMe | Gc |
| CH₂ - Q138 | H | COOMe | G3 |
| Q139 | H | COOMe | G3 |
| Q140 | H | COOMe | G1 |
| Q141 | H | COOMe | G3 |
| Q142 | H | COOMe | Gc |
| Q143 | H | COOMe | Gc |
| CH₂ - Q143 | H | COOMe | G3 |
| Q144 | H | COOMe | G3 |
| Q145 | H | COOMe | Gc |
| Q146 | H | COOMe | Gc |
| Q147 | H | COOMe | G3 |
| Q148 | H | COOMe | G1 |
| Q149 | H | COOMe | G3 |
| Q150 | H | COOMe | G3 |
| Q151 | H | COOMe | G2 |
| Q152 | H | COOMe | G1 |
| Q153 | H | COOMe | Gc |
| Q154 | H | COOMe | Gc |
| Q155 | H | COOMe | G3 |
| Q156 | H | COOMe | G3 |
| Q157 | H | COOMe | Gc |
| Q158 | H | COOMe | Ga |
| CH₂ - Q158 | H | COOMe | G3 |
| CHMe - Q158 | H | COOMe | G3 |
| Q159 | H | COOMe | G3 |
| Q160 | H | COOMe | Gc |
| Q161 | H | COOMe | Gc |
| Q162 | H | COOMe | Gc |
| Q163 | H | COOMe | G3 |
| Q164 | H | COOMe | Gc |
| Q165 | H | COOMe | Gc |
| Q166 | H | COOMe | Gc |
| Q167 | H | COOMe | G3 |
| Q168 | H | COOMe | G3 |
| Q169 | H | COOMe | Gc |
| CH₂ - Q169 | H | COOMe | G3 |
| CHMe - Q169 | H | COOMe | G3 |
| Q170 | H | COOMe | Gc |
| Q171 | H | COOMe | Gc |
| Q172 | H | COOMe | Gc |
| Q173 | H | COOMe | Gc |
| Q174 | H | COOMe | Gc |
| Q175 | H | COOMe | Gc |
| Q176 | H | COOMe | Gc |
| Q177 | H | COOMe | Gc |
| CH₂ - Q177 | H | COOMe | G3 |

TABLE 2-continued

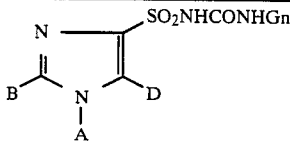

| A | B | D | Gn |
|---|---|---|---|
| CHMe - Q177 | H | COOMe | G3 |
| Q178 | H | COOMe | G3 |
| Q179 | H | COOMe | G3 |
| Q180 | H | COOMe | Gc |
| CH2 - Q180 | H | COOMe | G3 |
| Q181 | H | COOMe | G1 |
| Q182 | H | COOMe | G3 |
| Q183 | H | COOMe | G3 |
| Q184 | H | COOMe | Gc |
| CH2 - Q184 | H | COOMe | G3 |
| CHMe - Q184 | H | COOMe | G3 |
| Q185 | H | COOMe | G3 |
| Q186 | H | COOMe | G3 |
| Q187 | H | COOMe | G3 |
| Q188 | H | COOMe | Gb |
| Q189 | H | COOMe | Gb |
| Q1 | H | COOEt | Gb |
| CH2 - Q1 | H | COOEt | Gc |
| CHMe - Q1 | H | COOEt | G3 |
| Q2 | H | COOEt | Gb |
| Q3 | H | COOEt | Gb |
| Q4 | H | COOEt | Gb |
| Q5 | H | COOEt | Ga |
| CH2 - Q5 | H | COOEt | Gc |
| CHMe - Q5 | H | COOEt | G3 |
| Q6 | H | COOEt | G3 |
| Q7 | H | COOEt | G3 |
| Q8 | H | COOEt | G3 |
| Q9 | H | COOEt | Gc |
| CH2 - Q9 | H | COOEt | Gc |
| Q10 | H | COOEt | Gc |
| Q11 | H | COOEt | G3 |
| Q12 | H | COOEt | G3 |
| Q13 | H | COOEt | G3 |
| Q14 | H | COOEt | G1 |
| Q15 | H | COOEt | G3 |
| Q16 | H | COOEt | Gc |
| Q17 | H | COOEt | Gc |
| Q18 | H | COOEt | G3 |
| Q19 | H | COOEt | Gc |
| Q20 | H | COOEt | Gc |
| Q21 | H | COOEt | Gc |
| Q22 | H | COOEt | G3 |
| Q23 | H | COOEt | Gc |
| CH2 - Q23 | H | COOEt | G3 |
| Q24 | H | COOEt | Gc |
| Q25 | H | COOEt | Gb |
| Q26 | H | COOEt | Ga |
| CH2 - Q26 | H | COOEt | G3 |
| CHMe - Q26 | H | COOEt | G3 |
| Q27 | H | COOEt | G3 |
| Q28 | H | COOEt | G3 |
| Q29 | H | COOEt | Gc |
| CH2 - Q29 | H | COOEt | G3 |
| Q30 | H | COOEt | G3 |
| Q31 | H | COOEt | Gc |
| Q32 | H | COOEt | Gc |
| CH2 - Q32 | H | COOEt | G3 |
| Q33 | H | COOEt | G3 |
| Q34 | H | COOEt | G3 |
| Q35 | H | COOEt | G3 |
| Q36 | H | COOEt | G3 |
| Q37 | H | COOEt | Gc |
| Q38 | H | COOEt | Gc |
| Q39 | H | COOEt | G3 |
| Q40 | H | COOEt | Gc |
| Q41 | H | COOEt | Gc |
| Q42 | H | COOEt | Gc |
| Q43 | H | COOEt | G3 |
| Q44 | H | COOEt | Gc |
| Q45 | H | COOEt | Gc |
| Q46 | H | COOEt | Gc |
| Q47 | H | COOEt | Gc |

TABLE 2-continued

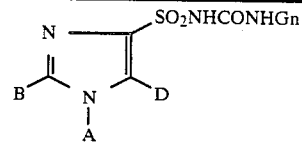

| A | B | D | Gn |
|---|---|---|---|
| Q48 | H | COOEt | Gc |
| Q49 | H | COOEt | G3 |
| Q50 | H | COOEt | Gc |
| CH2 - Q50 | H | COOEt | G3 |
| Q51 | H | COOEt | Gc |
| Q52 | H | COOEt | G3 |
| Q53 | H | COOEt | G3 |
| Q54 | H | COOEt | Gc |
| Q55 | H | COOEt | Gc |
| Q56 | H | COOEt | Gc |
| Q57 | H | COOEt | G3 |
| Q58 | H | COOEt | Gc |
| Q59 | H | COOEt | Gc |
| CH2 - Q59 | H | COOEt | G3 |
| Q60 | H | COOEt | Ga |
| Q61 | H | COOEt | Ga |
| CH2 - Q61 | H | COOEt | Gb |
| CHMe - Q61 | H | COOEt | Gc |
| Q62 | H | COOEt | Gc |
| Q63 | H | COOEt | Gc |
| Q64 | H | COOEt | Gb |
| CH2 - Q64 | H | COOEt | G3 |
| CHMe - Q64 | H | COOEt | G3 |
| Q65 | H | COOEt | G3 |
| Q66 | H | COOEt | G3 |
| Q67 | H | COOEt | G3 |
| Q68 | H | COOEt | G3 |
| Q69 | H | COOEt | Gc |
| Q70 | H | COOEt | Gc |
| Q71 | H | COOEt | Gc |
| Q72 | H | COOEt | Gc |
| CH2 - Q72 | H | COOEt | G3 |
| CHMe - Q72 | H | COOEt | G3 |
| Q73 | H | COOEt | Gc |
| CH2 - Q73 | H | COOEt | G3 |
| Q74 | H | COOEt | Gc |
| Q75 | H | COOEt | G3 |
| Q76 | H | COOEt | G3 |
| Q77 | H | COOEt | Gc |
| CH2 - Q77 | H | COOEt | G3 |
| Q78 | H | COOEt | Gc |
| Q79 | H | COOEt | Gc |
| Q80 | H | COOEt | Gc |
| Q81 | H | COOEt | G3 |
| Q82 | H | COOEt | G3 |
| Q83 | H | COOEt | G1 |
| Q84 | H | COOEt | G2 |
| Q85 | H | COOEt | G3 |
| Q86 | H | COOEt | Gc |
| Q87 | H | COOEt | G2 |
| Q88 | H | COOEt | Gc |
| Q89 | H | COOEt | Gc |
| Q90 | H | COOEt | Gc |
| Q91 | H | COOEt | Gc |
| Q92 | H | COOEt | G3 |
| Q93 | H | COOEt | Gc |
| Q94 | H | COOEt | G3 |
| Q95 | H | COOEt | Gc |
| Q96 | H | COOEt | G3 |
| Q97 | H | COOEt | Gc |
| Q98 | H | COOEt | Gc |
| Q99 | H | COOEt | Gc |
| Q100 | H | COOEt | Gc |
| Q101 | H | COOEt | Gc |
| CH2 - Q101 | H | COOEt | G3 |
| Q102 | H | COOEt | G3 |
| Q103 | H | COOEt | G3 |
| Q104 | H | COOEt | G3 |
| Q105 | H | COOEt | Gc |
| Q106 | H | COOEt | G3 |
| Q107 | H | COOEt | Gc |
| Q108 | H | COOEt | G1 |
| Q109 | H | COOEt | G3 |

TABLE 2-continued structure: imidazole with SO₂NHCONHGn at 4-position, D at 5-position, B at 2-position, A at N1

| A | B | D | Gn |
|---|---|---|---|
| Q110 | H | COOEt | G3 |
| Q111 | H | COOEt | G3 |
| Q112 | H | COOEt | Gc |
| Q113 | H | COOEt | Gc |
| Q114 | H | COOEt | G2 |
| Q115 | H | COOEt | Gc |
| Q116 | H | COOEt | Gc |
| Q117 | H | COOEt | G3 |
| Q118 | H | COOEt | Gc |
| Q119 | H | COOEt | Gc |
| Q120 | H | COOEt | G2 |
| Q121 | H | COOEt | Gc |
| Q122 | H | COOEt | Gc |
| Q123 | H | COOEt | Gc |
| Q124 | H | COOEt | Gc |
| Q125 | H | COOEt | Gc |
| Q126 | H | COOEt | Gc |
| Q127 | H | COOEt | Gc |
| Q128 | H | COOEt | Gc |
| Q129 | H | COOEt | Gc |
| Q130 | H | COOEt | G2 |
| Q131 | H | COOEt | Gc |
| Q132 | H | COOEt | Gc |
| Q133 | H | COOEt | G3 |
| Q134 | H | COOEt | G3 |
| Q135 | H | COOEt | Gc |
| Q136 | H | COOEt | G3 |
| Q137 | H | COOEt | G1 |
| $CH_2$ - Q138 | H | COOEt | G3 |
| Q139 | H | COOEt | G3 |
| Q140 | H | COOEt | G1 |
| Q141 | H | COOEt | G3 |
| Q142 | H | COOEt | Gc |
| Q143 | H | COOEt | Gc |
| $CH_2$ - Q143 | H | COOEt | G3 |
| Q144 | H | COOEt | G3 |
| Q145 | H | COOEt | Gc |
| Q146 | H | COOEt | Gc |
| Q147 | H | COOEt | G3 |
| Q148 | H | COOEt | G1 |
| Q149 | H | COOEt | G3 |
| Q150 | H | COOEt | G3 |
| Q151 | H | COOEt | G2 |
| Q152 | H | COOEt | G1 |
| Q153 | H | COOEt | Gc |
| Q154 | H | COOEt | Gc |
| Q155 | H | COOEt | G3 |
| Q156 | H | COOEt | G3 |
| Q157 | H | COOEt | Gc |
| Q158 | H | COOEt | Ga |
| $CH_2$ - Q158 | H | COOEt | G3 |
| CHMe - Q158 | H | COOEt | G3 |
| Q159 | H | COOEt | G3 |
| Q160 | H | COOEt | Gc |
| Q161 | H | COOEt | Gc |
| Q162 | H | COOEt | Gc |
| Q163 | H | COOEt | G3 |
| Q164 | H | COOEt | Gc |
| Q165 | H | COOEt | Gc |
| Q166 | H | COOEt | Gc |
| Q167 | H | COOEt | G3 |
| Q168 | H | COOEt | G3 |
| $CH_2$ - Q169 | H | COOEt | Gc |
| CHMe - Q169 | H | COOEt | G3 |
| Q170 | H | COOEt | Gc |
| Q171 | H | COOEt | Gc |
| Q172 | H | COOEt | Gc |
| Q173 | H | COOEt | Gc |
| Q174 | H | COOEt | Gc |
| Q175 | H | COOEt | Gc |
| Q176 | H | COOEt | Gc |
| Q177 | H | COOEt | Gc |
| $CH_2$ - Q177 | H | COOEt | G3 |
| CHMe - Q177 | H | COOEt | G3 |
| Q178 | H | COOEt | G3 |
| Q179 | H | COOEt | G3 |
| Q180 | H | COOEt | Gc |
| $CH_2$ - Q180 | H | COOEt | G3 |
| Q181 | H | COOEt | G1 |
| Q182 | H | COOEt | G3 |
| Q183 | H | COOEt | G3 |
| Q184 | H | COOEt | Gc |
| $CH_2$ - Q184 | H | COOEt | G3 |
| CHMe - Q184 | H | COOEt | G3 |
| Q185 | H | COOEt | G3 |
| Q186 | H | COOEt | G3 |
| Q187 | H | COOEt | G3 |
| Q188 | H | COOEt | Gb |
| Q189 | H | COOEt | Gb |
| Q5 | H | COOPr—i | G3 |
| Q26 | H | COOPr—i | G3 |
| Q61 | H | COOPr—i | G3 |
| Q158 | H | COOPr—i | G3 |
| Q5 | H | COOCH₂CH₂Cl | G3 |
| Q26 | H | COOCH₂CH₂Cl | G3 |
| Q61 | H | COOCH₂CH₂Cl | G3 |
| Q158 | H | COOCH₂CH₂Cl | G3 |
| Q5 | H | COOCH₂CH=CH₂ | G3 |
| Q26 | H | COOCH₂CH=CH₂ | G3 |
| Q61 | H | COOCH₂CH=CH₂ | G3 |
| Q158 | H | COOCH₂CH=CH₂ | G3 |
| Q5 | H | COOCH₂C≡CH | G3 |
| Q26 | H | COOCH₂C≡CH | G3 |
| Q61 | H | COOCH₂C≡CH | G3 |
| Q158 | H | COOCH₂C≡CH | G3 |
| Q1 | H | COOPr—i | G3 |
| Q2 | H | COOCH₂CH₂Cl | G3 |
| Q4 | H | COOCH₂CH=CH₂ | G3 |
| Q7 | H | COOCH₂C≡CH | G3 |
| Q9 | H | COOPr—i | G3 |
| Q10 | H | COOCH₂CH₂Cl | G3 |
| Q19 | H | COOPr—i | G3 |
| Q23 | H | COOCH₂CH=CH₂ | G3 |
| Q32 | H | COOCH₂C≡CH | G3 |
| Q41 | H | COOPr—i | G3 |
| Q45 | H | COOCH₂CH₂Cl | G3 |
| Q50 | H | COOCH₂C≡CH | G3 |
| Q69 | H | COOPr—i | G3 |
| Q79 | H | COOCH₂CH₂Cl | G3 |
| Q83 | H | COOCH₂C≡CH | G3 |
| Q96 | H | COOPr—i | G3 |
| Q124 | H | COOCH₂CH₂Cl | G3 |
| Q131 | H | COOCH₂CH=CH₂ | G3 |
| Q132 | H | COOCH₂C≡CH | G3 |
| Q135 | H | COOPr—i | G3 |
| Q138 | H | COOPr—i | G3 |
| Q142 | H | COOCH₂CH=CH₂ | G3 |
| Q157 | H | COOPr—i | G3 |
| Q159 | H | COOCH₂CH₂Cl | G3 |
| Q177 | H | COOCH₂CH=CH₂ | G3 |
| Q180 | H | COOCH₂C≡CH | G3 |
| Q184 | H | COOPr—i | G3 |
| Q5 | H | COOH | G3 |
| Q26 | H | COOH | G3 |
| Q61 | H | COOH | G3 |
| Q158 | H | COOH | G3 |
| Q5 | H | CONHMe | G3 |
| Q26 | H | CONHMe | G3 |
| Q61 | H | CONHMe | G3 |
| Q158 | H | CONHMe | G3 |
| Q5 | H | CONMe₂ | G3 |
| Q26 | H | CONMe₂ | G3 |
| Q61 | H | CONMe₂ | G3 |
| Q158 | H | CONMe₂ | G3 |

TABLE 2-continued

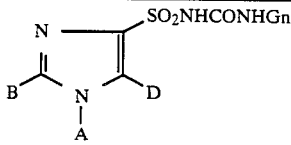

| A | B | D | Gn |
|---|---|---|---|
| Q5 | H | COMe | G3 |
| Q26 | H | COMe | G3 |
| Q61 | H | COMe | G3 |
| Q158 | H | COMe | G3 |
| Q189 | H | COMe | Gb |
| Q5 | H | COEt | G3 |
| Q26 | H | COEt | G3 |
| Q61 | H | COEt | G3 |
| Q158 | H | COEt | G3 |
| Q189 | H | COEt | Gb |
| Q5 | H | COPr—i | G3 |
| Q26 | H | COPr—i | G3 |
| Q61 | H | COPr—i | G3 |
| Q158 | H | COPr—i | G3 |
| Q5 | H | COPh | G3 |
| Q26 | H | COPh | G3 |
| Q61 | H | COPh | G3 |
| Q158 | H | COPh | G3 |
| Q1 | H | COMe | G3 |
| Q2 | H | COEt | G3 |
| Q4 | H | COMe | G3 |
| Q7 | H | COMe | G3 |
| Q9 | H | COEt | G3 |
| Q10 | H | COPr—i | G3 |
| Q19 | H | COPh | G3 |
| Q23 | H | COMe | G3 |
| Q32 | H | COMe | G3 |
| Q41 | H | COPr—i | G3 |
| Q45 | H | COPh | G3 |
| Q50 | H | COMe | G3 |
| Q69 | H | COEt | G3 |
| Q79 | H | COPr—i | G3 |
| Q83 | H | COPh | G3 |
| Q96 | H | COMe | G3 |
| Q124 | H | COEt | G3 |
| Q131 | H | COMe | G3 |
| Q132 | H | COMe | G3 |
| Q135 | H | COEt | G3 |
| Q138 | H | COPr—i | G3 |
| Q142 | H | COPh | G3 |
| Q157 | H | COMe | G3 |
| Q159 | H | COEt | G3 |
| Q177 | H | COMe | G3 |
| Q180 | H | COMe | G3 |
| Q184 | H | COPr—i | G3 |
| Q4 | H | CN | G3 |
| Q5 | H | CN | G3 |
| Q7 | H | CN | G3 |
| Q9 | H | CN | G3 |
| Q23 | H | CN | G3 |
| Q26 | H | CN | G3 |
| Q32 | H | CN | G3 |
| Q61 | H | CN | G3 |
| Q96 | H | CN | G3 |
| Q142 | H | CN | G3 |
| Q158 | H | CN | G3 |
| Q5 | H | H | G3 |
| Q26 | H | H | G3 |
| Q61 | H | H | G3 |
| Q158 | H | H | G3 |
| Q5 | H | Me | G3 |
| Q26 | H | Me | G3 |
| Q61 | H | Me | G3 |
| Q158 | H | Me | G3 |
| Q5 | H | Et | G3 |
| Q26 | H | Et | G3 |
| Q61 | H | Et | G3 |
| Q158 | H | Et | G3 |
| Q5 | H | Pr—i | G3 |
| Q26 | H | Pr—i | G3 |
| Q61 | H | Pr—i | G3 |
| Q158 | H | Pr—i | G3 |
| Q5 | H | CH=CH$_2$ | G3 |

TABLE 2-continued

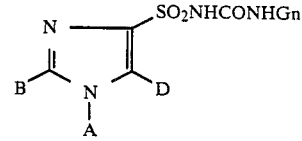

| A | B | D | Gn |
|---|---|---|---|
| Q26 | H | CH=CH$_2$ | G3 |
| Q61 | H | CH=CHMe | G3 |
| Q158 | H | CH=CHMe | G3 |
| Q5 | H | CH$_2$CH=CH$_2$ | G3 |
| Q26 | H | CH$_2$CH=CH$_2$ | G3 |
| Q61 | H | CH$_2$CH=CH$_2$ | G3 |
| Q158 | H | CH$_2$CH=CH$_2$ | G3 |
| Q1 | H | H | G3 |
| Q2 | H | Me | G3 |
| Q4 | H | Me | G3 |
| Q7 | H | Me | G3 |
| Q9 | H | Et | G3 |
| Q10 | H | Pr—i | G3 |
| Q19 | H | Me | G3 |
| Q23 | H | CH$_2$CH=CH$_2$ | G3 |
| Q32 | H | H | G3 |
| Q41 | H | Me | G3 |
| Q45 | H | Me | G3 |
| Q50 | H | Et | G3 |
| Q69 | H | Pr—i | G3 |
| Q79 | H | Me | G3 |
| Q83 | H | Et | G3 |
| Q96 | H | Me | G3 |
| Q124 | H | Et | G3 |
| Q131 | H | Me | G3 |
| Q132 | H | CH$_2$CH=CH$_2$ | G3 |
| Q135 | H | Et | G3 |
| Q138 | H | Pr—i | G3 |
| Q142 | H | H | G3 |
| Q157 | H | Me | G3 |
| Q159 | H | Me | G3 |
| Q177 | H | H | G3 |
| Q180 | H | Me | G3 |
| Q184 | H | Me | G3 |
| Q5 | H | CH$_2$Cl | G3 |
| Q26 | H | CH$_2$Cl | G3 |
| Q61 | H | CH$_2$Cl | G3 |
| Q158 | H | CH$_2$Cl | G3 |
| Q5 | H | CH$_2$CH$_2$Cl | G3 |
| Q26 | H | CH$_2$CH$_2$Cl | G3 |
| Q61 | H | CH$_2$CH$_2$Cl | G3 |
| Q158 | H | CH$_2$CH$_2$Cl | G3 |
| Q5 | H | CF$_3$ | G3 |
| Q26 | H | CF$_3$ | G3 |
| Q61 | H | CF$_3$ | G3 |
| Q158 | H | CF$_3$ | G3 |
| Q5 | H | CF=CFCl | G3 |
| Q26 | H | CF=CFCl | G3 |
| Q61 | H | CH$_2$Ph | G3 |
| Q158 | H | CH$_2$Ph | G3 |
| Q5 | H | Ph | G3 |
| Q26 | H | Ph | G3 |
| Q61 | H | Ph | G3 |
| Q158 | H | Ph | G3 |
| Q5 | H | Ph—2-Cl | G3 |
| Q26 | H | Ph—2-Me | G3 |
| Q61 | H | Ph—2-Cl | G3 |
| Q158 | H | Ph—2-Me | G3 |
| Q1 | H | Ph | G3 |
| Q2 | H | CH$_2$Cl | G3 |
| Q4 | H | CH$_2$CH$_2$Cl | G3 |
| Q7 | H | Ph | G3 |
| Q9 | H | CF$_3$ | G3 |
| Q10 | H | CF$_3$ | G3 |
| Q19 | H | CF=CFCl | G3 |
| Q23 | H | CH$_2$CH$_2$Cl | G3 |
| Q32 | H | Ph | G3 |
| Q41 | H | Ph—2-Cl | G3 |
| Q45 | H | Ph—2-Me | G3 |
| Q50 | H | CH$_2$CH$_2$Cl | G3 |
| Q69 | H | Ph | G3 |
| Q79 | H | CF$_3$ | G3 |
| Q83 | H | CF$_3$ | G3 |

TABLE 2-continued

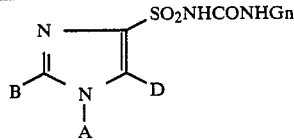

| A | B | D | Gn |
|---|---|---|---|
| Q96 | H | Ph | G3 |
| Q124 | H | Ph—2-Cl | G3 |
| Q131 | H | Ph—2-Me | G3 |
| Q132 | H | CH$_2$CH$_2$Cl | G3 |
| Q135 | H | Ph | G3 |
| Q138 | H | CF$_3$ | G3 |
| Q142 | H | CF$_3$ | G3 |
| Q157 | H | CF=CFCl | G3 |
| Q159 | H | CH$_2$Cl | G3 |
| Q177 | H | CH$_2$CH$_2$Cl | G3 |
| Q180 | H | Ph | G3 |
| Q184 | H | Ph—2-Cl | G3 |
| Q5 | H | Cl | G3 |
| Q26 | H | Cl | G3 |
| Q61 | H | Cl | G3 |
| Q158 | H | Cl | G3 |
| Q5 | H | Br | G3 |
| Q26 | H | Br | G3 |
| Q61 | H | Br | G3 |
| Q158 | H | Br | G3 |
| Q5 | H | F | G3 |
| Q26 | H | F | G3 |
| Q61 | H | I | G3 |
| Q158 | H | I | G3 |
| Q1 | H | Cl | G3 |
| Q2 | H | Cl | G3 |
| Q4 | H | Cl | G3 |
| Q7 | H | Br | G3 |
| Q9 | H | F | G3 |
| Q10 | H | I | G3 |
| Q19 | H | Cl | G3 |
| Q23 | H | Cl | G3 |
| Q32 | H | Cl | G3 |
| Q41 | H | Br | G3 |
| Q45 | H | Br | G3 |
| Q50 | H | F | G3 |
| Q69 | H | Cl | G3 |
| Q79 | H | F | G3 |
| Q83 | H | Cl | G3 |
| Q96 | H | Cl | G3 |
| Q124 | H | Cl | G3 |
| Q131 | H | Br | G3 |
| Q132 | H | Br | G3 |
| Q135 | H | F | G3 |
| Q138 | H | Br | G3 |
| Q142 | H | Cl | G3 |
| Q157 | H | Cl | G3 |
| Q159 | H | Cl | G3 |
| Q177 | H | Br | G3 |
| Q180 | H | Br | G3 |
| Q184 | H | Cl | G3 |
| Q4 | H | NO$_2$ | G3 |
| Q5 | H | NO$_2$ | G3 |
| Q7 | H | NO$_2$ | G3 |
| Q9 | H | NO$_2$ | G3 |
| Q23 | H | NO$_2$ | G3 |
| Q26 | H | NO$_2$ | G3 |
| Q32 | H | NO$_2$ | G3 |
| Q61 | H | NO$_2$ | G3 |
| Q96 | H | NO$_2$ | G3 |
| Q142 | H | NO$_2$ | G3 |
| Q158 | H | NO$_2$ | G3 |
| Q5 | H | NH$_2$ | G3 |
| Q26 | H | NH$_2$ | G3 |
| Q61 | H | NH$_2$ | G3 |
| Q158 | H | NH$_2$ | G3 |
| Q5 | H | NHMe | G3 |
| Q26 | H | NHMe | G3 |
| Q61 | H | NHMe | G3 |
| Q158 | H | NHMe | G3 |
| Q5 | H | NMe$_2$ | G3 |
| Q26 | H | NMe$_2$ | G3 |
| Q61 | H | NMe$_2$ | G3 |

TABLE 2-continued

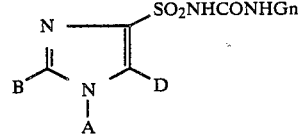

| A | B | D | Gn |
|---|---|---|---|
| Q158 | H | NMe$_2$ | G3 |
| Q5 | H | NMeEt | G3 |
| Q26 | H | NMeEt | G3 |
| Q61 | H | NMeEt | G3 |
| Q158 | H | NMeEt | G3 |
| Q5 | H | NHSO$_2$Me | G3 |
| Q26 | H | NHSO$_2$Me | G3 |
| Q61 | H | NHSO$_2$Me | G3 |
| Q158 | H | NHSO$_2$Me | G3 |
| Q1 | H | NH$_2$ | G3 |
| Q2 | H | NH$_2$ | G3 |
| Q4 | H | NH$_2$ | G3 |
| Q7 | H | NHMe | G3 |
| Q9 | H | NHMe | G3 |
| Q10 | H | NMe$_2$ | G3 |
| Q19 | H | NMeEt | G3 |
| Q23 | H | NMe$_2$ | G3 |
| Q32 | H | NMeEt | G3 |
| Q41 | H | NH$_2$ | G3 |
| Q45 | H | NH$_2$ | G3 |
| Q50 | H | NHMe | G3 |
| Q69 | H | NHMe | G3 |
| Q79 | H | NMe$_2$ | G3 |
| Q83 | H | NMeEt | G3 |
| Q96 | H | NHSO$_2$Me | G3 |
| Q124 | H | NMe$_2$ | G3 |
| Q131 | H | NMeEt | G3 |
| Q132 | H | NH$_2$ | G3 |
| Q135 | H | NH$_2$ | G3 |
| Q138 | H | NHMe | G3 |
| Q142 | H | NHMe | G3 |
| Q157 | H | NHSO$_2$Me | G3 |
| Q159 | H | NMe$_2$ | G3 |
| Q177 | H | NMeEt | G3 |
| Q180 | H | NH$_2$ | G3 |
| Q184 | H | NH$_2$ | G3 |
| Q4 | H | NHCOMe | G3 |
| Q5 | H | NHCOMe | G3 |
| Q7 | H | NHCOMe | G3 |
| Q9 | H | NHCOMe | G3 |
| Q23 | H | NHCOMe | G3 |
| Q26 | H | NHCOMe | G3 |
| Q32 | H | NHCOMe | G3 |
| Q61 | H | NHCOMe | G3 |
| Q96 | H | NHCOMe | G3 |
| Q142 | H | NHCOMe | G3 |
| Q158 | H | NHCOMe | G3 |
| Q5 | H | NHCOEt | G3 |
| Q26 | H | NHCOEt | G3 |
| Q61 | H | NHCOEt | G3 |
| Q158 | H | NHCOEt | G3 |
| Q5 | H | OMe | G3 |
| Q26 | H | OMe | G3 |
| Q61 | H | OMe | G3 |
| Q158 | H | OMe | G3 |
| Q5 | H | OEt | G3 |
| Q26 | H | OEt | G3 |
| Q61 | H | OEt | G3 |
| Q158 | H | OEt | G3 |
| Q5 | H | CH$_2$OMe | G3 |
| Q26 | H | CH$_2$OMe | G3 |
| Q61 | H | CH$_2$OMe | G3 |
| Q158 | H | CH$_2$OMe | G3 |
| Q5 | H | SMe | G3 |
| Q26 | H | SMe | G3 |
| Q61 | H | SMe | G3 |
| Q158 | H | SMe | G3 |
| Q5 | H | SO$_2$Me | G3 |
| Q26 | H | SO$_2$Me | G3 |
| Q61 | H | SO$_2$Me | G3 |
| Q158 | H | SO$_2$Me | G3 |
| Q1 | H | OMe | G3 |
| Q2 | H | OMe | G3 |

TABLE 2-continued

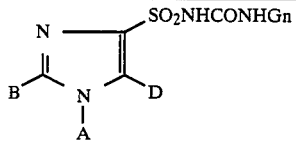

| A | B | D | Gn |
|---|---|---|---|
| Q4 | H | OEt | G3 |
| Q7 | H | SO2OMe | G3 |
| Q9 | H | CH2OMe | G3 |
| Q10 | H | SMe | G3 |
| Q19 | H | SO2OMe | G3 |
| Q23 | H | OMe | G3 |
| Q32 | H | OEt | G3 |
| Q41 | H | SO2OMe | G3 |
| Q45 | H | CH2OMe | G3 |
| Q50 | H | SMe | G3 |
| Q69 | H | SO2OMe | G3 |
| Q79 | H | OMe | G3 |
| Q83 | H | OEt | G3 |
| Q96 | H | CH2OMe | G3 |
| Q124 | H | SMe | G3 |
| Q131 | H | OMe | G3 |
| Q132 | H | OEt | G3 |
| Q135 | H | CH2OMe | G3 |
| Q138 | H | SMe | G3 |
| Q142 | H | SO2OMe | G3 |
| Q157 | H | OMe | G3 |
| Q159 | H | OEt | G3 |
| Q177 | H | SO2OMe | G3 |
| Q180 | H | OMe | G3 |
| Q184 | H | OEt | G3 |
| Q4 | H | SO2Me | G3 |
| Q5 | H | SO2Me | G3 |
| Q7 | H | SO2Me | G3 |
| Q9 | H | SO2Me | G3 |
| Q23 | H | SO2Me | G3 |
| Q26 | H | SO2Me | G3 |
| Q32 | H | SO2Me | G3 |
| Q61 | H | SO2Me | G3 |
| Q96 | H | SO2Me | G3 |
| Q142 | H | SO2Me | G3 |
| Q158 | H | SO2Me | G3 |
| Q188 | H | SO2Me | Gb |
| Q189 | H | SO2Me | Gb |
| Q5 | H | SO2Ph | G3 |
| Q26 | H | SO2Ph | G3 |
| Q61 | H | SO2Ph | G3 |
| Q158 | H | SO2Ph | G3 |
| Q5 | H | SO2NH2 | G3 |
| Q26 | H | SO2NH2 | G3 |
| Q61 | H | SO2NH2 | G3 |
| Q158 | H | SO2NH2 | G3 |
| Q5 | H | SO2NHMe | G3 |
| Q26 | H | SO2NHMe | G3 |
| Q61 | H | SO2NHMe | G3 |
| Q158 | H | SO2NHMe | G3 |
| Q5 | H | SO2NMe2 | G3 |
| Q26 | H | SO2NMe2 | G3 |
| Q61 | H | SO2NMe2 | G3 |
| Q158 | H | SO2NMe2 | G3 |
| Q1 | H | SO2Me | G3 |
| Q2 | H | SO2Me | G3 |
| Q4 | H | SO2Ph | G3 |
| Q7 | H | SO2NH2 | G3 |
| Q9 | H | SO2NH2 | G3 |
| Q10 | H | SO2Ph | G3 |
| Q19 | H | SO2Me | G3 |
| Q23 | H | SO2Ph | G3 |
| Q32 | H | SO2NHMe | G3 |
| Q41 | H | SO2NMe2 | G3 |
| Q45 | H | SO2Me | G3 |
| Q50 | H | SO2NH2 | G3 |
| Q69 | H | SO2Me | G3 |
| Q79 | H | SO2Ph | G3 |
| Q83 | H | SO2Me | G3 |
| Q96 | H | SO2NMe2 | G3 |
| Q124 | H | SO2NH2 | G3 |
| Q131 | H | SO2Me | G3 |
| Q132 | H | SO2Me | G3 |

TABLE 2-continued

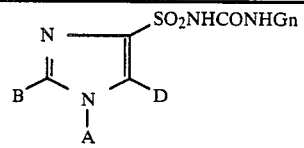

| A | B | D | Gn |
|---|---|---|---|
| Q135 | H | SO2NHMe | G3 |
| Q138 | H | SO2NMe2 | G3 |
| Q142 | H | SO2NH2 | G3 |
| Q157 | H | SO2Me | G3 |
| Q159 | H | SO2Me | G3 |
| Q177 | H | SO2NHMe | G3 |
| Q180 | H | SO2NMe2 | G3 |
| Q184 | H | SO2Me | G3 |
| Q1 | Me | COOMe | G3 |
| Q2 | Me | COOMe | G3 |
| Q4 | Me | COOMe | G3 |
| Q5 | Me | COOMe | G3 |
| Q7 | Me | COOMe | G3 |
| Q9 | Me | COOMe | G3 |
| Q10 | Me | COOMe | G3 |
| Q19 | Me | COOMe | G3 |
| Q23 | Me | COOMe | G3 |
| Q26 | Me | COOMe | G3 |
| Q32 | Me | COOMe | G3 |
| Q41 | Me | COOMe | G3 |
| Q45 | Me | COOMe | G3 |
| Q50 | Me | COOMe | G3 |
| Q61 | Me | COOMe | G3 |
| Q69 | Me | COOMe | G3 |
| Q79 | Me | COOMe | G3 |
| Q83 | Me | COOMe | G3 |
| Q96 | Me | COOMe | G3 |
| Q124 | Me | COOMe | G3 |
| Q131 | Me | COOMe | G3 |
| Q132 | Me | COOMe | G3 |
| Q135 | Me | COOMe | G3 |
| Q138 | Me | COOMe | G3 |
| Q142 | Me | COOMe | G3 |
| Q157 | Me | COOMe | G3 |
| Q158 | Me | COOMe | G3 |
| Q159 | Me | COOMe | G3 |
| Q177 | Me | COOMe | G3 |
| Q180 | Me | COOMe | G3 |
| Q184 | Me | COOMe | G3 |
| Q1 | Me | COOEt | G3 |
| Q2 | Me | COOEt | G3 |
| Q4 | Me | COOEt | G3 |
| Q5 | Me | COOEt | G3 |
| Q7 | Me | COOEt | G3 |
| Q9 | Me | COOEt | G3 |
| Q10 | Me | COOEt | G3 |
| Q19 | Me | COOEt | G3 |
| Q23 | Me | COOEt | G3 |
| Q26 | Me | COOEt | G3 |
| Q32 | Me | COOEt | G3 |
| Q41 | Me | COOEt | G3 |
| Q45 | Me | COOEt | G3 |
| Q50 | Me | COOEt | G3 |
| Q61 | H | COOEt | G3 |
| Q69 | Me | COOEt | G3 |
| Q79 | Me | COOEt | G3 |
| Q83 | Me | COOEt | G3 |
| Q96 | Me | COOEt | G3 |
| Q124 | Me | COOEt | G3 |
| Q131 | Me | COOEt | G3 |
| Q132 | Me | COOEt | G3 |
| Q135 | Me | COOEt | G3 |
| Q138 | Me | COOEt | G3 |
| Q142 | Me | COOEt | G3 |
| Q157 | Me | COOEt | G3 |
| Q158 | Me | COOEt | G3 |
| Q159 | Me | COOEt | G3 |
| Q177 | Me | COOEt | G3 |
| Q180 | Me | COOEt | G3 |
| Q184 | Me | COOEt | G3 |
| Q158 | Me | COOEt | G3 |
| Q5 | Me | COOPr—i | G3 |
| Q26 | Me | COOPr—i | G3 |

TABLE 2-continued

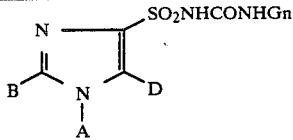

| A | B | D | Gn |
|---|---|---|---|
| Q61 | Me | COOPr—i | G3 |
| Q158 | Me | COOPr—i | G3 |
| Q5 | Me | COOCH₂CH₂Cl | G3 |
| Q26 | Me | COOCH₂CH₂Cl | G3 |
| Q61 | Me | COOCH₂CH₂Cl | G3 |
| Q158 | Me | COOCH₂CH₂Cl | G3 |
| Q5 | Me | COOCH₂CH=CH₂ | G3 |
| Q26 | Me | COOCH₂CH=CH₂ | G3 |
| Q61 | Me | COOCH₂CH=CH₂ | G3 |
| Q158 | Me | COOCH₂CH=CH₂ | G3 |
| Q5 | Me | COOCH₂C≡CH | G3 |
| Q26 | Me | COOCH₂C≡CH | G3 |
| Q61 | Me | COOCH₂C≡CH | G3 |
| Q158 | Me | COOCH₂C≡CH | G3 |
| Q5 | Me | CONHMe | G3 |
| Q26 | Me | CONHMe | G3 |
| Q61 | Me | CONHMe | G3 |
| Q158 | Me | CONHMe | G3 |
| Q5 | Me | CONMe₂ | G3 |
| Q26 | Me | CONMe₂ | G3 |
| Q61 | Me | CONMe₂ | G3 |
| Q158 | Me | CONMe₂ | G3 |
| Q1 | Me | COOPr—i | G3 |
| Q2 | Me | COOPr—i | G3 |
| Q4 | Me | COOCH₂CH₂Cl | G3 |
| Q7 | Me | COOCH₂CH=CH₂ | G3 |
| Q9 | Me | COOCH₂C≡CH | G3 |
| Q10 | Me | COOCH₂CH₂Cl | G3 |
| Q19 | Me | COOPr—i | G3 |
| Q23 | Me | COOCH₂CH₂Cl | G3 |
| Q32 | Me | CONMe₂ | G3 |
| Q41 | Me | COOPr—i | G3 |
| Q45 | Me | CONHMe | G3 |
| Q50 | Me | CONMe₂ | G3 |
| Q69 | Me | COOCH₂CH₂Cl | G3 |
| Q79 | Me | COOCH₂CH=CH₂ | G3 |
| Q83 | Me | COOPr—i | G3 |
| Q96 | Me | COOCH₂CH₂Cl | G3 |
| Q124 | Me | COOPr—i | G3 |
| Q131 | Me | COOCH₂CH₂Cl | G3 |
| Q132 | Me | CONHMe | G3 |
| Q135 | Me | CONMe₂ | G3 |
| Q138 | Me | COOCH₂C≡CH | G3 |
| Q142 | Me | COOPr—i | G3 |
| Q157 | Me | COOPr—i | G3 |
| Q159 | Me | COOCH₂CH=CH₂ | G3 |
| Q177 | Me | COOCH₂C≡CH | G3 |
| Q180 | Me | COOPr—i | G3 |
| Q184 | Me | COOCH₂CH₂Cl | G3 |
| Q5 | Me | COMe | G3 |
| Q26 | Me | COMe | G3 |
| Q61 | Me | COMe | G3 |
| Q158 | Me | COMe | G3 |
| Q5 | Me | COEt | G3 |
| Q26 | Me | COEt | G3 |
| Q61 | Me | COEt | G3 |
| Q158 | Me | COEt | G3 |
| Q5 | Me | COPr—i | G3 |
| Q26 | Me | COPr—i | G3 |
| Q61 | Me | COPr—i | G3 |
| Q158 | Me | COPr—i | G3 |
| Q5 | Me | CN | G3 |
| Q26 | Me | CN | G3 |
| Q61 | Me | CN | G3 |
| Q158 | Me | CN | G3 |
| Q5 | Me | H | G3 |
| Q26 | Me | H | G3 |
| Q61 | Me | H | G3 |
| Q158 | Me | H | G3 |
| Q5 | Me | Me | G3 |
| Q26 | Me | Me | G3 |
| Q61 | Me | Me | G3 |
| Q158 | Me | Me | G3 |

TABLE 2-continued

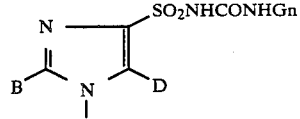

| A | B | D | Gn |
|---|---|---|---|
| Q5 | Me | Et | G3 |
| Q26 | Me | Et | G3 |
| Q61 | Me | Et | G3 |
| Q158 | Me | Et | G3 |
| Q5 | Me | Pr—i | G3 |
| Q26 | Me | Pr—i | G3 |
| Q61 | Me | CH=CH₂ | G3 |
| Q158 | Me | CH=CH₂ | G3 |
| Q5 | Me | CH=CHMe | G3 |
| Q26 | Me | CH₂CH=CH₂ | G3 |
| Q61 | Me | CH=CHMe | G3 |
| Q158 | Me | CH₂CH=CH₂ | G3 |
| Q1 | Me | COMe | G3 |
| Q2 | Me | COEt | G3 |
| Q4 | Me | CH=CHMe | G3 |
| Q7 | Me | CH₂CH=CH₂ | G3 |
| Q9 | Me | CN | G3 |
| Q10 | Me | H | G3 |
| Q19 | Me | Me | G3 |
| Q23 | Me | COMe | G3 |
| Q32 | Me | COEt | G3 |
| Q41 | Me | H | G3 |
| Q45 | Me | Me | G3 |
| Q50 | Me | COPr—i | G3 |
| Q69 | Me | CN | G3 |
| Q79 | Me | Et | G3 |
| Q83 | Me | Pr—i | G3 |
| Q96 | Me | COMe | G3 |
| Q124 | Me | COEt | G3 |
| Q131 | Me | CH₂CH=CH₂ | G3 |
| Q132 | Me | Me | G3 |
| Q135 | Me | COPr-i | G3 |
| Q138 | Me | CN | G3 |
| Q142 | Me | Et | G3 |
| Q157 | Me | CH₂CH=CH₂ | G3 |
| Q159 | Me | COMe | G3 |
| Q177 | Me | COEt | G3 |
| Q180 | Me | CH=CHMe | G3 |
| Q184 | Me | COMe | G3 |
| Q5 | Me | CH₂Cl | G3 |
| Q26 | Me | CH₂Cl | G3 |
| Q5 | Me | CH₂CH₂Cl | G3 |
| Q26 | Me | CH₂CH₂Cl | G3 |
| Q61 | Me | CH₂CH₂Cl | G3 |
| Q158 | Me | CH₂CH₂Cl | G3 |
| Q5 | Me | CF₃ | G3 |
| Q26 | Me | CF₃ | G3 |
| Q61 | Me | CF₃ | G3 |
| Q158 | Me | CF₃ | G3 |
| Q5 | Me | CF=CFCl | G3 |
| Q26 | Me | CF=CFCl | G3 |
| Q61 | Me | CH₂Ph | G3 |
| Q158 | Me | CH₂Ph | G3 |
| Q5 | Me | Ph | G3 |
| Q26 | Me | Ph | G3 |
| Q61 | Me | Ph | G3 |
| Q158 | Me | Ph | G3 |
| Q5 | Me | Ph—2-Cl | G3 |
| Q26 | Me | Ph—2-Cl | G3 |
| Q61 | Me | Ph—2-Me | G3 |
| Q158 | Me | Ph—2-Me | G3 |
| Q5 | Me | Cl | G3 |
| Q26 | Me | Cl | G3 |
| Q61 | Me | Cl | G3 |
| Q158 | Me | Cl | G3 |
| Q5 | Me | Br | G3 |
| Q26 | Me | Br | G3 |
| Q61 | Me | Br | G3 |
| Q158 | Me | Br | G3 |
| Q5 | Me | F | G3 |
| Q26 | Me | F | G3 |
| Q61 | Me | I | G3 |
| Q158 | Me | I | G3 |

TABLE 2-continued

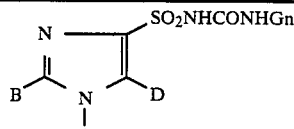

| A | B | D | Gn |
|---|---|---|---|
| Q1 | Me | Ph | G3 |
| Q2 | Me | Cl | G3 |
| Q4 | Me | CH$_2$CH$_2$Cl | G3 |
| Q7 | Me | Ph | G3 |
| Q9 | Me | Ph | G3 |
| Q10 | Me | Cl | G3 |
| Q19 | Me | Cl | G3 |
| Q23 | Me | Br | G3 |
| Q32 | Me | CH$_2$Cl | G3 |
| Q41 | Me | CH$_2$CH$_2$Cl | G3 |
| Q45 | Me | CF$_3$ | G3 |
| Q50 | Me | Cl | G3 |
| Q69 | Me | Cl | G3 |
| Q79 | Me | Br | G3 |
| Q83 | Me | Ph | G3 |
| Q96 | Me | CF$_3$ | G3 |
| Q124 | Me | CF$_3$ | G3 |
| Q131 | Me | CH$_2$CH$_2$Cl | G3 |
| Q132 | Me | Ph | G3 |
| Q135 | Me | Br | G3 |
| Q138 | Me | Ph | G3 |
| Q142 | Me | Ph | G3 |
| Q157 | Me | Cl | G3 |
| Q159 | Me | Br | G3 |
| Q177 | Me | CF$_3$ | G3 |
| Q180 | Me | CH$_2$CH$_2$Cl | G3 |
| Q184 | Me | Ph | G3 |
| Q5 | Me | NO$_2$ | G3 |
| Q26 | Me | NO$_2$ | G3 |
| Q61 | Me | NO$_2$ | G3 |
| Q158 | Me | NO$_2$ | G3 |
| Q5 | Me | NH$_2$ | G3 |
| Q26 | Me | NH$_2$ | G3 |
| Q61 | Me | NH$_2$ | G3 |
| Q158 | Me | NH$_2$ | G3 |
| Q5 | Me | NHMe | G3 |
| Q26 | Me | NHMe | G3 |
| Q61 | Me | NHMe | G3 |
| Q158 | Me | NHMe | G3 |
| Q5 | Me | NMe$_2$ | G3 |
| Q26 | Me | NMe$_2$ | G3 |
| Q61 | Me | NMe$_2$ | G3 |
| Q158 | Me | NMe$_2$ | G3 |
| Q5 | Me | NMeEt | G3 |
| Q26 | Me | NMeEt | G3 |
| Q5 | Me | NHCOMe | G3 |
| Q26 | Me | NHCOMe | G3 |
| Q61 | Me | NHCOMe | G3 |
| Q158 | Me | NHCOMe | G3 |
| Q5 | Me | NHCOEt | G3 |
| Q26 | Me | NHCOEt | G3 |
| Q61 | Me | NHSO$_2$Me | G3 |
| Q158 | Me | NHSO$_2$Me | G3 |
| Q5 | Me | OMe | G3 |
| Q26 | Me | OMe | G3 |
| Q61 | Me | OMe | G3 |
| Q158 | Me | OMe | G3 |
| Q5 | Me | OEt | G3 |
| Q26 | Me | OEt | G3 |
| Q61 | Me | CH$_2$OMe | G3 |
| Q158 | Me | CH$_2$OMe | G3 |
| Q1 | Me | NO$_2$ | G3 |
| Q2 | Me | NHCOMe | G3 |
| Q4 | Me | NHCOEt | G3 |
| Q7 | Me | NHMe | G3 |
| Q9 | Me | NO$_2$ | G3 |
| Q10 | Me | NH$_2$ | G3 |
| Q19 | Me | NHCOMe | G3 |
| Q23 | Me | OMe | G3 |
| Q32 | Me | NHCOMe | G3 |
| Q41 | Me | NHCOEt | G3 |
| Q45 | Me | CH$_2$OMe | G3 |
| Q50 | Me | OMe | G3 |

TABLE 2-continued

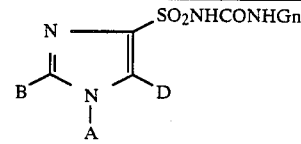

| A | B | D | Gn |
|---|---|---|---|
| Q69 | Me | OEt | G3 |
| Q79 | Me | NO$_2$ | G3 |
| Q83 | Me | NH$_2$ | G3 |
| Q96 | Me | NMe$_2$ | G3 |
| Q124 | Me | NMeEt | G3 |
| Q131 | Me | NHCOMe | G3 |
| Q132 | Me | NHCOEt | G3 |
| Q135 | Me | NO$_2$ | G3 |
| Q138 | Me | OMe | G3 |
| Q142 | Me | OEt | G3 |
| Q157 | Me | NO$_2$ | G3 |
| Q159 | Me | NH$_2$ | G3 |
| Q177 | Me | OMe | G3 |
| Q180 | Me | NHCOMe | G3 |
| Q184 | Me | NO$_2$ | G3 |
| Q26 | Me | SMe | G3 |
| Q61 | Me | SMe | G3 |
| Q5 | Me | SO$_2$Me | G3 |
| Q26 | Me | SO$_2$Me | G3 |
| Q61 | Me | SO$_2$Me | G3 |
| Q158 | Me | SO$_2$Me | G3 |
| Q5 | Me | SO$_2$Ph | G3 |
| Q26 | Me | SO$_2$Ph | G3 |
| Q61 | Me | SO$_2$Ph | G3 |
| Q158 | Me | SO$_2$Ph | G3 |
| Q5 | Me | SO$_2$OMe | G3 |
| Q26 | Me | SO$_2$OMe | G3 |
| Q61 | Me | SO$_2$NH$_2$ | G3 |
| Q158 | Me | SO$_2$NH$_2$ | G3 |
| Q5 | Me | SO$_2$NHMe | G3 |
| Q26 | Me | SO$_2$NHMe | G3 |
| Q61 | Me | SO$_2$NHMe | G3 |
| Q158 | Me | SO$_2$NHMe | G3 |
| Q5 | Me | SO$_2$NMe$_2$ | G3 |
| Q26 | Me | SO$_2$NMe$_2$ | G3 |
| Q61 | Me | SO$_2$NMe$_2$ | G3 |
| Q158 | Me | SO$_2$NMe$_2$ | G3 |
| Q1 | Me | SO$_2$Ph | G3 |
| Q2 | Me | SO$_2$OMe | G3 |
| Q4 | Me | SO$_2$NHMe | G3 |
| Q7 | Me | SO$_2$NMe$_2$ | G3 |
| Q9 | Me | SO$_2$Me | G3 |
| Q10 | Me | SO$_2$Me | G3 |
| Q19 | Me | SMe | G3 |
| Q23 | Me | SO$_2$Me | G3 |
| Q32 | Me | SO$_2$OMe | G3 |
| Q41 | Me | SO$_2$NMe$_2$ | G3 |
| Q45 | Me | SO$_2$NHMe | G3 |
| Q50 | Me | SO$_2$NMe$_2$ | G3 |
| Q69 | Me | SO$_2$Me | G3 |
| Q79 | Me | SO$_2$Me | G3 |
| Q83 | Me | SO$_2$Ph | G3 |
| Q96 | Me | SO$_2$OMe | G3 |
| Q124 | Me | SO$_2$NMe$_2$ | G3 |
| Q131 | Me | SO$_2$NHMe | G3 |
| Q132 | Me | SO$_2$NMe$_2$ | G3 |
| Q135 | Me | SO$_2$Ph | G3 |
| Q138 | Me | SO$_2$Ph | G3 |
| Q142 | Me | SO$_2$Me | G3 |
| Q157 | Me | SO$_2$Me | G3 |
| Q159 | Me | SO$_2$NHMe | G3 |
| Q177 | Me | SO$_2$NMe$_2$ | G3 |
| Q180 | Me | SO$_2$NMe$_2$ | G3 |
| Q184 | Me | SO$_2$Me$_2$ | G3 |
| Q5 | Et | COOMe | G3 |
| Q26 | Et | COOMe | G3 |
| Q61 | Et | COOMe | G3 |
| Q142 | Et | COOMe | G3 |
| Q158 | Et | COOMe | G3 |
| Q159 | Et | COOMe | G3 |
| Q4 | Et | COOEt | G3 |
| Q5 | Et | COOEt | G3 |
| Q9 | Et | COOEt | G3 |

TABLE 2-continued

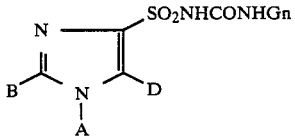

| A | B | D | Gn |
|---|---|---|---|
| Q26 | Et | COOEt | G3 |
| Q32 | Et | COOEt | G3 |
| Q61 | Et | COOEt | G3 |
| Q69 | Et | COOEt | G3 |
| Q96 | Et | COOEt | G3 |
| Q158 | Et | COOEt | G3 |
| Q61 | Et | COOPr—i | G3 |
| Q158 | Et | COOPr—i | G3 |
| Q5 | Et | COOCH$_2$CH$_2$Cl | G3 |
| Q26 | Et | COOCH$_2$CH$_2$Cl | G3 |
| Q5 | Et | COOCH$_2$CH=CH$_2$ | G3 |
| Q158 | Et | COOCH$_2$CH=CH$_2$ | G3 |
| Q5 | Et | COOCH$_2$C≡CH | G3 |
| Q26 | Et | COOCH$_2$C≡CH | G3 |
| Q5 | Et | CONHMe | G3 |
| Q26 | Et | CONMe$_2$ | G3 |
| Q1 | Et | COOPr—i | G3 |
| Q4 | Et | COOCH$_2$CH$_2$Cl | G3 |
| Q69 | Et | COOCH$_2$CH$_2$Cl | G3 |
| Q79 | Et | COOCH$_2$CH=CH$_2$ | G3 |
| Q83 | Et | COOPr—i | G3 |
| Q96 | Et | COOCH$_2$CH$_2$Cl | G3 |
| Q131 | Et | COOCH$_2$CH$_2$Cl | G3 |
| Q157 | Et | COOPr—i | G3 |
| Q159 | Et | COOCH$_2$CH=CH$_2$ | G3 |
| Q184 | Et | COOCH$_2$CH$_2$Cl | G3 |
| Q5 | Et | COMe | G3 |
| Q26 | Et | COMe | G3 |
| Q158 | Et | COEt | G3 |
| Q5 | Et | COPr—i | G3 |
| Q26 | Et | CN | G3 |
| Q61 | Et | H | G3 |
| Q26 | Et | Me | G3 |
| Q158 | Et | Et | G3 |
| Q5 | Et | Pr—i | G3 |
| Q1 | Et | COMe | G3 |
| Q2 | Et | COEt | G3 |
| Q9 | Et | CN | G3 |
| Q23 | Et | COMe | G3 |
| Q96 | Et | COMe | G3 |
| Q124 | Et | COEt | G3 |
| Q135 | Et | COPr—i | G3 |
| Q138 | Et | CN | G3 |
| Q5 | Et | CH$_2$CH$_2$Cl | G3 |
| Q26 | Et | CH$_2$CH$_2$Cl | G3 |
| Q158 | Et | CF$_3$ | G3 |
| Q5 | Et | Ph | G3 |
| Q26 | Et | Ph | G3 |
| Q158 | Et | Ph—2-Me | G3 |
| Q26 | Et | Cl | G3 |
| Q61 | Et | Cl | G3 |
| Q5 | Et | Br | G3 |
| Q1 | Et | Ph | G3 |
| Q2 | Et | Cl | G3 |
| Q9 | Et | Ph | G3 |
| Q5 | Et | NO$_2$ | G3 |
| Q5 | Et | NH$_2$ | G3 |
| Q5 | Et | NHMe | G3 |
| Q26 | Et | NMe$_2$ | G3 |
| Q61 | Et | NHCOMe | G3 |
| Q158 | Et | NHSO$_2$Me | G3 |
| Q2 | Et | NHCOMe | G3 |
| Q23 | Et | OMe | G3 |
| Q32 | Et | NHCOMe | G3 |
| Q96 | Et | NMe$_2$ | G3 |
| Q26 | Et | SO$_2$Me | G3 |
| Q61 | Et | SO$_2$Me | G3 |
| Q5 | Et | SO$_2$Ph | G3 |
| Q26 | Et | SO$_2$OMe | G3 |
| Q61 | Et | SO$_2$NH$_2$ | G3 |
| Q5 | Et | SO$_2$NHMe | G3 |
| Q26 | Et | SO$_2$NMe$_2$ | G3 |
| Q4 | Et | SO$_2$NHMe | G3 |
| Q7 | Et | SO$_2$NMe$_2$ | G3 |
| Q9 | Et | SO$_2$Me | G3 |
| Q142 | Et | SO$_2$Me | G3 |
| Q159 | Et | SO$_2$NMe$_2$ | G3 |
| Q5 | Cl | COOMe | G3 |
| Q26 | Cl | COOMe | G3 |
| Q61 | Cl | COOMe | G3 |
| Q5 | Cl | COOEt | G3 |
| Q26 | Cl | COOEt | G3 |
| Q61 | Cl | COOEt | G3 |
| Q96 | Cl | COOEt | G3 |
| Q158 | Cl | COOEt | G3 |
| Q61 | Cl | COOPr—i | G3 |
| Q5 | Cl | COMe | G3 |
| Q158 | Cl | COEt | G3 |
| Q5 | Cl | COPr—i | G3 |
| Q26 | Cl | CN | G3 |
| Q61 | Cl | H | G3 |
| Q26 | Cl | Me | G3 |
| Q158 | Cl | Et | G3 |
| Q5 | Cl | Pr—i | G3 |
| Q1 | Cl | COMe | G3 |
| Q26 | Cl | CH$_2$CH$_2$Cl | G3 |
| Q158 | Cl | CF$_3$ | G3 |
| Q5 | Cl | Ph | G3 |
| Q26 | Cl | Cl | G3 |
| Q5 | Cl | Br | G3 |
| Q2 | Cl | Cl | G3 |
| Q9 | Cl | Ph | G3 |
| Q5 | Cl | NO$_2$ | G3 |
| Q5 | Cl | NH$_2$ | G3 |
| Q5 | Cl | NHMe | G3 |
| Q26 | Cl | NMe$_2$ | G3 |
| Q61 | Cl | NHCOMe | G3 |
| Q158 | Cl | NHSO$_2$Me | G3 |
| Q2 | Cl | NHCOMe | G3 |
| Q26 | Cl | SO$_2$Me | G3 |
| Q61 | Cl | SO$_2$Me | G3 |
| Q5 | Cl | SO$_2$Ph | G3 |
| Q61 | Cl | SO$_2$NH$_2$ | G3 |
| Q5 | Cl | SO$_2$NHMe | G3 |
| Q26 | Cl | SO$_2$NMe$_2$ | G3 |
| Q5 | Br | COOMe | G3 |
| Q26 | Br | COOMe | G3 |
| Q61 | Br | COOMe | G3 |
| Q5 | Br | COOEt | G3 |
| Q26 | Br | COOEt | G3 |
| Q61 | Br | COOEt | G3 |
| Q61 | Br | COOPr—i | G3 |
| Q5 | Br | COMe | G3 |
| Q158 | Br | COEt | G3 |
| Q26 | Br | CN | G3 |
| Q26 | Br | Me | G3 |
| Q158 | Br | Et | G3 |
| Q26 | Br | CH$_2$CH$_2$Cl | G3 |
| Q158 | Br | CF$_3$ | G3 |
| Q5 | Br | Ph | G3 |
| Q26 | Br | Cl | G3 |
| Q5 | Br | Br | G3 |
| Q5 | Br | NO$_2$ | G3 |
| Q5 | Br | NH$_2$ | G3 |
| Q26 | Br | NMe$_2$ | G3 |
| Q61 | Br | NHCOMe | G3 |
| Q61 | Br | SO$_2$Me | G3 |
| Q5 | Br | SO$_2$Ph | G3 |
| Q61 | Br | SO$_2$NH$_2$ | G3 |
| Q26 | Br | SO$_2$NMe$_2$ | G3 |
| Q5 | SMe | COOMe | G3 |
| Q26 | SMe | COOMe | G3 |
| Q61 | SMe | COOMe | G3 |
| Q5 | SMe | COOEt | G3 |
| Q26 | SMe | COOEt | G3 |
| Q61 | SMe | COOEt | G3 |

TABLE 2-continued

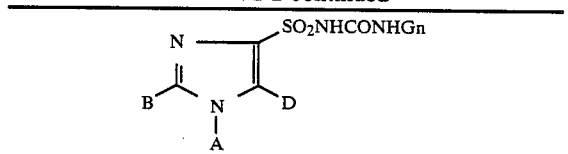

| A | B | D | Gn |
|---|---|---|---|
| Q61 | SMe | COOPr—i | G3 |
| Q5 | SMe | COMe | G3 |
| Q158 | SMe | COEt | G3 |
| Q26 | SMe | CN | G3 |
| Q26 | SMe | Me | G3 |
| Q158 | SMe | Et | G3 |
| Q26 | SMe | CH$_2$CH$_2$Cl | G3 |
| Q158 | SMe | CF$_3$ | G3 |
| Q5 | SMe | Ph | G3 |
| Q26 | SMe | Cl | G3 |
| Q5 | SMe | Br | G3 |
| Q5 | SMe | NO$_2$ | G3 |
| Q5 | SMe | NH$_2$ | G3 |
| Q26 | SMe | NMe$_2$ | G3 |
| Q61 | SMe | NHCOMe | G3 |
| Q61 | SMe | SO$_2$Me | G3 |
| Q5 | SMe | SO$_2$Ph | G3 |
| Q61 | SMe | SO$_2$NH$_2$ | G3 |
| Q26 | SMe | SO$_2$NMe$_2$ | G3 |
| Q5 | SO$_2$Me | COOMe | G3 |
| Q26 | SO$_2$Me | COOMe | G3 |
| Q61 | SO$_2$Me | COOMe | G3 |
| Q5 | SO$_2$Me | COOEt | G3 |
| Q26 | SO$_2$Me | COOEt | G3 |
| Q61 | SO$_2$Me | COOEt | G3 |
| Q96 | SO$_2$Me | COOEt | G3 |
| Q158 | SO$_2$Me | COOEt | G3 |
| Q61 | SO$_2$Me | COOPr—i | G3 |
| Q5 | SO$_2$Me | COMe | G3 |
| Q158 | SO$_2$Me | COEt | G3 |
| Q5 | SO$_2$Me | COPr—i | G3 |
| Q26 | SO$_2$Me | CN | G3 |
| Q61 | SO$_2$Me | H | G3 |
| Q26 | SO$_2$Me | Me | G3 |
| Q158 | SO$_2$Me | Et | G3 |
| Q5 | SO$_2$Me | Pr—i | G3 |
| Q1 | SO$_2$Me | COMe | G3 |
| Q26 | SO$_2$Me | CH$_2$CH$_2$Cl | G3 |
| Q158 | SO$_2$Me | CF$_3$ | G3 |
| Q5 | SO$_2$Me | Ph | G3 |
| Q26 | SO$_2$Me | Cl | G3 |
| Q5 | SO$_2$Me | Br | G3 |
| Q2 | SO$_2$Me | Cl | G3 |
| Q9 | SO$_2$Me | Ph | G3 |
| Q5 | SO$_2$Me | NO$_2$ | G3 |
| Q5 | SO$_2$Me | NH$_2$ | G3 |
| Q5 | SO$_2$Me | NHMe | G3 |
| Q26 | SO$_2$Me | NMe$_2$ | G3 |
| Q61 | SO$_2$Me | NHCOMe | G3 |
| Q158 | SO$_2$Me | NHSO$_2$Me | G3 |
| Q2 | SO$_2$Me | NHCOMe | G3 |
| Q26 | SO$_2$Me | SO$_2$Me | G3 |
| Q61 | SO$_2$Me | SO$_2$Me | G3 |
| Q5 | SO$_2$Me | SO$_2$Ph | G3 |
| Q61 | SO$_2$Me | SO$_2$NH$_2$ | G3 |
| Q5 | SO$_2$Me | SO$_2$NHMe | G3 |
| Q26 | SO$_2$Me | SO$_2$NMe$_2$ | G3 |
| Q5 | Ph | COOMe | G3 |
| Q26 | Ph | COOMe | G3 |
| Q61 | Ph | COOMe | G3 |
| Q5 | Ph | COOEt | G3 |
| Q26 | Ph | COOEt | G3 |
| Q61 | Ph | COOEt | G3 |
| Q61 | Ph | COOPr—i | G3 |
| Q5 | Ph | COMe | G3 |
| Q158 | Ph | COEt | G3 |
| Q26 | Ph | CN | G3 |
| Q26 | Ph | Me | G3 |
| Q158 | Ph | Et | G3 |
| Q26 | Ph | CH$_2$CH$_2$Cl | G3 |
| Q158 | Ph | CF$_3$ | G3 |
| Q5 | Ph | Ph | G3 |
| Q26 | Ph | Cl | G3 |

TABLE 2-continued

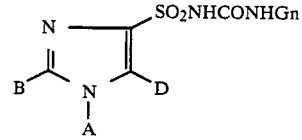

| A | B | D | Gn |
|---|---|---|---|
| Q5 | Ph | Br | G3 |
| Q5 | Ph | NO$_2$ | G3 |
| Q5 | Ph | NH$_2$ | G3 |
| Q26 | Ph | NMe$_2$ | G3 |
| Q61 | Ph | NHCOMe | G3 |
| Q61 | Ph | SO$_2$Me | G3 |
| Q5 | Ph | SO$_2$Ph | G3 |
| Q61 | Ph | SO$_2$NH$_2$ | G3 |
| Q26 | Ph | SO$_2$NMe$_2$ | G3 |
| Q201 | H | COOMe | Ga |
| CH$_2$ - Q201 | H | COOMe | Gb |
| CHMe - Q201 | H | COOMe | Gb |
| Q202 | H | COOMe | Gb |
| CH$_2$ - Q202 | H | COOMe | Gb |
| Q203 | H | COOMe | Gb |
| Q204 | H | COOMe | Gb |
| Q205 | H | COOMe | Gb |
| CH$_2$ - Q205 | H | COOMe | Gc |
| Q206 | H | COOMe | G$_3$ |
| Q207 | H | COOMe | Gc |
| Q208 | H | COOMe | G$_3$ |
| Q209 | H | COOMe | Gc |
| CH$_2$ - Q209 | H | COOMe | Gc |
| Q210 | H | COOMe | Gc |
| CH$_2$ - Q210 | H | COOMe | G$_3$ |
| Q211 | H | COOMe | G$_3$ |
| Q212 | H | COOMe | Gc |
| Q213 | H | COOMe | Gc |
| Q214 | H | COOMe | Gc |
| Q215 | H | COOMe | G$_1$ |
| Q216 | H | COOMe | Gc |
| Q217 | H | COOMe | Gc |
| Q218 | H | COOMe | G$_3$ |
| Q219 | H | COOMe | Gc |
| Q220 | H | COOMe | Gc |
| Q221 | H | COOMe | G$_2$ |
| Q222 | H | COOMe | Gb |
| CH$_2$ - Q222 | H | COOMe | Gc |
| Q223 | H | COOMe | Gc |
| Q224 | H | COOMe | G$_3$ |
| Q225 | H | COOMe | Gb |
| CH$_2$ - Q225 | H | COOMe | Gc |
| Q226 | H | COOMe | G$_3$ |
| Q227 | H | COOMe | Gc |
| Q228 | H | COOMe | Gc |
| Q229 | H | COOMe | Gb |
| CH$_2$ - Q229 | H | COOMe | Gc |
| Q230 | H | COOMe | Gc |
| Q231 | H | COOMe | Gc |
| Q232 | H | COOMe | G$_3$ |
| Q233 | H | COOMe | Gc |
| Q234 | H | COOMe | Gc |
| Q235 | H | COOMe | Gc |
| Q236 | H | COOMe | G$_3$ |
| Q237 | H | COOMe | Gc |
| Q238 | H | COOMe | Gc |
| Q239 | H | COOMe | G$_2$ |
| Q240 | H | COOMe | Gc |
| Q241 | H | COOMe | Gc |
| Q242 | H | COOMe | Gc |
| Q243 | H | COOMe | G$_1$ |
| Q244 | H | COOMe | Gc |
| Q245 | H | COOMe | Gc |
| Q246 | H | COOMe | Gb |
| CH$_2$ - Q246 | H | COOMe | Gc |
| Q247 | H | COOMe | G$_3$ |
| Q248 | H | COOMe | Gc |
| Q249 | H | COOMe | Gc |
| Q250 | H | COOMe | Gc |
| CH$_2$ - Q250 | H | COOMe | G$_3$ |
| Q251 | H | COOMe | Gc |
| Q252 | H | COOMe | Gc |
| Q253 | H | COOMe | Gc |

TABLE 2-continued

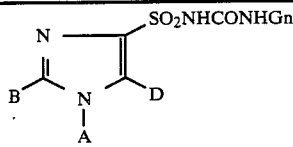

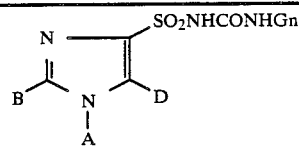

| A | B | D | Gn |
|---|---|---|---|
| Q254 | H | COOMe | G1 |
| Q255 | H | COOMe | Gc |
| Q256 | H | COOMe | Gc |
| Q257 | H | COOMe | G3 |
| Q258 | H | COOMe | Gc |
| Q259 | H | COOMe | Gc |
| CH2 - Q259 | H | COOMe | Gc |
| Q260 | H | COOMe | Gc |
| CH2 - Q260 | H | COOMe | Gc |
| Q261 | H | COOMe | G1 |
| Q262 | H | COOMe | Gc |
| Q263 | H | COOMe | Gc |
| Q264 | H | COOMe | G2 |
| Q201 | H | COOEt | Ga |
| CH2 - Q201 | H | COOEt | Gb |
| CHMe - Q201 | H | COOEt | Gb |
| Q202 | H | COOEt | Gb |
| CH2 - Q202 | H | COOEt | Gb |
| Q203 | H | COOEt | Gb |
| Q204 | H | COOEt | Gb |
| Q205 | H | COOEt | Gb |
| CH2 - Q205 | H | COOEt | Gc |
| Q206 | H | COOEt | G3 |
| Q207 | H | COOEt | Gc |
| Q208 | H | COOEt | G3 |
| Q209 | H | COOEt | Gc |
| CH2 - Q209 | H | COOEt | Gc |
| Q210 | H | COOEt | Gc |
| CH2 - 210 | H | COOEt | G3 |
| Q211 | H | COOEt | Gc |
| Q212 | H | COOEt | Gc |
| Q213 | H | COOEt | Gc |
| Q214 | H | COOEt | G1 |
| Q215 | H | COOEt | Gc |
| Q216 | H | COOEt | Gc |
| Q217 | H | COOEt | G2 |
| Q218 | H | COOEt | Gc |
| Q219 | H | COOEt | Gc |
| Q220 | H | COOEt | G3 |
| Q221 | H | COOEt | Gc |
| Q222 | H | COOEt | Gb |
| CH2 - Q222 | H | COOEt | Gc |
| Q223 | H | COOEt | Gc |
| Q224 | H | COOEt | Gc |
| Q225 | H | COOEt | Gb |
| CH2 - Q225 | H | COOEt | Gc |
| Q226 | H | COOEt | G3 |
| Q227 | H | COOEt | Gc |
| Q228 | H | COOEt | Gc |
| Q229 | H | COOEt | Gb |
| CH2 - Q229 | H | COOEt | Gc |
| Q230 | H | COOEt | Gc |
| Q231 | H | COOEt | Gc |
| Q232 | H | COOEt | G3 |
| Q233 | H | COOEt | Gc |
| Q234 | H | COOEt | Gc |
| CH2 - Q234 | H | COOEt | Gc |
| Q235 | H | COOEt | Gc |
| Q236 | H | COOEt | G3 |
| Q237 | H | COOEt | Gc |
| Q238 | H | COOEt | Gc |
| Q239 | H | COOEt | Gc |
| Q240 | H | COOEt | G1 |
| Q241 | H | COOEt | Gc |
| Q242 | H | COOEt | Gc |
| Q243 | H | COOEt | Gc |
| Q244 | H | COOEt | G2 |
| Q245 | H | COOEt | Gc |
| Q246 | H | COOEt | Gb |
| CH2 - Q246 | H | COOEt | Gc |
| Q247 | H | COOEt | Gc |
| Q248 | H | COOEt | Gc |
| Q249 | H | COOEt | G3 |
| Q250 | H | COOEt | Gc |
| CH2 - Q250 | H | COOEt | Gc |
| Q251 | H | COOEt | Gc |
| Q252 | H | COOEt | G3 |
| Q253 | H | COOEt | Gc |
| Q254 | H | COOEt | Gc |
| Q255 | H | COOEt | Gc |
| Q256 | H | COOEt | Gc |
| Q257 | H | COOEt | Gc |
| Q258 | H | COOEt | G1 |
| Q259 | H | COOEt | Gc |
| CH2 - Q259 | H | COOEt | Gc |
| Q260 | H | COOEt | Gc |
| CH2 - Q260 | H | COOEt | Gc |
| Q261 | H | COOEt | G3 |
| Q262 | H | COOEt | Gc |
| Q263 | H | COOEt | Gc |
| Q264 | H | COOEt | G3 |
| Q201 | H | COOH | Gc |
| Q202 | H | COOH | Gc |
| Q222 | H | COOH | Gc |
| Q225 | H | COOH | G3 |
| Q229 | H | COOH | Gc |
| Q246 | H | COOH | G3 |
| Q201 | H | COOPr—i | Gc |
| Q202 | H | COOPr—i | G3 |
| Q205 | H | COOPr—i | Gc |
| Q209 | H | COOPr—i | Gc |
| Q222 | H | COOPr—i | Gc |
| Q225 | H | COOPr—i | Gc |
| Q229 | H | COOPr—i | G3 |
| Q246 | H | COOPr—i | Gc |
| Q201 | H | COOCH2CH2Cl | Gc |
| Q202 | H | COOCH2CH2Cl | G3 |
| Q205 | H | COOCH2CH2Cl | Gc |
| Q209 | H | COOCH2CH2Cl | Gc |
| Q222 | H | COOCH2CH2Cl | G3 |
| Q225 | H | COOCH2CH2Cl | Gc |
| Q229 | H | COOCH2CH2Cl | Gc |
| Q246 | H | COOCH2CH2Cl | G1 |
| Q201 | H | COOCH2CH=CH2 | Gc |
| Q202 | H | COOCH2CH=CH2 | Gc |
| Q205 | H | COOCH2CH=CH2 | G3 |
| Q209 | H | COOCH2CH=CH2 | Gc |
| Q222 | H | COOCH2CH=CH2 | Gc |
| Q225 | H | COOCH2CH=CH2 | Gc |
| Q229 | H | COOCH2CH=CH2 | G3 |
| Q246 | H | COOCH2CH=CH2 | Gc |
| Q201 | H | COOCH2C≡CH | Gc |
| Q202 | H | COOCH2C≡CH | G3 |
| Q205 | H | COOCH2C≡CH | Gc |
| Q209 | H | COOCH2C≡CH | Gc |
| Q222 | H | COOCH2C≡CH | Gc |
| Q225 | H | COOCH2C≡CH | G3 |
| Q229 | H | COOCH2C≡CH | Gc |
| Q246 | H | COOCH2C≡CH | G3 |
| Q201 | H | CONHMe | Gc |
| Q202 | H | CONHMe | G3 |
| Q205 | H | CONHMe | Gc |
| Q209 | H | CONHMe | Gc |
| Q222 | H | CONHMe | G3 |
| Q225 | H | CONHMe | Gc |
| Q229 | H | CONHMe | Gc |
| Q246 | H | CONHMe | G3 |
| Q201 | H | CONMe2 | Gc |
| Q202 | H | CONMe2 | G3 |
| Q205 | H | CONMe2 | Gc |
| Q209 | H | CONMe2 | Gc |
| Q222 | H | CONMe2 | Gc |
| Q225 | H | CONMe2 | G3 |
| Q229 | H | CONMe2 | Gc |
| Q246 | H | CONMe2 | G2 |
| Q201 | H | COMe | Gc |

TABLE 2-continued

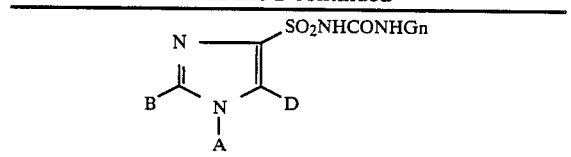

| A | B | D | Gn |
|---|---|---|---|
| CH₂ - Q201 | H | COMe | G₃ |
| Q202 | H | COMe | G₃ |
| Q205 | H | COMe | Gc |
| Q207 | H | COMe | G₃ |
| Q222 | H | COMe | Gc |
| Q225 | H | COMe | Gc |
| Q229 | H | COMe | Gc |
| Q230 | H | COMe | G₂ |
| Q231 | H | COMe | G₃ |
| Q237 | H | COMe | Gc |
| Q246 | H | COMe | Gc |
| Q247 | H | COMe | G₃ |
| Q250 | H | COMe | Gc |
| Q259 | H | COMe | Gc |
| Q260 | H | COMe | Gc |
| Q263 | H | COMe | G₃ |
| Q201 | H | COEt | Gc |
| Q202 | H | COEt | G₃ |
| Q205 | H | COEt | Gc |
| Q209 | H | COEt | Gc |
| Q222 | H | COEt | Gc |
| Q225 | H | COEt | G₃ |
| Q229 | H | COEt | Gc |
| Q246 | H | COEt | G₃ |
| Q201 | H | COPr—i | Gc |
| Q202 | H | COPr—i | G₃ |
| Q205 | H | COPr—i | Gc |
| Q209 | H | COPr—i | Gc |
| Q222 | H | COPr—i | Gc |
| Q225 | H | COPr—i | G₃ |
| Q229 | H | COPr—i | Gc |
| Q246 | H | COPr—i | Gc |
| Q201 | H | COPh | Gc |
| Q202 | H | COPh | G₃ |
| Q205 | H | COPh | Gc |
| Q209 | H | COPh | Gc |
| Q222 | H | COPh | G₃ |
| Q225 | H | COPh | Gc |
| Q229 | H | COPh | Gc |
| Q246 | H | COPh | G₃ |
| Q201 | H | CN | Gc |
| CH₂ - Q201 | H | CN | G₃ |
| Q202 | H | CN | Gc |
| Q205 | H | CN | Gc |
| Q209 | H | CN | Gc |
| Q222 | H | CN | Gc |
| Q225 | H | CN | Gc |
| Q229 | H | CN | Gc |
| Q246 | H | CN | G₃ |
| Q201 | H | H | Gc |
| Q202 | H | H | G₃ |
| Q205 | H | H | Gc |
| Q207 | H | H | Gc |
| Q222 | H | H | Gc |
| Q225 | H | H | G₃ |
| Q229 | H | H | Gc |
| Q230 | H | H | Gc |
| Q231 | H | H | G₃ |
| Q237 | H | H | Gc |
| Q246 | H | H | Gc |
| Q247 | H | H | G₃ |
| Q250 | H | H | Gc |
| Q259 | H | H | G₃ |
| Q260 | H | H | Gc |
| Q263 | H | H | G₃ |
| Q201 | H | Me | Gc |
| Q202 | H | Me | G₃ |
| Q205 | H | Me | Gc |
| Q207 | H | Me | G₃ |
| Q222 | H | Me | Gc |
| Q225 | H | Me | Gc |
| Q229 | H | Me | Gc |
| Q230 | H | Me | G₃ |
| Q231 | H | Me | Gc |
| Q237 | H | Me | Gc |
| Q246 | H | Me | Gc |
| Q247 | H | Me | G₃ |
| Q250 | H | Me | Gc |
| Q259 | H | Me | Gc |
| Q260 | H | Me | Gc |
| Q263 | H | Me | G₃ |
| Q201 | H | Et | Gc |
| Q202 | H | Et | G₁ |
| Q205 | H | Et | Gc |
| Q209 | H | Et | Gc |
| Q222 | H | Et | G₃ |
| Q225 | H | Et | Gc |
| Q229 | H | Et | Gc |
| Q246 | H | Et | G₂ |
| Q201 | H | Pr—i | Gc |
| Q205 | H | Pr—i | Gc |
| Q209 | H | Pr—i | Gc |
| Q222 | H | Pr—i | G₃ |
| Q229 | H | Pr—i | Gc |
| Q201 | H | CH=CH₂ | Gc |
| Q205 | H | CH=CH₂ | G₃ |
| Q209 | H | CH=CH₂ | Gc |
| Q229 | H | CH=CH₂ | G₃ |
| Q201 | H | CH=CHMe | Gc |
| Q205 | H | CH=CHMe | Gc |
| Q201 | H | CH₂CH=CH₂ | Gc |
| Q205 | H | CH₂CH=CH₂ | G₃ |
| Q209 | H | CH₂CH=CH₂ | Gc |
| Q229 | H | CH₂CH=CH₂ | Gc |
| Q201 | H | CH₂Cl | Gc |
| Q205 | H | CH₂Cl | G₃ |
| Q209 | H | CH₂Cl | Gc |
| Q229 | H | CH₂Cl | Gc |
| Q201 | H | CH₂CH₂Cl | Gc |
| Q205 | H | CH₂CH₂Cl | G₃ |
| Q209 | H | CH₂CH₂Cl | Gc |
| Q229 | H | CH₂CH₂Cl | G₂ |
| Q201 | H | CF₃ | Gc |
| Q205 | H | CF₃ | G₃ |
| Q209 | H | CF₃ | Gc |
| Q222 | H | CF₃ | Gc |
| Q225 | H | CF₃ | G₃ |
| Q229 | H | CF₃ | G₁ |
| Q201 | H | CF=CFCl | Gc |
| Q205 | H | CF=CFCl | Gc |
| Q229 | H | CF=CFCl | G₃ |
| Q201 | H | CH₂Ph | Gc |
| Q205 | H | CH₂Ph | Gc |
| Q209 | H | CH₂Ph | G₃ |
| Q201 | H | Ph | Gc |
| Q202 | H | Ph | G₁ |
| Q205 | H | Ph | Gc |
| Q209 | H | Ph | Gc |
| Q222 | H | Ph | G₃ |
| Q225 | H | Ph | Gc |
| Q229 | H | Ph | Gc |
| Q246 | H | Ph | G₂ |
| Q201 | H | Ph—2-Cl | Gc |
| Q205 | H | Ph—2-Cl | G₁ |
| Q209 | H | Ph—2-Cl | Gc |
| Q201 | H | Ph—2-Me | Gc |
| Q205 | H | Ph—2-Me | G₃ |
| Q209 | H | Ph—2-Me | Gc |
| Q225 | H | Ph—2-Me | Gc |
| Q229 | H | Ph—2-Me | G₃ |
| Q201 | H | Cl | Gc |
| Q205 | H | Cl | Gc |
| Q207 | H | Cl | G₃ |
| Q222 | H | Cl | Gc |
| Q225 | H | Cl | Gc |
| Q229 | H | Cl | G₁ |

TABLE 2-continued $$\underset{A}{\overset{N}{\underset{B}{\bigwedge}}}\overset{SO_2NHCONHGn}{\underset{D}{\bigvee}}$$

| A | B | D | Gn |
|---|---|---|---|
| Q231 | H | Cl | Gc |
| Q246 | H | Cl | Gc |
| Q250 | H | Cl | $G_3$ |
| Q259 | H | Cl | Gc |
| Q260 | H | Cl | Gc |
| Q201 | H | Br | Gc |
| Q205 | H | Br | $G_3$ |
| Q207 | H | Br | Gc |
| Q229 | H | Br | Gc |
| Q231 | H | Br | $G_3$ |
| Q250 | H | Br | Gc |
| Q259 | H | Br | Gc |
| Q260 | H | Br | $G_3$ |
| Q201 | H | F | Gc |
| Q205 | H | F | $G_3$ |
| Q209 | H | F | Gc |
| Q229 | H | F | Gc |
| Q246 | H | F | $G_3$ |
| Q201 | H | I | Gc |
| Q205 | H | I | Gc |
| Q209 | H | I | Gc |
| Q222 | H | I | Gc |
| Q201 | H | $NO_2$ | Gc |
| $CH_2$ - Q201 | H | $NO_2$ | $G_3$ |
| Q202 | H | $NO_2$ | $G_3$ |
| Q205 | H | $NO_2$ | Gc |
| Q207 | H | $NO_2$ | Gc |
| Q222 | H | $NO_2$ | $G_3$ |
| Q225 | H | $NO_2$ | Gc |
| Q229 | H | $NO_2$ | Gc |
| Q230 | H | $NO_2$ | $G_1$ |
| Q231 | H | $NO_2$ | Gc |
| Q237 | H | $NO_2$ | Gc |
| Q246 | H | $NO_2$ | Gc |
| Q247 | H | $NO_2$ | $G_2$ |
| Q250 | H | $NO_2$ | Gc |
| Q259 | H | $NO_2$ | Gc |
| Q260 | H | $NO_2$ | $G_3$ |
| Q263 | H | $NO_2$ | Gc |
| Q201 | H | $NH_2$ | Gc |
| Q202 | H | $NH_2$ | $G_3$ |
| Q205 | H | $NH_2$ | Gc |
| Q209 | H | $NH_2$ | Gc |
| Q222 | H | $NH_2$ | $G_3$ |
| Q225 | H | $NH_2$ | Gc |
| Q229 | H | $NH_2$ | Gc |
| Q246 | H | $NH_2$ | $G_3$ |
| Q201 | H | NHMe | Gc |
| Q205 | H | NHMe | Gc |
| Q209 | H | NHMe | Gc |
| Q225 | H | NHMe | Gc |
| Q229 | H | NHMe | $G_3$ |
| Q201 | H | $NMe_2$ | Gc |
| Q205 | H | $NMe_2$ | Gc |
| Q209 | H | $NMe_2$ | Gc |
| Q222 | H | $NMe_2$ | $G_1$ |
| Q225 | H | $NMe_2$ | Gc |
| Q229 | H | $NMe_2$ | Gc |
| Q246 | H | $NMe_2$ | $G_3$ |
| Q201 | H | NMeEt | Gc |
| Q205 | H | NMeEt | Gc |
| Q209 | H | NMeEt | $G_3$ |
| Q222 | H | NMeEt | Gc |
| Q225 | H | NMeEt | Gc |
| Q229 | H | NMeEt | $G_2$ |
| Q201 | H | NHCOMe | Gc |
| Q202 | H | NHCOMe | $G_3$ |
| Q205 | H | NHCOMe | Gc |
| Q209 | H | NHCOMe | Gc |
| Q222 | H | NHCOMe | $G_3$ |
| Q225 | H | NHCOMe | Gc |
| Q229 | H | NHCOMe | Gc |
| Q246 | H | NHCOMe | $G_3$ |
| Q201 | H | NHCOEt | Gc |
| Q205 | H | NHCOEt | Gc |
| Q209 | H | NHCOEt | Gc |
| Q222 | H | NHCOEt | $G_1$ |
| Q225 | H | NHCOEt | Gc |
| Q229 | H | NHCOEt | $G_3$ |
| Q201 | H | $NHSO_2Me$ | Gc |
| Q205 | H | $NHSO_2Me$ | Gc |
| Q209 | H | $NHSO_2Me$ | Gc |
| Q225 | H | $NHSO_2Me$ | $G_3$ |
| Q229 | H | $NHSO_2Me$ | $G_3$ |
| Q201 | H | OMe | Gc |
| Q205 | H | OMe | Gc |
| Q209 | H | OMe | $G_3$ |
| Q222 | H | OMe | Gc |
| Q225 | H | OMe | Gc |
| Q229 | H | OMe | $G_2$ |
| Q246 | H | OMe | $G_1$ |
| Q201 | H | OEt | Gc |
| Q205 | H | OEt | Gc |
| Q209 | H | OEt | Gc |
| Q222 | H | OEt | $G_3$ |
| Q229 | H | OEt | Gc |
| Q201 | H | $CH_2OMe$ | Gc |
| Q205 | H | $CH_2OMe$ | Gc |
| Q209 | H | $CH_2OMe$ | $G_3$ |
| Q222 | H | $CH_2OMe$ | Gc |
| Q201 | H | SMe | Gc |
| Q205 | H | SMe | Gc |
| Q209 | H | SMe | Gc |
| Q222 | H | SMe | $G_1$ |
| Q225 | H | SMe | Gc |
| Q229 | H | SMe | $G_3$ |
| Q201 | H | $SO_2Me$ | Gc |
| $CH_2$ - Q201 | H | $SO_2Me$ | $G_3$ |
| Q202 | H | $SO_2Me$ | Gc |
| Q205 | H | $SO_2Me$ | Gc |
| Q209 | H | $SO_2Me$ | Gc |
| Q222 | H | $SO_2Me$ | $G_3$ |
| Q225 | H | $SO_2Me$ | Gc |
| Q229 | H | $SO_2Me$ | Gc |
| Q246 | H | $SO_2Me$ | $G_3$ |
| Q201 | H | $SO_2Ph$ | Gc |
| Q202 | H | $SO_2Ph$ | $G_1$ |
| Q205 | H | $SO_2Ph$ | Gc |
| Q209 | H | $SO_2Ph$ | Gc |
| Q222 | H | $SO_2Ph$ | Gc |
| Q225 | H | $SO_2Ph$ | $G_3$ |
| Q229 | H | $SO_2Ph$ | Gc |
| Q246 | H | $SO_2Ph$ | $G_1$ |
| Q201 | H | $SO_2OMe$ | Gc |
| Q205 | H | $SO_2OMe$ | Gc |
| Q209 | H | $SO_2OMe$ | Gc |
| Q222 | H | $SO_2OMe$ | Gc |
| Q229 | H | $SO_2OMe$ | $G_3$ |
| Q201 | H | $SO_2NH_2$ | Gc |
| Q205 | H | $SO_2NH_2$ | Gc |
| Q209 | H | $SO_2NH_2$ | $G_3$ |
| Q225 | H | $SO_2NH_2$ | Gc |
| Q229 | H | $SO_2NH_2$ | Gc |
| Q246 | H | $SO_2NH_2$ | $G_1$ |
| Q201 | H | $SO_2NHMe$ | Gc |
| Q205 | H | $SO_2NHMe$ | Gc |
| Q209 | H | $SO_2NHMe$ | $G_3$ |
| Q222 | H | $SO_2NHMe$ | Gc |
| Q225 | H | $SO_2NHMe$ | Gc |
| Q229 | H | $SO_2NHMe$ | Gc |
| Q246 | H | $SO_2NHMe$ | $G_2$ |
| Q201 | H | $SO_2NMe_2$ | Gc |
| Q202 | H | $SO_2NMe_2$ | $G_3$ |
| Q205 | H | $SO_2NMe_2$ | Gc |
| Q209 | H | $SO_2NMe_2$ | Gc |
| Q222 | H | $SO_2NMe_2$ | $G_2$ |

TABLE 2-continued

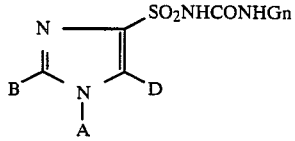

| A | B | D | Gn |
|---|---|---|---|
| Q225 | H | SO₂NMe₂ | Gc |
| Q229 | H | SO₂NMe₂ | Gc |
| Q246 | H | SO₂NMe₂ | G₃ |
| Q201 | Me | COOMe | Gc |
| CH₂-Q201 | Me | COOMe | G₃ |
| Q201 | Me | COOMe | G₁ |
| Q205 | Me | COOMe | Gc |
| Q207 | Me | COOMe | G₃ |
| Q209 | Me | COOMe | Gc |
| Q222 | Me | COOMe | Gc |
| Q225 | Me | COOMe | G₂ |
| Q229 | Me | COOMe | Gc |
| Q230 | Me | COOMe | Gc |
| Q231 | Me | COOMe | G₃ |
| Q237 | Me | COOMe | Gc |
| Q246 | Me | COOMe | Gc |
| Q247 | Me | COOMe | G₃ |
| Q250 | Me | COOMe | Gc |
| Q259 | Me | COOMe | G₁ |
| Q260 | Me | COOMe | Gc |
| Q263 | Me | COOMe | G₃ |
| Q201 | Me | COOEt | Gc |
| CH₂-Q201 | Me | COOEt | G₂ |
| Q222 | Me | COOEt | Gc |
| Q205 | Me | COOEt | Gc |
| Q207 | Me | COOEt | G₃ |
| Q209 | Me | COOEt | Gc |
| Q222 | Me | COOEt | Gc |
| Q225 | Me | COOEt | G₃ |
| Q229 | Me | COOEt | Gc |
| Q230 | Me | COOEt | Gc |
| Q231 | Me | COOEt | Gc |
| Q237 | Me | COOEt | G₁ |
| Q246 | Me | COOEt | Gc |
| Q247 | Me | COOEt | Gc |
| Q250 | Me | COOEt | Gc |
| Q259 | Me | COOEt | G₃ |
| Q260 | Me | COOEt | Gc |
| Q263 | Me | COOEt | G₃ |
| Q201 | Me | COOH | G₁ |
| Q205 | Me | COOH | Gc |
| Q201 | Me | COOPr—i | Gc |
| Q202 | Me | COOPr—i | G₃ |
| Q205 | Me | COOPr—i | Gc |
| Q209 | Me | COOPr—i | Gc |
| Q222 | Me | COOPr—i | G₃ |
| Q225 | Me | COOPr—i | Gc |
| Q229 | Me | COOPr—i | Gc |
| Q246 | Me | COOPr—i | G₁ |
| Q201 | Me | COOCH₂CH₂Cl | Gc |
| Q205 | Me | COOCH₂CH₂Cl | G₃ |
| Q222 | Me | COOCH₂CH₂Cl | Gc |
| Q229 | Me | COOCH₂CH₂Cl | G₁ |
| Q201 | Me | COOCH₂CH=CH₂ | Gc |
| Q205 | Me | COOCH₂CH=CH₂ | G₃ |
| Q222 | Me | COOCH₂CH=CH₂ | Gc |
| Q229 | Me | COOCH₂CH=CH₂ | G₁ |
| Q201 | Me | COOCH₂C≡CH | Gc |
| Q205 | Me | COOCH₂C≡CH | G₂ |
| Q222 | Me | COOCH₂C≡CH | Gc |
| Q229 | Me | COOCH₂C≡CH | Gc |
| Q201 | Me | CONHMe | Gc |
| Q205 | Me | CONHMe | G₃ |
| Q222 | Me | CONHMe | Gc |
| Q229 | Me | CONHMe | Gc |
| Q201 | Me | CONMe₂ | Gc |
| Q205 | Me | CONMe₂ | G₃ |
| Q222 | Me | CONMe₂ | Gc |
| Q229 | Me | CONMe₂ | Gc |
| Q201 | Me | COMe | Gc |
| Q202 | Me | COMe | G₃ |
| Q205 | Me | COMe | Gc |
| Q207 | Me | COMe | Gc |

TABLE 2-continued

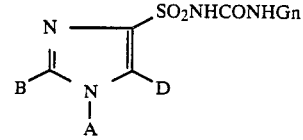

| A | B | D | Gn |
|---|---|---|---|
| Q222 | Me | COMe | G₃ |
| Q225 | Me | COMe | Gc |
| Q229 | Me | COMe | Gc |
| Q230 | Me | COMe | G₃ |
| Q231 | Me | COMe | Gc |
| Q237 | Me | COMe | Gc |
| Q246 | Me | COMe | Gc |
| Q247 | Me | COMe | G₂ |
| Q250 | Me | COMe | Gc |
| Q259 | Me | COMe | Gc |
| Q260 | Me | COMe | G₁ |
| Q263 | Me | COMe | Gc |
| Q201 | Me | COEt | Gc |
| Q205 | Me | COEt | G₃ |
| Q222 | Me | COEt | Gc |
| Q229 | Me | COEt | Gc |
| Q201 | Me | COPr—i | Gc |
| Q205 | Me | COPr—i | G₃ |
| Q222 | Me | COPr—i | Gc |
| Q229 | Me | COPr—i | G₁ |
| Q201 | Me | COPh | Gc |
| Q205 | Me | COPh | Gc |
| Q222 | Me | COPh | G₃ |
| Q229 | Me | COPh | Gc |
| Q201 | Me | CN | Gc |
| Q202 | Me | CN | G₃ |
| Q205 | Me | CN | Gc |
| Q209 | Me | CN | Gc |
| Q222 | Me | CN | G₃ |
| Q225 | Me | CN | Gc |
| Q229 | Me | CN | Gc |
| Q246 | Me | CN | G₁ |
| Q201 | Me | H | Gc |
| Q205 | Me | H | Gc |
| Q222 | Me | H | G₃ |
| Q229 | Me | H | Gc |
| Q201 | Me | Me | Gc |
| Q202 | Me | Me | G₃ |
| Q205 | Me | Me | Gc |
| Q209 | Me | Me | Gc |
| Q222 | Me | Me | Gc |
| Q225 | Me | Me | Gc |
| Q229 | Me | Me | G₃ |
| Q246 | Me | Me | Gc |
| Q201 | Me | Et | Gc |
| Q205 | Me | Et | Gc |
| Q222 | Me | Et | G₃ |
| Q229 | Me | Et | Gc |
| Q201 | Me | Pr—i | Gc |
| Q205 | Me | Pr—i | G₂ |
| Q201 | Me | CH=CH₂ | Gc |
| Q205 | Me | CH=CH₂ | G₃ |
| Q201 | Me | CH=CHMe | G₃ |
| Q205 | Me | CH=CHMe | Gc |
| Q201 | Me | CH₂CH=CH₂ | Gc |
| Q205 | Me | CH₂CH=CH₂ | G₃ |
| Q201 | Me | CH₂Cl | Gc |
| Q205 | Me | CH₂Cl | G₂ |
| Q222 | Me | CH₂Cl | Gc |
| Q229 | Me | CH₂Cl | G₃ |
| Q201 | Me | CH₂CH₂Cl | Gc |
| Q205 | Me | CH₂CH₂Cl | Gc |
| Q222 | Me | CH₂CH₂Cl | G₃ |
| Q229 | Me | CH₂CH₂Cl | Gc |
| Q201 | Me | CF₃ | Gc |
| Q205 | Me | CF₃ | G₃ |
| Q222 | Me | CF₃ | G₃ |
| Q229 | Me | CF₃ | Gc |
| Q201 | Me | CF=CFCl | Gc |
| Q205 | Me | CF=CFCl | G₃ |
| Q201 | Me | CH₂Ph | Gc |
| Q205 | Me | CH₂Ph | G₃ |
| Q201 | Me | Ph | Gc |

TABLE 2-continued

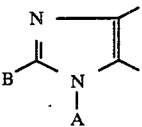

| A | B | D | Gn |
|---|---|---|---|
| Q202 | Me | Ph | Gc |
| Q205 | Me | Ph | Gc |
| Q209 | Me | Ph | Gc |
| Q222 | Me | Ph | $G_3$ |
| Q225 | Me | Ph | $G_3$ |
| Q229 | Me | Ph | Gc |
| Q246 | Me | Ph | $G_3$ |
| Q201 | Me | Ph—2-Cl | Gc |
| Q205 | Me | Ph—2-Cl | $G_3$ |
| Q201 | Me | Ph—2-Me | Gc |
| Q205 | Me | Ph—2-Me | Gc |
| Q229 | Me | Ph—2-Me | $G_3$ |
| Q201 | Me | Cl | Gc |
| Q202 | Me | Cl | $G_3$ |
| Q205 | Me | Cl | Gc |
| Q209 | Me | Cl | Gc |
| Q222 | Me | Cl | $G_3$ |
| Q225 | Me | Cl | Gc |
| Q229 | Me | Cl | Gc |
| Q246 | Me | Cl | $G_3$ |
| Q201 | Me | Br | Gc |
| Q205 | Me | Br | $G_3$ |
| Q222 | Me | Br | Gc |
| Q229 | Me | Br | $G_1$ |
| Q201 | Me | F | $G_1$ |
| Q205 | Me | F | $G_1$ |
| Q201 | Me | I | $G_1$ |
| Q205 | Me | I | $G_1$ |
| Q201 | Me | $NO_2$ | Gc |
| Q202 | Me | $NO_2$ | $G_3$ |
| Q205 | Me | $NO_2$ | Gc |
| Q209 | Me | $NO_2$ | Gc |
| Q222 | Me | $NO_2$ | Gc |
| Q225 | Me | $NO_2$ | $G_3$ |
| Q229 | Me | $NO_2$ | Gc |
| Q246 | Me | $NO_2$ | Gc |
| Q201 | Me | $NH_2$ | Gc |
| Q205 | Me | $NH_2$ | $G_3$ |
| Q222 | Me | $NH_2$ | Gc |
| Q229 | Me | $NH_2$ | $G_3$ |
| Q201 | Me | NHMe | Gc |
| Q205 | Me | NHMe | Gc |
| Q229 | Me | NHMe | $G_3$ |
| Q201 | Me | $NMe_2$ | Gc |
| Q205 | Me | $NMe_2$ | Gc |
| Q229 | Me | $NMe_2$ | $G_3$ |
| Q201 | Me | NMeEt | Gc |
| Q205 | Me | NMeEt | Gc |
| Q201 | Me | NHCOMe | Gc |
| Q205 | Me | NHCOMe | Gc |
| Q222 | Me | NHCOMe | $G_3$ |
| Q229 | Me | NHCOMe | Gc |
| Q201 | Me | NHCOEt | Gc |
| Q205 | Me | NHCOEt | $G_3$ |
| Q201 | Me | $NHSO_2Me$ | Gc |
| Q205 | Me | $NHSO_2Me$ | Gc |
| Q229 | Me | $NHSO_2Me$ | $G_2$ |
| Q201 | Me | OMe | Gc |
| Q205 | Me | OMe | $G_3$ |
| Q222 | Me | OMe | Gc |
| Q229 | Me | OMe | $G_1$ |
| Q201 | Me | OEt | Gc |
| Q205 | Me | OEt | $G_3$ |
| Q201 | Me | $CH_2OMe$ | Gc |
| Q205 | Me | $CH_2OMe$ | Gc |
| Q229 | Me | $CH_2OMe$ | $G_3$ |
| Q201 | Me | SMe | Gc |
| Q205 | Me | SMe | $G_3$ |
| Q201 | Me | $SO_2Me$ | Gc |
| Q205 | Me | $SO_2Me$ | Gc |
| Q222 | Me | $SO_2Me$ | $G_1$ |
| Q229 | Me | $SO_2Me$ | $G_3$ |
| Q201 | Me | $SO_2Ph$ | Gc |

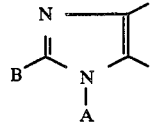

| A | B | D | Gn |
|---|---|---|---|
| Q205 | Me | $SO_2Ph$ | Gc |
| Q222 | Me | $SO_2Ph$ | $G_3$ |
| Q229 | Me | $SO_2Ph$ | Gc |
| Q201 | Me | $SO_2OMe$ | Gc |
| Q205 | Me | $SO_2OMe$ | $G_3$ |
| Q229 | Me | $SO_2OMe$ | Gc |
| Q201 | Me | $SO_2NH_2$ | Gc |
| Q205 | Me | $SO_2NH_2$ | Gc |
| Q229 | Me | $SO_2NH_2$ | $G_3$ |
| Q201 | Me | $SO_2NHMe$ | Gc |
| Q205 | Me | $SO_2NHMe$ | Gc |
| Q222 | Me | $SO_2NHMe$ | $G_1$ |
| Q229 | Me | $SO_2NHMe$ | Gc |
| Q201 | Me | $SO_2NMe_2$ | Gc |
| Q205 | Me | $SO_2NMe_2$ | $G_3$ |
| Q222 | Me | $SO_2NMe_2$ | Gc |
| Q229 | Me | $SO_2NMe_2$ | $G_1$ |
| Q201 | Et | COOMe | Gc |
| Q205 | Et | COOMe | Gc |
| Q229 | Et | COOMe | $G_3$ |
| Q246 | Et | COOMe | $G_3$ |
| Q201 | Et | COOEt | Gc |
| Q202 | Et | COOEt | $G_2$ |
| Q209 | Et | COOEt | Gc |
| Q222 | Et | COOEt | $G_3$ |
| Q225 | Et | COOEt | Gc |
| Q201 | Et | COOPr—i | $G_3$ |
| Q205 | Et | COOPr—i | Gc |
| Q201 | Et | $COOCH_2CHCl$ | Gc |
| Q205 | Et | $COOCH_2CH=CH_2$ | $G_3$ |
| Q201 | Et | $COOCH_2C\equiv CH$ | Gc |
| Q201 | Et | CONHMe | Gc |
| Q201 | Et | $CONMe_2$ | Gc |
| Q201 | Et | COMe | Gc |
| Q205 | Et | COMe | $G_3$ |
| Q229 | Et | COMe | Gc |
| Q201 | Et | COEt | Gc |
| Q201 | Et | COPh | Gc |
| Q201 | Et | CN | Gc |
| Q205 | Et | CN | $G_3$ |
| Q229 | Et | CN | Gc |
| Q201 | Et | H | Gc |
| Q205 | Et | H | $G_3$ |
| Q201 | Et | Me | Gc |
| Q205 | Et | Me | $G_3$ |
| Q201 | Et | Et | Gc |
| Q205 | Et | Pr—i | Gc |
| Q201 | Et | CH=CHMe | Gc |
| Q201 | Et | $CH_2CH_2Cl$ | Gc |
| Q201 | Et | $CH_2Ph$ | $G_3$ |
| Q201 | Et | Ph | Gc |
| Q205 | Et | Ph | Gc |
| Q209 | Et | Ph | Gc |
| Q229 | Et | Ph | $G_3$ |
| Q201 | Et | Ph—2-Cl | Gc |
| Q205 | Et | Ph—2-Me | Gc |
| Q201 | Et | Cl | Gc |
| Q205 | Et | Cl | $G_2$ |
| Q201 | Et | Br | Gc |
| Q205 | Et | Br | $G_1$ |
| Q201 | Et | F | Gc |
| Q201 | Et | $NO_2$ | Gc |
| Q205 | Et | $NO_2$ | $G_3$ |
| Q209 | Et | $NO_2$ | Gc |
| Q201 | Et | $NH_2$ | Gc |
| Q201 | Et | NHMe | Gc |
| Q201 | Et | $NMe_2$ | Gc |
| Q205 | Et | $NMe_2$ | $G_3$ |
| Q201 | Et | NHCOMe | Gc |
| Q205 | Et | NHCOMe | Gc |
| Q201 | Et | NHCOEt | Gc |
| Q201 | Et | $NHSO_2Me$ | Gc |
| Q201 | Et | OMe | Gc |

TABLE 2-continued

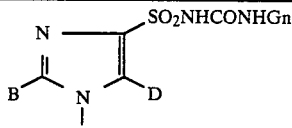

| A | B | D | Gn |
|---|---|---|---|
| Q205 | Et | OEt | G₃ |
| Q201 | Et | CH₂OMe | Gc |
| Q201 | Et | SMe | Gc |
| Q201 | Et | SO₂Me | Gc |
| Q205 | Et | SO₂Me | G₃ |
| Q201 | Et | SO₂Ph | Gc |
| Q205 | Et | SO₂Ph | G₃ |
| Q201 | Et | SO₂OMe | Gc |
| Q201 | Et | SO₂NH₂ | Gc |
| Q205 | Et | SO₂NHMe | G₃ |
| Q201 | Et | SO₂NMe₂ | Gc |
| Q205 | Et | SO₂NMe₂ | G₃ |
| Q201 | Cl | COOMe | Gc |
| Q209 | Cl | COOMe | G₃ |
| Q229 | Cl | COOMe | Gc |
| Q246 | Cl | COOMe | G₃ |
| Q201 | Cl | COOEt | Gc |
| Q205 | Cl | COOEt | Gc |
| Q222 | Cl | COOEt | G₁ |
| Q225 | Cl | COOEt | Gc |
| Q246 | Cl | COOEt | G₃ |
| Q201 | Cl | COOPr—i | Gc |
| Q205 | Cl | COOPr—i | G₃ |
| Q205 | Cl | COOCH₂CH₂Cl | G₃ |
| Q201 | Cl | COOCH₂CH=CH₂ | Gc |
| Q201 | Cl | COOCH₂C≡CH | G₃ |
| Q201 | Cl | CONHMe | Gc |
| Q201 | Cl | CONMe₂ | G₃ |
| Q201 | Cl | COMe | Gc |
| Q205 | Cl | COMe | Gc |
| Q201 | Cl | COEt | G₃ |
| Q201 | Cl | COPr—i | Gc |
| Q201 | Cl | COPh | G₃ |
| Q201 | Cl | CN | Gc |
| Q205 | Cl | CN | Gc |
| Q201 | Cl | H | G₃ |
| Q201 | Cl | Me | Gc |
| Q205 | Cl | Me | G₃ |
| Q205 | Cl | Et | Gc |
| Q201 | Cl | Pr—i | G₃ |
| Q201 | Cl | CH=CHMe | Gc |
| Q201 | Cl | CH₂CH=CH₂ | G₁ |
| Q205 | Cl | CH₂CH₂Cl | Gc |
| Q201 | Cl | Ph | Gc |
| Q205 | Cl | Ph | Gc |
| Q209 | Cl | Ph | G₃ |
| Q201 | Cl | Ph—2-Cl | Gc |
| Q205 | Cl | Ph—2-Me | G₃ |
| Q201 | Cl | Cl | Gc |
| Q205 | Cl | Cl | G₃ |
| Q201 | Cl | Br | Gc |
| Q201 | Cl | NO₂ | Gc |
| Q205 | Cl | NO₂ | G₃ |
| Q209 | Cl | NO₂ | Gc |
| Q201 | Cl | NH₂ | Gc |
| Q201 | Cl | NHMe | G₁ |
| Q201 | Cl | NMe₂ | G₃ |
| Q201 | Cl | NHCOMe | Gc |
| Q205 | Cl | NHCOEt | Gc |
| Q201 | Cl | NHSO₂Me | G₃ |
| Q201 | Cl | OMe | Gc |
| Q201 | Cl | CH₂OMe | G₃ |
| Q201 | Cl | SO₂Me | Gc |
| Q201 | Cl | SO₂Ph | Gc |
| Q201 | Cl | SO₂NH₂ | G₃ |
| Q201 | Cl | SO₂NMe₂ | Gc |
| Q205 | Cl | SO₂NMe₂ | Gc |
| Q201 | Br | COOMe | Gc |
| Q205 | Br | COOMe | G₃ |
| Q209 | Br | COOMe | G₃ |
| Q201 | Br | COOEt | Gc |
| Q209 | Br | COOEt | Gc |
| Q229 | Br | COOEt | G₃ |
| Q201 | Br | COOPr—i | G₃ |
| Q201 | Br | COOCH₂CHCl | Gc |
| Q201 | Br | COOCH₂CH=CH₂ | G₃ |
| Q201 | Br | CONHMe | Gc |
| Q201 | Br | CONMe₂ | G₃ |
| Q201 | Br | COMe | Gc |
| Q205 | Br | COMe | G₃ |
| Q201 | Br | COEt | Gc |
| Q201 | Br | COPh | G₃ |
| Q201 | Br | CN | Gc |
| Q205 | Br | CN | Gc |
| Q201 | Br | H | G₃ |
| Q201 | Br | Me | G₂ |
| Q201 | Br | Et | G₁ |
| Q201 | Br | CH₂CH₂Cl | G₃ |
| Q201 | Br | Ph | Gc |
| Q205 | Br | Ph | Gc |
| Q209 | Br | Ph | G₃ |
| Q201 | Br | Ph—2-Cl | G₃ |
| Q201 | Br | Cl | Gc |
| Q201 | Br | Br | Gc |
| Q205 | Br | Br | G₃ |
| Q201 | Br | NO₂ | Gc |
| Q209 | Br | NO₂ | Gc |
| Q201 | Br | NH₂ | Gc |
| Q201 | Br | NMe₂ | G₃ |
| Q201 | Br | NHCOMe | Gc |
| Q201 | Br | OMe | G₃ |
| Q201 | Br | CH₂OMe | Gc |
| Q201 | Br | SMe | Gc |
| Q201 | Br | SO₂Me | Gc |
| Q201 | Br | SO₂NH₂ | G₃ |
| Q201 | Br | SO₂NHMe | Gc |
| Q201 | Br | SO₂NMe₂ | G₃ |
| Q201 | SMe | COOMe | Gc |
| Q205 | SMe | COOMe | Gc |
| Q209 | SMe | COOMe | G₃ |
| Q201 | SMe | COOEt | Gc |
| Q205 | SMe | COOEt | Gc |
| Q209 | SMe | COOEt | Gc |
| Q229 | SMe | COOEt | G₃ |
| Q246 | SMe | COOEt | Gc |
| Q201 | SMe | COOPr—i | Gc |
| Q205 | SMe | COOPr—i | G₃ |
| Q201 | SMe | COOCH₂CH₂Cl | Gc |
| Q201 | SMe | COOCH₂CH=CH₂ | Gc |
| Q201 | SMe | CONHMe | Gc |
| Q201 | SMe | CONMe₂ | G₁ |
| Q201 | SMe | COMe | Gc |
| Q205 | SMe | COMe | Gc |
| Q201 | SMe | COEt | G₃ |
| Q201 | SMe | COPr—i | Gc |
| Q201 | SMe | COPh | G₃ |
| Q201 | SMe | CN | Gc |
| Q205 | SMe | CN | Gc |
| Q229 | SMe | CN | G₃ |
| Q201 | SMe | H | Gc |
| Q201 | SMe | Me | Gc |
| Q205 | SMe | Me | G₃ |
| Q201 | SMe | Et | Gc |
| Q205 | SMe | Et | Gc |
| Q201 | SMe | CH₂CH₂Cl | G₃ |
| Q201 | SMe | Ph | Gc |
| Q205 | SMe | Ph | Gc |
| Q209 | SMe | Ph | G₃ |
| Q201 | SMe | Ph—2-Cl | Gc |
| Q201 | SMe | Cl | Gc |
| Q205 | SMe | Cl | G₃ |
| Q201 | SMe | Br | Gc |
| Q201 | SMe | NO₂ | Gc |
| Q205 | SMe | NO₂ | Gc |
| Q209 | SMe | NO₂ | G₃ |
| Q201 | SMe | NH₂ | Gc |

TABLE 2-continued

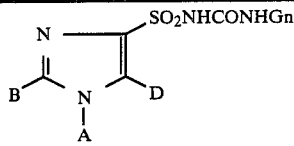

| A | B | D | Gn |
|---|---|---|---|
| Q205 | SMe | NH₂ | Gc |
| Q201 | SMe | NHMe | G₃ |
| Q201 | SMe | NMe₂ | Gc |
| Q205 | SMe | NMe₂ | Gc |
| Q201 | SMe | NHCOMe | Gc |
| Q205 | SMe | NHCOMe | G₃ |
| Q201 | SMe | NHSO₂Me | Gc |
| Q201 | SMe | OMe | Gc |
| Q201 | SMe | CH₂OMe | Gc |
| Q201 | SMe | SMe | Gc |
| Q201 | SMe | SO₂Me | Gc |
| Q205 | SMe | SO₂Me | G₃ |
| Q201 | SMe | SO₂Ph | Gc |
| Q201 | SMe | SO₂NH₂ | Gc |
| Q201 | SMe | SO₂NHMe | G₃ |
| Q201 | SMe | SO₂NMe₂ | Gc |
| Q201 | SO₂Me | COOMe | Gc |
| Q205 | SO₂Me | COOMe | Gc |
| Q209 | SO₂Me | COOMe | G₃ |
| Q229 | SO₂Me | COOMe | G₃ |
| Q246 | SO₂Me | COOMe | G₁ |
| Q201 | SO₂Me | COOEt | Gc |
| Q205 | SO₂Me | COOEt | Gc |
| Q209 | SO₂Me | COOEt | G₃ |
| Q222 | SO₂Me | COOEt | Gc |
| Q225 | SO₂Me | COOEt | Gc |
| Q201 | SO₂Me | COOPr—i | G₃ |
| Q205 | SO₂Me | COOPr—i | Gc |
| Q201 | SO₂Me | COOCH₂CH₂Cl | Gc |
| Q201 | SO₂Me | COOCH₂CH=CH₂ | G₃ |
| Q201 | SO₂Me | COOCH₂C≡CH | Gc |
| Q201 | SO₂Me | CONHMe | Gc |
| Q201 | SO₂Me | CONMe₂ | G₂ |
| Q201 | SO₂Me | COMe | Gc |
| Q205 | SO₂Me | COMe | Gc |
| Q229 | SO₂Me | COMe | G₃ |
| Q201 | SO₂Me | COEt | Gc |
| Q205 | SO₂Me | COEt | Gc |
| Q201 | SO₂Me | COPr—i | G₃ |
| Q201 | SO₂Me | COPh | Gc |
| Q201 | SO₂Me | CN | Gc |
| Q205 | SO₂Me | CN | Gc |
| Q222 | SO₂Me | CN | Gc |
| Q229 | SO₂Me | CN | Gc |
| Q201 | SO₂Me | H | G₂ |
| Q201 | SO₂Me | Me | Gc |
| Q205 | SO₂Me | Me | Gc |
| Q201 | SO₂Me | Et | G₃ |
| Q201 | SO₂Me | Pr—i | Gc |
| Q201 | SO₂Me | CH=CH₂ | Gc |
| Q201 | SO₂Me | CH=CHMe | G₁ |
| Q201 | SO₂Me | CH₂CH₂Cl | Gc |
| Q205 | SO₂Me | CH₂CH₂Cl | G₃ |
| Q201 | SO₂Me | CH₂Ph | G₃ |
| Q201 | SO₂Me | Ph | Gc |
| Q205 | SO₂Me | Ph | Gc |
| Q209 | SO₂Me | Ph | Gc |
| Q229 | SO₂Me | Ph | G₃ |
| Q246 | SO₂Me | Ph | G₃ |
| Q201 | SO₂Me | Ph—2-Cl | Gc |
| Q205 | SO₂Me | Ph—2-Me | Gc |
| Q201 | SO₂Me | Cl | Gc |
| Q205 | SO₂Me | Cl | Gc |
| Q229 | SO₂Me | Cl | G₃ |
| Q201 | SO₂Me | Br | G₃ |
| Q205 | SO₂Me | Br | Gc |
| Q201 | SO₂Me | NO₂ | Gc |
| Q205 | SO₂Me | NO₂ | Gc |
| Q209 | SO₂Me | NO₂ | Gc |
| Q229 | SO₂Me | NO₂ | G₃ |
| Q201 | SO₂Me | NH₂ | Gc |
| Q205 | SO₂Me | NH₂ | G₃ |
| Q201 | SO₂Me | NHMe | Gc |

TABLE 2-continued

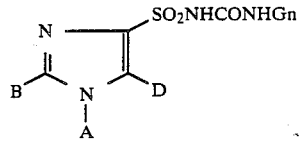

| A | B | D | Gn |
|---|---|---|---|
| Q201 | SO₂Me | NMe₂ | Gc |
| Q205 | SO₂Me | NMe₂ | G₁ |
| Q201 | SO₂Me | NHCOMe | Gc |
| Q205 | SO₂Me | NHCOMe | Gc |
| Q201 | SO₂Me | NHCOEt | G₃ |
| Q201 | SO₂Me | NHSO₂Me | Gc |
| Q201 | SO₂Me | OMe | G₁ |
| Q201 | SO₂Me | CH₂OMe | Gc |
| Q205 | SO₂Me | CH₂OMe | Gc |
| Q201 | SO₂Me | SO₂Me | Gc |
| Q205 | SO₂Me | SO₂Me | Gc |
| Q201 | SO₂Me | SO₂Ph | G₃ |
| Q201 | SO₂Me | SO₂OMe | Gc |
| Q201 | SO₂Me | SO₂NH₂ | Gc |
| Q201 | SO₂Me | SO₂NHMe | G₃ |
| Q201 | SO₂Me | SO₂NMe₂ | Gc |
| Q201 | Ph | COOMe | Gc |
| Q205 | Ph | COOMe | G₃ |
| Q209 | Ph | COOMe | Gc |
| Q201 | Ph | COOEt | Gc |
| Q205 | Ph | COOEt | Gc |
| Q209 | Ph | COOEt | G₃ |
| Q229 | Ph | COOEt | Gc |
| Q201 | Ph | COOPr—i | G₃ |
| Q201 | Ph | COOCH₂CH₂Cl | Gc |
| Q201 | Ph | COOCH₂CH=CH₂ | Gc |
| Q201 | Ph | COOCH₂C≡CH | G₃ |
| Q201 | Ph | CONMe₂ | Gc |
| Q201 | Ph | COMe | Gc |
| Q205 | Ph | COMe | Gc |
| Q201 | Ph | COEt | G₃ |
| Q201 | Ph | CN | Gc |
| Q205 | Ph | CN | Gc |
| Q201 | Ph | H | G₃ |
| Q201 | Ph | Me | Gc |
| Q201 | Ph | Et | Gc |
| Q201 | Ph | CH₂CH₂Cl | G₃ |
| Q201 | Ph | Ph | Gc |
| Q205 | Ph | Ph | Gc |
| Q209 | Ph | Ph | G₃ |
| Q201 | Ph | Cl | Gc |
| Q201 | Ph | Br | G₃ |
| Q201 | Ph | NO₂ | Gc |
| Q201 | Ph | NH₂ | Gc |
| Q201 | Ph | NHMe | G₃ |
| Q201 | Ph | NMe₂ | Gc |
| Q201 | Ph | NHCOMe | Gc |
| Q201 | Ph | NHSO₂Me | G₁ |
| Q201 | Ph | CH₂OMe | Gc |
| Q201 | Ph | SO₂Me | G₃ |
| Q201 | Ph | SO₂NH₂ | Gc |
| Q201 | Ph | SO₂NHMe | Gc |
| Q201 | Ph | SO₂NMe₂ | G₃ |

TABLE 3

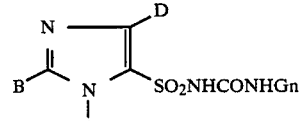

| A | B | D | Gn |
|---|---|---|---|
| Q1 | H | COOMe | Gb |
| CH₂ - Q1 | H | COOMe | Gc |
| CHMe - Q1 | H | COOMe | G3 |
| Q2 | H | COOMe | Gb |
| Q3 | H | COOMe | Gb |
| Q4 | H | COOMe | Gb |
| Q5 | H | COOMe | Ga |

TABLE 3-continued

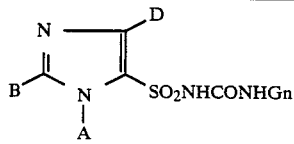

| A | B | D | Gn |
|---|---|---|---|
| CH$_2$ - Q5 | H | COOMe | Gc |
| CHMe - Q5 | H | COOMe | G3 |
| Q6 | H | COOMe | G3 |
| Q7 | H | COOMe | G3 |
| Q8 | H | COOMe | G3 |
| Q9 | H | COOMe | Gc |
| CH$_2$ - Q9 | H | COOMe | Gc |
| Q10 | H | COOMe | Gc |
| Q11 | H | COOMe | G3 |
| Q12 | H | COOMe | G3 |
| Q13 | H | COOMe | G3 |
| Q14 | H | COOMe | G1 |
| Q15 | H | COOMe | G3 |
| Q16 | H | COOMe | Gc |
| Q17 | H | COOMe | Gc |
| Q18 | H | COOMe | G3 |
| Q19 | H | COOMe | Gc |
| Q20 | H | COOMe | Gc |
| Q21 | H | COOMe | Gc |
| Q22 | H | COOMe | G3 |
| Q23 | H | COOMe | Gc |
| CH$_2$ - Q23 | H | COOMe | G3 |
| Q24 | H | COOMe | Gc |
| Q25 | H | COOMe | Gb |
| Q26 | H | COOMe | Ga |
| CH$_2$ - Q26 | H | COOMe | G3 |
| CHMe - Q26 | H | COOMe | G3 |
| Q27 | H | COOMe | G3 |
| Q28 | H | COOMe | G3 |
| Q29 | H | COOMe | Gc |
| CH$_2$ - Q29 | H | COOMe | G3 |
| Q30 | H | COOMe | G3 |
| Q31 | H | COOMe | Gc |
| Q32 | H | COOMe | Gc |
| CH$_2$ - Q32 | H | COOMe | G3 |
| Q33 | H | COOMe | G3 |
| Q34 | H | COOMe | G3 |
| Q35 | H | COOMe | G3 |
| Q36 | H | COOMe | G3 |
| Q37 | H | COOMe | Gc |
| Q38 | H | COOMe | Gc |
| Q39 | H | COOMe | G3 |
| Q40 | H | COOMe | Gc |
| Q41 | H | COOMe | Gc |
| Q42 | H | COOMe | Gc |
| Q43 | H | COOMe | G3 |
| Q44 | H | COOMe | Gc |
| Q45 | H | COOMe | Gc |
| Q46 | H | COOMe | Gc |
| Q47 | H | COOMe | Gc |
| Q48 | H | COOMe | Gc |
| Q49 | H | COOMe | G3 |
| Q50 | H | COOMe | Gc |
| CH$_2$ - Q50 | H | COOMe | G3 |
| Q51 | H | COOMe | Gc |
| Q52 | H | COOMe | G3 |
| Q53 | H | COOMe | G3 |
| Q54 | H | COOMe | Gc |
| Q55 | H | COOMe | Gc |
| Q56 | H | COOMe | Gc |
| Q57 | H | COOMe | G3 |
| Q58 | H | COOMe | Gc |
| Q59 | H | COOMe | Gc |
| CH$_2$ - Q59 | H | COOMe | G3 |
| Q60 | H | COOMe | Gc |
| Q61 | H | COOMe | Ga |
| CH$_2$ - Q61 | H | COOMe | Gb |
| CHMe - Q61 | H | COOMe | Gc |
| Q62 | H | COOMe | Gc |
| Q63 | H | COOMe | Gc |
| Q64 | H | COOMe | Gb |
| CH$_2$ - Q64 | H | COOMe | G3 |
| CHMe - Q64 | H | COOMe | G3 |

TABLE 3-continued

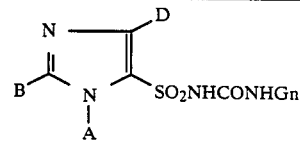

| A | B | D | Gn |
|---|---|---|---|
| Q65 | H | COOMe | G3 |
| Q66 | H | COOMe | G3 |
| Q67 | H | COOMe | G3 |
| Q68 | H | COOMe | G3 |
| Q69 | H | COOMe | Gc |
| Q70 | H | COOMe | Gc |
| Q71 | H | COOMe | Gc |
| Q72 | H | COOMe | Gc |
| CH$_2$ - Q72 | H | COOMe | G3 |
| CHMe - Q72 | H | COOMe | G3 |
| Q73 | H | COOMe | Gc |
| CH$_2$ - Q73 | H | COOMe | G3 |
| Q74 | H | COOMe | Gc |
| Q75 | H | COOMe | G3 |
| Q76 | H | COOMe | G3 |
| Q77 | H | COOMe | Gc |
| CH$_2$ - Q77 | H | COOMe | G3 |
| Q78 | H | COOMe | Gc |
| Q79 | H | COOMe | Gc |
| Q80 | H | COOMe | Gc |
| Q81 | H | COOMe | G3 |
| Q82 | H | COOMe | G3 |
| Q83 | H | COOMe | G1 |
| Q84 | H | COOMe | G2 |
| Q85 | H | COOMe | G3 |
| Q86 | H | COOMe | Gc |
| Q87 | H | COOMe | G2 |
| Q88 | H | COOMe | Gc |
| Q89 | H | COOMe | Gc |
| Q90 | H | COOMe | Gc |
| Q91 | H | COOMe | G3 |
| Q92 | H | COOMe | G3 |
| Q93 | H | COOMe | Gc |
| Q94 | H | COOMe | G3 |
| Q95 | H | COOMe | Gc |
| Q96 | H | COOMe | G3 |
| Q97 | H | COOMe | Gc |
| Q98 | H | COOMe | Gc |
| Q99 | H | COOMe | Gc |
| Q100 | H | COOMe | Gc |
| Q101 | H | COOMe | Gc |
| CH$_2$ - Q101 | H | COOMe | G3 |
| Q102 | H | COOMe | G3 |
| Q103 | H | COOMe | G3 |
| Q104 | H | COOMe | G3 |
| Q105 | H | COOMe | Gc |
| Q106 | H | COOMe | G3 |
| Q107 | H | COOMe | Gc |
| Q108 | H | COOMe | G1 |
| Q109 | H | COOMe | G3 |
| Q110 | H | COOMe | G3 |
| Q111 | H | COOMe | G3 |
| Q112 | H | COOMe | Gc |
| Q113 | H | COOMe | Gc |
| Q114 | H | COOMe | Gc |
| Q115 | H | COOMe | G2 |
| Q116 | H | COOMe | Gc |
| Q117 | H | COOMe | Gc |
| Q118 | H | COOMe | G3 |
| Q119 | H | COOMe | Gc |
| Q120 | H | COOMe | Gc |
| Q121 | H | COOMe | G2 |
| Q122 | H | COOMe | Gc |
| Q123 | H | COOMe | Gc |
| Q124 | H | COOMe | Gc |
| Q125 | H | COOMe | Gc |
| Q126 | H | COOMe | Gc |
| Q127 | H | COOMe | Gc |
| Q128 | H | COOMe | Gc |
| Q129 | H | COOMe | Gc |
| Q130 | H | COOMe | G2 |
| Q131 | H | COOMe | Gc |
| Q132 | H | COOMe | Gc |

TABLE 3-continued

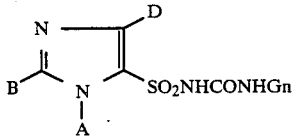

| A | B | D | Gn |
|---|---|---|---|
| Q133 | H | COOMe | G3 |
| Q134 | H | COOMe | Gc |
| Q135 | H | COOMe | G3 |
| Q136 | H | COOMe | G1 |
| Q137 | H | COOMe | G1 |
| Q138 | H | COOMe | Gc |
| CH2 - Q138 | H | COOMe | G3 |
| Q139 | H | COOMe | G3 |
| Q140 | H | COOMe | G1 |
| Q141 | H | COOMe | G3 |
| Q142 | H | COOMe | Gc |
| Q143 | H | COOMe | Gc |
| CH2 - Q143 | H | COOMe | G3 |
| Q144 | H | COOMe | G3 |
| Q145 | H | COOMe | Gc |
| Q146 | H | COOMe | Gc |
| Q147 | H | COOMe | G3 |
| Q148 | H | COOMe | G1 |
| Q149 | H | COOMe | G3 |
| Q150 | H | COOMe | G3 |
| Q151 | H | COOMe | G2 |
| Q152 | H | COOMe | G1 |
| Q153 | H | COOMe | Gc |
| Q154 | H | COOMe | Gc |
| Q155 | H | COOMe | G3 |
| Q156 | H | COOMe | G3 |
| Q157 | H | COOMe | Gc |
| Q158 | H | COOMe | Ga |
| CH2 - Q158 | H | COOMe | G3 |
| CHMe - Q158 | H | COOMe | G3 |
| Q159 | H | COOMe | G3 |
| Q160 | H | COOMe | Gc |
| Q161 | H | COOMe | Gc |
| Q162 | H | COOMe | Gc |
| Q163 | H | COOMe | G3 |
| Q164 | H | COOMe | Gc |
| Q165 | H | COOMe | Gc |
| Q166 | H | COOMe | Gc |
| Q167 | H | COOMe | G3 |
| Q168 | H | COOMe | G3 |
| Q169 | H | COOMe | Gc |
| CH2 - Q169 | H | COOMe | G3 |
| CHMe - Q169 | H | COOMe | G3 |
| Q170 | H | COOMe | Gc |
| Q171 | H | COOMe | Gc |
| Q172 | H | COOMe | Gc |
| Q173 | H | COOMe | Gc |
| Q174 | H | COOMe | Gc |
| Q175 | H | COOMe | Gc |
| Q176 | H | COOMe | Gc |
| Q177 | H | COOMe | Gc |
| CH2 - Q177 | H | COOMe | G3 |
| CHMe - Q177 | H | COOMe | G3 |
| Q178 | H | COOMe | G3 |
| Q179 | H | COOMe | G3 |
| Q180 | H | COOMe | Gc |
| CH2 - Q180 | H | COOMe | G3 |
| Q181 | H | COOMe | G1 |
| Q182 | H | COOMe | G3 |
| Q183 | H | COOMe | G3 |
| Q184 | H | COOMe | Gc |
| CH2 - Q184 | H | COOMe | G3 |
| CHMe - Q184 | H | COOMe | G3 |
| Q185 | H | COOMe | G3 |
| Q186 | H | COOMe | G3 |
| Q187 | H | COOMe | G3 |
| Q188 | H | COOMe | Gb |
| Q189 | H | COOMe | Gb |
| Q1 | H | COOEt | Gb |
| CH2 - Q1 | H | COOEt | Gc |
| CHMe - Q1 | H | COOEt | G3 |
| Q2 | H | COOEt | Gb |
| Q3 | H | COOEt | Gb |

TABLE 3-continued

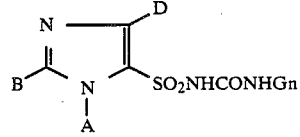

| A | B | D | Gn |
|---|---|---|---|
| Q4 | H | COOEt | Gb |
| Q5 | H | COOEt | Ga |
| CH2 - Q5 | H | COOEt | Gc |
| CHMe - Q5 | H | COOEt | G3 |
| Q6 | H | COOEt | G3 |
| Q7 | H | COOEt | G3 |
| Q8 | H | COOEt | G3 |
| Q9 | H | COOEt | Gc |
| CH2 - Q9 | H | COOEt | Gc |
| Q10 | H | COOEt | Gc |
| Q11 | H | COOEt | G3 |
| Q12 | H | COOEt | G3 |
| Q13 | H | COOEt | G3 |
| Q14 | H | COOEt | G1 |
| Q15 | H | COOEt | G3 |
| Q16 | H | COOEt | Gc |
| Q17 | H | COOEt | Gc |
| Q18 | H | COOEt | G3 |
| Q19 | H | COOEt | Gc |
| Q20 | H | COOEt | Gc |
| Q21 | H | COOEt | Gc |
| Q22 | H | COOEt | G3 |
| Q23 | H | COOEt | Gc |
| CH2 - Q23 | H | COOEt | G3 |
| Q24 | H | COOEt | Gc |
| Q25 | H | COOEt | Gb |
| Q26 | H | COOEt | Ga |
| CH2 - Q26 | H | COOEt | G3 |
| CHMe - Q26 | H | COOEt | G3 |
| Q27 | H | COOEt | G3 |
| Q28 | H | COOEt | G3 |
| Q29 | H | COOEt | Gc |
| CH2 - Q29 | H | COOEt | G3 |
| Q30 | H | COOEt | G3 |
| Q31 | H | COOEt | Gc |
| Q32 | H | COOEt | Gc |
| CH2 - Q32 | H | COOEt | G3 |
| Q33 | H | COOEt | G3 |
| Q34 | H | COOEt | G3 |
| Q35 | H | COOEt | G3 |
| Q36 | H | COOEt | G3 |
| Q37 | H | COOEt | Gc |
| Q38 | H | COOEt | Gc |
| Q39 | H | COOEt | G3 |
| Q40 | H | COOEt | Gc |
| Q41 | H | COOEt | Gc |
| Q42 | H | COOEt | Gc |
| Q43 | H | COOEt | G3 |
| Q44 | H | COOEt | Gc |
| Q45 | H | COOEt | Gc |
| Q46 | H | COOEt | Gc |
| Q47 | H | COOEt | Gc |
| Q48 | H | COOEt | Gc |
| Q49 | H | COOEt | G3 |
| Q50 | H | COOEt | Gc |
| CH2 - Q50 | H | COOEt | G3 |
| Q51 | H | COOEt | Gc |
| Q52 | H | COOEt | G3 |
| Q53 | H | COOEt | G3 |
| Q54 | H | COOEt | Gc |
| Q55 | H | COOEt | Gc |
| Q56 | H | COOEt | Gc |
| Q57 | H | COOEt | G3 |
| Q58 | H | COOEt | Gc |
| Q59 | H | COOEt | Gc |
| CH2 - Q59 | H | COOEt | G3 |
| Q60 | H | COOEt | Gc |
| Q61 | H | COOEt | Ga |
| CH2 - Q61 | H | COOEt | Gb |
| CHMe - Q61 | H | COOEt | Gc |
| Q62 | H | COOEt | Gc |
| Q63 | H | COOEt | Gc |
| Q64 | H | COOEt | Gb |

TABLE 3-continued

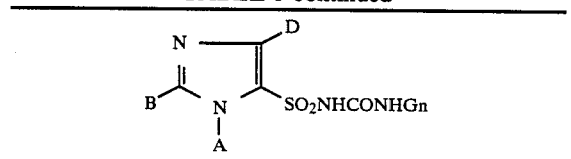

| A | B | D | Gn |
|---|---|---|---|
| CH₂ - Q64 | H | COOEt | G3 |
| CHMe - Q64 | H | COOEt | G3 |
| Q65 | H | COOEt | G3 |
| Q66 | H | COOEt | G3 |
| Q67 | H | COOEt | G3 |
| Q68 | H | COOEt | G3 |
| Q69 | H | COOEt | Gc |
| Q70 | H | COOEt | Gc |
| Q71 | H | COOEt | Gc |
| Q72 | H | COOEt | Gc |
| CH₂ - Q72 | H | COOEt | G3 |
| CHMe - Q72 | H | COOEt | G3 |
| Q73 | H | COOEt | Gc |
| CH₂ - Q73 | H | COOEt | G3 |
| Q74 | H | COOEt | Gc |
| Q75 | H | COOEt | G3 |
| Q76 | H | COOEt | G3 |
| Q77 | H | COOEt | Gc |
| CH₂ - Q77 | H | COOEt | G3 |
| Q78 | H | COOEt | Gc |
| Q79 | H | COOEt | Gc |
| Q80 | H | COOEt | Gc |
| Q81 | H | COOEt | G3 |
| Q82 | H | COOEt | G3 |
| Q83 | H | COOEt | G1 |
| Q84 | H | COOEt | G2 |
| Q85 | H | COOEt | G3 |
| Q86 | H | COOEt | Gc |
| Q87 | H | COOEt | G2 |
| Q88 | H | COOEt | Gc |
| Q89 | H | COOEt | Gc |
| Q90 | H | COOEt | Gc |
| Q91 | H | COOEt | Gc |
| Q92 | H | COOEt | G3 |
| Q93 | H | COOEt | Gc |
| Q94 | H | COOEt | G3 |
| Q95 | H | COOEt | Gc |
| Q96 | H | COOEt | G3 |
| Q97 | H | COOEt | Gc |
| Q98 | H | COOEt | Gc |
| Q99 | H | COOEt | Gc |
| Q100 | H | COOEt | Gc |
| Q101 | H | COOEt | Gc |
| CH₂ - Q101 | H | COOEt | G3 |
| Q102 | H | COOEt | G3 |
| Q103 | H | COOEt | G3 |
| Q104 | H | COOEt | G3 |
| Q105 | H | COOEt | Gc |
| Q106 | H | COOEt | G3 |
| Q107 | H | COOEt | Gc |
| Q108 | H | COOEt | G1 |
| Q109 | H | COOEt | G3 |
| Q110 | H | COOEt | G3 |
| Q111 | H | COOEt | G3 |
| Q112 | H | COOEt | Gc |
| Q113 | H | COOEt | Gc |
| Q114 | H | COOEt | Gc |
| Q115 | H | COOEt | G2 |
| Q116 | H | COOEt | Gc |
| Q117 | H | COOEt | Gc |
| Q118 | H | COOEt | G3 |
| Q119 | H | COOEt | Gc |
| Q120 | H | COOEt | Gc |
| Q121 | H | COOEt | G2 |
| Q122 | H | COOEt | Gc |
| Q123 | H | COOEt | Gc |
| Q124 | H | COOEt | Gc |
| Q125 | H | COOEt | Gc |
| Q126 | H | COOEt | Gc |
| Q127 | H | COOEt | Gc |
| Q128 | H | COOEt | Gc |
| Q129 | H | COOEt | Gc |
| Q130 | H | COOEt | G2 |
| Q131 | H | COOEt | Gc |
| Q132 | H | COOEt | Gc |
| Q133 | H | COOEt | G3 |
| Q134 | H | COOEt | G3 |
| Q135 | H | COOEt | Gc |
| Q136 | H | COOEt | G3 |
| Q137 | H | COOEt | G1 |
| Q138 | H | COOEt | Gc |
| CH₂ - Q138 | H | COOEt | G3 |
| Q139 | H | COOEt | G3 |
| Q140 | H | COOEt | G1 |
| Q141 | H | COOEt | G3 |
| Q142 | H | COOEt | Gc |
| Q143 | H | COOEt | Gc |
| CH₂ - Q143 | H | COOEt | G3 |
| Q144 | H | COOEt | G3 |
| Q145 | H | COOEt | Gc |
| Q146 | H | COOEt | Gc |
| Q147 | H | COOEt | G3 |
| Q148 | H | COOEt | G1 |
| Q149 | H | COOEt | G3 |
| Q150 | H | COOEt | G3 |
| Q151 | H | COOEt | G2 |
| Q152 | H | COOEt | G1 |
| Q153 | H | COOEt | Gc |
| Q154 | H | COOEt | Gc |
| Q155 | H | COOEt | G3 |
| Q156 | H | COOEt | G3 |
| Q157 | H | COOEt | Gc |
| Q158 | H | COOEt | Ga |
| CH₂ - Q158 | H | COOEt | G3 |
| CHMe - Q158 | H | COOEt | G3 |
| Q159 | H | COOEt | G3 |
| Q160 | H | COOEt | Gc |
| Q161 | H | COOEt | Gc |
| Q162 | H | COOEt | Gc |
| Q163 | H | COOEt | G3 |
| Q164 | H | COOEt | Gc |
| Q165 | H | COOEt | Gc |
| Q166 | H | COOEt | Gc |
| Q167 | H | COOEt | G3 |
| Q168 | H | COOEt | G3 |
| Q169 | H | COOEt | Gc |
| CH₂ - Q169 | H | COOEt | G3 |
| CHMe - Q169 | H | COOEt | G3 |
| Q170 | H | COOEt | Gc |
| Q171 | H | COOEt | Gc |
| Q172 | H | COOEt | Gc |
| Q173 | H | COOEt | Gc |
| Q174 | H | COOEt | Gc |
| Q175 | H | COOEt | Gc |
| Q176 | H | COOEt | Gc |
| Q177 | H | COOEt | Gc |
| CH₂ - Q177 | H | COOEt | G3 |
| CHMe - Q177 | H | COOEt | G3 |
| Q178 | H | COOEt | G3 |
| Q179 | H | COOEt | G3 |
| Q180 | H | COOEt | Gc |
| CH₂ - Q180 | H | COOEt | G3 |
| Q181 | H | COOEt | G1 |
| Q182 | H | COOEt | G3 |
| Q183 | H | COOEt | G3 |
| Q184 | H | COOEt | Gc |
| CH₂ - Q184 | H | COOEt | G3 |
| CHMe - Q184 | H | COOEt | G3 |
| Q185 | H | COOEt | G3 |
| Q186 | H | COOEt | G3 |
| Q187 | H | COOEt | G3 |
| Q188 | H | COOEt | Gb |
| Q189 | H | COOEt | Gb |
| Q5 | H | COOPr—i | G3 |
| Q26 | H | COOPr—i | G3 |
| Q61 | H | COOPr—i | G3 |

TABLE 3-continued

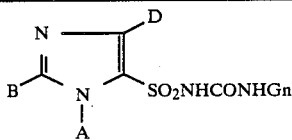

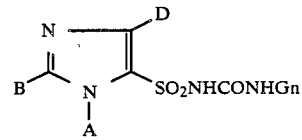

| A | B | D | Gn |
|---|---|---|---|
| Q158 | H | COOPr—i | G3 |
| Q5 | H | COOCH₂CH₂Cl | G3 |
| Q26 | H | COOCH₂CH₂Cl | G3 |
| Q61 | H | COOCH₂CH₂Cl | G3 |
| Q158 | H | COOCH₂CH₂Cl | G3 |
| Q189 | H | COOCH₂CH₂Cl | G3 |
| Q5 | H | COOCH₂CH=CH₂ | G3 |
| Q26 | H | COOCH₂CH=CH₂ | G3 |
| Q61 | H | COOCH₂CH=CH₂ | G3 |
| Q158 | H | COOCH₂CH=CH₂ | G3 |
| Q5 | H | COOCH₂C≡CH | G3 |
| Q26 | H | COOCH₂C≡CH | G3 |
| Q61 | H | COOCH₂C≡CH | G3 |
| Q158 | H | COOCH₂C≡CH | G3 |
| Q1 | H | COOPr—i | G3 |
| Q2 | H | COOCH₂CH₂Cl | G3 |
| Q4 | H | COOCH₂CH=CH₂ | G3 |
| Q7 | H | COOCH₂C≡CH | G3 |
| Q9 | H | COOPr—i | G3 |
| Q10 | H | COOCH₂CH₂Cl | G3 |
| Q19 | H | COOPr—i | G3 |
| Q23 | H | COOCH₂CH=CH₂ | G3 |
| Q32 | H | COOCH₂C≡CH | G3 |
| Q41 | H | COOPr—i | G3 |
| Q45 | H | COOCH₂CH₂Cl | G3 |
| Q50 | H | COOCH₂C≡CH | G3 |
| Q69 | H | COOPr—i | G3 |
| Q79 | H | COOCH₂CH₂Cl | G3 |
| Q83 | H | COOCH₂C≡CH | G3 |
| Q96 | H | COOPr—i | G3 |
| Q124 | H | COOCH₂CH₂Cl | G3 |
| Q131 | H | COOCH₂CH=CH₂ | G3 |
| Q132 | H | COOCH₂C≡CH | G3 |
| Q135 | H | COOPr—i | G3 |
| Q138 | H | COOPr—i | G3 |
| Q142 | H | COOCH₂CH=CH₂ | G3 |
| Q157 | H | COOPr—i | G3 |
| Q159 | H | COOCH₂CH₂Cl | G3 |
| Q177 | H | COOCH₂CH=CH₂ | G3 |
| Q180 | H | COOCH₂C≡CH | G3 |
| Q184 | H | COOPr—i | G3 |
| Q5 | H | COOH | G3 |
| Q26 | H | COOH | G3 |
| Q61 | H | COOH | G3 |
| Q158 | H | COOH | G3 |
| Q5 | H | CONHMe | G3 |
| Q26 | H | CONHMe | G3 |
| Q61 | H | CONHMe | G3 |
| Q158 | H | CONHMe | G3 |
| Q5 | H | CONMe₂ | G3 |
| Q26 | H | CONMe₂ | G3 |
| Q61 | H | CONMe₂ | G3 |
| Q158 | H | CONMe₂ | G3 |
| Q5 | H | COMe | G3 |
| Q26 | H | COMe | G3 |
| Q61 | H | COMe | G3 |
| Q188 | H | COMe | Gb |
| Q189 | H | COMe | Gb |
| Q158 | H | COMe | G3 |
| Q5 | H | COEt | G3 |
| Q26 | H | COEt | G3 |
| Q61 | H | COEt | G3 |
| Q158 | H | COEt | G3 |
| Q188 | H | COEt | Gb |
| Q189 | H | COEt | Gb |
| Q5 | H | COPr—i | G3 |
| Q26 | H | COPr—i | G3 |
| Q61 | H | COPr—i | G3 |
| Q158 | H | COPr—i | G3 |
| Q5 | H | COPh | G3 |
| Q26 | H | COPh | G3 |
| Q61 | H | COPh | G3 |
| Q158 | H | COPh | G3 |
| Q1 | H | COMe | G3 |
| Q2 | H | COMe | G3 |
| Q4 | H | COMe | G3 |
| Q7 | H | COMe | G3 |
| Q9 | H | COEt | G3 |
| Q10 | H | COPr—i | G3 |
| Q19 | H | COPh | G3 |
| Q23 | H | COMe | G3 |
| Q32 | H | COMe | G3 |
| Q41 | H | COPr—i | G3 |
| Q45 | H | COPh | G3 |
| Q50 | H | COMe | G3 |
| Q69 | H | COEt | G3 |
| Q79 | H | COPr—i | G3 |
| Q83 | H | COPh | G3 |
| Q96 | H | COMe | G3 |
| Q124 | H | COEt | G3 |
| Q131 | H | COMe | G3 |
| Q132 | H | COMe | G3 |
| Q135 | H | COEt | G3 |
| Q138 | H | COPr—i | G3 |
| Q142 | H | COPh | G3 |
| Q157 | H | COMe | G3 |
| Q159 | H | COEt | G3 |
| Q177 | H | COMe | G3 |
| Q180 | H | COMe | G3 |
| Q184 | H | COPr—i | G3 |
| Q4 | H | CN | G3 |
| Q5 | H | CN | G3 |
| Q7 | H | CN | G3 |
| Q9 | H | CN | G3 |
| Q23 | H | CN | G3 |
| Q26 | H | CN | G3 |
| Q32 | H | CN | G3 |
| Q61 | H | CN | G3 |
| Q96 | H | CN | G3 |
| Q142 | H | CN | G3 |
| Q158 | H | CN | G3 |
| Q5 | H | H | G3 |
| Q26 | H | H | G3 |
| Q61 | H | H | G3 |
| Q158 | H | H | G3 |
| Q5 | H | Me | G3 |
| Q26 | H | Me | G3 |
| Q61 | H | Me | G3 |
| Q158 | H | Me | G3 |
| Q5 | H | Et | G3 |
| Q26 | H | Et | G3 |
| Q61 | H | Et | G3 |
| Q158 | H | Et | G3 |
| Q5 | H | Pr—i | G3 |
| Q26 | H | Pr—i | G3 |
| Q61 | H | Pr—i | G3 |
| Q158 | H | Pr—i | G3 |
| Q5 | H | CH=CH₂ | G3 |
| Q26 | H | CH=CH₂ | G3 |
| Q61 | H | CH=CHMe | G3 |
| Q158 | H | CH=CHMe | G3 |
| Q5 | H | CH₂CH=CH₂ | G3 |
| Q26 | H | CH₂CH=CH₂ | G3 |
| Q61 | H | CH₂CH=CH₂ | G3 |
| Q158 | H | CH₂CH=CH₂ | G3 |
| Q1 | H | H | G3 |
| Q2 | H | Me | G3 |
| Q4 | H | Me | G3 |
| Q7 | H | Me | G3 |
| Q9 | H | Et | G3 |
| Q10 | H | Pr—i | G3 |
| Q19 | H | Me | G3 |
| Q23 | H | CH₂CH=CH₂ | G3 |
| Q32 | H | H | G3 |
| Q41 | H | Me | G3 |
| Q45 | H | Me | G3 |

TABLE 3-continued

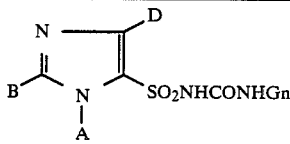

| A | B | D | Gn |
|---|---|---|---|
| Q50 | H | Et | G3 |
| Q69 | H | Pr—i | G3 |
| Q79 | H | Me | G3 |
| Q83 | H | Et | G3 |
| Q96 | H | Me | G3 |
| Q124 | H | Et | G3 |
| Q131 | H | Me | G3 |
| Q132 | H | CH$_2$CH=CH$_2$ | G3 |
| Q135 | H | Et | G3 |
| Q138 | H | Pr—i | G3 |
| Q142 | H | H | G3 |
| Q157 | H | Me | G3 |
| Q159 | H | Me | G3 |
| Q177 | H | H | G3 |
| Q180 | H | Me | G3 |
| Q184 | H | Me | G3 |
| Q5 | H | CH$_2$Cl | G3 |
| Q26 | H | CH$_2$Cl | G3 |
| Q61 | H | CH$_2$Cl | G3 |
| Q158 | H | CH$_2$Cl | G3 |
| Q5 | H | CH$_2$CH$_2$Cl | G3 |
| Q26 | H | CH$_2$CH$_2$Cl | G3 |
| Q61 | H | CH$_2$CH$_2$Cl | G3 |
| Q158 | H | CH$_2$CH$_2$Cl | G3 |
| Q5 | H | CF$_3$ | G3 |
| Q26 | H | CF$_3$ | G3 |
| Q61 | H | CF$_3$ | G3 |
| Q158 | H | CF$_3$ | G3 |
| Q5 | H | CF=CFCl | G3 |
| Q26 | H | CF=CFCl | G3 |
| Q61 | H | CH$_2$Ph | G3 |
| Q158 | H | CH$_2$Ph | G3 |
| Q5 | H | Ph | G3 |
| Q26 | H | Ph | G3 |
| Q61 | H | Ph | G3 |
| Q158 | H | Ph | G3 |
| Q5 | H | Ph—2-Cl | G3 |
| Q26 | H | Ph—2-Me | G3 |
| Q61 | H | Ph—2-Cl | G3 |
| Q158 | H | Ph—2-Me | G3 |
| Q1 | H | Ph | G3 |
| Q2 | H | CH$_2$Cl | G3 |
| Q4 | H | CH$_2$CH$_2$Cl | G3 |
| Q7 | H | Ph | G3 |
| Q9 | H | CF$_3$ | G3 |
| Q10 | H | CF$_3$ | G3 |
| Q19 | H | CF=CFCl | G3 |
| Q23 | H | CH$_2$CH$_2$Cl | G3 |
| Q32 | H | Ph | G3 |
| Q41 | H | Ph—2-Cl | G3 |
| Q45 | H | Ph—2-Me | G3 |
| Q50 | H | CH$_2$CH$_2$Cl | G3 |
| Q69 | H | Ph | G3 |
| Q79 | H | CF$_3$ | G3 |
| Q83 | H | CF$_3$ | G3 |
| Q96 | H | Ph | G3 |
| Q124 | H | Ph—2-Cl | G3 |
| Q131 | H | Ph—2-Me | G3 |
| Q132 | H | CH$_2$CH$_2$Cl | G3 |
| Q135 | H | Ph | G3 |
| Q138 | H | CF$_3$ | G3 |
| Q142 | H | CF$_3$ | G3 |
| Q157 | H | CF=CFCl | G3 |
| Q159 | H | CH$_2$Cl | G3 |
| Q177 | H | CH$_2$CH$_2$Cl | G3 |
| Q180 | H | Ph | G3 |
| Q184 | H | Ph—2-Cl | G3 |
| Q5 | H | Cl | G3 |
| Q26 | H | Cl | G3 |
| Q61 | H | Cl | G3 |
| Q158 | H | Cl | G3 |
| Q5 | H | Br | G3 |
| Q26 | H | Br | G3 |

TABLE 3-continued

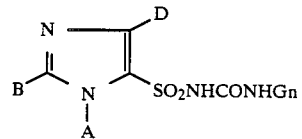

| A | B | D | Gn |
|---|---|---|---|
| Q61 | H | Br | G3 |
| Q158 | H | Br | G3 |
| Q5 | H | F | G3 |
| Q26 | H | F | G3 |
| Q61 | H | I | G3 |
| Q158 | H | I | G3 |
| Q1 | H | Cl | G3 |
| Q2 | H | Cl | G3 |
| Q4 | H | Cl | G3 |
| Q7 | H | Br | G3 |
| Q9 | H | F | G3 |
| Q10 | H | I | G3 |
| Q19 | H | Cl | G3 |
| Q23 | H | Cl | G3 |
| Q32 | H | Cl | G3 |
| Q41 | H | Br | G3 |
| Q45 | H | Br | G3 |
| Q50 | H | F | G3 |
| Q69 | H | Cl | G3 |
| Q79 | H | F | G3 |
| Q83 | H | Cl | G3 |
| Q96 | H | Cl | G3 |
| Q124 | H | Cl | G3 |
| Q131 | H | Br | G3 |
| Q132 | H | Br | G3 |
| Q135 | H | F | G3 |
| Q138 | H | Br | G3 |
| Q142 | H | Cl | G3 |
| Q157 | H | Cl | G3 |
| Q159 | H | Cl | G3 |
| Q177 | H | Br | G3 |
| Q180 | H | Br | G3 |
| Q184 | H | Cl | G3 |
| Q4 | H | NO$_2$ | G3 |
| Q5 | H | NO$_2$ | G3 |
| Q7 | H | NO$_2$ | G3 |
| Q9 | H | NO$_2$ | G3 |
| Q23 | H | NO$_2$ | G3 |
| Q26 | H | NO$_2$ | G3 |
| Q32 | H | NO$_2$ | G3 |
| Q61 | H | NO$_2$ | G3 |
| Q96 | H | NO$_2$ | G3 |
| Q142 | H | NO$_2$ | G3 |
| Q158 | H | NO$_2$ | G3 |
| Q5 | H | NH$_2$ | G3 |
| Q26 | H | NH$_2$ | G3 |
| Q61 | H | NH$_2$ | G3 |
| Q158 | H | NH$_2$ | G3 |
| Q5 | H | NHMe | G3 |
| Q26 | H | NHMe | G3 |
| Q61 | H | NHMe | G3 |
| Q158 | H | NHMe | G3 |
| Q5 | H | NMe$_2$ | G3 |
| Q26 | H | NMe$_2$ | G3 |
| Q61 | H | NMe$_2$ | G3 |
| Q158 | H | NMe$_2$ | G3 |
| Q5 | H | NMeEt | G3 |
| Q26 | H | NMeEt | G3 |
| Q61 | H | NMeEt | G3 |
| Q158 | H | NMeEt | G3 |
| Q5 | H | NHSO$_2$Me | G3 |
| Q26 | H | NHSO$_2$Me | G3 |
| Q61 | H | NHSO$_2$Me | G3 |
| Q158 | H | NHSO$_2$Me | G3 |
| Q1 | H | NH$_2$ | G3 |
| Q2 | H | NH$_2$ | G3 |
| Q4 | H | NH$_2$ | G3 |
| Q7 | H | NHMe | G3 |
| Q9 | H | NHMe | G3 |
| Q10 | H | NMe$_2$ | G3 |
| Q19 | H | NMeEt | G3 |
| Q23 | H | NMe$_2$ | G3 |
| Q32 | H | NMeEt | G3 |

TABLE 3-continued

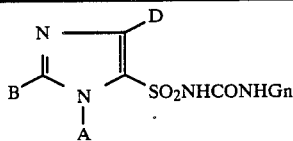
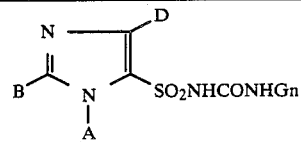

| A | B | D | Gn | A | B | D | Gn |
|---|---|---|---|---|---|---|---|
| Q41 | H | NH₂ | G3 | Q138 | H | SMe | G3 |
| Q45 | H | NH₂ | G3 | Q142 | H | SO₂OMe | G3 |
| Q50 | H | NHMe | G3 | Q157 | H | OMe | G3 |
| Q69 | H | NHMe | G3 | Q159 | H | OEt | G3 |
| Q79 | H | NMe₂ | G3 | Q177 | H | SO₂OMe | G3 |
| Q83 | H | NMeEt | G3 | Q180 | H | OMe | G3 |
| Q96 | H | NHSO₂Me | G3 | Q184 | H | OEt | G3 |
| Q124 | H | NMe₂ | G3 | Q4 | H | SO₂Me | G3 |
| Q131 | H | NMeEt | G3 | Q5 | H | SO₂Me | G3 |
| Q132 | H | NH₂ | G3 | Q7 | H | SO₂Me | G3 |
| Q135 | H | NH₂ | G3 | Q9 | H | SO₂Me | G3 |
| Q138 | H | NHMe | G3 | Q23 | H | SO₂Me | G3 |
| Q142 | H | NHMe | G3 | Q26 | H | SO₂Me | G3 |
| Q157 | H | NHSO₂Me | G3 | Q32 | H | SO₂Me | G3 |
| Q159 | H | NMe₂ | G3 | Q61 | H | SO₂Me | G3 |
| Q177 | H | NMeEt | G3 | Q96 | H | SO₂Me | G3 |
| Q180 | H | NH₂ | G3 | Q142 | H | SO₂Me | G3 |
| Q184 | H | NH₂ | G3 | Q158 | H | SO₂Me | G3 |
| Q4 | H | NHCOMe | G3 | Q188 | H | SO₂Me | Gb |
| Q5 | H | NHCOMe | G3 | Q189 | H | SO₂Me | Gb |
| Q7 | H | NHCOMe | G3 | Q5 | H | SO₂Ph | G3 |
| Q9 | H | NHCOMe | G3 | Q26 | H | SO₂Ph | G3 |
| Q23 | H | NHCOMe | G3 | Q61 | H | SO₂Ph | G3 |
| Q26 | H | NHCOMe | G3 | Q158 | H | SO₂Ph | G3 |
| Q32 | H | NHCOMe | G3 | Q5 | H | SO₂NH₂ | G3 |
| Q61 | H | NHCOMe | G3 | Q26 | H | SO₂NH₂ | G3 |
| Q96 | H | NHCOMe | G3 | Q61 | H | SO₂NH₂ | G3 |
| Q142 | H | NHCOMe | G3 | Q158 | H | SO₂NH₂ | G3 |
| Q158 | H | NHCOMe | G3 | Q5 | H | SO₂NHMe | G3 |
| Q5 | H | NHCOEt | G3 | Q26 | H | SO₂NHMe | G3 |
| Q26 | H | NHCOEt | G3 | Q61 | H | SO₂NHMe | G3 |
| Q61 | H | NHCOEt | G3 | Q158 | H | SO₂NHMe | G3 |
| Q158 | H | NHCOEt | G3 | Q5 | H | SO₂NMe₂ | G3 |
| Q5 | H | OMe | G3 | Q26 | H | SO₂NMe₂ | G3 |
| Q26 | H | OMe | G3 | Q61 | H | SO₂NMe₂ | G3 |
| Q61 | H | OMe | G3 | Q158 | H | SO₂NMe₂ | G3 |
| Q158 | H | OMe | G3 | Q188 | H | SO₂NMe₂ | Gb |
| Q5 | H | OEt | G3 | Q189 | H | SO₂NMe₂ | Gb |
| Q26 | H | OEt | G3 | Q1 | H | SO₂Me | G3 |
| Q61 | H | OEt | G3 | Q2 | H | SO₂Me | G3 |
| Q158 | H | OEt | G3 | Q4 | H | SO₂NH₂ | G3 |
| Q5 | H | CH₂OMe | G3 | Q7 | H | SO₂NH₂ | G3 |
| Q26 | H | CH₂OMe | G3 | Q9 | H | SO₂NH₂ | G3 |
| Q61 | H | CH₂OMe | G3 | Q10 | H | SO₂Ph | G3 |
| Q158 | H | CH₂OMe | G3 | Q19 | H | SO₂Me | G3 |
| Q5 | H | SMe | G3 | Q23 | H | SO₂Ph | G3 |
| Q26 | H | SMe | G3 | Q32 | H | SO₂NHMe | G3 |
| Q61 | H | SMe | G3 | Q41 | H | SO₂NMe₂ | G3 |
| Q158 | H | SMe | G3 | Q45 | H | SO₂Me | G3 |
| Q5 | H | SO₂OMe | G3 | Q50 | H | SO₂NH₂ | G3 |
| Q26 | H | SO₂OMe | G3 | Q69 | H | SO₂Me | G3 |
| Q61 | H | SO₂OMe | G3 | Q79 | H | SO₂Ph | G3 |
| Q158 | H | SO₂OMe | G3 | Q83 | H | SO₂Me | G3 |
| Q1 | H | OMe | G3 | Q96 | H | SO₂NMe₂ | G3 |
| Q2 | H | OMe | G3 | Q124 | H | SO₂NH₂ | G3 |
| Q4 | H | OEt | G3 | Q131 | H | SO₂Me | G3 |
| Q7 | H | SO₂OMe | G3 | Q132 | H | SO₂Me | G3 |
| Q9 | H | CH₂OMe | G3 | Q135 | H | SO₂NHMe | G3 |
| Q10 | H | SMe | G3 | Q138 | H | SO₂NMe₂ | G3 |
| Q19 | H | SO₂OMe | G3 | Q142 | H | SO₂NH₂ | G3 |
| Q23 | H | OMe | G3 | Q157 | H | SO₂Me | G3 |
| Q32 | H | OEt | G3 | Q159 | H | SO₂Me | G3 |
| Q41 | H | SO₂OMe | G3 | Q177 | H | SO₂NHMe | G3 |
| Q45 | H | CH₂OMe | G3 | Q180 | H | SO₂NHMe₂ | G3 |
| Q50 | H | SMe | G3 | Q184 | H | SO₂Me | G3 |
| Q69 | H | SO₂OMe | G3 | Q1 | Me | COOMe | G3 |
| Q79 | H | OMe | G3 | Q2 | Me | COOMe | G3 |
| Q83 | H | OEt | G3 | Q4 | Me | COOMe | G3 |
| Q96 | H | CH₂OMe | G3 | Q5 | Me | COOMe | G3 |
| Q124 | H | SMe | G3 | Q7 | Me | COOMe | G3 |
| Q131 | H | OMe | G3 | Q9 | Me | COOMe | G3 |
| Q132 | H | OEt | G3 | Q10 | Me | COOMe | G3 |
| Q135 | H | CH₂OMe | G3 | Q19 | Me | COOMe | G3 |

TABLE 3-continued

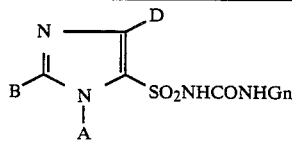

| A | B | D | Gn |
|---|---|---|---|
| Q23 | Me | COOMe | G3 |
| Q26 | Me | COOMe | G3 |
| Q32 | Me | COOMe | G3 |
| Q41 | Me | COOMe | G3 |
| Q45 | Me | COOMe | G3 |
| Q50 | Me | COOMe | G3 |
| Q61 | Me | COOMe | G3 |
| Q69 | Me | COOMe | G3 |
| Q79 | Me | COOMe | G3 |
| Q83 | Me | COOMe | G3 |
| Q96 | Me | COOMe | G3 |
| Q124 | Me | COOMe | G3 |
| Q131 | Me | COOMe | G3 |
| Q132 | Me | COOMe | G3 |
| Q135 | Me | COOMe | G3 |
| Q138 | Me | COOMe | G3 |
| Q142 | Me | COOMe | G3 |
| Q157 | Me | COOMe | G3 |
| Q158 | Me | COOMe | G3 |
| Q159 | Me | COOMe | G3 |
| Q177 | Me | COOMe | G3 |
| Q180 | Me | COOMe | G3 |
| Q184 | Me | COOMe | G3 |
| Q1 | Me | COOEt | G3 |
| Q2 | Me | COOEt | G3 |
| Q4 | Me | COOEt | G3 |
| Q5 | Me | COOEt | G3 |
| Q7 | Me | COOEt | G3 |
| Q9 | Me | COOEt | G3 |
| Q10 | Me | COOEt | G3 |
| Q19 | Me | COOEt | G3 |
| Q23 | Me | COOEt | G3 |
| Q26 | Me | COOEt | G3 |
| Q32 | Me | COOEt | G3 |
| Q41 | Me | COOEt | G3 |
| Q45 | Me | COOEt | G3 |
| Q50 | Me | COOEt | G3 |
| Q61 | H | COOEt | G3 |
| Q69 | Me | COOEt | G3 |
| Q79 | Me | COOEt | G3 |
| Q83 | Me | COOEt | G3 |
| Q96 | Me | COOEt | G3 |
| Q124 | Me | COOEt | G3 |
| Q131 | Me | COOEt | G3 |
| Q132 | Me | COOEt | G3 |
| Q135 | Me | COOEt | G3 |
| Q138 | Me | COOEt | G3 |
| Q142 | Me | COOEt | G3 |
| Q157 | Me | COOEt | G3 |
| Q158 | Me | COOEt | G3 |
| Q159 | Me | COOEt | G3 |
| Q177 | Me | COOEt | G3 |
| Q180 | Me | COOEt | G3 |
| Q184 | Me | COOEt | G3 |
| Q158 | Me | COOEt | G3 |
| Q5 | Me | COOPr—i | G3 |
| Q26 | Me | COOPr—i | G3 |
| Q61 | Me | COOPr—i | G3 |
| Q158 | Me | COOPr—i | G3 |
| Q5 | Me | COOCH$_2$CH$_2$Cl | G3 |
| Q26 | Me | COOCH$_2$CH$_2$Cl | G3 |
| Q61 | Me | COOCH$_2$CH$_2$Cl | G3 |
| Q158 | Me | COOCH$_2$CH$_2$Cl | G3 |
| Q5 | Me | COOCH$_2$CH=CH$_2$ | G3 |
| Q26 | Me | COOCH$_2$CH=CH$_2$ | G3 |
| Q61 | Me | COOCH$_2$CH=CH$_2$ | G3 |
| Q158 | Me | COOCH$_2$CH=CH$_2$ | G3 |
| Q5 | Me | COOCH$_2$C≡CH | G3 |
| Q26 | Me | COOCH$_2$C≡CH | G3 |
| Q61 | Me | COOCH$_2$C≡CH | G3 |
| Q158 | Me | COOCH$_2$C≡CH | G3 |
| Q5 | Me | CONHMe | G3 |
| Q26 | Me | CONHMe | G3 |
| Q61 | Me | CONHMe | G3 |
| Q158 | Me | CONHMe | G3 |
| Q5 | Me | CONMe$_2$ | G3 |
| Q26 | Me | CONMe$_2$ | G3 |
| Q61 | Me | CONMe$_2$ | G3 |
| Q158 | Me | CONMe$_2$ | G3 |
| Q1 | Me | COOPr—i | G3 |
| Q2 | Me | COOPr—i | G3 |
| Q4 | Me | COOCH$_2$CH$_2$Cl | G3 |
| Q7 | Me | COOCH$_2$CH=CH$_2$ | G3 |
| Q9 | Me | COOCH$_2$C≡CH | G3 |
| Q10 | Me | COOCH$_2$CH$_2$Cl | G3 |
| Q19 | Me | COOPr—i | G3 |
| Q23 | Me | COOCH$_2$CH$_2$Cl | G3 |
| Q32 | Me | CONMe$_2$ | G3 |
| Q41 | Me | COOPr—i | G3 |
| Q45 | Me | CONHMe | G3 |
| Q50 | Me | CONMe$_2$ | G3 |
| Q69 | Me | COOCH$_2$CH$_2$Cl | G3 |
| Q79 | Me | COOCH$_2$CH=CH$_2$ | G3 |
| Q83 | Me | COOPr—i | G3 |
| Q96 | Me | COOCH$_2$CH$_2$Cl | G3 |
| Q124 | Me | COOPr—i | G3 |
| Q131 | Me | COOCH$_2$CH$_2$Cl | G3 |
| Q132 | Me | CONHMe | G3 |
| Q135 | Me | CONMe$_2$ | G3 |
| Q138 | Me | COOCH$_2$C≡CH | G3 |
| Q142 | Me | COOPr—i | G3 |
| Q157 | Me | COOPr—i | G3 |
| Q159 | Me | COOCH$_2$CH=CH$_2$ | G3 |
| Q177 | Me | COOCH$_2$C≡CH | G3 |
| Q180 | Me | COOPr—i | G3 |
| Q184 | Me | COOCH$_2$CH$_2$Cl | G3 |
| Q5 | Me | COMe | G3 |
| Q26 | Me | COMe | G3 |
| Q61 | Me | COMe | G3 |
| Q158 | Me | COMe | G3 |
| Q5 | Me | COEt | G3 |
| Q26 | Me | COEt | G3 |
| Q61 | Me | COEt | G3 |
| Q158 | Me | COEt | G3 |
| Q5 | Me | COPr—i | G3 |
| Q26 | Me | COPr—i | G3 |
| Q61 | Me | COPr—i | G3 |
| Q158 | Me | COPr—i | G3 |
| Q5 | Me | CN | G3 |
| Q26 | Me | CN | G3 |
| Q61 | Me | CN | G3 |
| Q158 | Me | CN | G3 |
| Q5 | Me | H | G3 |
| Q26 | Me | H | G3 |
| Q61 | Me | H | G3 |
| Q158 | Me | H | G3 |
| Q5 | Me | Me | G3 |
| Q26 | Me | Me | G3 |
| Q61 | Me | Me | G3 |
| Q158 | Me | Me | G3 |
| Q5 | Me | Et | G3 |
| Q26 | Me | Et | G3 |
| Q61 | Me | Et | G3 |
| Q158 | Me | Et | G3 |
| Q5 | Me | Pr—i | G3 |
| Q26 | Me | Pr—i | G3 |
| Q61 | Me | CH=CH$_2$ | G3 |
| Q158 | Me | CH=CH$_2$ | G3 |
| Q5 | Me | CH=CHMe | G3 |
| Q26 | Me | CH$_2$CH=CH$_2$ | G3 |
| Q61 | Me | CH=CHMe | G3 |
| Q158 | Me | CH$_2$CH=CH$_2$ | G3 |
| Q1 | Me | COMe | G3 |
| Q2 | Me | COEt | G3 |
| Q4 | Me | CH=CHMe | G3 |
| Q7 | Me | CH$_2$CH=CH$_2$ | G3 |

TABLE 3-continued

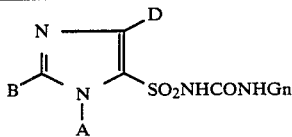

| A | B | D | Gn |
|---|---|---|---|
| Q9 | Me | CN | G3 |
| Q10 | Me | H | G3 |
| Q19 | Me | Me | G3 |
| Q23 | Me | COMe | G3 |
| Q32 | Me | COEt | G3 |
| Q41 | Me | H | G3 |
| Q45 | Me | Me | G3 |
| Q50 | Me | COPr—i | G3 |
| Q69 | Me | CN | G3 |
| Q79 | Me | Et | G3 |
| Q83 | Me | Pr—i | G3 |
| Q96 | Me | COMe | G3 |
| Q124 | Me | COEt | G3 |
| Q131 | Me | CH$_2$CH=CH$_2$ | G3 |
| Q132 | Me | Me | G3 |
| Q135 | Me | COPr-i | G3 |
| Q138 | Me | CN | G3 |
| Q142 | Me | Et | G3 |
| Q157 | Me | CH$_2$CH=CH$_2$ | G3 |
| Q159 | Me | COMe | G3 |
| Q177 | Me | COEt | G3 |
| Q180 | Me | CH=CHMe | G3 |
| Q184 | Me | COMe | G3 |
| Q5 | Me | CH$_2$Cl | G3 |
| Q26 | Me | CH$_2$Cl | G3 |
| Q5 | Me | CH$_2$CH$_2$Cl | G3 |
| Q26 | Me | CH$_2$CH$_2$Cl | G3 |
| Q61 | Me | CH$_2$CH$_2$Cl | G3 |
| Q158 | Me | CH$_2$CH$_2$Cl | G3 |
| Q5 | Me | CF$_3$ | G3 |
| Q26 | Me | CF$_3$ | G3 |
| Q61 | Me | CF$_3$ | G3 |
| Q158 | Me | CF$_3$ | G3 |
| Q5 | Me | CF=CFCl | G3 |
| Q26 | Me | CF=CFCl | G3 |
| Q61 | Me | CH$_2$Ph | G3 |
| Q158 | Me | CH$_2$Ph | G3 |
| Q5 | Me | Ph | G3 |
| Q26 | Me | Ph | G3 |
| Q61 | Me | Ph | G3 |
| Q158 | Me | Ph | G3 |
| Q5 | Me | Ph—2-Cl | G3 |
| Q26 | Me | Ph—2-Cl | G3 |
| Q61 | Me | Ph—2-Me | G3 |
| Q158 | Me | Ph—2-Me | G3 |
| Q5 | Me | Cl | G3 |
| Q26 | Me | Cl | G3 |
| Q61 | Me | Cl | G3 |
| Q158 | Me | Cl | G3 |
| Q5 | Me | Br | G3 |
| Q26 | Me | Br | G3 |
| Q61 | Me | Br | G3 |
| Q158 | Me | Br | G3 |
| Q5 | Me | F | G3 |
| Q26 | Me | F | G3 |
| Q61 | Me | I | G3 |
| Q158 | Me | I | G3 |
| Q1 | Me | Ph | G3 |
| Q2 | Me | Cl | G3 |
| Q4 | Me | CH$_2$CH$_2$Cl | G3 |
| Q7 | Me | Ph | G3 |
| Q9 | Me | Ph | G3 |
| Q10 | Me | Cl | G3 |
| Q19 | Me | Cl | G3 |
| Q23 | Me | Br | G3 |
| Q32 | Me | CH$_2$Cl | G3 |
| Q41 | Me | CH$_2$CH$_2$Cl | G3 |
| Q45 | Me | CF$_3$ | G3 |
| Q50 | Me | Cl | G3 |
| Q69 | Me | Cl | G3 |
| Q79 | Me | Br | G3 |
| Q83 | Me | Ph | G3 |
| Q96 | Me | CF$_3$ | G3 |
| Q124 | Me | CF$_3$ | G3 |
| Q131 | Me | CH$_2$CH$_2$Cl | G3 |
| Q132 | Me | Ph | G3 |
| Q135 | Me | Br | G3 |
| Q138 | Me | Ph | G3 |
| Q142 | Me | Ph | G3 |
| Q157 | Me | Cl | G3 |
| Q159 | Me | Br | G3 |
| Q177 | Me | CF$_3$ | G3 |
| Q180 | Me | CH$_2$CH$_2$Cl | G3 |
| Q184 | Me | Ph | G3 |
| Q5 | Me | NO$_2$ | G3 |
| Q26 | Me | NO$_2$ | G3 |
| Q61 | Me | NO$_2$ | G3 |
| Q158 | Me | NO$_2$ | G3 |
| Q5 | Me | NH$_2$ | G3 |
| Q26 | Me | NH$_2$ | G3 |
| Q61 | Me | NH$_2$ | G3 |
| Q158 | Me | NH$_2$ | G3 |
| Q5 | Me | NHMe | G3 |
| Q26 | Me | NHMe | G3 |
| Q61 | Me | NHMe | G3 |
| Q158 | Me | NHMe | G3 |
| Q5 | Me | NMe$_2$ | G3 |
| Q26 | Me | NMe$_2$ | G3 |
| Q61 | Me | NMe$_2$ | G3 |
| Q158 | Me | NMe$_2$ | G3 |
| Q5 | Me | NMeEt | G3 |
| Q26 | Me | NMeEt | G3 |
| Q5 | Me | NHCOMe | G3 |
| Q26 | Me | NHCOMe | G3 |
| Q61 | Me | NHCOMe | G3 |
| Q158 | Me | NHCOMe | G3 |
| Q5 | Me | NHCOEt | G3 |
| Q26 | Me | NHCOEt | G3 |
| Q61 | Me | NHSO$_2$Me | G3 |
| Q158 | Me | NHSO$_2$Me | G3 |
| Q5 | Me | OMe | G3 |
| Q26 | Me | OMe | G3 |
| Q61 | Me | OMe | G3 |
| Q158 | Me | OMe | G3 |
| Q5 | Me | OEt | G3 |
| Q26 | Me | OEt | G3 |
| Q61 | Me | CH$_2$OMe | G3 |
| Q158 | Me | CH$_2$OMe | G3 |
| Q1 | Me | NO$_2$ | G3 |
| Q2 | Me | NHCOMe | G3 |
| Q4 | Me | NHCOEt | G3 |
| Q7 | Me | NHMe | G3 |
| Q9 | Me | NO$_2$ | G3 |
| Q10 | Me | NH$_2$ | G3 |
| Q19 | Me | NHCOMe | G3 |
| Q23 | Me | OMe | G3 |
| Q32 | Me | NHCOMe | G3 |
| Q41 | Me | NHCOEt | G3 |
| Q45 | Me | CH$_2$OMe | G3 |
| Q50 | Me | OMe | G3 |
| Q69 | Me | OEt | G3 |
| Q79 | Me | NO$_2$ | G3 |
| Q83 | Me | NH$_2$ | G3 |
| Q96 | Me | NMe$_2$ | G3 |
| Q124 | Me | NMeEt | G3 |
| Q131 | Me | NHCOMe | G3 |
| Q132 | Me | NHCOEt | G3 |
| Q135 | Me | NO$_2$ | G3 |
| Q138 | Me | OMe | G3 |
| Q142 | Me | OEt | G3 |
| Q157 | Me | NO$_2$ | G3 |
| Q159 | Me | NH$_2$ | G3 |
| Q177 | Me | OMe | G3 |
| Q180 | Me | NHCOMe | G3 |
| Q184 | Me | NO$_2$ | G3 |
| Q26 | Me | SMe | G3 |

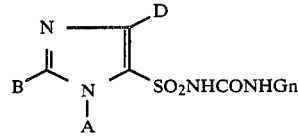

TABLE 3-continued

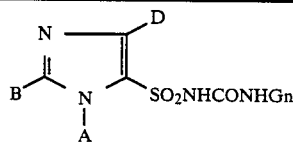

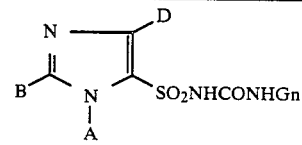

| A | B | D | Gn |
|---|---|---|---|
| Q61 | Me | SMe | G3 |
| Q5 | Me | SO$_2$Me | G3 |
| Q26 | Me | SO$_2$Me | G3 |
| Q61 | Me | SO$_2$Me | G3 |
| Q158 | Me | SO$_2$Me | G3 |
| Q5 | Me | SO$_2$Ph | G3 |
| Q26 | Me | SO$_2$Ph | G3 |
| Q61 | Me | SO$_2$Ph | G3 |
| Q158 | Me | SO$_2$Ph | G3 |
| Q5 | Me | SO$_2$OMe | G3 |
| Q26 | Me | SO$_2$OMe | G3 |
| Q61 | Me | SO$_2$NH$_2$ | G3 |
| Q158 | Me | SO$_2$NH$_2$ | G3 |
| Q5 | Me | SO$_2$NMe | G3 |
| Q26 | Me | SO$_2$NMe | G3 |
| Q61 | Me | SO$_2$NMe | G3 |
| Q158 | Me | SO$_2$NMe | G3 |
| Q5 | Me | SO$_2$NHMe$_2$ | G3 |
| Q26 | Me | SO$_2$NHMe$_2$ | G3 |
| Q61 | Me | SO$_2$NHMe$_2$ | G3 |
| Q158 | Me | SO$_2$NHMe$_2$ | G3 |
| Q1 | Me | SO$_2$Ph | G3 |
| Q2 | Me | SO$_2$OMe | G3 |
| Q4 | Me | SO$_2$NHMe | G3 |
| Q7 | Me | SO$_2$NMe$_2$ | G3 |
| Q9 | Me | SO$_2$Me | G3 |
| Q10 | Me | SO$_2$Me | G3 |
| Q19 | Me | SMe | G3 |
| Q23 | Me | SO$_2$Me | G3 |
| Q32 | Me | SO$_2$OMe | G3 |
| Q41 | Me | SO$_2$NMe$_2$ | G3 |
| Q45 | Me | SO$_2$NHMe | G3 |
| Q50 | Me | SO$_2$NMe$_2$ | G3 |
| Q69 | Me | SO$_2$Me | G3 |
| Q79 | Me | SO$_2$Me | G3 |
| Q83 | Me | SO$_2$Ph | G3 |
| Q96 | Me | SO$_2$OMe | G3 |
| Q124 | Me | SO$_2$NMe$_2$ | G3 |
| Q131 | Me | SO$_2$NHMe | G3 |
| Q132 | Me | SO$_2$NMe$_2$ | G3 |
| Q135 | Me | SO$_2$Ph | G3 |
| Q138 | Me | SO$_2$Ph | G3 |
| Q142 | Me | SO$_2$Me | G3 |
| Q157 | Me | SO$_2$Me | G3 |
| Q159 | Me | SO$_2$NHMe | G3 |
| Q177 | Me | SO$_2$NMe$_2$ | G3 |
| Q180 | Me | SO$_2$NMe$_2$ | G3 |
| Q184 | Me | SO$_2$Me$_2$ | G3 |
| Q5 | Et | COOMe | G3 |
| Q26 | Et | COOMe | G3 |
| Q61 | Et | COOMe | G3 |
| Q142 | Et | COOMe | G3 |
| Q158 | Et | COOMe | G3 |
| Q159 | Et | COOMe | G3 |
| Q4 | Et | COOEt | G3 |
| Q5 | Et | COOEt | G3 |
| Q9 | Et | COOEt | G3 |
| Q26 | Et | COOEt | G3 |
| Q32 | Et | COOEt | G3 |
| Q61 | Et | COOEt | G3 |
| Q69 | Et | COOEt | G3 |
| Q96 | Et | COOEt | G3 |
| Q158 | Et | COOEt | G3 |
| Q61 | Et | COOPr—i | G3 |
| Q158 | Et | COOPr—i | G3 |
| Q5 | Et | COOCH$_2$CH$_2$Cl | G3 |
| Q26 | Et | COOCH$_2$CH$_2$Cl | G3 |
| Q5 | Et | COOCH$_2$CH=CH$_2$ | G3 |
| Q158 | Et | COOCH$_2$CH=CH$_2$ | G3 |
| Q5 | Et | COOCH$_2$C≡CH | G3 |
| Q26 | Et | COOCH$_2$C≡CH | G3 |
| Q5 | Et | CONHMe | G3 |
| Q26 | Et | CONMe$_2$ | G3 |
| Q1 | Et | COOPr—i | G3 |
| Q4 | Et | COOCH$_2$CH$_2$Cl | G3 |
| Q69 | Et | COOCH$_2$CH$_2$Cl | G3 |
| Q79 | Et | COOCH$_2$CH=CH$_2$ | G3 |
| Q83 | Et | COOPr—i | G3 |
| Q96 | Et | COOCH$_2$CH$_2$Cl | G3 |
| Q131 | Et | COOCH$_2$CH$_2$Cl | G3 |
| Q157 | Et | COOPr—i | G3 |
| Q159 | Et | COOCH$_2$CH=CH$_2$ | G3 |
| Q184 | Et | COOCH$_2$CH$_2$Cl | G3 |
| Q5 | Et | COMe | G3 |
| Q26 | Et | COMe | G3 |
| Q158 | Et | COEt | G3 |
| Q5 | Et | COPr—i | G3 |
| Q26 | Et | CN | G3 |
| Q61 | Et | H | G3 |
| Q26 | Et | Me | G3 |
| Q158 | Et | Et | G3 |
| Q5 | Et | Pr—i | G3 |
| Q1 | Et | COMe | G3 |
| Q2 | Et | COEt | G3 |
| Q9 | Et | CN | G3 |
| Q23 | Et | COMe | G3 |
| Q96 | Et | COMe | G3 |
| Q124 | Et | COEt | G3 |
| Q135 | Et | COPr—i | G3 |
| Q138 | Et | CN | G3 |
| Q5 | Et | CH$_2$CH$_2$Cl | G3 |
| Q26 | Et | CH$_2$CH$_2$Cl | G3 |
| Q158 | Et | CF$_3$ | G3 |
| Q5 | Et | Ph | G3 |
| Q26 | Et | Ph | G3 |
| Q158 | Et | Ph—2-Me | G3 |
| Q26 | Et | Cl | G3 |
| Q61 | Et | Cl | G3 |
| Q5 | Et | Br | G3 |
| Q1 | Et | Ph | G3 |
| Q2 | Et | Cl | G3 |
| Q9 | Et | Ph | G3 |
| Q5 | Et | NO$_2$ | G3 |
| Q5 | Et | NH$_2$ | G3 |
| Q5 | Et | NHMe | G3 |
| Q26 | Et | NMe$_2$ | G3 |
| Q61 | Et | NHCOMe | G3 |
| Q158 | Et | NHSO$_2$Me | G3 |
| Q2 | Et | NHCOMe | G3 |
| Q23 | Et | OMe | G3 |
| Q32 | Et | NHCOMe | G3 |
| Q96 | Et | NMe$_2$ | G3 |
| Q26 | Et | SO$_2$Me | G3 |
| Q61 | Et | SO$_2$Me | G3 |
| Q5 | Et | SO$_2$Ph | G3 |
| Q26 | Et | SO$_2$OMe | G3 |
| Q61 | Et | SO$_2$NH$_2$ | G3 |
| Q5 | Et | SO$_2$NHMe | G3 |
| Q26 | Et | SO$_2$NMe$_2$ | G3 |
| Q4 | Et | SO$_2$NHMe | G3 |
| Q7 | Et | SO$_2$NMe$_2$ | G3 |
| Q9 | Et | SO$_2$Me | G3 |
| Q142 | Et | SO$_2$Me | G3 |
| Q159 | Et | SO$_2$NMe$_2$ | G3 |
| Q5 | Cl | COOMe | G3 |
| Q26 | Cl | COOMe | G3 |
| Q61 | Cl | COOMe | G3 |
| Q5 | Cl | COOEt | G3 |
| Q26 | Cl | COOEt | G3 |
| Q61 | Cl | COOEt | G3 |
| Q96 | Cl | COOEt | G3 |
| Q158 | Cl | COOEt | G3 |
| Q61 | Cl | COOPr—i | G3 |
| Q5 | Cl | COMe | G3 |
| Q158 | Cl | COEt | G3 |
| Q5 | Cl | COPr—i | G3 |

TABLE 3-continued

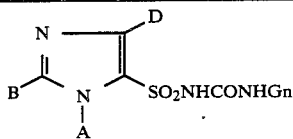

| A | B | D | Gn |
|---|---|---|---|
| Q26 | Cl | CN | G3 |
| Q61 | Cl | H | G3 |
| Q26 | Cl | Me | G3 |
| Q158 | Cl | Et | G3 |
| Q5 | Cl | Pr—i | G3 |
| Q1 | Cl | COMe | G3 |
| Q26 | Cl | CH$_2$CH$_2$Cl | G3 |
| Q158 | Cl | CF$_3$ | G3 |
| Q5 | Cl | Ph | G3 |
| Q26 | Cl | Cl | G3 |
| Q5 | Cl | Br | G3 |
| Q2 | Cl | Cl | G3 |
| Q9 | Cl | Ph | G3 |
| Q5 | Cl | NO$_2$ | G3 |
| Q5 | Cl | NH$_2$ | G3 |
| Q5 | Cl | NHMe | G3 |
| Q26 | Cl | NMe$_2$ | G3 |
| Q61 | Cl | NHCOMe | G3 |
| Q158 | Cl | NHSO$_2$Me | G3 |
| Q2 | Cl | NHCOMe | G3 |
| Q26 | Cl | SO$_2$Me | G3 |
| Q61 | Cl | SO$_2$Me | G3 |
| Q5 | Cl | SO$_2$Ph | G3 |
| Q61 | Cl | SO$_2$NH$_2$ | G3 |
| Q5 | Cl | SO$_2$NHMe | G3 |
| Q26 | Cl | SO$_2$NMe$_2$ | G3 |
| Q5 | Br | COOMe | G3 |
| Q26 | Br | COOMe | G3 |
| Q61 | Br | COOMe | G3 |
| Q5 | Br | COOEt | G3 |
| Q26 | Br | COOEt | G3 |
| Q61 | Br | COOEt | G3 |
| Q61 | Br | COOPr—i | G3 |
| Q5 | Br | COMe | G3 |
| Q158 | Br | COEt | G3 |
| Q26 | Br | CN | G3 |
| Q26 | Br | Me | G3 |
| Q158 | Br | Et | G3 |
| Q26 | Br | CH$_2$CH$_2$Cl | G3 |
| Q158 | Br | CF$_3$ | G3 |
| Q5 | Br | Ph | G3 |
| Q26 | Br | Cl | G3 |
| Q5 | Br | Br | G3 |
| Q5 | Br | NO$_2$ | G3 |
| Q5 | Br | NH$_2$ | G3 |
| Q26 | Br | NMe$_2$ | G3 |
| Q61 | Br | NHCOMe | G3 |
| Q61 | Br | SO$_2$Me | G3 |
| Q5 | Br | SO$_2$Ph | G3 |
| Q61 | Br | SO$_2$NH$_2$ | G3 |
| Q26 | Br | SO$_2$NMe$_2$ | G3 |
| Q5 | SMe | COOMe | G3 |
| Q26 | SMe | COOMe | G3 |
| Q61 | SMe | COOMe | G3 |
| Q5 | SMe | COOEt | G3 |
| Q26 | SMe | COOEt | G3 |
| Q61 | SMe | COOEt | G3 |
| Q61 | SMe | COOPr—i | G3 |
| Q5 | SMe | COMe | G3 |
| Q158 | SMe | COEt | G3 |
| Q26 | SMe | CN | G3 |
| Q26 | SMe | Me | G3 |
| Q158 | SMe | Et | G3 |
| Q26 | SMe | CH$_2$CH$_2$Cl | G3 |
| Q158 | SMe | CF$_3$ | G3 |
| Q5 | SMe | Ph | G3 |
| Q26 | SMe | Cl | G3 |
| Q5 | SMe | Br | G3 |
| Q5 | SMe | NO$_2$ | G3 |
| Q5 | SMe | NH$_2$ | G3 |
| Q26 | SMe | NMe$_2$ | G3 |
| Q61 | SMe | NHCOMe | G3 |
| Q61 | SMe | SO$_2$Me | G3 |
| Q5 | SMe | SO$_2$Ph | G3 |
| Q61 | SMe | SO$_2$NH$_2$ | G3 |
| Q26 | SMe | SO$_2$NMe$_2$ | G3 |
| Q5 | SO$_2$Me | COOMe | G3 |
| Q26 | SO$_2$Me | COOMe | G3 |
| Q61 | SO$_2$Me | COOMe | G3 |
| Q5 | SO$_2$Me | COOEt | G3 |
| Q26 | SO$_2$Me | COOEt | G3 |
| Q61 | SO$_2$Me | COOEt | G3 |
| Q96 | SO$_2$Me | COOEt | G3 |
| Q158 | SO$_2$Me | COOEt | G3 |
| Q61 | SO$_2$Me | COOPr—i | G3 |
| Q5 | SO$_2$Me | COMe | G3 |
| Q158 | SO$_2$Me | COEt | G3 |
| Q5 | SO$_2$Me | COPr—i | G3 |
| Q26 | SO$_2$Me | CN | G3 |
| Q61 | SO$_2$Me | H | G3 |
| Q26 | SO$_2$Me | Me | G3 |
| Q158 | SO$_2$Me | Et | G3 |
| Q5 | SO$_2$Me | Pr—i | G3 |
| Q1 | SO$_2$Me | COMe | G3 |
| Q26 | SO$_2$Me | CH$_2$CH$_2$Cl | G3 |
| Q158 | SO$_2$Me | CF$_3$ | G3 |
| Q5 | SO$_2$Me | Ph | G3 |
| Q26 | SO$_2$Me | Cl | G3 |
| Q5 | SO$_2$Me | Br | G3 |
| Q2 | SO$_2$Me | Cl | G3 |
| Q9 | SO$_2$Me | Ph | G3 |
| Q5 | SO$_2$Me | NO$_2$ | G3 |
| Q5 | SO$_2$Me | NH$_2$ | G3 |
| Q5 | SO$_2$Me | NHMe | G3 |
| Q26 | SO$_2$Me | NMe$_2$ | G3 |
| Q61 | SO$_2$Me | NHCOMe | G3 |
| Q158 | SO$_2$Me | NHSO$_2$Me | G3 |
| Q2 | SO$_2$Me | NHCOMe | G3 |
| Q26 | SO$_2$Me | SO$_2$Me | G3 |
| Q61 | SO$_2$Me | SO$_2$Me | G3 |
| Q5 | SO$_2$Me | SO$_2$Ph | G3 |
| Q61 | SO$_2$Me | SO$_2$NH$_2$ | G3 |
| Q5 | SO$_2$Me | SO$_2$NHMe | G3 |
| Q26 | SO$_2$Me | SO$_2$NMe$_2$ | G3 |
| Q5 | Ph | COOMe | G3 |
| Q26 | Ph | COOMe | G3 |
| Q61 | Ph | COOMe | G3 |
| Q5 | Ph | COOEt | G3 |
| Q26 | Ph | COOEt | G3 |
| Q61 | Ph | COOEt | G3 |
| Q61 | Ph | COOPr—i | G3 |
| Q5 | Ph | COMe | G3 |
| Q158 | Ph | COEt | G3 |
| Q26 | Ph | CN | G3 |
| Q26 | Ph | Me | G3 |
| Q158 | Ph | Et | G3 |
| Q26 | Ph | CH$_2$CH$_2$Cl | G3 |
| Q158 | Ph | CF$_3$ | G3 |
| Q5 | Ph | Ph | G3 |
| Q26 | Ph | Cl | G3 |
| Q5 | Ph | Br | G3 |
| Q5 | Ph | NO$_2$ | G3 |
| Q5 | Ph | NH$_2$ | G3 |
| Q26 | Ph | NMe$_2$ | G3 |
| Q61 | Ph | NHCOMe | G3 |
| Q61 | Ph | SO$_2$Me | G3 |
| Q5 | Ph | SO$_2$Ph | G3 |
| Q61 | Ph | SO$_2$NH$_2$ | G3 |
| Q26 | Ph | SO$_2$NMe$_2$ | G3 |
| Q201 | H | COOMe | Ga |
| CH$_2$ - Q201 | H | COOMe | Gb |
| CHMe - Q201 | H | COOMe | Gb |
| Q202 | H | COOMe | Gb |
| CH$_2$ - Q202 | H | COOMe | Gb |
| Q203 | H | COOMe | Gb |
| Q204 | H | COOMe | Gb |

TABLE 3-continued

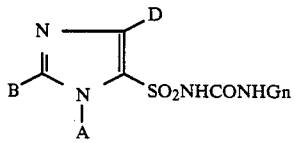

| A | B | D | Gn |
|---|---|---|---|
| Q205 | H | COOMe | Gb |
| CH$_2$ - Q205 | H | COOMe | Gc |
| Q206 | H | COOMe | G$_3$ |
| Q207 | H | COOMe | Gc |
| Q208 | H | COOMe | G$_3$ |
| Q209 | H | COOMe | Gc |
| CH$_2$ - Q209 | H | COOMe | Gc |
| Q210 | H | COOMe | Gc |
| CH$_2$ - Q210 | H | COOMe | G$_3$ |
| Q211 | H | COOMe | G$_3$ |
| Q212 | H | COOMe | Gc |
| Q213 | H | COOMe | Gc |
| Q214 | H | COOMe | Gc |
| Q215 | H | COOMe | G$_1$ |
| Q216 | H | COOMe | Gc |
| Q217 | H | COOMe | Gc |
| Q218 | H | COOMe | G$_3$ |
| Q219 | H | COOMe | Gc |
| Q220 | H | COOMe | Gc |
| Q221 | H | COOMe | G$_2$ |
| Q222 | H | COOMe | Gb |
| CH$_2$ - Q222 | H | COOMe | Gc |
| Q223 | H | COOMe | Gc |
| Q224 | H | COOMe | G$_3$ |
| Q225 | H | COOMe | Gb |
| CH$_2$ - Q225 | H | COOMe | Gc |
| Q226 | H | COOMe | G$_3$ |
| Q227 | H | COOMe | Gc |
| Q228 | H | COOMe | Gc |
| Q229 | H | COOMe | Gb |
| CH$_2$ - Q229 | H | COOMe | Gc |
| Q230 | H | COOMe | Gc |
| Q231 | H | COOMe | Gc |
| Q232 | H | COOMe | G$_3$ |
| Q233 | H | COOMe | Gc |
| Q234 | H | COOMe | Gc |
| Q235 | H | COOMe | Gc |
| Q236 | H | COOMe | G$_3$ |
| Q237 | H | COOMe | Gc |
| Q238 | H | COOMe | Gc |
| Q239 | H | COOMe | G$_2$ |
| Q240 | H | COOMe | Gc |
| Q241 | H | COOMe | Gc |
| Q242 | H | COOMe | Gc |
| Q243 | H | COOMe | G$_1$ |
| Q244 | H | COOMe | Gc |
| Q245 | H | COOMe | Gc |
| Q246 | H | COOMe | Gb |
| CH$_2$ - Q246 | H | COOMe | Gc |
| Q247 | H | COOMe | G$_3$ |
| Q248 | H | COOMe | Gc |
| Q249 | H | COOMe | Gc |
| Q250 | H | COOMe | Gc |
| CH$_2$ - Q250 | H | COOMe | G$_3$ |
| Q251 | H | COOMe | Gc |
| Q252 | H | COOMe | Gc |
| Q253 | H | COOMe | Gc |
| Q254 | H | COOMe | G$_1$ |
| Q255 | H | COOMe | Gc |
| Q256 | H | COOMe | Gc |
| Q257 | H | COOMe | G$_3$ |
| Q258 | H | COOMe | Gc |
| Q259 | H | COOMe | Gc |
| CH$_2$ - Q259 | H | COOMe | Gc |
| Q260 | H | COOMe | Gc |
| CH$_2$ - Q260 | H | COOMe | Gc |
| Q261 | H | COOMe | G$_1$ |
| Q262 | H | COOMe | Gc |
| Q263 | H | COOMe | Gc |
| Q264 | H | COOMe | G$_2$ |
| Q201 | H | COOEt | Ga |
| CH$_2$ - Q201 | H | COOEt | Gb |
| CHMe - Q201 | H | COOEt | Gb |

TABLE 3-continued

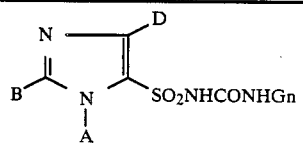

| A | B | D | Gn |
|---|---|---|---|
| Q202 | H | COOEt | Gb |
| CH$_2$ - Q202 | H | COOEt | Gb |
| Q203 | H | COOEt | Gb |
| Q204 | H | COOEt | Gb |
| Q205 | H | COOEt | Gb |
| CH$_2$ - Q205 | H | COOEt | Gc |
| Q206 | H | COOEt | G$_3$ |
| Q207 | H | COOEt | Gc |
| Q208 | H | COOEt | G$_3$ |
| Q209 | H | COOEt | Gc |
| CH$_2$ - Q209 | H | COOEt | Gc |
| Q210 | H | COOEt | Gc |
| CH$_2$ - 210 | H | COOEt | G$_3$ |
| Q211 | H | COOEt | Gc |
| Q212 | H | COOEt | Gc |
| Q213 | H | COOEt | Gc |
| Q214 | H | COOEt | G$_1$ |
| Q215 | H | COOEt | Gc |
| Q216 | H | COOEt | G$_2$ |
| Q217 | H | COOEt | Gc |
| Q218 | H | COOEt | Gc |
| Q219 | H | COOEt | G$_3$ |
| Q220 | H | COOEt | Gc |
| Q221 | H | COOEt | Gb |
| Q222 | H | COOEt | Gc |
| CH$_2$ - Q222 | H | COOEt | Gc |
| Q223 | H | COOEt | Gc |
| Q224 | H | COOEt | Gb |
| Q225 | H | COOEt | Gc |
| CH$_2$ - Q225 | H | COOEt | G$_3$ |
| Q226 | H | COOEt | Gc |
| Q227 | H | COOEt | Gc |
| Q228 | H | COOEt | Gb |
| Q229 | H | COOEt | Gc |
| CH$_2$ - Q229 | H | COOEt | Gc |
| Q230 | H | COOEt | Gc |
| Q231 | H | COOEt | Gc |
| Q232 | H | COOEt | G$_3$ |
| Q233 | H | COOEt | Gc |
| CH$_2$ - Q234 | H | COOEt | Gc |
| Q235 | H | COOEt | Gc |
| Q236 | H | COOEt | G$_3$ |
| Q237 | H | COOEt | Gc |
| Q238 | H | COOEt | Gc |
| Q239 | H | COOEt | Gc |
| Q240 | H | COOEt | G$_1$ |
| Q241 | H | COOEt | Gc |
| Q242 | H | COOEt | Gc |
| Q243 | H | COOEt | Gc |
| Q244 | H | COOEt | G$_2$ |
| Q245 | H | COOEt | Gc |
| Q246 | H | COOEt | Gb |
| CH$_2$ - Q246 | H | COOEt | Gc |
| Q247 | H | COOEt | Gc |
| Q248 | H | COOEt | Gc |
| Q249 | H | COOEt | G$_3$ |
| Q250 | H | COOEt | Gc |
| CH$_2$ - Q250 | H | COOEt | Gc |
| Q251 | H | COOEt | Gc |
| Q252 | H | COOEt | G$_3$ |
| Q253 | H | COOEt | Gc |
| Q254 | H | COOEt | Gc |
| Q255 | H | COOEt | Gc |
| Q256 | H | COOEt | Gc |
| Q257 | H | COOEt | Gc |
| Q258 | H | COOEt | G$_1$ |
| Q259 | H | COOEt | Gc |
| CH$_2$ - Q259 | H | COOEt | Gc |
| Q260 | H | COOEt | Gc |
| CH$_2$ - Q260 | H | COOEt | Gc |
| Q261 | H | COOEt | G$_3$ |
| Q262 | H | COOEt | Gc |

TABLE 3-continued

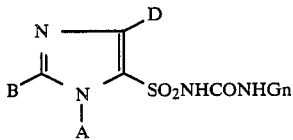

| A | B | D | Gn |
|---|---|---|---|
| Q263 | H | COOEt | Gc |
| Q264 | H | COOEt | G3 |
| Q201 | H | COOH | Gc |
| Q202 | H | COOH | Gc |
| Q222 | H | COOH | Gc |
| Q225 | H | COOH | G3 |
| Q229 | H | COOH | Gc |
| Q246 | H | COOH | G3 |
| Q201 | H | COOPr—i | Gc |
| Q202 | H | COOPr—i | G3 |
| Q205 | H | COOPr—i | Gc |
| Q209 | H | COOPr—i | Gc |
| Q222 | H | COOPr—i | Gc |
| Q225 | H | COOPr—i | Gc |
| Q229 | H | COOPr—i | G3 |
| Q246 | H | COOPr—i | Gc |
| Q201 | H | COOCH2CH2Cl | Gc |
| Q202 | H | COOCH2CH2Cl | G3 |
| Q205 | H | COOCH2CH2Cl | Gc |
| Q209 | H | COOCH2CH2Cl | Gc |
| Q222 | H | COOCH2CH2Cl | G3 |
| Q225 | H | COOCH2CH2Cl | Gc |
| Q229 | H | COOCH2CH2Cl | Gc |
| Q246 | H | COOCH2CH2Cl | G1 |
| Q201 | H | COOCH2CH=CH2 | Gc |
| Q202 | H | COOCH2CH=CH2 | Gc |
| Q205 | H | COOCH2CH=CH2 | G3 |
| Q209 | H | COOCH2CH=CH2 | Gc |
| Q222 | H | COOCH2CH=CH2 | Gc |
| Q225 | H | COOCH2CH=CH2 | Gc |
| Q229 | H | COOCH2CH=CH2 | G3 |
| Q246 | H | COOCH2CH=CH2 | Gc |
| Q201 | H | COOCH2C≡CH | Gc |
| Q202 | H | COOCH2C≡CH | G3 |
| Q205 | H | COOCH2C≡CH | Gc |
| Q209 | H | COOCH2C≡CH | Gc |
| Q222 | H | COOCH2C≡CH | Gc |
| Q225 | H | COOCH2C≡CH | G3 |
| Q229 | H | COOCH2C≡CH | Gc |
| Q246 | H | COOCH2C≡CH | G3 |
| Q201 | H | CONHMe | Gc |
| Q202 | H | CONHMe | G3 |
| Q205 | H | CONHMe | Gc |
| Q209 | H | CONHMe | Gc |
| Q222 | H | CONHMe | G3 |
| Q225 | H | CONHMe | Gc |
| Q229 | H | CONHMe | Gc |
| Q246 | H | CONHMe | G3 |
| Q201 | H | CONMe2 | Gc |
| Q202 | H | CONMe2 | G3 |
| Q205 | H | CONMe2 | Gc |
| Q209 | H | CONMe2 | Gc |
| Q222 | H | CONMe2 | Gc |
| Q225 | H | COMe | Gc |
| Q229 | H | COMe | Gc |
| Q230 | H | COMe | G2 |
| Q231 | H | COMe | G3 |
| Q237 | H | COMe | Gc |
| Q246 | H | COMe | Gc |
| Q247 | H | COMe | G3 |
| Q250 | H | COMe | Gc |
| Q259 | H | COMe | Gc |
| Q260 | H | COMe | Gc |
| Q263 | H | COMe | G3 |
| Q201 | H | COEt | Gc |
| Q202 | H | COEt | G3 |
| Q205 | H | COEt | Gc |
| Q209 | H | COEt | Gc |
| Q222 | H | COEt | Gc |
| Q225 | H | COEt | G3 |
| Q229 | H | COEt | Gc |
| Q246 | H | COEt | G3 |
| Q201 | H | COPr—i | Gc |

TABLE 3-continued

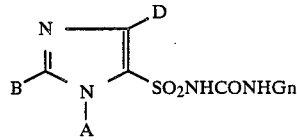

| A | B | D | Gn |
|---|---|---|---|
| Q202 | H | COPr—i | G3 |
| Q205 | H | COPr—i | Gc |
| Q209 | H | COPr—i | Gc |
| Q222 | H | COPr—i | Gc |
| Q225 | H | COPr—i | G3 |
| Q229 | H | COPr—i | Gc |
| Q246 | H | COPr—i | Gc |
| Q201 | H | COPh | Gc |
| Q202 | H | COPh | G3 |
| Q205 | H | COPh | Gc |
| Q209 | H | COPh | Gc |
| Q222 | H | COPh | G3 |
| Q225 | H | COPh | Gc |
| Q229 | H | COPh | Gc |
| Q246 | H | COPh | G3 |
| Q201 | H | CN | Gc |
| CH2 - Q201 | H | CN | G3 |
| Q202 | H | CN | Gc |
| Q205 | H | CN | Gc |
| Q209 | H | CN | Gc |
| Q222 | H | CN | Gc |
| Q225 | H | CN | Gc |
| Q229 | H | CN | Gc |
| Q246 | H | CN | G3 |
| Q201 | H | H | Gc |
| Q202 | H | H | G3 |
| Q205 | H | H | Gc |
| Q207 | H | H | Gc |
| Q222 | H | H | Gc |
| Q225 | H | H | G3 |
| Q229 | H | H | Gc |
| Q230 | H | H | Gc |
| Q231 | H | H | G3 |
| Q237 | H | H | Gc |
| Q246 | H | H | Gc |
| Q247 | H | H | G3 |
| Q250 | H | H | Gc |
| Q259 | H | H | G3 |
| Q260 | H | H | Gc |
| Q263 | H | H | G3 |
| Q201 | H | Me | Gc |
| Q202 | H | Me | G3 |
| Q205 | H | Me | Gc |
| Q207 | H | Me | G3 |
| Q222 | H | Me | Gc |
| Q225 | H | Me | Gc |
| Q229 | H | Me | Gc |
| Q230 | H | Me | G3 |
| Q231 | H | Me | Gc |
| Q237 | H | Me | Gc |
| Q246 | H | Me | Gc |
| Q247 | H | Me | G3 |
| Q250 | H | Me | Gc |
| Q259 | H | Me | Gc |
| Q260 | H | Me | Gc |
| Q263 | H | Me | G3 |
| Q201 | H | Et | Gc |
| Q202 | H | Et | G1 |
| Q205 | H | Et | Gc |
| Q209 | H | Et | Gc |
| Q222 | H | Et | G3 |
| Q225 | H | Et | Gc |
| Q229 | H | Et | Gc |
| Q246 | H | Et | G2 |
| Q201 | H | Pr—i | Gc |
| Q205 | H | Pr—i | Gc |
| Q209 | H | Pr—i | Gc |
| Q222 | H | Pr—i | G3 |
| Q229 | H | Pr—i | Gc |
| Q201 | H | CH=CH2 | Gc |
| Q205 | H | CH=CH2 | G3 |
| Q209 | H | CH=CH2 | Gc |
| Q229 | H | CH=CH2 | G3 |

TABLE 3-continued

![Structure: N=B-N(A)-C(SO2NHCONHGn)=C(D) pyrazole-like ring]

| A | B | D | Gn |
|---|---|---|---|
| Q201 | H | CH=CHMe | Gc |
| Q205 | H | CH=CHMe | Gc |
| Q201 | H | CH2CH=CH2 | Gc |
| Q205 | H | CH2CH=CH2 | G3 |
| Q209 | H | CH2CH=CH2 | Gc |
| Q229 | H | CH2CH=CH2 | Gc |
| Q201 | H | CH2Cl | Gc |
| Q205 | H | CH2Cl | G3 |
| Q209 | H | CH2Cl | Gc |
| Q229 | H | CH2Cl | Gc |
| Q201 | H | CH2CH2Cl | Gc |
| Q205 | H | CH2CH2Cl | G3 |
| Q209 | H | CH2CH2Cl | Gc |
| Q229 | H | CH2CH2Cl | G2 |
| Q201 | H | CF3 | Gc |
| Q205 | H | CF3 | G3 |
| Q209 | H | CF3 | Gc |
| Q222 | H | CF3 | Gc |
| Q225 | H | CF3 | G3 |
| Q229 | H | CF3 | G1 |
| Q201 | H | CF=CFCl | Gc |
| Q205 | H | CF=CFCl | Gc |
| Q229 | H | CF=CFCl | G3 |
| Q201 | H | CH2Ph | Gc |
| Q205 | H | CH2Ph | Gc |
| Q209 | H | CH2Ph | G3 |
| Q201 | H | Ph | Gc |
| Q202 | H | Ph | G1 |
| Q205 | H | Ph | Gc |
| Q209 | H | Ph | Gc |
| Q222 | H | Ph | G3 |
| Q225 | H | Ph | Gc |
| Q229 | H | Ph | Gc |
| Q246 | H | Ph | G2 |
| Q201 | H | Ph—2-Cl | Gc |
| Q205 | H | Ph—2-Cl | G1 |
| Q209 | H | Ph—2-Cl | Gc |
| Q201 | H | Ph—2-Me | Gc |
| Q205 | H | Ph—2-Me | G3 |
| Q209 | H | Ph—2-Me | Gc |
| Q225 | H | Ph—2-Me | Gc |
| Q229 | H | Ph—2-Me | G3 |
| Q201 | H | Cl | Gc |
| Q205 | H | Cl | Gc |
| Q207 | H | Cl | G3 |
| Q222 | H | Cl | Gc |
| Q225 | H | Cl | Gc |
| Q229 | H | Cl | G1 |
| Q231 | H | Cl | Gc |
| Q246 | H | Cl | Gc |
| Q250 | H | Cl | G3 |
| Q259 | H | Cl | Gc |
| Q260 | H | Cl | Gc |
| Q201 | H | Br | Gc |
| Q205 | H | Br | G3 |
| Q207 | H | Br | Gc |
| Q229 | H | Br | Gc |
| Q231 | H | Br | G3 |
| Q250 | H | Br | Gc |
| Q259 | H | Br | Gc |
| Q260 | H | Br | G3 |
| Q201 | H | F | Gc |
| Q205 | H | F | G3 |
| Q209 | H | F | Gc |
| Q229 | H | F | Gc |
| Q246 | H | F | G3 |
| Q201 | H | I | Gc |
| Q205 | H | I | Gc |
| Q209 | H | I | Gc |
| Q222 | H | I | Gc |
| Q201 | H | NO2 | Gc |
| CH2-Q201 | H | NO2 | G3 |
| Q202 | H | NO2 | G3 |
| Q205 | H | NO2 | Gc |
| Q207 | H | NO2 | Gc |
| Q222 | H | NO2 | G3 |
| Q225 | H | NO2 | Gc |
| Q229 | H | NO2 | Gc |
| Q230 | H | NO2 | G1 |
| Q231 | H | NO2 | Gc |
| Q237 | H | NO2 | Gc |
| Q246 | H | NO2 | Gc |
| Q247 | H | NO2 | G2 |
| Q250 | H | NO2 | Gc |
| Q259 | H | NO2 | Gc |
| Q260 | H | NO2 | G3 |
| Q263 | H | NO2 | Gc |
| Q201 | H | NH2 | Gc |
| Q202 | H | NH2 | G3 |
| Q205 | H | NH2 | Gc |
| Q209 | H | NH2 | Gc |
| Q222 | H | NH2 | G3 |
| Q225 | H | NH2 | Gc |
| Q229 | H | NH2 | Gc |
| Q246 | H | NH2 | G3 |
| Q201 | H | NHMe | Gc |
| Q205 | H | NHMe | Gc |
| Q209 | H | NHMe | Gc |
| Q225 | H | NHMe | Gc |
| Q229 | H | NHMe | G3 |
| Q201 | H | NMe2 | Gc |
| Q205 | H | NMe2 | Gc |
| Q209 | H | NMe2 | Gc |
| Q222 | H | NMe2 | G1 |
| Q225 | H | NMe2 | Gc |
| Q229 | H | NMe2 | Gc |
| Q246 | H | NMe2 | G3 |
| Q201 | H | NMeEt | Gc |
| Q205 | H | NMeEt | Gc |
| Q209 | H | NMeEt | G3 |
| Q222 | H | NMeEt | Gc |
| Q225 | H | NMeEt | Gc |
| Q229 | H | NMeEt | G2 |
| Q201 | H | NHCOMe | Gc |
| Q202 | H | NHCOMe | G3 |
| Q205 | H | NHCOMe | Gc |
| Q209 | H | NHCOMe | Gc |
| Q222 | H | NHCOMe | G3 |
| Q225 | H | NHCOMe | Gc |
| Q229 | H | NHCOMe | Gc |
| Q246 | H | NHCOMe | G3 |
| Q201 | H | NHCOEt | Gc |
| Q205 | H | NHCOEt | Gc |
| Q209 | H | NHCOEt | Gc |
| Q222 | H | NHCOEt | G1 |
| Q225 | H | NHCOEt | Gc |
| Q229 | H | NHCOEt | G3 |
| Q201 | H | NHSO2Me | Gc |
| Q205 | H | NHSO2Me | Gc |
| Q209 | H | NHSO2Me | Gc |
| Q225 | H | NHSO2Me | G3 |
| Q229 | H | NHSO2Me | G3 |
| Q201 | H | OMe | Gc |
| Q205 | H | OMe | Gc |
| Q209 | H | OMe | G3 |
| Q222 | H | OMe | Gc |
| Q225 | H | OMe | Gc |
| Q229 | H | OMe | G2 |
| Q246 | H | OMe | G1 |
| Q201 | H | OEt | Gc |
| Q205 | H | OEt | Gc |
| Q209 | H | OEt | Gc |
| Q222 | H | OEt | G3 |
| Q229 | H | OEt | Gc |
| Q201 | H | CH2OMe | Gc |
| Q205 | H | CH2OMe | Gc |

TABLE 3-continued

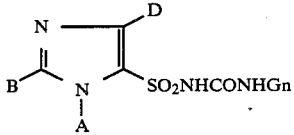

| A | B | D | Gn |
|---|---|---|---|
| Q209 | H | CH₂OMe | G₃ |
| Q222 | H | CH₂OMe | Gc |
| Q201 | H | SMe | Gc |
| Q205 | H | SMe | Gc |
| Q209 | H | SMe | Gc |
| Q222 | H | SMe | G₁ |
| Q225 | H | SMe | Gc |
| Q229 | H | SMe | G₃ |
| Q201 | H | SO₂Me | Gc |
| CH₂-Q201 | H | SO₂Me | G₃ |
| Q202 | H | SO₂Me | Gc |
| Q205 | H | SO₂Me | Gc |
| Q209 | H | SO₂Me | Gc |
| Q222 | H | SO₂Me | G₃ |
| Q225 | H | SO₂Me | Gc |
| Q229 | H | SO₂Me | Gc |
| Q246 | H | SO₂Me | G₃ |
| Q201 | H | SO₂Ph | Gc |
| Q202 | H | SO₂Ph | G₁ |
| Q205 | H | SO₂Ph | Gc |
| Q209 | H | SO₂Ph | Gc |
| Q222 | H | SO₂Ph | Gc |
| Q225 | H | SO₂Ph | G₃ |
| Q229 | H | SO₂Ph | Gc |
| Q246 | H | SO₂Ph | G₁ |
| Q201 | H | SO₂OMe | Gc |
| Q205 | H | SO₂OMe | Gc |
| Q209 | H | SO₂OMe | Gc |
| Q222 | H | SO₂OMe | Gc |
| Q229 | H | SO₂OMe | G₃ |
| Q201 | H | SO₂NH₂ | Gc |
| Q205 | H | SO₂NH₂ | Gc |
| Q209 | H | SO₂NH₂ | G₃ |
| Q225 | H | SO₂NH₂ | Gc |
| Q229 | H | SO₂NH₂ | Gc |
| Q246 | H | SO₂NH₂ | G₁ |
| Q201 | H | SO₂NHMe | Gc |
| Q205 | H | SO₂NHMe | Gc |
| Q209 | H | SO₂NHMe | G₃ |
| Q222 | H | SO₂NHMe | Gc |
| Q225 | H | SO₂NHMe | Gc |
| Q229 | H | SO₂NHMe | Gc |
| Q246 | H | SO₂NHMe | G₂ |
| Q201 | H | SO₂NMe₂ | Gc |
| Q202 | H | SO₂NMe₂ | G₃ |
| Q205 | H | SO₂NMe₂ | Gc |
| Q209 | H | SO₂NMe₂ | Gc |
| Q222 | H | SO₂NMe₂ | G₂ |
| Q225 | H | SO₂NMe₂ | Gc |
| Q229 | H | SO₂NMe₂ | Gc |
| Q246 | H | SO₂NMe₂ | G₃ |
| Q201 | Me | COOMe | Gc |
| CH₂-Q201 | Me | COOMe | G₃ |
| Q202 | Me | COOMe | G₁ |
| Q205 | Me | COOMe | Gc |
| Q207 | Me | COOMe | G₃ |
| Q209 | Me | COOMe | Gc |
| Q222 | Me | COOMe | Gc |
| Q225 | Me | COOMe | G₂ |
| Q229 | Me | COOMe | Gc |
| Q230 | Me | COOMe | Gc |
| Q231 | Me | COOMe | G₃ |
| Q237 | Me | COOMe | Gc |
| Q246 | Me | COOMe | Gc |
| Q247 | Me | COOMe | G₃ |
| Q250 | Me | COOMe | Gc |
| Q259 | Me | COOMe | G₁ |
| Q260 | Me | COOMe | Gc |
| Q263 | Me | COOMe | G₃ |
| Q201 | Me | COOEt | Gc |
| CH₂-Q201 | Me | COOEt | G₂ |
| Q222 | Me | COOEt | Gc |
| Q205 | Me | COOEt | Gc |
| Q207 | Me | COOEt | G₃ |
| Q209 | Me | COOEt | Gc |
| Q222 | Me | COOEt | Gc |
| Q225 | Me | COOEt | G₃ |
| Q229 | Me | COOEt | Gc |
| Q230 | Me | COOEt | Gc |
| Q231 | Me | COOEt | Gc |
| Q237 | Me | COOEt | G₁ |
| Q246 | Me | COOEt | Gc |
| Q247 | Me | COOEt | Gc |
| Q250 | Me | COOEt | Gc |
| Q259 | Me | COOEt | G₃ |
| Q260 | Me | COOEt | Gc |
| Q263 | Me | COOEt | G₃ |
| Q201 | Me | COOH | G₁ |
| Q205 | Me | COOH | Gc |
| Q201 | Me | COOPr—i | Gc |
| Q202 | Me | COOPr—i | G₃ |
| Q205 | Me | COOPr—i | Gc |
| Q209 | Me | COOPr—i | Gc |
| Q222 | Me | COOPr—i | G₃ |
| Q225 | Me | COOPr—i | Gc |
| Q229 | Me | COOPr—i | Gc |
| Q246 | Me | COOPr—i | G₁ |
| Q201 | Me | COOCH₂CH₂Cl | Gc |
| Q205 | Me | COOCH₂CH₂Cl | G₃ |
| Q222 | Me | COOCH₂CH₂Cl | Gc |
| Q229 | Me | COOCH₂CH₂Cl | G₁ |
| Q201 | Me | COOCH₂CH=CH₂ | Gc |
| Q205 | Me | COOCH₂CH=CH₂ | G₃ |
| Q222 | Me | COOCH₂CH=CH₂ | Gc |
| Q229 | Me | COOCH₂CH=CH₂ | G₁ |
| Q201 | Me | COOCH₂C≡CH | Gc |
| Q205 | Me | COOCH₂C≡CH | G₂ |
| Q222 | Me | COOCH₂C≡CH | Gc |
| Q229 | Me | COOCH₂C≡CH | Gc |
| Q201 | Me | CONHMe | Gc |
| Q205 | Me | CONHMe | G₃ |
| Q222 | Me | CONHMe | Gc |
| Q229 | Me | CONHMe | Gc |
| Q201 | Me | CONMe₂ | Gc |
| Q205 | Me | CONMe₂ | G₃ |
| Q222 | Me | CONMe₂ | Gc |
| Q229 | Me | CONMe₂ | Gc |
| Q201 | Me | COMe | Gc |
| Q202 | Me | COMe | G₃ |
| Q205 | Me | COMe | Gc |
| Q207 | Me | COMe | Gc |
| Q222 | Me | COMe | G₃ |
| Q225 | Me | COMe | Gc |
| Q229 | Me | COMe | Gc |
| Q230 | Me | COMe | G₃ |
| Q231 | Me | COMe | Gc |
| Q237 | Me | COMe | Gc |
| Q246 | Me | COMe | Gc |
| Q247 | Me | COMe | G₂ |
| Q250 | Me | COMe | Gc |
| Q259 | Me | COMe | Gc |
| Q260 | Me | COMe | G₁ |
| Q263 | Me | COMe | Gc |
| Q201 | Me | COEt | Gc |
| Q205 | Me | COEt | G₃ |
| Q222 | Me | COEt | Gc |
| Q229 | Me | COEt | Gc |
| Q201 | Me | COPr—i | Gc |
| Q205 | Me | COPr—i | G₃ |
| Q222 | Me | COPr—i | Gc |
| Q229 | Me | COPr—i | G₁ |
| Q201 | Me | COPh | Gc |
| Q205 | Me | COPh | Gc |
| Q222 | Me | COPh | G₃ |
| Q229 | Me | COPh | Gc |
| Q201 | Me | CN | Gc |

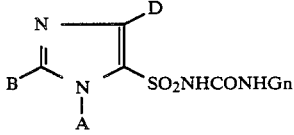

TABLE 3-continued

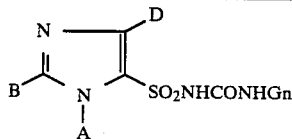

| A | B | D | Gn |
|---|---|---|---|
| Q202 | Me | CN | G3 |
| Q205 | Me | CN | Gc |
| Q209 | Me | CN | Gc |
| Q222 | Me | CN | G3 |
| Q225 | Me | CN | Gc |
| Q229 | Me | CN | Gc |
| Q246 | Me | CN | G1 |
| Q201 | Me | H | Gc |
| Q205 | Me | H | Gc |
| Q222 | Me | H | G3 |
| Q229 | Me | H | Gc |
| Q201 | Me | Me | Gc |
| Q202 | Me | Me | G3 |
| Q205 | Me | Me | Gc |
| Q209 | Me | Me | Gc |
| Q222 | Me | Me | Gc |
| Q225 | Me | Me | Gc |
| Q229 | Me | Me | G3 |
| Q246 | Me | Me | Gc |
| Q201 | Me | Et | Gc |
| Q205 | Me | Et | Gc |
| Q222 | Me | Et | G3 |
| Q229 | Me | Et | Gc |
| Q201 | Me | Pr—i | Gc |
| Q205 | Me | Pr—i | G2 |
| Q201 | Me | CH=CH2 | Gc |
| Q205 | Me | CH=CH2 | G3 |
| Q201 | Me | CH=CHMe | G3 |
| Q205 | Me | CH=CHMe | Gc |
| Q201 | Me | CH2CH=CH2 | Gc |
| Q205 | Me | CH2CH=CH2 | G3 |
| Q201 | Me | CH2Cl | Gc |
| Q205 | Me | CH2Cl | G2 |
| Q222 | Me | CH2Cl | Gc |
| Q229 | Me | CH2Cl | G3 |
| Q201 | Me | CH2CH2Cl | Gc |
| Q205 | Me | CH2CH2Cl | Gc |
| Q222 | Me | CH2CH2Cl | G3 |
| Q229 | Me | CH2CH2Cl | Gc |
| Q201 | Me | CF3 | Gc |
| Q205 | Me | CF3 | G3 |
| Q222 | Me | CF3 | G3 |
| Q229 | Me | CF3 | Gc |
| Q201 | Me | CF=CFCl | Gc |
| Q205 | Me | CF=CFCl | G3 |
| Q201 | Me | CH2Ph | Gc |
| Q205 | Me | CH2Ph | G3 |
| Q201 | Me | Ph | Gc |
| Q202 | Me | Ph | Gc |
| Q205 | Me | Ph | Gc |
| Q209 | Me | Ph | Gc |
| Q222 | Me | Ph | G3 |
| Q225 | Me | Ph | G3 |
| Q229 | Me | Ph | Gc |
| Q246 | Me | Ph | G3 |
| Q201 | Me | Ph—2-Cl | Gc |
| Q205 | Me | Ph—2-Cl | G3 |
| Q201 | Me | Ph—2-Me | Gc |
| Q205 | Me | Ph—2-Me | Gc |
| Q229 | Me | Ph—2-Me | G3 |
| Q201 | Me | Cl | Gc |
| Q202 | Me | Cl | G3 |
| Q205 | Me | Cl | Gc |
| Q209 | Me | Cl | Gc |
| Q222 | Me | Cl | G3 |
| Q225 | Me | Cl | Gc |
| Q229 | Me | Cl | Gc |
| Q246 | Me | Cl | G3 |
| Q201 | Me | Br | Gc |
| Q205 | Me | Br | G3 |
| Q222 | Me | Br | Gc |
| Q229 | Me | Br | G1 |
| Q201 | Me | F | G1 |

TABLE 3-continued

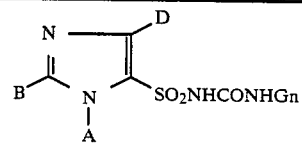

| A | B | D | Gn |
|---|---|---|---|
| Q205 | Me | F | G1 |
| Q201 | Me | I | G1 |
| Q205 | Me | I | G1 |
| Q201 | Me | NO2 | Gc |
| Q202 | Me | NO2 | G3 |
| Q205 | Me | NO2 | Gc |
| Q209 | Me | NO2 | Gc |
| Q222 | Me | NO2 | Gc |
| Q225 | Me | NO2 | G3 |
| Q229 | Me | NO2 | Gc |
| Q246 | Me | NO2 | Gc |
| Q201 | Me | NH2 | Gc |
| Q205 | Me | NH2 | G3 |
| Q222 | Me | NH2 | Gc |
| Q229 | Me | NH2 | G3 |
| Q201 | Me | NHMe | Gc |
| Q205 | Me | NHMe | Gc |
| Q229 | Me | NHMe | G3 |
| Q201 | Me | NMe2 | Gc |
| Q205 | Me | NMe2 | Gc |
| Q229 | Me | NMe2 | G3 |
| Q201 | Me | NMeEt | Gc |
| Q205 | Me | NMeEt | Gc |
| Q201 | Me | NHCOMe | Gc |
| Q205 | Me | NHCOMe | Gc |
| Q222 | Me | NHCOMe | G3 |
| Q229 | Me | NHCOMe | Gc |
| Q201 | Me | NHCOEt | Gc |
| Q205 | Me | NHCOEt | G3 |
| Q201 | Me | NHSO2Me | Gc |
| Q205 | Me | NHSO2Me | Gc |
| Q229 | Me | NHSO2Me | G2 |
| Q201 | Me | OMe | Gc |
| Q205 | Me | OMe | G3 |
| Q222 | Me | OMe | Gc |
| Q229 | Me | OMe | G1 |
| Q201 | Me | OEt | Gc |
| Q205 | Me | OEt | G3 |
| Q201 | Me | CH2OMe | Gc |
| Q205 | Me | CH2OMe | Gc |
| Q229 | Me | CH2OMe | G3 |
| Q201 | Me | SMe | Gc |
| Q205 | Me | SMe | G3 |
| Q201 | Me | SO2Me | Gc |
| Q205 | Me | SO2Me | Gc |
| Q222 | Me | SO2Me | G1 |
| Q229 | Me | SO2Me | G3 |
| Q201 | Me | SO2Ph | Gc |
| Q205 | Me | SO2Ph | Gc |
| Q222 | Me | SO2Ph | G3 |
| Q229 | Me | SO2Ph | Gc |
| Q201 | Me | SO2OMe | Gc |
| Q205 | Me | SO2OMe | G3 |
| Q229 | Me | SO2OMe | Gc |
| Q201 | Me | SO2NH2 | Gc |
| Q205 | Me | SO2NH2 | Gc |
| Q229 | Me | SO2NH2 | G3 |
| Q201 | Me | SO2NHMe | Gc |
| Q205 | Me | SO2NHMe | Gc |
| Q222 | Me | SO2NHMe | G1 |
| Q229 | Me | SO2NHMe | Gc |
| Q201 | Me | SO2NMe2 | Gc |
| Q205 | Me | SO2NMe2 | G3 |
| Q222 | Me | SO2NMe2 | Gc |
| Q229 | Me | SO2NMe2 | G1 |
| Q201 | Et | COOMe | Gc |
| Q205 | Et | COOMe | Gc |
| Q229 | Et | COOMe | G3 |
| Q246 | Et | COOMe | G3 |
| Q201 | Et | COOEt | Gc |
| Q202 | Et | COOEt | G2 |
| Q209 | Et | COOEt | Gc |
| Q222 | Et | COOEt | G3 |

TABLE 3-continued

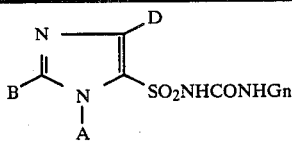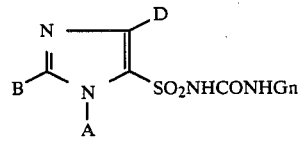

| A | B | D | Gn |
|---|---|---|---|
| Q225 | Et | COOEt | Gc |
| Q201 | Et | COOPr—i | G3 |
| Q205 | Et | COOPr—i | Gc |
| Q201 | Et | COOCH2CHCl | Gc |
| Q205 | Et | COOCH2CH=CH2 | G3 |
| Q201 | Et | COOCH2C≡CH | Gc |
| Q201 | Et | CONHMe | Gc |
| Q201 | Et | CONMe2 | Gc |
| Q201 | Et | COMe | Gc |
| Q205 | Et | COMe | G3 |
| Q229 | Et | COMe | Gc |
| Q201 | Et | COEt | Gc |
| Q201 | Et | COPh | Gc |
| Q201 | Et | CN | Gc |
| Q205 | Et | CN | G3 |
| Q229 | Et | CN | Gc |
| Q201 | Et | H | Gc |
| Q205 | Et | H | G3 |
| Q201 | Et | Me | Gc |
| Q205 | Et | Me | G3 |
| Q201 | Et | Et | Gc |
| Q205 | Et | Pr—i | Gc |
| Q201 | Et | CH=CHMe | Gc |
| Q201 | Et | CH2CH2Cl | Gc |
| Q201 | Et | CH2Ph | G3 |
| Q201 | Et | Ph | Gc |
| Q205 | Et | Ph | Gc |
| Q209 | Et | Ph | Gc |
| Q229 | Et | Ph | G3 |
| Q201 | Et | Ph—2-Cl | Gc |
| Q205 | Et | Ph—2-Me | Gc |
| Q201 | Et | Cl | Gc |
| Q205 | Et | Cl | G2 |
| Q201 | Et | Br | Gc |
| Q205 | Et | Br | G1 |
| Q201 | Et | F | Gc |
| Q201 | Et | NO2 | Gc |
| Q205 | Et | NO2 | G3 |
| Q209 | Et | NO2 | Gc |
| Q201 | Et | NH2 | Gc |
| Q201 | Et | NHMe | Gc |
| Q201 | Et | NMe2 | Gc |
| Q205 | Et | NMe2 | G3 |
| Q201 | Et | NHCOMe | Gc |
| Q205 | Et | NHCOMe | Gc |
| Q201 | Et | NHCOEt | Gc |
| Q201 | Et | NHSO2Me | Gc |
| Q201 | Et | OMe | Gc |
| Q205 | Et | OEt | G3 |
| Q201 | Et | CH2OMe | Gc |
| Q201 | Et | SMe | Gc |
| Q201 | Et | SO2Me | Gc |
| Q205 | Et | SO2Me | G3 |
| Q201 | Et | SO2Ph | Gc |
| Q205 | Et | SO2Ph | G3 |
| Q201 | Et | SO2OMe | Gc |
| Q201 | Et | SO2NH2 | Gc |
| Q205 | Et | SO2NHMe | G3 |
| Q201 | Et | SO2NMe2 | Gc |
| Q205 | Et | SO2NMe2 | G3 |
| Q201 | Cl | COOMe | Gc |
| Q209 | Cl | COOMe | G3 |
| Q229 | Cl | COOMe | Gc |
| Q246 | Cl | COOMe | G3 |
| Q201 | Cl | COOEt | Gc |
| Q205 | Cl | COOEt | Gc |
| Q222 | Cl | COOEt | G1 |
| Q225 | Cl | COOEt | Gc |
| Q246 | Cl | COOEt | G3 |
| Q201 | Cl | COOPr—i | Gc |
| Q205 | Cl | COOPr—i | G3 |
| Q205 | Cl | COOCH2CH2Cl | G3 |
| Q201 | Cl | COOCH2CH=CH2 | Gc |
| Q201 | Cl | COOCH2C≡CH | G3 |
| Q201 | Cl | CONHMe | Gc |
| Q201 | Cl | CONMe2 | G3 |
| Q201 | Cl | COMe | Gc |
| Q205 | Cl | COMe | Gc |
| Q201 | Cl | COEt | G3 |
| Q201 | Cl | COPr—i | Gc |
| Q201 | Cl | COPh | G3 |
| Q201 | Cl | CN | Gc |
| Q205 | Cl | CN | Gc |
| Q201 | Cl | H | G3 |
| Q201 | Cl | Me | Gc |
| Q205 | Cl | Me | G3 |
| Q205 | Cl | Et | Gc |
| Q201 | Cl | Pr—i | G3 |
| Q201 | Cl | CH=CHMe | Gc |
| Q201 | Cl | CH2CH=CH2 | G1 |
| Q205 | Cl | CH2CH2Cl | Gc |
| Q201 | Cl | Ph | Gc |
| Q205 | Cl | Ph | Gc |
| Q209 | Cl | Ph | G3 |
| Q201 | Cl | Ph—2-Cl | Gc |
| Q205 | Cl | Ph—2-Me | G3 |
| Q201 | Cl | Cl | Gc |
| Q205 | Cl | Cl | G3 |
| Q201 | Cl | Br | Gc |
| Q201 | Cl | NO2 | Gc |
| Q205 | Cl | NO2 | G3 |
| Q209 | Cl | NO2 | Gc |
| Q201 | Cl | NH2 | Gc |
| Q201 | Cl | NHMe | G1 |
| Q201 | Cl | NMe2 | G3 |
| Q201 | Cl | NHCOMe | Gc |
| Q205 | Cl | NHCOEt | Gc |
| Q201 | Cl | NHSO2Me | G3 |
| Q201 | Cl | OMe | Gc |
| Q201 | Cl | CH2OMe | G3 |
| Q201 | Cl | SO2Me | Gc |
| Q201 | Cl | SO2Ph | Gc |
| Q201 | Cl | SO2NH2 | G3 |
| Q201 | Cl | SO2NMe2 | Gc |
| Q205 | Cl | SO2NMe2 | Gc |
| Q201 | Br | COOMe | Gc |
| Q205 | Br | COOMe | G3 |
| Q209 | Br | COOMe | G3 |
| Q201 | Br | COOEt | Gc |
| Q209 | Br | COOEt | Gc |
| Q229 | Br | COOEt | G3 |
| Q201 | Br | COOPr—i | G3 |
| Q201 | Br | COOCH2CH2Cl | Gc |
| Q201 | Br | COOCH2CH=CH2 | G3 |
| Q201 | Br | CONHMe | Gc |
| Q201 | Br | CONMe2 | G3 |
| Q201 | Br | COMe | Gc |
| Q205 | Br | COMe | G3 |
| Q201 | Br | COEt | Gc |
| Q201 | Br | COPh | G3 |
| Q201 | Br | CN | Gc |
| Q205 | Br | CN | Gc |
| Q201 | Br | H | G3 |
| Q201 | Br | Me | G2 |
| Q201 | Br | Et | G1 |
| Q201 | Br | CH2CH2Cl | G3 |
| Q201 | Br | Ph | Gc |
| Q205 | Br | Ph | Gc |
| Q209 | Br | Ph | G3 |
| Q201 | Br | Ph—2-Cl | G3 |
| Q201 | Br | Cl | Gc |
| Q201 | Br | Br | Gc |
| Q205 | Br | Br | G3 |
| Q201 | Br | NO2 | Gc |
| Q209 | Br | NO2 | Gc |
| Q201 | Br | NH2 | Gc |

TABLE 3-continued $$\begin{array}{c} N \diagup D \\ \| \quad \| \\ B \diagdown N \diagup SO_2NHCONHGn \\ | \\ A \end{array}$$

| A | B | D | Gn |
|---|---|---|---|
| Q201 | Br | NMe₂ | G₃ |
| Q201 | Br | NHCOMe | Gc |
| Q201 | Br | OMe | G₃ |
| Q201 | Br | CH₂OMe | Gc |
| Q201 | Br | SMe | Gc |
| Q201 | Br | SO₂Me | Gc |
| Q201 | Br | SO₂NH₂ | G₃ |
| Q201 | Br | SO₂NHMe | Gc |
| Q201 | Br | SO₂NMe₂ | G₃ |
| Q201 | SMe | COOMe | Gc |
| Q205 | SMe | COOMe | Gc |
| Q209 | SMe | COOMe | G₃ |
| Q201 | SMe | COOEt | Gc |
| Q205 | SMe | COOEt | Gc |
| Q209 | SMe | COOEt | Gc |
| Q229 | SMe | COOEt | G₃ |
| Q246 | SMe | COOEt | Gc |
| Q201 | SMe | COOPr—i | Gc |
| Q205 | SMe | COOPr—i | G₃ |
| Q201 | SMe | COOCH₂CH₂Cl | Gc |
| Q201 | SMe | COOCH₂CH=CH₂ | Gc |
| Q201 | SMe | CONHMe | Gc |
| Q201 | SMe | CONMe₂ | G₁ |
| Q201 | SMe | COMe | Gc |
| Q205 | SMe | COMe | Gc |
| Q201 | SMe | COEt | G₃ |
| Q201 | SMe | COPr—i | Gc |
| Q201 | SMe | COPh | G₃ |
| Q201 | SMe | CN | Gc |
| Q205 | SMe | CN | Gc |
| Q229 | SMe | CN | G₃ |
| Q201 | SMe | H | Gc |
| Q201 | SMe | Me | Gc |
| Q205 | SMe | Me | G₃ |
| Q201 | SMe | Et | Gc |
| Q205 | SMe | Et | Gc |
| Q201 | SMe | CH₂CH₂Cl | G₃ |
| Q201 | SMe | Ph | Gc |
| Q205 | SMe | Ph | Gc |
| Q209 | SMe | Ph | G₃ |
| Q201 | SMe | Ph—2-Cl | Gc |
| Q201 | SMe | Cl | Gc |
| Q205 | SMe | Cl | G₃ |
| Q201 | SMe | Br | Gc |
| Q201 | SMe | NO₂ | Gc |
| Q205 | SMe | NO₂ | Gc |
| Q209 | SMe | NO₂ | G₃ |
| Q201 | SMe | NH₂ | Gc |
| Q205 | SMe | NH₂ | Gc |
| Q201 | SMe | NHMe | G₃ |
| Q201 | SMe | NMe₂ | Gc |
| Q205 | SMe | NMe₂ | Gc |
| Q201 | SMe | NHCOMe | Gc |
| Q205 | SMe | NHCOMe | G₃ |
| Q201 | SMe | NHSO₂Me | Gc |
| Q201 | SMe | OMe | Gc |
| Q201 | SMe | CH₂OMe | Gc |
| Q201 | SMe | SMe | Gc |
| Q201 | SMe | SO₂Me | Gc |
| Q205 | SMe | SO₂Me | G₃ |
| Q201 | SMe | SO₂Ph | Gc |
| Q201 | SMe | SO₂NH₂ | Gc |
| Q201 | SMe | SO₂NHMe | G₃ |
| Q201 | SMe | SO₂NMe₂ | Gc |
| Q201 | SO₂Me | COOMe | Gc |
| Q205 | SO₂Me | COOMe | Gc |
| Q209 | SO₂Me | COOMe | G₃ |
| Q229 | SO₂Me | COOMe | G₃ |
| Q246 | SO₂Me | COOMe | G₁ |
| Q201 | SO₂Me | COOEt | Gc |
| Q205 | SO₂Me | COOEt | Gc |
| Q209 | SO₂Me | COOEt | G₃ |
| Q222 | SO₂Me | COOEt | Gc |
| Q225 | SO₂Me | COOEt | Gc |
| Q201 | SO₂Me | COOPr—i | G₃ |
| Q205 | SO₂Me | COOPr—i | Gc |
| Q201 | SO₂Me | COOCH₂CH₂Cl | Gc |
| Q201 | SO₂Me | COOCH₂CH=CH₂ | G₃ |
| Q201 | SO₂Me | COOCH₂C≡CH | Gc |
| Q201 | SO₂Me | CONHMe | Gc |
| Q201 | SO₂Me | CONMe₂ | G₂ |
| Q201 | SO₂Me | COMe | Gc |
| Q205 | SO₂Me | COMe | Gc |
| Q229 | SO₂Me | COMe | G₃ |
| Q201 | SO₂Me | COEt | Gc |
| Q205 | SO₂Me | COEt | Gc |
| Q201 | SO₂Me | COPr—i | G₃ |
| Q201 | SO₂Me | COPh | Gc |
| Q201 | SO₂Me | CN | Gc |
| Q205 | SO₂Me | CN | Gc |
| Q222 | SO₂Me | CN | Gc |
| Q229 | SO₂Me | CN | Gc |
| Q201 | SO₂Me | H | G₂ |
| Q201 | SO₂Me | Me | Gc |
| Q205 | SO₂Me | Me | Gc |
| Q201 | SO₂Me | Et | G₃ |
| Q201 | SO₂Me | Pr—i | Gc |
| Q201 | SO₂Me | CH=CH₂ | Gc |
| Q201 | SO₂Me | CH=CHMe | G₁ |
| Q201 | SO₂Me | CH₂CH₂Cl | Gc |
| Q205 | SO₂Me | CH₂CH₂Cl | G₃ |
| Q201 | SO₂Me | CH₂Ph | G₃ |
| Q201 | SO₂Me | Ph | Gc |
| Q205 | SO₂Me | Ph | Gc |
| Q209 | SO₂Me | Ph | Gc |
| Q229 | SO₂Me | Ph | G₃ |
| Q246 | SO₂Me | Ph | G₃ |
| Q201 | SO₂Me | Ph—2-Cl | Gc |
| Q205 | SO₂Me | Ph—2-Me | Gc |
| Q201 | SO₂Me | Cl | Gc |
| Q205 | SO₂Me | Cl | Gc |
| Q229 | SO₂Me | Cl | G₃ |
| Q201 | SO₂Me | Br | G₃ |
| Q205 | SO₂Me | Br | Gc |
| Q201 | SO₂Me | NO₂ | Gc |
| Q205 | SO₂Me | NO₂ | Gc |
| Q209 | SO₂Me | NO₂ | Gc |
| Q229 | SO₂Me | NO₂ | G₃ |
| Q201 | SO₂Me | NH₂ | Gc |
| Q205 | SO₂Me | NH₂ | G₃ |
| Q201 | SO₂Me | NHMe | Gc |
| Q201 | SO₂Me | NMe₂ | Gc |
| Q205 | SO₂Me | NMe₂ | G₁ |
| Q201 | SO₂Me | NHCOMe | Gc |
| Q205 | SO₂Me | NHCOMe | Gc |
| Q201 | SO₂Me | NHCOEt | G₃ |
| Q201 | SO₂Me | NHSO₂Me | Gc |
| Q201 | SO₂Me | OMe | G₁ |
| Q201 | SO₂Me | CH₂OMe | Gc |
| Q205 | SO₂Me | CH₂OMe | Gc |
| Q201 | SO₂Me | SO₂Me | Gc |
| Q205 | SO₂Me | SO₂Me | Gc |
| Q201 | SO₂Me | SO₂Ph | G₃ |
| Q201 | SO₂Me | SO₂OMe | Gc |
| Q201 | SO₂Me | SO₂NH₂ | Gc |
| Q201 | SO₂Me | SO₂NHMe | G₃ |
| Q201 | SO₂Me | SO₂NMe₂ | Gc |
| Q201 | Ph | COOMe | Gc |
| Q205 | Ph | COOMe | G₃ |
| Q209 | Ph | COOMe | Gc |
| Q201 | Ph | COOEt | Gc |
| Q205 | Ph | COOEt | Gc |
| Q209 | Ph | COOEt | Gc |
| Q229 | Ph | COOEt | G₃ |
| Q201 | Ph | COOPr—i | G₃ |
| Q201 | Ph | COOCH₂CH₂Cl | Gc |

TABLE 3-continued

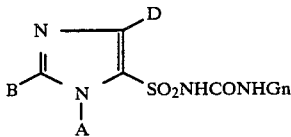

| A | B | D | Gn |
|---|---|---|---|
| Q201 | Ph | COOCH$_2$CH=CH$_2$ | Gc |
| Q201 | Ph | COOCH$_2$C≡CH | G$_3$ |
| Q201 | Ph | CONMe$_2$ | Gc |
| Q201 | Ph | COMe | Gc |
| Q205 | Ph | COMe | Gc |
| Q201 | Ph | COEt | G$_3$ |
| Q201 | Ph | CN | Gc |
| Q205 | Ph | CN | Gc |
| Q201 | Ph | H | G$_3$ |
| Q201 | Ph | Me | Gc |
| Q201 | Ph | Et | Gc |
| Q201 | Ph | CH$_2$CH$_2$Cl | G$_3$ |
| Q201 | Ph | Ph | Gc |
| Q205 | Ph | Ph | Gc |
| Q209 | Ph | Ph | G$_3$ |
| Q201 | Ph | Cl | Gc |
| Q201 | Ph | Br | G$_3$ |
| Q201 | Ph | NO$_2$ | Gc |
| Q201 | Ph | NH$_2$ | Gc |
| Q201 | Ph | NHMe | G$_3$ |
| Q201 | Ph | NMe$_2$ | Gc |
| Q201 | Ph | NHCOMe | Gc |
| Q201 | Ph | NHSO$_2$Me | G$_1$ |
| Q201 | Ph | CH$_2$OMe | Gc |
| Q201 | Ph | SO$_2$Me | G$_3$ |
| Q201 | Ph | SO$_2$NH$_2$ | Gc |
| Q201 | Ph | SO$_2$NHMe | Gc |
| Q201 | Ph | SO$_2$NMe$_2$ | G$_3$ |

TABLE 4

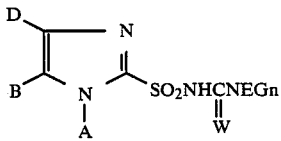

| A | B | D | E | W | Gn |
|---|---|---|---|---|---|
| Q5 | H | H | Me | O | Gc |
| CH$_2$—Q5 | H | H | Me | O | Gc |
| Q5 | H | H | Et | O | G3 |
| Q5 | H | H | Pr—n | O | G3 |
| Q5 | H | H | CH$_2$CH=CH$_2$ | O | G3 |
| Q5 | H | H | OMe | O | G3 |
| Q61 | H | H | Me | O | Gc |
| CH$_2$—Q61 | H | H | Me | O | Gc |
| Q61 | H | H | Et | O | G3 |
| Q61 | H | H | Pr—n | O | G3 |
| Q61 | H | H | CH$_2$CH=CH$_2$ | O | G3 |
| Q61 | H | H | OMe | O | G3 |
| Q26 | H | H | Me | O | G3 |
| Q26 | H | H | Et | O | G3 |
| Q26 | H | H | OMe | O | G3 |
| Q5 | H | H | H | S | Gc |
| CH$_2$—Q5 | H | H | H | S | G3 |
| Q26 | H | H | H | S | Gc |
| Q61 | H | H | H | S | Gc |
| CH$_2$—Q61 | H | H | H | S | G3 |
| Q5 | H | H | H | NH | Gc |
| CH$_2$—Q5 | H | H | H | NH | G3 |
| Q26 | H | H | H | NH | Gc |
| Q61 | H | H | H | NH | Gc |
| CH$_2$—Q61 | H | H | H | NH | G3 |
| Q5 | H | H | H | NOMe | Gc |
| CH$_2$—Q5 | H | H | H | NOMe | G3 |
| Q26 | H | H | H | NOMe | Gc |
| Q61 | H | H | H | NOMe | Gc |
| CH$_2$—Q61 | H | H | H | NOMe | G3 |
| Q201 | H | H | Me | O | Gc |
| CH$_2$—Q201 | H | H | Me | O | G3 |

TABLE 4-continued

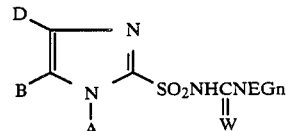

| A | B | D | E | W | Gn |
|---|---|---|---|---|---|
| Q201 | H | H | Et | O | Gc |
| Q201 | H | H | Pr—n | O | G3 |
| Q201 | H | H | CH$_2$CH=CH$_2$ | O | Gc |
| Q201 | H | H | OMe | O | Gc |
| Q205 | H | H | Me | O | G3 |
| Q205 | H | H | Et | O | G3 |
| Q205 | H | H | OMe | O | G3 |
| Q201 | H | H | H | S | Gb |
| CH$_2$—Q201 | H | H | H | S | G3 |
| Q205 | H | H | H | S | Gc |
| Q222 | H | H | H | S | G2 |
| Q229 | H | H | H | S | G3 |
| Q201 | H | H | H | NH | Gb |
| CH$_2$—Q201 | H | H | H | NH | G3 |
| Q205 | H | H | H | NH | Gc |
| Q222 | H | H | H | NH | Gc |
| Q229 | H | H | H | NH | G3 |
| Q201 | H | H | H | NOMe | Gb |
| CH$_2$—Q201 | H | H | H | NOMe | G3 |
| Q205 | H | H | H | NOMe | Gc |
| Q222 | H | H | H | NOMe | Gc |
| Q229 | H | H | H | NOMe | G3 |

TABLE 5

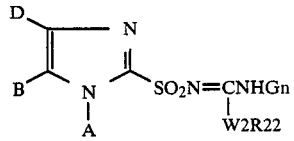

| A | B | D | W2 | R22 | Gn |
|---|---|---|----|-----|-----|
| Q5 | H | H | O | Me | Gc |
| CH$_2$—Q5 | H | H | O | Me | G3 |
| Q5 | H | H | O | Et | Gc |
| Q5 | H | H | O | Pr—n | G3 |
| Q26 | H | H | O | Me | Gc |
| Q26 | H | H | O | Et | G3 |
| Q61 | H | H | O | Me | Gc |
| CH$_2$—Q61 | H | H | O | Me | Gc |
| Q61 | H | H | O | Et | Gc |
| Q61 | H | H | O | Pr—n | G3 |
| Q158 | H | H | O | Et | G3 |
| Q158 | H | H | O | Me | G3 |
| Q5 | H | H | S | Me | Gc |
| CH$_2$—Q5 | H | H | S | Me | G3 |
| Q5 | H | H | S | Et | Gc |
| Q5 | H | H | S | Pr—n | G3 |
| Q26 | H | H | S | Me | Gc |
| Q26 | H | H | S | Et | G3 |
| Q61 | H | H | S | Me | Gc |
| CH$_2$—Q61 | H | H | S | Me | Gc |
| Q61 | H | H | S | Et | Gc |
| Q61 | H | H | S | Pr—n | G3 |
| Q158 | H | H | S | Et | G3 |
| Q158 | H | H | S | Me | G3 |
| Q201 | H | H | O | Me | Gc |
| CH$_2$—Q201 | H | H | O | Me | G$_3$ |
| Q201 | H | H | O | Et | Gc |
| Q201 | H | H | O | Pr—n | Gc |
| Q205 | H | H | O | Me | G$_3$ |
| Q205 | H | H | O | Et | Gc |
| Q222 | H | H | O | Me | Gc |
| Q222 | H | H | O | Et | G$_3$ |
| Q229 | H | H | O | Me | Gc |
| Q229 | H | H | O | Et | G$_3$ |
| Q201 | H | H | S | Me | Gc |
| CH$_2$—Q201 | H | H | S | Me | G$_3$ |
| Q201 | H | H | S | Et | Gc |
| Q201 | H | H | S | Pr—n | Gc |

TABLE 5-continued

Structure: D, B-N(A)- ring with N=C-SO₂N=CNHGn, W2R22

| A | B | D | W2 | R22 | Gn |
|---|---|---|----|----|----|
| Q205 | H | H | S | Me | Gc |
| Q205 | H | H | S | Et | Gc |
| Q222 | H | H | S | Me | G₃ |
| Q222 | H | H | S | Et | Gc |
| Q229 | H | H | S | Me | Gc |
| Q229 | H | H | S | Et | G₃ |

TABLE 6

Structure with SO₂N=CNHGn, Az

| A | B | D | Az | Gn |
|---|---|---|----|----|
| Q5 | H | H | Imidazol-1-yl | Gc |
| Q5 | H | H | Pyrazol-1-yl | Gc |
| CH₂—Q5 | H | H | Imidazol-1-yl | G3 |
| CH₂—Q5 | H | H | Pyrazol-1-yl | G3 |
| Q26 | H | H | Imidazol-1-yl | Gc |
| Q26 | H | H | Pyrazol-1-yl | Gc |
| Q61 | H | H | Imidazol-1-yl | Gc |
| Q61 | H | H | Pyrazol-1-yl | Gc |
| CH₂—Q61 | H | H | Imidazol-1-yl | G3 |
| CH₂—Q61 | H | H | Pyrazol-1-yl | G3 |
| Q158 | H | H | Imidazol-1-yl | G3 |
| Q158 | H | H | Pyrazol-1-yl | G3 |
| Q201 | H | H | Imidazol-1-yl | Gc |
| Q201 | H | H | Pyrazol-1-yl | Gc |
| CH₂—Q201 | H | H | Imidazol-1-yl | G₃ |
| CH₂—Q201 | H | H | Pyrazol-1-yl | G₃ |
| Q205 | H | H | Imidazol-1-yl | Gc |
| Q205 | H | H | Pyrazol-1-yl | Gc |
| Q222 | H | H | Imidazol-1-yl | G₃ |
| Q222 | H | H | Pyrazol-1-yl | G₃ |
| Q229 | H | H | Imidazol-1-yl | Gc |
| Q229 | H | H | Pyrazol-1-yl | Gc |

TABLE 7

Structure with SO₂N=CNHGn, N(J)R23

| A | B | D | J | R23 | Gn |
|---|---|---|---|-----|-----|
| Q5 | H | H | Me | H | Gc |
| Q5 | H | H | Me | Me | G3 |
| Q5 | H | H | Me | OMe | Gc |
| Q5 | H | H | Et | H | G3 |
| Q5 | H | H | Et | Me | G3 |
| Q5 | H | H | Et | OMe | Gc |
| Q5 | H | H | J1 | H | G3 |
| Q5 | H | H | J1 | Me | G1 |
| Q5 | H | H | J1 | OMe | G3 |
| Q201 | H | H | Me | H | Gc |
| Q201 | H | H | Me | Me | G₃ |
| Q201 | H | H | Me | OMe | Gc |
| Q201 | H | H | Et | H | G₃ |
| Q201 | H | H | Et | Me | G₃ |
| Q201 | H | H | Et | OMe | Gc |
| Q201 | H | H | J10 | H | G₃ |
| Q201 | H | H | J10 | Me | G₁ |

TABLE 7-continued

| A | B | D | J | R23 | Gn |
|---|---|---|---|-----|-----|
| Q201 | H | H | J10 | OMe | G₃ |

TABLE 8

Structure: SO₂NHCNEGn, W

| A | B | D | E | W | Gn |
|---|---|---|---|---|----|
| Q5 | H | COOMe | Me | O | Gc |
| CH₂—Q5 | H | COOMe | Me | O | G3 |
| Q5 | H | COOMe | Et | O | Gc |
| Q5 | H | COOMe | Pr—n | O | Gc |
| Q5 | H | COOMe | CH₂CH=CH₂ | O | G3 |
| Q5 | H | COOMe | OMe | O | Gc |
| Q26 | H | COOMe | Me | O | G3 |
| Q26 | H | COOMe | Et | O | Gc |
| Q26 | H | COOMe | OMe | O | Gc |
| Q61 | H | COOMe | Me | O | Gc |
| CH₂—Q61 | H | COOMe | Me | O | G3 |
| Q61 | H | COOMe | Et | O | Gc |
| Q61 | H | COOMe | Pr—n | O | Gc |
| Q61 | H | COOMe | CH₂CH=CH₂ | O | G3 |
| Q61 | H | COOMe | OMe | O | Gc |
| Q5 | H | COOMe | H | S | Gb |
| CH₂—Q5 | H | COOMe | H | S | G3 |
| Q26 | H | COOMe | H | S | Gc |
| Q61 | H | COOMe | H | S | Gc |
| CH₂—Q61 | H | COOMe | H | S | G3 |
| Q5 | H | COOMe | H | NH | Gb |
| CH₂—Q5 | H | COOMe | H | NH | G3 |
| Q26 | H | COOMe | H | NH | Gc |
| Q61 | H | COOMe | H | NH | Gc |
| CH₂—Q61 | H | COOMe | H | NH | G3 |
| Q5 | H | COOMe | H | NOMe | Gb |
| CH₂—Q5 | H | COOMe | H | NOMe | G3 |
| Q26 | H | COOMe | H | NOMe | Gc |
| Q61 | H | COOMe | H | NOMe | Gc |
| CH₂—Q61 | H | COOMe | H | NOMe | G3 |
| Q5 | H | COOEt | Me | O | Gc |
| CH₂—Q5 | H | COOEt | Me | O | G3 |
| Q5 | H | COOEt | Et | O | Gc |
| Q5 | H | COOEt | Pr—n | O | Gc |
| Q5 | H | COOEt | CH₂CH=CH₂ | O | G3 |
| Q5 | H | COOEt | OMe | O | Gc |
| Q26 | H | COOEt | Me | O | G3 |
| Q26 | H | COOEt | Et | O | Gc |
| Q26 | H | COOEt | OMe | O | Gc |
| Q61 | H | COOEt | Me | O | Gc |
| CH₂—Q61 | H | COOEt | Me | O | G3 |
| Q61 | H | COOEt | Et | O | Gc |
| Q61 | H | COOEt | Pr—n | O | Gc |
| Q61 | H | COOEt | CH₂CH=CH₂ | O | G3 |
| Q61 | H | COOEt | OMe | O | Gc |
| Q5 | H | COOEt | H | S | Gb |
| CH₂—Q5 | H | COOEt | H | S | G3 |
| Q26 | H | COOEt | H | S | Gc |
| Q61 | H | COOEt | H | S | Gc |
| CH₂—Q61 | H | COOEt | H | S | G3 |
| Q5 | H | COOEt | H | NH | Gb |
| CH₂—Q5 | H | COOEt | H | NH | G3 |
| Q26 | H | COOEt | H | NH | Gc |
| Q61 | H | COOEt | H | NH | Gc |
| CH₂—Q61 | H | COOEt | H | NH | G3 |
| Q5 | H | COOEt | H | NOMe | Gb |
| CH₂—Q5 | H | COOEt | H | NOMe | G3 |
| Q26 | H | COOEt | H | NOMe | Gc |

TABLE 8-continued

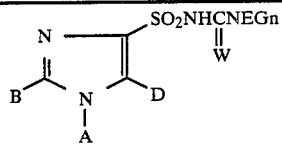

| A | B | D | E | W | Gn |
|---|---|---|---|---|---|
| Q61 | H | COOEt | H | NOMe | Gc |
| CH₂—Q61 | H | COOEt | H | NOMe | G3 |
| Q201 | H | COOMe | Me | O | Gc |
| CH₂—Q201 | H | COOMe | Me | O | G3 |
| Q201 | H | COOMe | Et | O | Gc |
| Q201 | H | COOMe | Pr—n | O | Gc |
| Q201 | H | COOMe | CH₂CH=CH₂ | O | G3 |
| Q201 | H | COOMe | OMe | O | Gc |
| Q205 | H | COOMe | Me | O | G3 |
| Q205 | H | COOMe | Et | O | Gc |
| Q205 | H | COOMe | OMe | O | Gc |
| Q201 | H | COOMe | H | S | Gb |
| CH₂—Q201 | H | COOMe | H | S | G3 |
| Q205 | H | COOMe | H | S | Gc |
| Q222 | H | COOMe | H | S | G3 |
| Q229 | H | COOMe | H | S | G1 |
| Q201 | H | COOMe | H | NH | Gb |
| CH₂—Q201 | H | COOMe | H | NH | G3 |
| Q205 | H | COOMe | H | NH | Gc |
| Q222 | H | COOMe | H | NH | Gc |
| Q229 | H | COOMe | H | NH | G3 |
| Q201 | H | COOMe | H | NOMe | Gb |
| CH₂—Q201 | H | COOMe | H | NOMe | G3 |
| Q205 | H | COOMe | H | NOMe | Gc |
| Q222 | H | COOMe | H | NOMe | Gc |
| Q229 | H | COOMe | H | NOMe | G3 |
| Q201 | H | COOEt | Me | O | Gc |
| CH₂—Q201 | H | COOEt | Me | O | G3 |
| Q201 | H | COOEt | Et | O | Gc |
| Q201 | H | COOEt | Pr—n | O | Gc |
| Q201 | H | COOEt | CH₂CH=CH₂ | O | Gc |
| Q201 | H | COOEt | OMe | O | Gc |
| Q205 | H | COOEt | Me | O | G3 |
| Q205 | H | COOEt | Et | O | G3 |
| Q205 | H | COOEt | OMe | O | Gc |
| Q201 | H | COOEt | H | S | Gb |
| CH₂—Q201 | H | COOEt | H | S | G3 |
| Q205 | H | COOEt | H | S | Gc |
| Q222 | H | COOEt | H | S | Gc |
| Q229 | H | COOEt | H | S | Gc |
| Q201 | H | COOEt | H | NH | Gb |
| CH₂—Q201 | H | COOEt | H | NH | G3 |
| Q205 | H | COOEt | H | NH | Gc |
| Q222 | H | COOEt | H | NH | Gc |
| Q229 | H | COOEt | H | NH | Gc |
| Q201 | H | COOEt | H | NOMe | Gb |
| CH₂—Q201 | H | COOEt | H | NOMe | G3 |
| Q205 | H | COOEt | H | NOMe | Gc |
| Q222 | H | COOEt | H | NOMe | Gc |
| Q229 | H | COOEt | H | NOMe | G3 |

TABLE 9

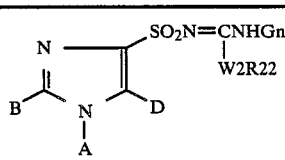

| A | B | D | W2 | R22 | Gn |
|---|---|---|----|-----|----|
| Q5 | H | COOMe | O | Me | Gc |
| CH₂—Q5 | H | COOMe | O | Me | G3 |
| Q5 | H | COOMe | O | Et | Gc |
| Q5 | H | COOMe | O | Pr—n | G3 |
| Q26 | H | COOMe | O | Me | Gc |
| Q26 | H | COOMe | O | Et | G3 |
| Q61 | H | COOMe | O | Me | Gc |
| CH₂—Q61 | H | COOMe | O | Me | G3 |
| Q61 | H | COOMe | O | Et | Gc |
| Q61 | H | COOMe | O | Pr—n | G3 |

TABLE 9-continued

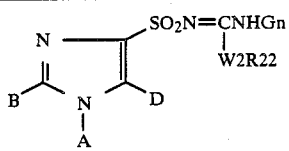

| A | B | D | W2 | R22 | Gn |
|---|---|---|----|-----|----|
| Q158 | H | COOMe | O | Me | Gc |
| Q158 | H | COOMe | O | Et | G3 |
| Q5 | H | COOMe | S | Me | Gc |
| CH₂—Q5 | H | COOMe | S | Me | G3 |
| Q5 | H | COOMe | S | Et | Gc |
| Q5 | H | COOMe | S | Pr—n | G3 |
| Q26 | H | COOMe | S | Me | Gc |
| Q26 | H | COOMe | S | Et | G3 |
| Q61 | H | COOMe | S | Me | Gc |
| CH₂—Q61 | H | COOMe | S | Me | G3 |
| Q61 | H | COOMe | S | Et | Gc |
| Q61 | H | COOMe | S | Pr—n | G3 |
| Q158 | H | COOMe | S | Me | Gc |
| Q158 | H | COOMe | S | Et | G3 |
| Q5 | H | COOEt | O | Me | Gc |
| CH₂—Q5 | H | COOEt | O | Me | G3 |
| Q5 | H | COOEt | O | Et | Gc |
| Q5 | H | COOEt | O | Pr—n | G3 |
| Q26 | H | COOEt | O | Me | Gc |
| Q26 | H | COOEt | O | Et | G3 |
| Q61 | H | COOEt | O | Me | Gc |
| CH₂—Q61 | H | COOEt | O | Me | G3 |
| Q61 | H | COOEt | O | Et | Gc |
| Q61 | H | COOEt | O | Pr—n | G3 |
| Q158 | H | COOEt | O | Me | Gc |
| Q158 | H | COOEt | O | Et | G3 |
| Q5 | H | COOEt | S | Me | Gc |
| CH₂—Q5 | H | COOEt | S | Me | G3 |
| Q5 | H | COOEt | S | Et | Gc |
| Q5 | H | COOEt | S | Pr—n | G3 |
| Q26 | H | COOEt | S | Me | Gc |
| Q26 | H | COOEt | S | Et | G3 |
| Q61 | H | COOEt | S | Me | Gc |
| CH₂—Q61 | H | COOEt | S | Me | G3 |
| Q61 | H | COOEt | S | Et | Gc |
| Q61 | H | COOEt | S | Pr—n | G3 |
| Q158 | H | COOEt | S | Me | Gc |
| Q158 | H | COOEt | S | Et | G3 |
| Q201 | H | COOMe | O | Me | Gc |
| CH₂—Q201 | H | COOMe | O | Me | G3 |
| Q201 | H | COOMe | O | Et | Gc |
| Q201 | H | COOMe | O | Pr—n | Gc |
| Q205 | H | COOMe | O | Me | Gc |
| Q205 | H | COOMe | O | Et | Gc |
| Q222 | H | COOMe | O | Me | Gc |
| Q222 | H | COOMe | O | Et | G3 |
| Q229 | H | COOMe | O | Me | Gc |
| Q229 | H | COOMe | O | Et | Gc |
| Q201 | H | COOMe | S | Me | Gc |
| CH₂—Q201 | H | COOMe | S | Me | G3 |
| Q201 | H | COOMe | S | Et | Gc |
| Q201 | H | COOMe | S | Pr—n | Gc |
| Q205 | H | COOMe | S | Me | Gc |
| Q205 | H | COOMe | S | Et | Gc |
| Q222 | H | COOMe | S | Me | Gc |
| Q222 | H | COOMe | S | Et | G3 |
| Q229 | H | COOMe | S | Me | Gc |
| Q229 | H | COOMe | S | Et | G3 |
| Q201 | H | COOEt | O | Me | Gc |
| CH₂—Q201 | H | COOEt | O | Me | G3 |
| Q201 | H | COOEt | O | Et | Gc |
| Q201 | H | COOEt | O | Pr—n | Gc |
| Q205 | H | COOEt | O | Me | Gc |
| Q205 | H | COOEt | O | Et | Gc |
| Q222 | H | COOEt | O | Me | Gc |
| Q222 | H | COOEt | O | Et | Gc |
| Q229 | H | COOEt | O | Me | Gc |
| Q229 | H | COOEt | O | Et | Gc |
| Q201 | H | COOEt | S | Me | Gc |
| CH₂—Q201 | H | COOEt | S | Me | G3 |
| Q201 | H | COOEt | S | Et | Gc |
| Q201 | H | COOEt | S | Pr—n | Gc |
| Q205 | H | COOEt | S | Me | Gc |

TABLE 9-continued

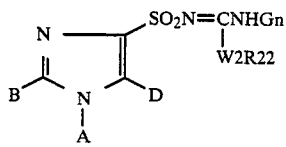

| A | B | D | W2 | R22 | Gn |
|---|---|---|---|---|---|
| Q205 | H | COOEt | S | Et | G3 |
| Q222 | H | COOEt | S | Me | Gc |
| Q222 | H | COOEt | S | Et | Gc |
| Q229 | H | COOEt | S | Me | G1 |
| Q229 | H | COOEt | S | Et | G1 |

TABLE 10

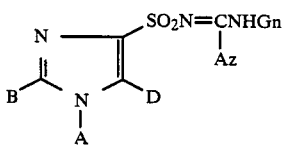

| A | B | D | Az | Gn |
|---|---|---|---|---|
| Q5 | H | COOMe | Imidazol-1-yl | Gc |
| Q5 | H | COOMe | Pyrazol-1-yl | Gc |
| CH2—Q5 | H | COOMe | Imidazol-1-yl | G1 |
| CH2—Q5 | H | COOMe | Pyrazol-1-yl | G1 |
| Q26 | H | COOMe | Imidazol-1-yl | Gc |
| Q26 | H | COOMe | Pyrazol-1-yl | Gc |
| Q61 | H | COOMe | Imidazol-1-yl | Gc |
| Q61 | H | COOMe | Pyrazol-1-yl | Gc |
| CH2—Q61 | H | COOMe | Imidazol-1-yl | G3 |
| CH2—Q61 | H | COOMe | Pyrazol-1-yl | G3 |
| Q5 | H | COOEt | Imidazol-1-yl | Gc |
| Q5 | H | COOEt | Pyrazol-1-yl | Gc |
| CH2—Q5 | H | COOEt | Imidazol-1-yl | G3 |
| CH2—Q5 | H | COOEt | Pyrazol-1-yl | G3 |
| Q26 | H | COOEt | Imidazol-1-yl | Gc |
| Q26 | H | COOEt | Pyrazol-1-yl | Gc |
| Q61 | H | COOEt | Imidazol-1-yl | Gc |
| Q61 | H | COOEt | Pyrazol-1-yl | Gc |
| CH2—Q61 | H | COOEt | Imidazol-1-yl | G3 |
| CH2—Q61 | H | COOEt | Pyrazol-1-yl | G3 |
| Q201 | H | COOMe | Imidazol-1-yl | Gc |
| Q201 | H | COOMe | Pyrazol-1-yl | Gc |
| CH2—Q201 | H | COOMe | Imidazol-1-yl | G1 |
| CH2—Q201 | H | COOMe | Pyrazol-1-yl | G1 |
| Q205 | H | COOMe | Imidazol-1-yl | Gc |
| Q205 | H | COOMe | Pyrazol-1-yl | Gc |
| Q222 | H | COOMe | Imidazol-1-yl | Gc |
| Q222 | H | COOMe | Pyrazol-1-yl | Gc |
| Q229 | H | COOMe | Imidazol-1-yl | G3 |
| Q229 | H | COOMe | Pyrazol-1-yl | G3 |
| Q201 | H | COOEt | Imidazol-1-yl | Gc |
| Q201 | H | COOEt | Pyrazol-1-yl | Gc |
| CH2—Q201 | H | COOEt | Imidazol-1-yl | G3 |
| CH2—Q201 | H | COOEt | Pyrazol-1-yl | G3 |
| Q205 | H | COOEt | Imidazol-1-yl | Gc |
| Q205 | H | COOEt | Pyrazol-1-yl | Gc |
| Q222 | H | COOEt | Imidazol-1-yl | Gc |
| Q222 | H | COOEt | Pyrazol-1-yl | Gc |
| Q229 | H | COOEt | Imidazol-1-yl | G3 |
| Q229 | H | COOEt | Pyrazol-1-yl | G3 |

TABLE 11

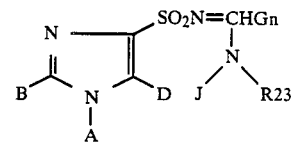

| A | B | D | J | R23 | Gn |
|---|---|---|---|---|---|
| Q5 | H | COOMe | Me | H | G3 |
| Q5 | H | COOMe | Me | Me | Gc |
| Q5 | H | COOMe | Me | OMe | Gc |
| Q5 | H | COOMe | Et | H | Gc |
| Q5 | H | COOMe | Et | Me | Gc |
| Q5 | H | COOMe | Et | OMe | G3 |
| Q5 | H | COOMe | J2 | H | Gc |
| Q5 | H | COOMe | J2 | Me | Gc |
| Q5 | H | COOMe | J2 | OMe | G3 |
| Q5 | H | COOEt | Me | H | Gc |
| Q5 | H | COOEt | Me | Me | G3 |
| Q5 | H | COOEt | Me | OMe | Gc |
| Q5 | H | COOEt | Et | H | Gc |
| Q5 | H | COOEt | Et | Me | G3 |
| Q5 | H | COOEt | Et | OMe | Gc |
| Q5 | H | COOEt | J3 | H | Gc |
| Q5 | H | COOEt | J3 | Me | Gc |
| Q5 | H | COOEt | J3 | OMe | Gc |
| CH2—Q5 | H | COOMe | Me | H | G3 |
| CH2—Q5 | H | COOEt | Me | OMe | Gc |
| Q26 | H | COOMe | Me | H | Gc |
| Q26 | H | COOEt | Me | OMe | Gc |
| Q61 | H | COOMe | Me | H | G3 |
| Q61 | H | COOMe | Me | Me | Gc |
| Q61 | H | COOMe | Me | OMe | Gc |
| Q61 | H | COOMe | Et | H | Gc |
| Q61 | H | COOMe | Et | Me | Gc |
| Q61 | H | COOMe | Et | OMe | G3 |
| Q61 | H | COOMe | J4 | H | Gc |
| Q61 | H | COOMe | J4 | Me | Gc |
| Q61 | H | COOMe | J4 | OMe | G3 |
| Q61 | H | COOEt | Me | H | Gc |
| Q61 | H | COOEt | Me | Me | G3 |
| Q61 | H | COOEt | Me | OMe | Gc |
| Q61 | H | COOEt | Et | H | Gc |
| Q61 | H | COOEt | Et | Me | G3 |
| Q61 | H | COOEt | Et | OMe | Gc |
| Q61 | H | COOEt | J5 | H | Gc |
| Q61 | H | COOEt | J5 | Me | Gc |
| Q61 | H | COOEt | J5 | OMe | Gc |
| CH2—Q61 | H | COOMe | Me | H | G3 |
| CH2—Q61 | H | COOEt | Me | OMe | Gc |
| Q201 | H | COOMe | Me | H | G3 |
| Q201 | H | COOMe | Me | Me | Gc |
| Q201 | H | COOMe | Me | OMe | Gc |
| Q201 | H | COOMe | Et | H | Gc |
| Q201 | H | COOMe | Et | Me | Gc |
| Q201 | H | COOMe | Et | OMe | G3 |
| Q201 | H | COOMe | J11 | H | Gc |
| Q201 | H | COOMe | J11 | Me | Gc |
| Q201 | H | COOMe | J11 | OMe | G3 |
| Q201 | H | COOEt | Me | H | Gc |
| Q201 | H | COOEt | Me | Me | G3 |
| Q201 | H | COOEt | Me | OMe | Gc |
| Q201 | H | COOEt | Et | H | Gc |
| Q201 | H | COOEt | Et | Me | G3 |
| Q201 | H | COOEt | Et | OMe | Gc |
| Q201 | H | COOEt | J12 | H | Gc |
| Q201 | H | COOEt | J12 | Me | Gc |
| Q201 | H | COOEt | J12 | OMe | Gc |
| CH2—Q201 | H | COOMe | Me | H | G3 |
| CH2—Q201 | H | COOEt | Me | OMe | Gc |
| Q205 | H | COOMe | Me | H | Gc |
| Q205 | H | COOEt | Me | OMe | Gc |
| Q229 | H | COOMe | Me | H | Gc |
| Q229 | H | COOEt | Me | OMe | G3 |

TABLE 12

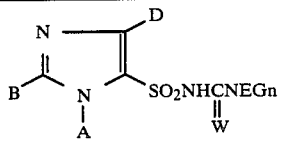

| A | B | D | E | W | Gn |
|---|---|---|---|---|---|
| Q5 | H | COOMe | Me | O | Gc |
| CH2—Q5 | H | COOMe | Me | O | G3 |
| Q5 | H | COOMe | Et | O | Gc |
| Q5 | H | COOMe | Pr—n | O | Gc |
| Q5 | H | COOMe | CH2CH=CH2 | O | G3 |
| Q5 | H | COOMe | OMe | O | Gc |
| Q26 | H | COOMe | Me | O | G3 |
| Q26 | H | COOMe | Et | O | Gc |
| Q26 | H | COOMe | OMe | O | Gc |
| Q61 | H | COOMe | Me | O | Gc |
| CH2—Q61 | H | COOMe | Me | O | G3 |
| Q61 | H | COOMe | Et | O | Gc |
| Q61 | H | COOMe | Pr—n | O | Gc |
| Q61 | H | COOMe | CH2CH=CH2 | O | G3 |
| Q61 | H | COOMe | OMe | O | Gc |
| Q5 | H | COOMe | H | S | Gb |
| CH2—Q5 | H | COOMe | H | S | G3 |
| Q26 | H | COOMe | H | S | Gc |
| Q61 | H | COOMe | H | S | Gc |
| CH2—Q61 | H | COOMe | H | S | G3 |
| Q5 | H | COOMe | H | NH | Gb |
| CH2—Q5 | H | COOMe | H | NH | G3 |
| Q26 | H | COOMe | H | NH | Gc |
| Q61 | H | COOMe | H | NH | Gc |
| CH2—Q61 | H | COOMe | H | NH | G3 |
| Q5 | H | COOMe | H | NOMe | Gb |
| CH2—Q5 | H | COOMe | H | NOMe | G3 |
| Q26 | H | COOMe | H | NOMe | Gc |
| Q61 | H | COOMe | H | NOMe | Gc |
| CH2—Q61 | H | COOMe | H | NOMe | G3 |
| Q5 | H | COOEt | Me | O | Gc |
| CH2—Q5 | H | COOEt | Me | O | G3 |
| Q5 | H | COOEt | Et | O | Gc |
| Q5 | H | COOEt | Pr—n | O | Gc |
| Q5 | H | COOEt | CH2CH=CH2 | O | G3 |
| Q5 | H | COOEt | OMe | O | Gc |
| Q26 | H | COOEt | Me | O | G3 |
| Q26 | H | COOEt | Et | O | Gc |
| Q26 | H | COOEt | OMe | O | Gc |
| Q61 | H | COOEt | Me | O | Gc |
| CH2—Q61 | H | COOEt | Me | O | G3 |
| Q61 | H | COOEt | Et | O | Gc |
| Q61 | H | COOEt | Pr—n | O | Gc |
| Q61 | H | COOEt | CH2CH=CH2 | O | G3 |
| Q61 | H | COOEt | OMe | O | Gc |
| Q5 | H | COOEt | H | S | Gb |
| CH2—Q5 | H | COOEt | H | S | G3 |
| Q26 | H | COOEt | H | S | Gc |
| Q61 | H | COOEt | H | S | Gc |
| CH2—Q61 | H | COOEt | H | S | G3 |
| Q5 | H | COOEt | H | NH | Gb |
| CH2—Q5 | H | COOEt | H | NH | G3 |
| Q26 | H | COOEt | H | NH | Gc |
| Q61 | H | COOEt | H | NH | Gc |
| CH2—Q61 | H | COOEt | H | NH | G3 |
| Q5 | H | COOEt | H | NOMe | Gb |
| CH2—Q5 | H | COOEt | H | NOMe | G3 |
| Q26 | H | COOEt | H | NOMe | Gc |
| Q61 | H | COOEt | H | NOMe | Gc |
| CH2—Q61 | H | COOEt | H | NOMe | G3 |
| Q201 | H | COOMe | Me | O | Gc |
| CH2—Q201 | H | COOMe | Me | O | G3 |
| Q201 | H | COOMe | Et | O | Gc |
| Q201 | H | COOMe | Pr—n | O | Gc |
| Q201 | H | COOMe | CH2CH=CH2 | O | G3 |
| Q201 | H | COOMe | OMe | O | Gc |
| Q205 | H | COOMe | Me | O | Gc |
| Q205 | H | COOMe | Et | O | Gc |
| Q205 | H | COOMe | OMe | O | Gc |
| Q201 | H | COOMe | H | S | Gb |
| CH2—Q201 | H | COOMe | H | S | G3 |
| Q205 | H | COOMe | H | S | Gc |
| Q222 | H | COOMe | H | S | G3 |
| Q229 | H | COOMe | H | S | G1 |
| Q201 | H | COOMe | H | NH | Gb |
| CH2—Q201 | H | COOMe | H | NH | G3 |
| Q205 | H | COOMe | H | NH | Gc |
| Q222 | H | COOMe | H | NH | Gc |
| Q229 | H | COOMe | H | NH | G3 |
| Q201 | H | COOMe | H | NOMe | Gb |
| CH2—Q201 | H | COOMe | H | NOMe | G3 |
| Q205 | H | COOMe | H | NOMe | Gc |
| Q222 | H | COOMe | H | NOMe | Gc |
| Q229 | H | COOMe | H | NOMe | G3 |
| Q201 | H | COOEt | Me | O | Gc |
| CH2—Q201 | H | COOEt | Me | O | G3 |
| Q201 | H | COOEt | Et | O | Gc |
| Q201 | H | COOEt | Pr—n | O | Gc |
| Q201 | H | COOEt | CH2CH=CH2 | O | Gc |
| Q201 | H | COOEt | OMe | O | Gc |
| Q205 | H | COOEt | Me | O | Gc |
| Q205 | H | COOEt | Et | O | G3 |
| Q205 | H | COOEt | OMe | O | Gc |
| Q201 | H | COOEt | H | S | Gb |
| CH2—Q201 | H | COOEt | H | S | G3 |
| Q205 | H | COOEt | H | S | Gc |
| Q222 | H | COOEt | H | S | Gc |
| Q229 | H | COOEt | H | S | Gc |
| Q201 | H | COOEt | H | NH | Gb |
| CH2—Q201 | H | COOEt | H | NH | G3 |
| Q205 | H | COOEt | H | NH | Gc |
| Q222 | H | COOEt | H | NH | Gc |
| Q229 | H | COOEt | H | NH | Gc |
| Q201 | H | COOEt | H | NOMe | Gb |
| CH2—Q201 | H | COOEt | H | NOMe | G3 |
| Q205 | H | COOEt | H | NOMe | Gc |
| Q222 | H | COOEt | H | NOMe | Gc |
| Q229 | H | COOEt | H | NOMe | G3 |

TABLE 13

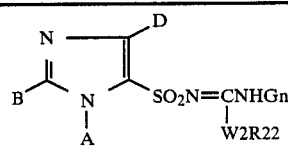

| A | B | D | W2 | R22 | Gn |
|---|---|---|---|---|---|
| Q5 | H | COOMe | O | Me | Gc |
| CH2 - Q5 | H | COOMe | O | Me | G3 |
| Q5 | H | COOMe | O | Et | Gc |
| Q5 | H | COOMe | O | Pr—n | G3 |
| Q26 | H | COOMe | O | Me | Gc |
| Q26 | H | COOMe | O | Et | G3 |
| Q61 | H | COOMe | O | Me | Gc |
| CH2 - Q61 | H | COOMe | O | Me | G3 |
| Q61 | H | COOMe | O | Et | Gc |
| Q61 | H | COOMe | O | Pr—n | G3 |
| Q158 | H | COOMe | O | Me | Gc |
| Q158 | H | COOMe | O | Et | G3 |
| Q5 | H | COOMe | S | Me | Gc |
| CH2 - Q5 | H | COOMe | S | Me | G3 |
| Q5 | H | COOMe | S | Et | Gc |
| Q5 | H | COOMe | S | Pr—n | G3 |
| Q26 | H | COOMe | S | Me | Gc |
| Q26 | H | COOMe | S | Et | G3 |
| Q61 | H | COOMe | S | Me | Gc |
| CH2 - Q61 | H | COOMe | S | Me | G3 |
| Q61 | H | COOMe | S | Et | Gc |
| Q61 | H | COOMe | S | Pr—n | G3 |
| Q158 | H | COOMe | S | Me | Gc |
| Q158 | H | COOMe | S | Et | G3 |
| Q5 | H | COOEt | O | Me | Gc |

TABLE 13-continued

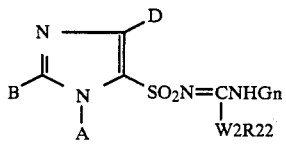

| A | B | D | W2 | R22 | Gn |
|---|---|---|---|---|---|
| CH2 - Q5 | H | COOEt | O | Me | G3 |
| Q5 | H | COOEt | O | Et | Gc |
| Q5 | H | COOEt | O | Pr—n | G3 |
| Q26 | H | COOEt | O | Me | Gc |
| Q26 | H | COOEt | O | Et | G3 |
| Q61 | H | COOEt | O | Me | Gc |
| CH2 - Q61 | H | COOEt | O | Me | G3 |
| Q61 | H | COOEt | O | Et | Gc |
| Q61 | H | COOEt | O | Pr—n | G3 |
| Q158 | H | COOEt | O | Me | Gc |
| Q158 | H | COOEt | O | Et | G3 |
| Q5 | H | COOEt | S | Me | Gc |
| CH2 - Q5 | H | COOEt | S | Me | G3 |
| Q5 | H | COOEt | S | Et | Gc |
| Q5 | H | COOEt | S | Pr—n | G3 |
| Q26 | H | COOEt | S | Me | Gc |
| Q26 | H | COOEt | S | Et | G3 |
| Q61 | H | COOEt | S | Me | Gc |
| CH2 - Q61 | H | COOEt | S | Me | G3 |
| Q61 | H | COOEt | S | Et | Gc |
| Q61 | H | COOEt | S | Pr—n | G3 |
| Q158 | H | COOEt | S | Me | Gc |
| Q158 | H | COOEt | S | Et | G3 |
| Q201 | H | COOMe | O | Me | Gc |
| CH2 - Q201 | H | COOMe | O | Me | G3 |
| Q201 | H | COOMe | O | Et | Gc |
| Q201 | H | COOMe | O | Pr—n | Gc |
| Q205 | H | COOMe | O | Me | Gc |
| Q205 | H | COOMe | O | Et | Gc |
| Q222 | H | COOMe | O | Me | Gc |
| Q222 | H | COOMe | O | Et | G3 |
| Q229 | H | COOMe | O | Me | G3 |
| Q229 | H | COOMe | O | Et | Gc |
| Q201 | H | COOMe | S | Me | Gc |
| CH2 - Q201 | H | COOMe | S | Me | G3 |
| Q201 | H | COOMe | S | Et | Gc |
| Q201 | H | COOMe | S | Pr—n | Gc |
| Q205 | H | COOMe | S | Me | Gc |
| Q205 | H | COOMe | S | Et | Gc |
| Q222 | H | COOMe | S | Me | Gc |
| Q222 | H | COOMe | S | Et | G3 |
| Q229 | H | COOMe | S | Me | Gc |
| Q229 | H | COOMe | S | Et | G3 |
| Q201 | H | COOEt | O | Me | Gc |
| CH2 - Q201 | H | COOEt | O | Me | G3 |
| Q201 | H | COOEt | O | Et | Gc |
| Q201 | H | COOEt | O | Pr—n | Gc |
| Q205 | H | COOEt | O | Me | Gc |
| Q205 | H | COOEt | O | Et | Gc |
| Q222 | H | COOEt | O | Me | Gc |
| Q222 | H | COOEt | O | Et | G3 |
| Q229 | H | COOEt | O | Me | Gc |
| Q229 | H | COOEt | O | Et | G3 |
| Q201 | H | COOEt | S | Me | Gc |
| CH2 - Q201 | H | COOEt | S | Me | G3 |
| Q201 | H | COOEt | S | Et | Gc |
| Q201 | H | COOEt | S | Pr—n | Gc |
| Q205 | H | COOEt | S | Me | Gc |
| Q205 | H | COOEt | S | Et | G3 |
| Q222 | H | COOEt | S | Me | Gc |
| Q222 | H | COOEt | S | Et | Gc |
| Q229 | H | COOEt | S | Me | G1 |
| Q229 | H | COOEt | S | Et | G1 |

TABLE 14

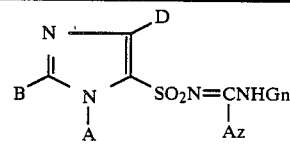

| A | B | D | Az | Gn |
|---|---|---|---|---|
| Q5 | H | COOMe | Imidazol-1-yl | Gc |
| Q5 | H | COOMe | Pyrazol-1-yl | Gc |
| CH2 - Q5 | H | COOMe | Imidazol-1-yl | G1 |
| CH2 - Q5 | H | COOMe | Pyrazol-1-yl | G1 |
| Q26 | H | COOMe | Imidazol-1-yl | Gc |
| Q26 | H | COOMe | Pyrazol-1-yl | Gc |
| Q61 | H | COOMe | Imidazol-1-yl | Gc |
| Q61 | H | COOMe | Pyrazol-1-yl | Gc |
| CH2 - Q61 | H | COOMe | Imidazol-1-yl | G3 |
| CH2 - Q61 | H | COOMe | Pyrazol-1-yl | G3 |
| Q5 | H | COOEt | Imidazol-1-yl | Gc |
| Q5 | H | COOEt | Pyrazol-1-yl | Gc |
| CH2 - Q5 | H | COOEt | Imidazol-1-yl | G3 |
| CH2 - Q5 | H | COOEt | Pyrazol-1-yl | G3 |
| Q26 | H | COOEt | Imidazol-1-yl | Gc |
| Q26 | H | COOEt | Pyrazol-1-yl | Gc |
| Q61 | H | COOEt | Imidazol-1-yl | Gc |
| Q61 | H | COOEt | Pyrazol-1-yl | Gc |
| CH2 - Q61 | H | COOEt | Imidazol-1-yl | G3 |
| CH2 - Q61 | H | COOEt | Pyrazol-1-yl | G3 |
| Q201 | H | COOMe | Imidazol-1-yl | Gc |
| Q201 | H | COOMe | Pyrazol-1-yl | Gc |
| CH2 - Q201 | H | COOMe | Imidazol-1-yl | G1 |
| CH2 - Q201 | H | COOMe | Pyrazol-1-yl | G1 |
| Q205 | H | COOMe | Imidazol-1-yl | Gc |
| Q205 | H | COOMe | Pyrazol-1-yl | Gc |
| Q222 | H | COOMe | Imidazol-1-yl | Gc |
| Q222 | H | COOMe | Pyrazol-1-yl | Gc |
| Q229 | H | COOMe | Imidazol-1-yl | G3 |
| Q229 | H | COOMe | Pyrazol-1-yl | G3 |
| Q201 | H | COOEt | Imidazol-1-yl | Gc |
| Q201 | H | COOEt | Pyrazol-1-yl | Gc |
| CH2 - Q201 | H | COOEt | Imidazol-1-yl | G3 |
| CH2 - Q201 | H | COOEt | Pyrazol-1-yl | G3 |
| Q205 | H | COOEt | Imidazol-1-yl | Gc |
| Q205 | H | COOEt | Pyrazol-1-yl | Gc |
| Q222 | H | COOEt | Imidazol-1-yl | Gc |
| Q222 | H | COOEt | Pyrazol-1-yl | Gc |
| Q229 | H | COOEt | Imidazol-1-yl | G3 |
| Q229 | H | COOEt | Pyrazol-1-yl | G3 |

TABLE 15

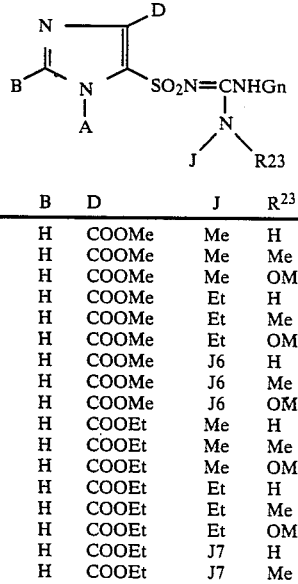

| A | B | D | J | R23 | Gn |
|---|---|---|---|---|---|
| Q5 | H | COOMe | Me | H | G3 |
| Q5 | H | COOMe | Me | Me | Gc |
| Q5 | H | COOMe | Me | OMe | Gc |
| Q5 | H | COOMe | Et | H | Gc |
| Q5 | H | COOMe | Et | Me | Gc |
| Q5 | H | COOMe | Et | OMe | G3 |
| Q5 | H | COOMe | J6 | H | Gc |
| Q5 | H | COOMe | J6 | Me | Gc |
| Q5 | H | COOMe | J6 | OMe | G3 |
| Q5 | H | COOEt | Me | H | Gc |
| Q5 | H | COOEt | Me | Me | G3 |
| Q5 | H | COOEt | Me | OMe | Gc |
| Q5 | H | COOEt | Et | H | Gc |
| Q5 | H | COOEt | Et | Me | G3 |
| Q5 | H | COOEt | Et | OMe | Gc |
| Q5 | H | COOEt | J7 | H | Gc |
| Q5 | H | COOEt | J7 | Me | Gc |
| Q5 | H | COOEt | J7 | OMe | Gc |
| CH2 - Q5 | H | COOMe | Me | H | G3 |

TABLE 15-continued $$\begin{array}{c} D \\ N \underset{\underset{A}{\mid}}{=} \\ B \underset{}{=} N \underset{}{-} SO_2N\!=\!CNHGn \\ \phantom{xxxxxxx} \underset{J}{\mid} \underset{R^{23}}{\diagdown} N \end{array}$$

| A | B | D | J | R²³ | Gn |
|---|---|---|---|---|---|
| CH₂ - Q5 | H | COOEt | Me | OMe | Gc |
| Q26 | H | COOMe | Me | H | Gc |
| Q26 | H | COOEt | Me | OMe | Gc |
| Q61 | H | COOMe | Me | H | G3 |
| Q61 | H | COOMe | Me | Me | Gc |
| Q61 | H | COOMe | Me | OMe | Gc |
| Q61 | H | COOMe | Et | H | Gc |
| Q61 | H | COOMe | Et | Me | Gc |
| Q61 | H | COOMe | Et | OMe | G3 |
| Q61 | H | COOMe | J8 | H | Gc |
| Q61 | H | COOMe | J8 | Me | Gc |
| Q61 | H | COOMe | J8 | OMe | G3 |
| Q61 | H | COOEt | Me | H | Gc |
| Q61 | H | COOEt | Me | Me | G3 |
| Q61 | H | COOEt | Me | OMe | Gc |
| Q61 | H | COOEt | Et | H | Gc |
| Q61 | H | COOEt | Et | Me | G3 |
| Q61 | H | COOEt | Et | OMe | Gc |
| Q61 | H | COOEt | J9 | H | Gc |
| Q61 | H | COOEt | J9 | Me | Gc |
| Q61 | H | COOEt | J9 | OMe | Gc |
| CH₂ - Q61 | H | COOMe | Me | H | G3 |
| CH₂ - Q61 | H | COOEt | Me | OMe | Gc |
| Q201 | H | COOMe | Me | H | G₃ |
| Q201 | H | COOMe | Me | Me | Gc |
| Q201 | H | COOMe | Me | OMe | Gc |
| Q201 | H | COOMe | Et | H | Gc |
| Q201 | H | COOMe | Et | Me | Gc |
| Q201 | H | COOMe | Et | OMe | G₃ |
| Q201 | H | COOMe | J13 | H | Gc |
| Q201 | H | COOMe | J13 | Me | Gc |
| Q201 | H | COOMe | J13 | OMe | G₃ |
| Q201 | H | COOEt | Me | H | Gc |
| Q201 | H | COOEt | Me | Me | G₃ |
| Q201 | H | COOEt | Me | OMe | Gc |
| Q201 | H | COOEt | Et | H | Gc |
| Q201 | H | COOEt | Et | Me | G₃ |
| Q201 | H | COOEt | Et | OMe | Gc |
| Q201 | H | COOEt | J14 | H | Gc |
| Q201 | H | COOEt | J14 | Me | Gc |
| Q201 | H | COOEt | J14 | OMe | Gc |
| CH₂ - Q201 | H | COOMe | Me | H | G₃ |
| CH₂ - Q201 | H | COOEt | Me | OMe | Gc |
| Q205 | H | COOMe | Me | H | Gc |
| Q205 | H | COOEt | Me | OMe | Gc |
| Q229 | H | COOMe | Me | H | Gc |
| Q229 | H | COOEt | Me | OMe | G₃ |

In application of the compounds of this invention as herbicides, they can be applied by mixing with suitable carriers such as solid carriers, including for example clay, talc, bentonite, diatomaceous earth and others, or liquid carriers, including for example water, alcohols (methanol, ethanol and the like), aromatic hydrocarbons (benzene, toluene, xylene and the like), chlorinated hydrocarbons, ethers, ketones, esters (ethyl acetate etc.), acid amides (dimethylformamide etc.) and others. They can be provided for practical use with addition of any desired additive selected from an emulsifier, a dispersing agent, a suspending agent, a penetrating agent, a spreader and a stabilizer and in any desired form such as a soluble concentrate, an emulsifiable concentrate, a wettable powder, a dust, a granule, a flowable, etc.

In the following, there are shown examples of formulations of herbicides containing the compounds of this invention as active ingredients, but they are not limitative of this invention. In the exemplary formulations shown below, "parts" means "parts by weight".

| Exemplary Formulation 1: Wettable powder | |
|---|---|
| Compound No. 11 of this invention | 20 parts |
| Zeeklite A | 76 parts |
| (kaolin type clay; trade name; produced by Zeeklite Kogyo Co., Ltd.) | |
| Solpol 5039 | 2 parts |
| (mixture of nonionic surfactant and anionic surfactant; trade name; produced by Toho Kagaku Co., Ltd.) | |
| Carplex (anticaking agent) | 2 parts |
| (white carbon; trade name, produced by Shionogi Seiyaku Co., Ltd.) | |

The above components are mixed and pulverized homogeneously to prepare a wettable powder.

| Exemplary Formulation 2: Wettable powder | |
|---|---|
| Compound No. 6 of this invention | 40 parts |
| Zeeklite A | 54 parts |
| (kaolin type clay; trade name; produced by Zeeklite Kogyo Co., Ltd.) | |
| Solpol 5039 | 2 parts |
| (mixture of nonionic surfactant and anionic surfactant; trade name; produced by Toho Kagaku Co., Ltd.) | |
| Carplex (anticaking agent) | 4 parts |
| (white carbon; trade name, produced by Shionogi Seiyaku Co., Ltd.) | |

The above components are mixed and pulverized homogeneously to prepare a wettable powder.

| Exemplary Formulation 3: Emulsifiable concentrate | |
|---|---|
| Compound No. 3 of this invention | 5 parts |
| Xylene | 75 parts |
| Dimethylformamide | 15 parts |
| Solpol 2680 | 5 parts |
| (mixture of nonionic surfactant and anionic surfactant; trade name; produced by Toho Kagaku Co., Ltd.) | |

The above components are homogeneously mixed to prepare an emulsifiable concentrate. In use, the above emulsifiable concentrate is diluted 10 to 10,000 times and sprayed in an amount of 0.005 to 10 kg per hectare in terms of the active ingredient.

| Exemplary Formulation 4: Flowable | |
|---|---|
| Compound No. 11 of this invention | 25 parts |
| Agrisol S-710 | 10 parts |
| (nonionic surfactant; trade name; produced by Kao Co., Ltd.) | |
| Runox 1000C | 0.5 part |
| (anionic surfactant; trade name; produced by Toho Kagaku Co., Ltd.) | |
| 1% Rhodopol water | 20 parts |
| (thickener; trade name; produced by Rhone-Poulenc Co., Ltd.) | |
| Water | 44.5 parts |

The above components are mixed homogeneously to provide a flowable agent.

| Exemplary Formulation 5: Flowable | |
|---|---|
| Compound No. 9 of this invention | 40 parts |
| Agrisol S-710 | 10 parts |
| (nonionic surfactant; trade name; produced by Kao Co., Ltd.) | |
| Runox 1000C | 0.5 part |

| Exemplary Formulation 5: Flowable | |
|---|---|
| (anionic surfactant; trade name; produced by Toho Kagaku Co., Ltd.) | |
| 1% Rhodopol water | 20 parts |
| (thickener; trade name, produced by Rhone-Poulenc Co., Ltd.) | |
| Water | 29.5 parts |

The above components are mixed homogeneously to provide a flowable agent.

| Exemplary Formulation 6: Granule | |
|---|---|
| Compound No. 8 of this invention | 1 part |
| Bentonite | 55 parts |
| Talc | 44 parts |

The above components are mixed and pulverized homogeneously, then a small amount of water is added and the whole is stirred, kneaded and granulated by excluding granulator, then dried to prepare a granule.

| Exemplary Formulation 7: Wettable powder | |
|---|---|
| Compound No. 24 of this invention | 20 parts |
| Zeeklite A | 76 parts |
| (kaolin type clay; trade name; produced by Zeeklite Kogyo Co., Ltd.) | |
| Solpol 5039 | 2 parts |
| (mixture of nonionic surfactant and anionic surfactant; trade name; produced by Toho Kagaku Co., Ltd.) | |
| Carplex (anticaking agent) | 2 parts |
| (white carbon; trade name, produced by Shionogi Seiyaku Co., Ltd.) | |

The above components are mixed and pulverized homogeneously to prepare a wettable powder.

| Exemplary Formulation 8: Wettable powder | |
|---|---|
| Compound No. 21 of this invention | 40 parts |
| Zeeklite A | 54 parts |
| (kaolin type clay; trade name; produced by Zeeklite Kogyo Co., Ltd.) | |
| Solpol 5039 | 2 parts |
| (mixture of nonionic surfactant and anionic surfactant; trade name; produced by Toho Kagaku Co., Ltd.) | |
| Carplex (anticaking agent) | 4 parts |
| (white carbon; trade name, produced by Shionogi Seiyaku Co., Ltd.) | |

The above components are mixed and pulverized homogeneously to prepare a wettable powder.

| Exemplary Formulation 9: Emulsifiable concentrate | |
|---|---|
| Compound No. 22 of this invention | 5 parts |
| Xylene | 75 parts |
| Dimethylformamide | 15 parts |
| Solpol 2680 | 5 parts |
| (mixture of nonionic surfactant and anionic surfactant; trade name; produced by Toho Kagaku Co., Ltd.) | |

The above components are homogeneously mixed to prepare an emulsifiable concentrate. In use, the above emulsifiable concentrate is diluted 10 to 10,000 times and sprayed in an amount of 0.005 to 10 kg per hectare in terms of the active ingredient.

| Exemplary Formulation 10: Flowable | |
|---|---|
| Compound No. 24 of this invention | 25 parts |
| Agrisol S-710 | 10 parts |
| (nonionic surfactant; trade name; produced by Kao Co., Ltd.) | |
| Runox 1000C | 0.5 part |
| (anionic surfactant; trade name; produced by Toho Kagaku Co., Ltd.) | |
| 1% Rhodopol water | 20 parts |
| (thickener; trade name, produced by Rhone-Poulenc Co., Ltd.) | |
| Water | 44.5 parts |

The above components are mixed homogeneously to provide a flowable agent.

| Exemplary Formulation 11: Flowable | |
|---|---|
| Compound No. 21 of this invention | 40 parts |
| Agrisol S-710 | 10 parts |
| (nonionic surfactant; trade name; produced by Kao Co., Ltd.) | |
| Runox 1000C | 0.5 part |
| (anionic surfactant; trade name; produced by Toho Kagaku Co., Ltd.) | |
| 1% Rhodopol water | 20 parts |
| (thickener; trade name, produced by Rhone-Poulenc Co., Ltd.) | |
| Water | 29.5 parts |

The above components are mixed homogeneously to provide a flowable agent.

| Exemplary Formulation 12: Granule | |
|---|---|
| Compound No. 23 of this invention | 1 part |
| Bentonite | 55 parts |
| Talc | 44 parts |

The above components are mixed and pulverized homogeneously, then a small amount of water is added and the whole is stirred, kneaded and granulated by excluding granulator, then dried to prepare a granule.

If desired, the compound of this invention may be applied as a mixture with other kinds of herbicides, various insecticides, sterilizers or adjuvants during preparation or before spraying.

Such other kinds of herbicides as mentioned above include compounds as described in Farm Chemicals Handbook (1986).

The compounds of this invention can also be applied not only to the agricultural and horticultural fields such as farm fields, paddy fields, fruit gardens and the like, but to the non-agricultural fields such as athletic grounds, vacant lands, belts along railroads and others in order to prevent and eliminate various weeds. The amounts of the herbicide to be applied, which may differ depending on the scenes to be applied, the time of application, the application method, the kinds of the objective grasses and the crops harvested, may generally range suitably from about 0.005 to 10 kg per hectare in terms of the active ingredient.

The following test examples are set forth for illustrating specifically the effectiveness of the compounds of this invention as herbicides.

TEST EXAMPLE 1

Herbicidal effect test by soil treatment

In a plastic box of 15 cm length, 22 cm width and 6 cm depth, there was placed a sterilized deluvium soil, and seeds of (A) barnyardgrass (*Echinochloa crusgalli*), (B) large crabgrass (*Digitaria adscendens*), (C) annual sedge (*Cyperus microiria*), (D) black nightshade (*Solanum nigrum L.*), (E) hairly galinosoga (*Galinosoga ciliata*), (F) yellows cress (*Rorippa atrovirens*), (G) rice (*Oryza sativa*), (H) corn (*Zea mays*), (I) wheat (*Triticum vulgare*), (J) soybean (*Glysine max*), (K) cotton (*Gossypium spp*) and (L) sugar beet (*Beta vulgaris*) were sown mixedly. After covering the seeds with soil to about 1.5 cm, herbicides were sprayed evenly on the soil surface respectively such that a predetermined proportion of the active ingredient may be applied.

In spraying, the wettable powder as shown in the foregoing exemplary formulations was diluted with water and sprayed over the entire surface by means of a small sprayer. Four weeks after spraying, the herbicidal effect on crops and each of the weeds were examined according to the judgment criteria shown below. Provided that, in the following Table, a mark "-" was shown in the column of activity when beet was omitted from the crops to be tested.

The results are shown in Table 16.

Some of the compounds of this invention show the selectivity on certain crops.

Judgment criteria:

5 ... Growth control rates of more than 90% (almost completely withered)
4 ... Growth control rates of 70 to 90%
3 ... Growth control rates of 40 to 70%
2 ... Growth control rates of 20 to 40%
1 ... Growth control rates of 5 to 20%
0 ... Growth control rates of less than 5% (substantially no effect)

The above growth control rates are determined by measuring the top fresh weights of the treated plants and those of the non-treated plants, and calculated from the following formula:

$$\text{Growth control rate (\%)} = \left(1 - \frac{\text{Top fresh weight of the treated plants}}{\text{Top fresh weight of the non-treated plants}}\right) \times 100$$

TABLE 16

| Compound No. | Amount of active ingredient applied kg/ha | (A) | (B) | (C) | (D) | (E) | (F) | (G) | (H) | (I) | (J) | (K) | (L) |
|---|---|---|---|---|---|---|---|---|---|---|---|---|---|
| 3 | 0.32 | 5 | 4 | 5 | 4 | 4 | 5 | 5 | 5 | 5 | 5 | 0 | — |
| 6 | 0.32 | 5 | 5 | 5 | 5 | 5 | 5 | 5 | 5 | 5 | 5 | 0 | — |
| 9 | 0.16 | 5 | 5 | 5 | 5 | 5 | 5 | 5 | 5 | 5 | 5 | 0 | — |
|   | 0.32 | 5 | 5 | 5 | 5 | 5 | 5 | 5 | 5 | 5 | 5 | 0 | — |
| 11 | 0.08 | 5 | 5 | 5 | 5 | 5 | 5 | 5 | 5 | 5 | 5 | 5 | 0 |
|   | 0.16 | 5 | 5 | 5 | 5 | 5 | 5 | 5 | 5 | 5 | 5 | 5 | 0 |
| 13 | 0.16 | 5 | 5 | 5 | 5 | 5 | 5 | 5 | 5 | 5 | 5 | 5 | 0 |
| 16 | 0.08 | 5 | 3 | 5 | 5 | 5 | 5 | 5 | 5 | 3 | 3 | 0 | 0 |
|   | 0.16 | 5 | 4 | 5 | 5 | 5 | 5 | 5 | 5 | 4 | 4 | 1 | 0 |
| 19 | 0.04 | 4 | 3 | 5 | 5 | 5 | 5 | 5 | 5 | 5 | 5 | 5 | — |
|   | 0.08 | 5 | 4 | 5 | 5 | 5 | 5 | 5 | 5 | 5 | 5 | 5 | — |
|   | 0.16 | 5 | 5 | 5 | 5 | 5 | 5 | 5 | 5 | 5 | 5 | 5 | — |
| 21 | 0.04 | 4 | 4 | 4 | 4 | 5 | 5 | 5 | 4 | 0 | 4 | 0 | — |
|   | 0.08 | 5 | 5 | 5 | 5 | 5 | 5 | 5 | 5 | 1 | 5 | 0 | — |
|   | 0.16 | 5 | 5 | 5 | 5 | 5 | 5 | 5 | 5 | 2 | 5 | 1 | — |
| 24 | 0.02 | 5 | 4 | 5 | 5 | 5 | 5 | 5 | 5 | 5 | 5 | 0 | — |
|   | 0.04 | 5 | 5 | 5 | 5 | 5 | 5 | 5 | 5 | 5 | 5 | 0 | — |
|   | 0.08 | 5 | 5 | 5 | 5 | 5 | 5 | 5 | 5 | 5 | 5 | 0 | — |

(A) barnyardgrass (*Echinochloa crusgalli*),
(B) large crabgrass (*Digitaria adscendens*),
(C) annual sedge (*Cyperus microiria*),
(D) black nightshade (*Solanum nigrum L.*),
(E) hairly galinosoga (*Galinosoga ciliata*),
(F) yellows cress (*Rorippa atrovirens*),
(G) rice (*Oryza sativa*),
(H) corn (*Zea mays*),
(I) wheat (*Triticum vulgare*),
(J) soybean (*Glysine max*),
(K) cotton (*Gossypium spp*),
(L) sugar beet (*Beta vulgaris*).

TEST EXAMPLE 2

Herbicidal effect test by foliage treatment

In a plastic box of 15 cm length, 22 cm width and 6 cm depth, there was placed a sterilized deluvium soil, and seeds of (A) barnyardgrass (*Echinochloa crusgalli*), (B) large crabgrass (*Digitaria adscendens*), (C) annual sedge (*Cyperus microiria*), (D) black nightshade (*Solanum nigrum L.*), (E) hairly galinosoga (*Galinosoga ciliata*), (F) yellows cress (*Rorippa atrovirens*), (G) rice (*Oryza sativa*), (H) corn (*Zea mays*), (I) wheat (*Triticum vulgare*), (J) soybean (*Glysine max*), (K) cotton (*Gossypium spp*) and (L) sugar beet (*Beta vulgaris*) were sown in spots. After covering the seeds with soil to about 1.5 cm, herbicides were sprayed evenly on the soil surface such that a predetermined proportion of the active ingredient may be applied.

In spraying, the wettable powder as shown in the foregoing exemplary formulations was diluted with water and sprayed over the entire surface of the foliage portions of each crop and weed by means of a small sprayer. Four weeks after spraying, the herbicidal effect on crops etc. and each of the weeds were examined according to the judgment criteria shown in Test Example 1.

The results are shown in Table 17.

TABLE 17

| Compound No. | Amount of active ingredient applied kg/ha | (A) | (B) | (C) | (D) | (E) | (F) | (G) | (H) | (I) | (J) | (K) | (L) |
|---|---|---|---|---|---|---|---|---|---|---|---|---|---|
| 3 | 0.08 | 5 | 2 | 5 | 5 | 5 | 5 | 5 | 5 | 5 | 5 | 0 | 5 |
|  | 0.16 | 5 | 3 | 5 | 5 | 5 | 5 | 5 | 5 | 5 | 5 | 1 | 5 |
| 5 | 0.32 | 5 | 5 | 5 | 5 | 5 | 5 | 5 | 5 | 5 | 5 | 5 | — |
| 6 | 0.04 | 5 | 1 | 4 | 5 | 5 | 5 | 5 | 5 | 0 | 5 | 5 | 5 |
|  | 0.08 | 5 | 2 | 5 | 5 | 5 | 5 | 5 | 5 | 1 | 5 | 5 | 5 |
|  | 0.16 | 5 | 3 | 5 | 5 | 5 | 5 | 5 | 5 | 2 | 5 | 5 | 5 |
| 8 | 0.08 | 4 | 1 | 5 | 5 | 5 | 5 | 5 | 4 | 0 | 5 | 4 | 5 |
|  | 0.16 | 5 | 2 | 5 | 5 | 5 | 5 | 5 | 5 | 0 | 5 | 5 | 5 |
| 9 | 0.04 | 5 | 3 | 4 | 5 | 5 | 5 | 5 | 5 | 4 | 5 | 5 | 5 |
|  | 0.08 | 5 | 4 | 5 | 5 | 5 | 5 | 5 | 5 | 5 | 5 | 5 | 5 |
|  | 0.16 | 5 | 5 | 5 | 5 | 5 | 5 | 5 | 5 | 5 | 5 | 5 | 5 |
| 11 | 0.04 | 5 | 4 | 5 | 5 | 5 | 5 | 5 | 5 | 5 | 5 | 5 | 0 |
|  | 0.08 | 5 | 5 | 5 | 5 | 5 | 5 | 5 | 5 | 5 | 5 | 5 | 0 |
|  | 0.16 | 5 | 5 | 5 | 5 | 5 | 5 | 5 | 5 | 5 | 5 | 5 | 0 |
| 13 | 0.16 | 5 | 5 | 5 | 5 | 5 | 5 | 5 | 5 | 5 | 5 | 5 | 0 |
| 16 | 0.08 | 5 | 4 | 5 | 5 | 5 | 5 | 5 | 5 | 5 | 5 | 5 | 0 |
|  | 0.16 | 5 | 5 | 5 | 5 | 5 | 5 | 5 | 5 | 5 | 5 | 5 | 0 |
| 19 | 0.04 | 5 | 4 | 5 | 5 | 5 | 5 | 5 | 5 | 5 | 5 | 5 | 5 |
|  | 0.08 | 5 | 5 | 5 | 5 | 5 | 5 | 5 | 5 | 5 | 5 | 5 | 5 |
|  | 0.16 | 5 | 5 | 5 | 5 | 5 | 5 | 5 | 5 | 5 | 5 | 5 | 5 |
| 21 | 0.02 | 3 | 2 | 5 | 5 | 5 | 5 | 5 | 5 | 4 | 5 | 4 | 5 |
|  | 0.04 | 4 | 3 | 5 | 5 | 5 | 5 | 5 | 5 | 5 | 5 | 5 | 5 |
|  | 0.08 | 5 | 4 | 5 | 5 | 5 | 5 | 5 | 5 | 5 | 5 | 5 | 5 |
| 24 | 0.01 | 5 | 4 | 5 | 5 | 5 | 5 | 5 | 5 | 4 | 5 | 4 | 5 |
|  | 0.02 | 5 | 5 | 5 | 5 | 5 | 5 | 5 | 5 | 5 | 5 | 5 | 5 |
|  | 0.04 | 5 | 5 | 5 | 5 | 5 | 5 | 5 | 5 | 5 | 5 | 5 | 5 |

(A) barnyardgrass (*Echinochloa crusgalli*),
(B) large crabgrass (*Digitaria adscendens*),
(C) annual sedge (*Cyperus microiria*),
(D) black nightshade (*Solanum nigrum* L.),
(E) hairly galinosoga (*Galinosoga ciliata*),
(F) yellows cress (*Rorippa atrovirens*),
(G) rice (*Oryza sativa*),
(H) corn (*Zea mays*),
(I) wheat (*Triticum vulgare*),
(J) soybean (*Glysine max*),
(K) cotton (Gossypium spp),
(L) sugar beet (*Beta vulgaris*).

We claim:

1. An imidazolesulfonamide derivative represented by the formula (I):

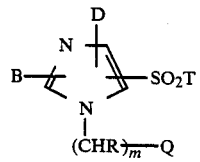

(I)

wherein Q represents a group of:

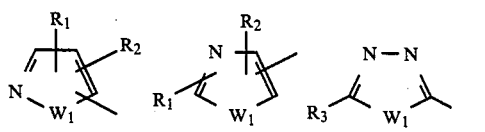

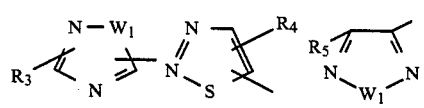

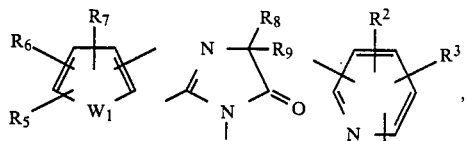

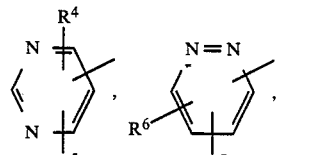

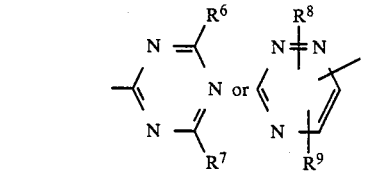

wherein $R^1$, $R^2$ and $R^3$ each independently represent a hydrogen atom, a halogen atom, a nitro group, a lower alkyl group, a halogenated lower alkyl group, a cyano group, a group of $COOR^{10}$, a group of $S(O)_nR^{11}$, a group of $NR^{12}R^{13}$, a lower alkoxy group, a group of $SO_2NR^8R^9$, a group of $SO_2OR^{11}$ or a phenyl group which may be substituted by a halogen atom, a nitro group, a group of COOR$^{10}$, a lower alkoxy group or a lower alkyl group;

R$^4$ and R$^5$ each independently represent a hydrogen atom, a halogen atom, a lower alkyl group, a halogenated lower alkyl group, a nitro group, a cyano group, a group of COOR$^{10}$, a group of S(O)$_n$R$^{11}$, a lower alkoxy group or a phenyl group which may be substituted by a halogen atom, a group of COOR$^{10}$, a nitro group, a lower alkoxy group or a lower alkyl group;

R$^6$ and R$^7$ each independently represent a hydrogen atom, a halogen atom, a lower alkyl group, a lower alkoxy group, a nitro group or a group of COOR$^{10}$;

R$^8$ and R$^9$ each independently represent a hydrogen atom, a lower alkyl group or a phenyl group;

W$^1$ represents an oxygen atom, a sulfur atom or a group of N—R$^{10}$;

R$^{10}$ represents a hydrogen atom or a lower alkyl group;

R$^{11}$ represents a lower alkyl group and n represents an integer of 0, 1 or 2; and R$^{12}$ and R$^{13}$ each independently represent a hydrogen atom or a lower alkyl group;

m represents an integer of 0, 1 or 2;

R represents a hydrogen atom or a lower alkyl group;

B and D each independently represent a hydrogen atom, a halogen atom, a nitro group, a lower alkyl group, a lower aralkyl group, a lower alkoxy group, a halogenated lower alkyl group, a halogenated lower alkenyl group, a lower alkoxyalkyl group, an alkylcarbonyl group, a group of COOR$^{14}$, a group of CONR$^{15}$R$^{16}$, a group of S(O)$_n$R$^{17}$, a cyano group, a group of NR$^{18}$R$^{19}$, a group of SO$_2$NR$^{20}$R$^{21}$, a group of OH, a benzoyl group which may be substituted by a halogen atom or a lower alkyl group or a phenyl group which may substituted by is selected from a halogen atom, a nitro group, a group of COOR$^{10}$, a lower alkoxy group or a lower alkyl group;

R$^{14}$ represents a hydrogen atom, a lower alkyl group which may be substituted by a group of OR$^{10}$, a halogen atom, a halogenated lower alkoxy group, a cyano group, a phenoxy group, a lower alkoxycarbonyl group, a group of NR$^{10}$R$^{11}$, a lower cycloalkyl group, a lower alkylthio group or a lower alkylcarbonyl group, a lower alkenyl group, a halogenated lower alkenyl group, a lower alkynyl group, a halogenated lower alkynyl group, a lower cycloalkyl group or a benzyl group;

R$^{15}$ represents a hydrogen atom, a lower alkyl group or a phenyl group; and R$^{16}$ represents a hydrogen atom, a lower alkyl group or a lower alkoxy group;

R$^{17}$ represents a lower alkyl group, a lower alkoxy group, a phenyl group, a halogenated alkyl group, a lower alkenyloxy group or a lower alkynyloxy group; and n represents an integer of 0, 1 or 2;

R$^{18}$ and R$^{19}$ each independently represent a hydrogen atom, a lower alkyl group, a lower alkylcarbonyl group or a lower alkylsulfonyl group;

R$^{20}$ and R$^{21}$ each independently represent a hydrogen atom, a lower alkyl group, a lower alkenyl group or a lower alkynyl group;

T represents a group of

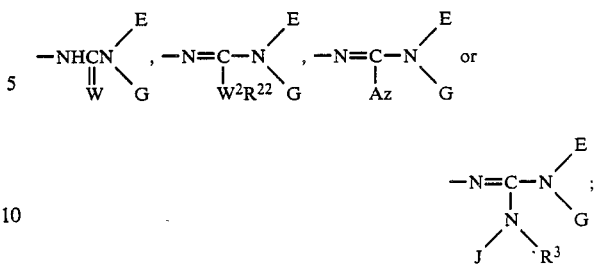

E represents a hydrogen atom, a lower alkyl group, a lower alkenyl group, a lower alkynyl group or a lower alkoxy group;

G represents a group of;

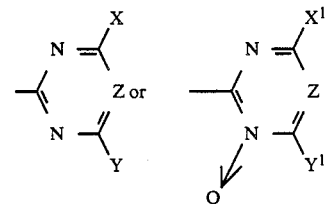

wherein X and Y each independently represent a hydrogen atom, a halogen atom, a lower alkyl group, a lower alkoxy group, a lower alkoxyalkyl group, a halogenated alkyl group, a halogenated lower alkoxy group, a group of NR$^{24}$R$^{25}$, a group of OCH(R$^{10}$)—COOR$^{10}$, a group of COOR$^{10}$, a cyclopropyl group, a group of CH(OR$^{26}$)$_2$, a lower alkylthio group or a halogenated lower alkylthio group;

R$^{24}$ and R$^{25}$ each independently represent a hydrogen atom, a lower alkyl group or a lower alkoxy group;

R$^{26}$ represents a lower alkyl group;

X$^1$ and Y$^1$ each independently represent a hydrogen atom, a halogen atom, a lower alkyl group, a halogenated alkyl group or a lower alkoxy group;

Z represents a group of C—R$^{27}$;

H$^{27}$ represents a hydrogen atom, a lower alkyl group, a halogenated lower alkyl group, a halogen atom, a lower alkoxy group or a 5-membered ring structure containing an oxygen atom together with Y or Y$^1$;

W represents an oxygen atom, a sulfur atom or a group of N—R$^{28}$ where R$^{28}$ represents a hydrogen atom or a lower alkoxy group;

W$^2$ represents an oxygen atom or a sulfur atom;

R$^{22}$ represents a lower alkyl group;

Az represents a halogen atom, a nitro group, or an imidazolyl group, an imidazolynyl group, a pyrazolyl group, a triazolyl group or a benzimidazolyl group each of which may be mono-, di- or tri-substituted by a lower alkyl group;

J represents a lower alkyl group or a group of;

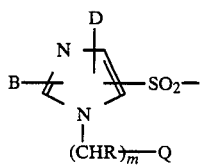

wherein Q, R, m, B and D have the same meanings as defined above;
$R^{23}$ represents a hydrogen atom, a lower alkyl group or a lower alkoxy group.

2. The compound of claim 1, which is represented by the formula:

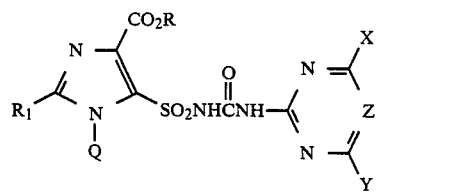

wherein $R_1$ represents a hydrogen atom, a methyl group or a halogen atom; R represents a methyl group or an ethyl group; Q is selected from the group of Q5, Q6, Q7, Q9, Q15, Q21, Q26, Q29, Q32, Q50, Q54, Q61, Q68, Q88, Q127, Q138, Q142, Q188, Q189, Q201, Q202, Q204, Q205, Q209, Q222, Q225, Q229, Q230, Q246 and Q250 as shown below:

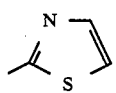 Q5

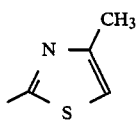 Q6

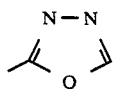 Q7

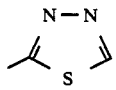 Q9

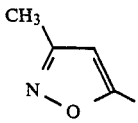 Q15

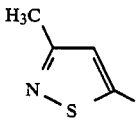 Q21

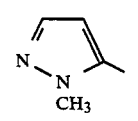 Q26

-continued

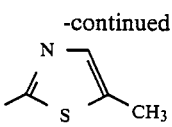 Q29

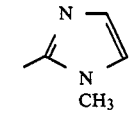 Q32

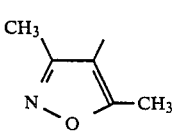 Q50

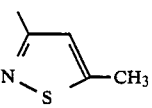 Q54

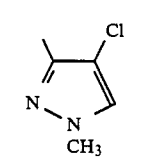 Q61

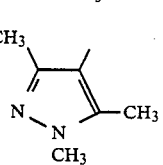 Q68

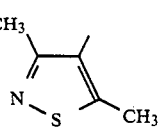 Q88

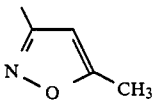 Q127

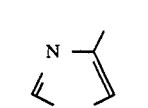 Q138

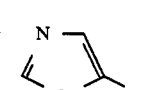 Q142

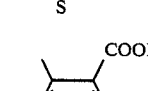 Q188

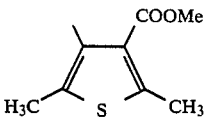 Q189

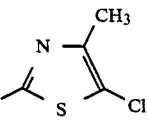 Q201

-continued

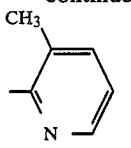  Q202

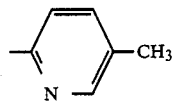  Q204

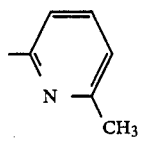  Q205

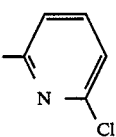  Q209

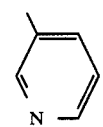  Q222

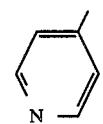  Q225

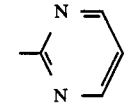  Q229

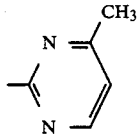  Q230

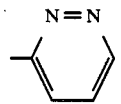  Q246

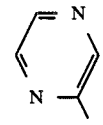  Q250

X and Y are each independently a halogen atom, a methyl group, a methoxy group; and Z is —CH=.

3. The compound of claim 2, which is N-[(4,6-dimethoxypyrimidin-2-yl)aminocarbonyl]-4-ethoxycarbonyl-1-(2-thiazolyl)imidazole-5-sulfonamide.

4. The compound of claim 2, which is N-[(4,6-dimethoxypyrimidin-2-yl)aminocarbonyl]-4-methoxycarbonyl-1-(2-thiazolyl)imidazole-5-sulfonamide.

5. The compound of claim 2, which is N-[(4,6-dimethoxypyrimidin-2-yl)aminocarbonyl]-4-methoxycarbonyl-1-(1,3,4-thiadiazol-2-yl)imidazole-5-sulfonamide.

6. The compound of claim 2, which is N-[(4,6-dimethylpyrimidin-2-yl)aminocarbonyl]-4-methoxycarbonyl-1-(2-pyridyl)imidazole-5-sulfonamide.

7. The compound of claim 2, which is N-[(4,6-dimethoxypyrimidin-2-yl)aminocarbonyl]-4-methoxycarbonyl-1-(2-pyrimidyl)imidazole-5-sulfonamide.

8. The compound of claim 1, which is represented by the formula:

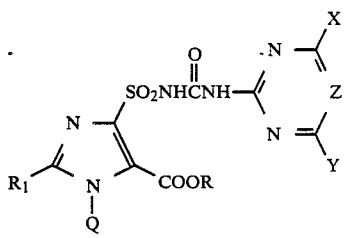

wherein $R_1$ represents a hydrogen atom or a methyl group; R represents a methyl group or an ethyl group; Q is selected from the group of Q5, Q6, Q7, Q9, Q15, Q21, Q26, Q29, Q32, Q50, Q54, Q61, Q68, Q88, Q127, Q138, Q142, Q188, Q189, Q201, Q202, Q204, Q205, Q209, Q222, Q225, Q229, Q230, Q246 and Q250 as shown below:

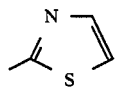  Q5

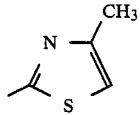  Q6

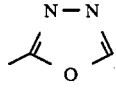  Q7

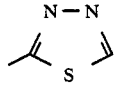  Q9

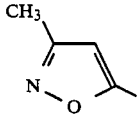  Q15

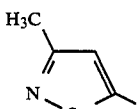  Q21

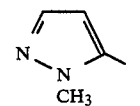  Q26

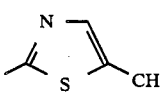  Q29

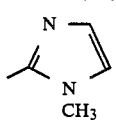 Q32
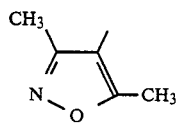 Q50
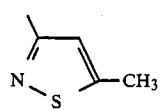 Q54
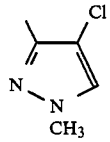 Q61
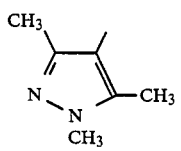 Q68
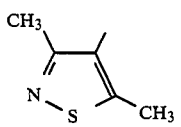 Q88
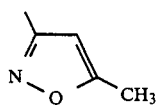 Q127
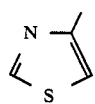 Q138
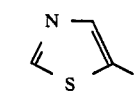 Q142
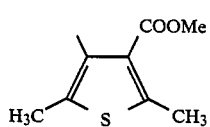 Q188
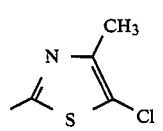 Q189
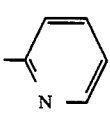 Q201
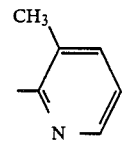 Q202
Q204
Q205
Q209
Q222
Q225
Q229
Q230
Q246
Q250
X and Y are each independently a halogen atom, a methyl group, a methoxy group; and Z is —CH=.
9. The compound of claim 1, which is represented by the formula:

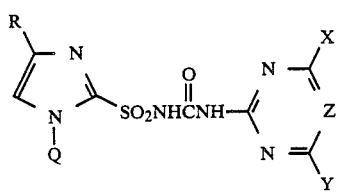
wherein $R_1$ represents a hydrogen atom, a methyl group, a halogen atom or a nitro group; R represents a methyl group or an ethyl group; Q is selected from the group of Q5, Q6, Q7, Q9, Q15, Q21, Q26, Q29, Q32, Q50, Q54, Q61, Q68, Q88, Q127, Q138, Q142, Q188, Q189, Q201, Q202, Q204, Q205, Q209, Q222, Q225, Q229, Q230, Q246 and Q250 as shown below:
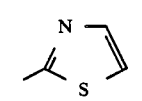 Q5
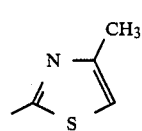 Q6
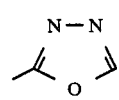 Q7
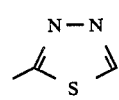 Q9
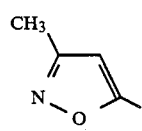 Q15
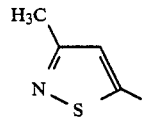 Q21
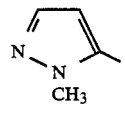 Q26
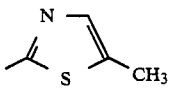 Q29
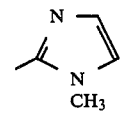 Q32
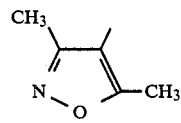 Q50
-continued
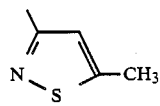 Q54
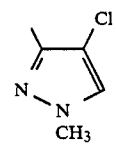 Q61
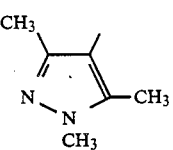 Q68
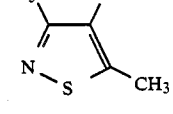 Q88
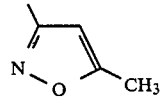 Q127
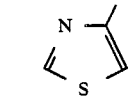 Q138
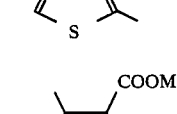 Q142
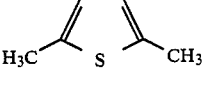 Q188
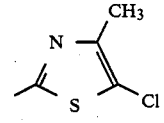 Q189
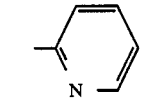 Q201
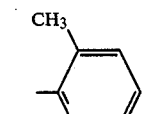 Q202
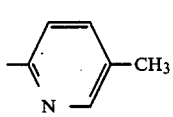 Q204

-continued

Q205 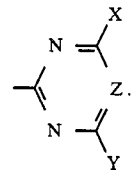

Q209 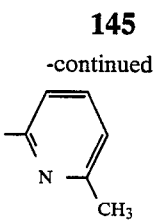

Q222

Q225

Q229

Q230

Q246

Q250

X and Y are each independently a halogen atom, a methyl group, a methoxy group; and Z is —CH=.

10. The compound of claim 2, which is N-[(4,6-dimethoxypyrimidin-2-yl)aminocarbonyl]-4-ethoxycarbonyl-1-(2-pyridyl)imidazole-5-sulfonamide.

11. The compound of claim 2, which is the compound where R is an ethyl group, $R_1$ is a hydrogen atom and Q is Q204.

12. The compound of claim 11, wherein X and Y are each independently selected from methyl and methoxy.

13. The compound of claim 12, wherein X and Y are each methoxy.

14. The compound of claim 2, which is the compound where R is an ethyl group, $R_1$ is a hydrogen atom and Q is Q222.

15. The compound of claim 14, wherein X and Y are each independently selected from methyl and methoxy.

16. The compound of claim 15, wherein X and Y are each methoxy.

17. The compound of claim 1, wherein G is

18. A method for inhibiting growth of undesirable plants by using the compound represented by the formula (I):

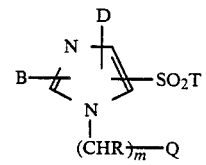 (I)

wherein Q represents a group of:

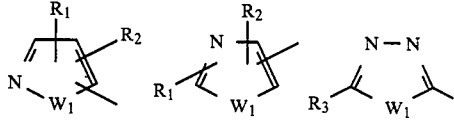

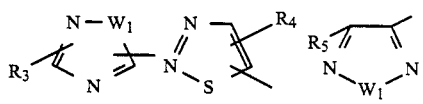

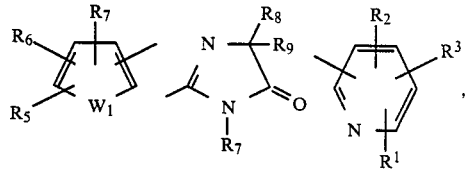

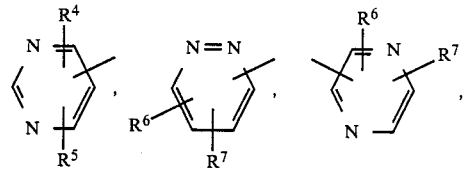

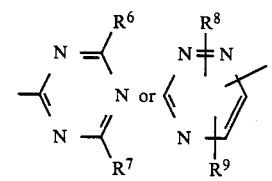

wherein $R^1$, $R^2$ and $R^3$ each independently represent a hydrogen atom, a halogen atom, a nitro group, a lower alkyl group, a halogenated lower alkyl group, a cyano group, a group of $COOR^{10}$, a group of $S(O)_nR^{11}$, a group of $NR^{12}R^{13}$, a lower alkoxy group, a group of $SO_2NR^8R^9$, a group of $SO_2OR^{11}$ or a phenyl group which may be substituted by a halogen atom, a nitro group, a group of $COOR^{10}$, a lower alkoxy group or a lower alkyl group;

R[4] and R[5] each independently represent a hydrogen atom, a halogen atom, a lower alkyl group, a halogenated lower alkyl group, a nitro group, a cyano group, a group of COOR[10], a group of S(O)$_n$R[11], a lower alkoxy group or a phenyl group which may be substituted by a halogen atom, a group of COOR[10], a nitro group, a lower alkoxy group or a lower alkyl group;

R[6] and R[7] each independently represent a hydrogen atom, a halogen atom, a lower alkyl group, a lower alkoxy group, a nitro group or a group of COOR[10];

R[8] and R[9] each independently represent a hydrogen atom, a lower alkyl group or a phenyl group;

W[1] represents an oxygen atom, a sulfur atom or a group of N—R[10];

R[10] represents a hydrogen atom or a lower alkyl group;

R[11] represents a lower alkyl group and n represents an integer of 0, 1 or 2; and R[12] and R[13] each independently represent a hydrogen atom or a lower alkyl group;

m represents an integer of 0, 1 or 2;

R represents a hydrogen atom or a lower alkyl group;

B and D each independently represent a hydrogen atom, a halogen atom, a nitro group, a lower alkyl group, a lower aralkyl group, a lower alkoxy group, a halogenated lower alkyl group, a halogenated lower alkenyl group, a lower alkoxyalkyl group, an alkylcarbonyl group, a group of COOR[14], a group of CONR[15]R[16], a group of S(O)$_n$R[17], a cyano group, a group of NR[18]R[19], a group of SO$_2$NR[20]R[21], a group of OH, a benzoyl group which may be substituted by a halogen atom or a lower alkyl group or a phenyl group which may substituted by is selected from a halogen atom, a nitro group, a group of COOR[10], a lower alkoxy group or a lower alkyl group;

R[14] represents a hydrogen atom, a lower alkyl group which may be substituted by a group of OR[10], a halogen atom, a halogenated lower alkoxy group, a cyano group, a phenoxy group, a lower alkoxycarbonyl group, a group of NR[10]R[11], a lower cycloalkyl group, a lower alkylthio group or a lower alkylcarbonyl group, a lower alkenyl group, a halogenated lower alkenyl group, a lower alkynyl group, a halogenated lower alkynyl group, a lower cycloalkyl group or a benzyl group;

R[15] represents a hydrogen atom, a lower alkyl group or a phenyl group; and R[16] represents a hydrogen atom, a lower alkyl group or a lower alkoxy group;

R[17] represents a lower alkyl group, a lower alkoxy group, a phenyl group, a halogenated alkyl group, a lower alkenyloxy group or a lower alkynyloxy group; and n represents an integer of 0, 1 or 2;

R[18] and R[19] each independently represent a hydrogen atom, a lower alkyl group, a lower alkylcarbonyl group or a lower alkylsulfonyl group;

R[20] and R[21] each independently represent a hydrogen atom, a lower alkyl group, a lower alkenyl group or a lower alkynyl group;

T represents a group of

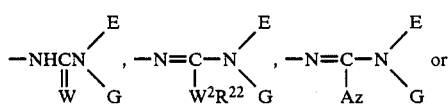

or

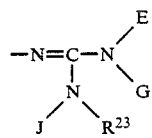

E represents a hydrogen atom, a lower alkyl group, a lower alkenyl group, a lower alkynyl group or a lower alkoxy group;

G represents a group of:

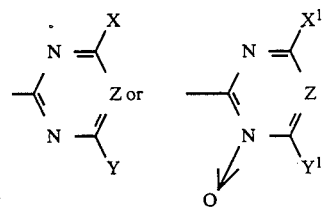

wherein X and Y each independently represent a hydrogen atom, a halogen atom, a lower alkyl group, a lower alkoxy group, a lower alkoxyalkyl group, a halogenated alkyl group, a halogenated lower alkoxy group, a group of NR[24]R[25], a group of OCH(R[10])—COOR[10], a group of COOR[10], a cyclopropyl group, a group of CH(OR[26])$_2$, a lower alkylthio group or a halogenated lower alkylthio group;

R[24] and R[25] each independently represent a hydrogen atom, a lower alkyl group or a lower alkoxy group;

R[26] represents a lower alkyl group;

X[1] and Y[1] each independently represent a hydrogen atom, a halogen atom, a lower alkyl group; a halogenated alkyl group or a lower alkoxy group;

Z represents a group of C—R[27];

R[27] represents a hydrogen atom, a lower alkyl group, a halogenated lower alkyl group, a halogen atom, a lower alkoxy group or a 5-membered ring structure containing an oxygen atom together with Y or Y[1];

W represents an oxygen atom, a sulfur atom or a group of N—R[28] where R[28] represents a hydrogen atom or a lower alkoxy group;

W[2] represents an oxygen atom or a sulfur atom;

R[22] represents a lower alkyl group;

Az represents a halogen atom, a nitro group, or an imidazolyl group, an imidazolynyl group, a pyrazolyl group, a triazolyl group or a benzimidazolyl group each of which may be mono-, di- or tri-substituted by a lower alkyl group;

J represents a lower alkyl group or a group of;

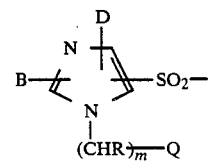

wherein Q, R, m, B and D have the same meanings as defined above;

$R^{23}$ represents a hydrogen atom, a lower alkyl group or a lower alkoxy group.

19. The method of claim 18, wherein G is

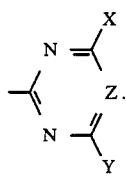

20. A herbicide which comprises a herbicidal carrier and as an effective ingredient, a compound represented by the formula (I):

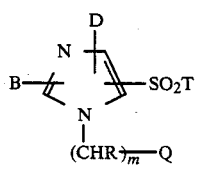

wherein Q represents a group of;

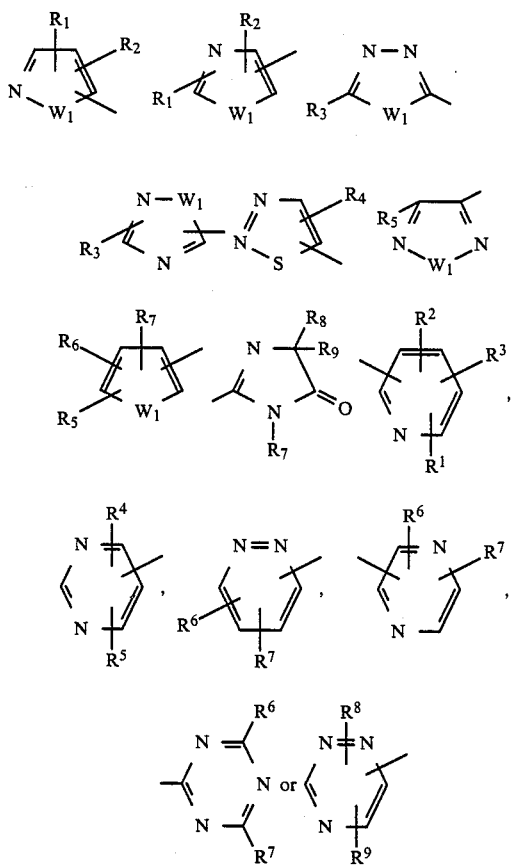

wherein $R^1$, $R^2$ and $R^3$ each independently represent a hydrogen atom, a halogen atom, a nitro group, a lower alkyl group, a halogenated lower alkyl group, a cyano group, a group of $COOR^{10}$, a group of $S(O)_nR^{11}$, a group of $NR^{12}R^{13}$, a lower alkoxy group, a group of $SO_2NR^8R^9$, a group of $SO_2OR^{11}$ or a phenyl group which may be substituted by a halogen atom, a nitro group, a group of $COOR^{10}$, a lower alkoxy group or a lower alkyl group;

$R^4$ and $R^5$ each independently represent a hydrogen atom, a halogen atom, a lower alkyl group, a halogenated lower alkyl group, a nitro group, a cyano group, a group of $COOR^{10}$, a group of $S(O)_nR^{11}$, a lower alkoxy group or a phenyl group which may be substituted by a halogen atom, a group of $COOR^{10}$, a nitro group, a lower alkoxy group or a lower alkyl group;

$R^6$ and $R^7$ each independently represent a hydrogen atom, a halogen atom, a lower alkyl group, a lower alkoxy group, a nitro group or a group of $COOR^{10}$;

$R^8$ and $R^9$ each independently represent a hydrogen atom, a lower alkyl group or a phenyl group;

$W^1$ represents an oxygen atom, a sulfur atom or a group of $N-R^{10}$;

$R^{10}$ represents a hydrogen atom or a lower alkyl group;

$R^{11}$ represents a lower alkyl group and n represents an integer of 0, 1 or 2; and $R^{12}$ and $R^{13}$ each independently represent a hydrogen atom or a lower alkyl group;

m represents an integer of 0, 1 or 2;

R represents a hydrogen atom or a lower alkyl group;

B and D each independently represent a hydrogen atom, a halogen atom, a nitro group, a lower alkyl group, a lower aralkyl group, a lower alkoxy group, a halogenated lower alkyl group, a halogenated lower alkenyl group, a lower alkoxyalkyl group, an alkylcarbonyl group, a group of $COOR^{14}$, a group of $CONR^{15}R^{16}$, a group of $S(O)_nR^{17}$, a cyano group, a group of $NR^{18}R^{19}$, a group of $SO_2NR^{20}R^{21}$, a group of OH, a benzoyl group which may be substituted by a halogen atom or a lower alkyl group or a phenyl group which may substituted by is selected from a halogen atom, a nitro group, a group of $COOR^{10}$, a lower alkoxy group or a lower alkyl group;

$R^{14}$ represents a hydrogen atom, a lower alkyl group which may be substituted by a group of $OR^{10}$, a halogen atom, a halogenated lower alkoxy group, a cyano group, a phenoxy group, a lower alkoxycarbonyl group, a group of $NR^{10}R^{11}$, a lower cycloalkyl group, a lower alkylthio group or a lower alkylcarbonyl group, a lower alkenyl group, a halogenated lower alkenyl group, a lower alkynyl group, a halogenated lower alkynyl group, a lower cycloalkyl group or a benzyl group;

$R^{15}$ represents a hydrogen atom, a lower alkyl group or a phenyl group; and $R^{16}$ represents a hydrogen atom, a lower alkyl group or a lower alkoxy group;

$R^{17}$ represents a lower alkyl group, a lower alkoxy group, a phenyl group, a halogenated alkyl group, a lower alkenyloxy group or a lower alkynyloxy group; and n represents an integer of 0, 1 or 2;

$R^{18}$ and $R^{19}$ each independently represent a hydrogen atom, a lower alkyl group, a lower alkylcarbonyl group or a lower alkylsulfonyl group;

$R^{20}$ and $R^{21}$ each independently represent a hydrogen atom, a lower alkyl group, a lower alkenyl group or a lower alkynyl group;

T represents a group of

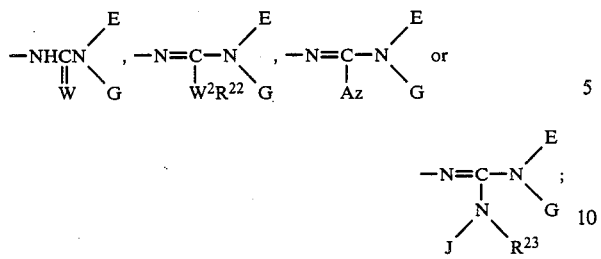

E represents a hydrogen atom, a lower alkyl group, a lower alkenyl group, a lower alkynyl group or a lower alkoxy group;

G represents a group of;

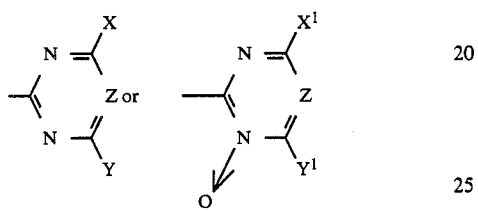

wherein X and Y each independently represent a hydrogen atom, a halogen atom, a lower alkyl group, a lower alkoxy group, a lower alkoxyalkyl group, a halogenated alkyl group, a halogenated lower alkoxy group, a group of $NR^{24}R^{25}$, a group of $OCH(R^{10})$—$COOR^{10}$, a group of $COOR^{10}$, a cyclopropyl group, a group of $CH(OR^{26})_2$, a lower alkylthio group or a halogenated lower alkylthio group;

$R^{24}$ and $R^{25}$ each independently represent a hydrogen atom, a lower alkyl group or a lower alkoxy group;

$R^{26}$ represents a lower alkyl group;

$X^1$ and $Y^1$ each independently represent a hydrogen atom, a halogen atom, a lower alkyl group, a halogenated alkyl group or a lower alkoxy group;

Z represents a group of C—$R^{27}$;

$R^{27}$ represents a hydrogen atom, a lower alkyl group, a halogenated lower alkyl group, a halogen atom, a lower alkoxy group or a 5-membered ring structure containing an oxygen atom together with Y or $Y^1$;

W represents an oxygen atom, a sulfur atom or a group of N—$R^{28}$ where $R^{28}$ represents a hydrogen atom or a lower alkoxy group;

$W^2$ represents an oxygen atom or a sulfur atom;

$R^{22}$ represents a lower alkyl group;

Az represents a halogen atom, a nitro group, or an imidazolyl group, an imidazolynyl group, a pyrazolyl group, a triazolyl group or a benzimidazolyl group each of which may be mono-, di- or tri-substituted by a lower alkyl group;

J represents a lower alkyl group or a group of;

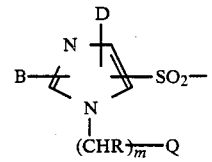

wherein Q, R, m, B and D have the same meanings as defined above;

$R^{23}$ represents a hydrogen atom, a lower alkyl group or a lower alkoxy group.

21. The herbicide of claim 20, wherein G is

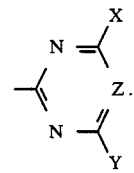

* * * * *

UNITED STATES PATENT AND TRADEMARK OFFICE
CERTIFICATE OF CORRECTION

PATENT NO. : 4,830,660

DATED : May 16, 1989

INVENTOR(S) : YAMAMOTO et al

It is certified that error appears in the above-identified patent and that said Letters Patent is hereby corrected as shown below:

Column 136, line 10:

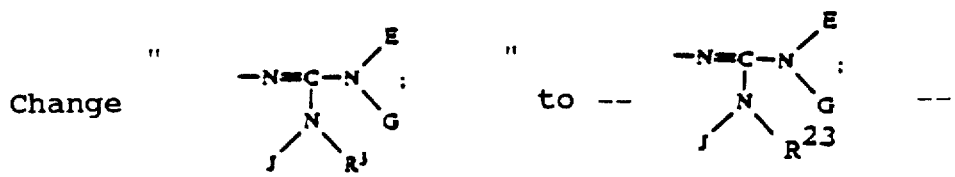

Column 136, line 50, change "$H^{27}$" to -- $R^{27}$ --.

Signed and Sealed this

Thirtieth Day of June, 1992

*Attest:*

DOUGLAS B. COMER

*Attesting Officer*     *Acting Commissioner of Patents and Trademarks*